(12) United States Patent
Zhou et al.

(10) Patent No.: US 10,351,511 B2
(45) Date of Patent: Jul. 16, 2019

(54) CYCLIC VINYLOGOUS AMIDES AS BROMODOMAIN INHIBITORS

(71) Applicant: ICAHN SCHOOL OF MEDICINE AT MOUNT SINAI, New York, NY (US)

(72) Inventors: Ming-Ming Zhou, Old Greenwich, CT (US); Michael Ohlmeyer, Plainsboro, NJ (US); Adam Vincek, Tarrytown, NY (US); Nilesh Zaware, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/842,032

(22) Filed: Dec. 14, 2017

(65) Prior Publication Data
US 2018/0105485 A1    Apr. 19, 2018

Related U.S. Application Data

(62) Division of application No. 14/914,672, filed as application No. PCT/US2014/053527 on Aug. 29, 2014, now Pat. No. 9,884,806.

(Continued)

(51) Int. Cl.
| | | |
|---|---|---|
| *A61K 31/136* | (2006.01) | |
| *A61K 31/166* | (2006.01) | |
| *A61K 31/18* | (2006.01) | |
| *A61K 31/195* | (2006.01) | |
| *A61K 31/196* | (2006.01) | |
| *A61K 31/245* | (2006.01) | |
| *A61K 31/277* | (2006.01) | |
| *A61K 31/404* | (2006.01) | |
| *A61K 31/4184* | (2006.01) | |
| *A61K 31/4192* | (2006.01) | |
| *A61K 31/44* | (2006.01) | |
| *A61K 31/4402* | (2006.01) | |
| *A61K 31/4406* | (2006.01) | |
| *A61K 31/4409* | (2006.01) | |

(Continued)

(52) U.S. Cl.
CPC .......... *C07C 225/20* (2013.01); *A61K 31/136* (2013.01); *A61K 31/166* (2013.01); *A61K 31/18* (2013.01); *A61K 31/195* (2013.01); *A61K 31/196* (2013.01); *A61K 31/245* (2013.01); *A61K 31/277* (2013.01); *A61K 31/404* (2013.01); *A61K 31/4184* (2013.01); *A61K 31/4192* (2013.01); *A61K 31/44* (2013.01); *A61K 31/4402* (2013.01); *A61K 31/4406* (2013.01); *A61K 31/4409* (2013.01); *A61K 31/4468* (2013.01); *A61K 31/47* (2013.01); *A61K 31/498* (2013.01); *A61K 31/4965* (2013.01); *A61K 31/517* (2013.01); *A61K 31/5375* (2013.01); *A61K 45/06* (2013.01); *C07C 229/48* (2013.01); *C07C 229/56* (2013.01); *C07C 229/60* (2013.01); *C07C 229/68* (2013.01); *C07C 237/30* (2013.01); *C07C 237/40* (2013.01); *C07C 255/58* (2013.01); *C07C 311/38* (2013.01); *C07D 209/08* (2013.01); *C07D 209/40* (2013.01); *C07D 211/58* (2013.01); *C07D 213/74* (2013.01); *C07D 213/75* (2013.01); *C07D 213/76* (2013.01); *C07D 215/06* (2013.01); *C07D 215/38* (2013.01); *C07D 217/02* (2013.01); *C07D 235/26* (2013.01); *C07D 239/74* (2013.01); *C07D 241/20* (2013.01); *C07D 241/42* (2013.01); *C07D 249/04* (2013.01); *C07D 249/06* (2013.01); *C07D 295/16* (2013.01); *C07D 295/21* (2013.01)

(58) Field of Classification Search
None
See application file for complete search history.

(56) References Cited

U.S. PATENT DOCUMENTS

| 4,338,466 A | 7/1982 | Nelson |
| 5,110,925 A | 5/1992 | Kusase et al. |

(Continued)

FOREIGN PATENT DOCUMENTS

| WO | 2007016643 A2 | 2/2007 |
| WO | 2013027168 A1 | 2/2013 |

OTHER PUBLICATIONS

Sengupta et al., Trends in Pharmacological Sciences, Jun. 2011, vol. 32, No. 6, pp. 337-344.*

(Continued)

*Primary Examiner* — Alicia L Otton
(74) *Attorney, Agent, or Firm* — Heslin Rothenberg Farley & Mesiti P.C.

(57) ABSTRACT

Cyclic vinylogous amides of Formula I are disclosed

I

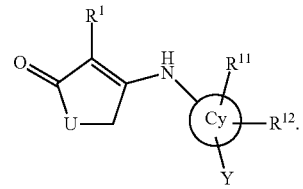

The compounds are useful for treating diseases that arise from inappropriate activity of proteins containing an acetyl-lysine. The compositions comprise a genus of cyclic vinylogous amides that are inhibitors of bromodomain.

18 Claims, 1 Drawing Sheet

Related U.S. Application Data

(60) Provisional application No. 61/872,303, filed on Aug. 30, 2013.

(51) Int. Cl.

| | | |
|---|---|---|
| A61K 31/4468 | (2006.01) |
| A61K 31/47 | (2006.01) |
| A61K 31/4965 | (2006.01) |
| A61K 31/498 | (2006.01) |
| A61K 31/517 | (2006.01) |
| A61K 31/5375 | (2006.01) |
| C07C 225/20 | (2006.01) |
| C07C 229/48 | (2006.01) |
| C07C 229/56 | (2006.01) |
| C07C 229/60 | (2006.01) |
| C07C 229/68 | (2006.01) |
| C07C 237/30 | (2006.01) |
| C07C 237/40 | (2006.01) |
| C07C 255/58 | (2006.01) |
| C07C 311/38 | (2006.01) |
| C07D 209/08 | (2006.01) |
| C07D 211/58 | (2006.01) |
| C07D 213/74 | (2006.01) |
| C07D 215/06 | (2006.01) |
| C07D 217/02 | (2006.01) |
| C07D 235/26 | (2006.01) |
| C07D 239/74 | (2006.01) |
| C07D 241/20 | (2006.01) |
| C07D 241/42 | (2006.01) |
| C07D 249/04 | (2006.01) |
| C07D 295/16 | (2006.01) |
| A61K 45/06 | (2006.01) |
| C07D 213/75 | (2006.01) |
| C07D 213/76 | (2006.01) |
| C07D 215/38 | (2006.01) |
| C07D 249/06 | (2006.01) |
| C07D 209/40 | (2006.01) |
| C07D 295/21 | (2006.01) |

(56) References Cited

U.S. PATENT DOCUMENTS

| | | |
|---|---|---|
| 6,235,736 B1 | 5/2001 | Ina et al. |
| 6,828,464 B2 | 12/2004 | Liang et al. |
| 2008/0194696 A1 | 8/2008 | Skolnick et al. |
| 2009/0035784 A1 | 2/2009 | Ioannou et al. |

OTHER PUBLICATIONS

Pooneh Salari & Mohammad Abdollahi (2012) Expert Opinion on Investigational Drugs, 21:3, 261-264.*
Edmondson et al., Org. Letter, 2000, 2 (8), pp. 1109-1112.
Gardette et al., Can. J. Chem., vol. 67, 1989.
PubChem-CID-11182899, Create Date: Oct. 26, 2006, p. 3.
International Search Report for International Application No. PCT/US14/53527 dated Feb. 4, 2015.

* cited by examiner

CYCLIC VINYLOGOUS AMIDES AS BROMODOMAIN INHIBITORS

CROSS REFERENCE TO RELATED APPLICATIONS

This application is a divisional application of U.S. patent application Ser. No. 14/914,672, filed Feb. 26, 2016, now allowed. U.S. patent application Ser. No. 14/914,672 is a national phase filing under 35 U.S.C. § 371 of PCT International Application PCT/US2014/053527, filed Aug. 29, 2014, and published under PCT Article 21(2) in English as WO 2015/031824 A1 on Mar. 5, 2015. This application claims priority from U.S. provisional application 61/872,303, filed Aug. 30, 2013. The entire disclosures of all of these applications are hereby incorporated herein by reference.

GOVERNMENT RIGHTS STATEMENT

This invention was made with government support under grant numbers HG004508, CA087658 and DA029963 awarded by National Institutes of Health. The government has certain rights in the invention.

BACKGROUND OF THE INVENTION

Technical Field

The present application relates generally to compositions for treating diseases that arise from inappropriate activity of proteins containing an acetyl-lysine. The compositions comprise a genus of cyclic vinylogous amides that are inhibitors of bromodomain.

Background Information

BRD4 is a member of the bromodomains and extra terminal domain (BET) family of proteins that recognize acetylated chromatin structures through their bromodomains and act as transcriptional activators. Brd4 functions as an associated factor and positive regulator of P-TEFb, a Cdk9-cyclin T heterodimer that stimulates transcriptional elongation by RNA polymerase II. Bromodomain-containing protein 4 (BRD4) contains two tandem bromodomains (BrD1 and BrD2) that bind preferentially to acetylated lysine residues found in histones and nonhistone proteins. This molecular recognition allows Brd4 to associate with acetylated chromatin throughout the cell cycle and regulates transcription at targeted loci.

Acute myeloid leukemia (AML) is a life-threatening stem cell disease characterized by uncontrolled proliferation and accumulation of myeloblasts. In a recent current study, Herrmann et al. [Oncotarget. 2012 December; 3(12):1588-99] showed that inhibition of BRD4 by a small-molecule inhibitor, JQ1, leads to growth-inhibition and apoptosis in primary human AML stem- and progenitor cells, including cells derived from relapsed or refractory patients. In addition, JQ1 was found to induce apoptosis in CD34+/CD38− and CD34+/CD38+ stem- and progenitor cells in all donors. BRD4-inhibition is therefore recognized as promising new therapeutic approach in AML.

NF-κB-mediated inflammation is the major pathology in chronic kidney diseases, including HIV-associated nephropathy that ultimately progresses to end stage renal disease. HIV infection in the kidney induces NF-κB activation, leading to the production of proinflammatory chemokines, cytokines, and adhesion molecules. In a study published in the Journal of Biological Chemistry, Zhang et al. [J Biol Chem. 2012 Nov. 9; 287(46):38956] showed that a Bromodomain and Extra-Terminal domain-specific bromodomain inhibitor MS417 effectively ameliorated inflammation and kidney injury in HIV-1 transgenic mice, an animal model for HIV-associated nephropathy.

Thus, there is a need for inhibitors of BRD4 as therapeutic agents for leukemia and HIV-associated nephropathy.

SUMMARY OF THE INVENTION

In one aspect, the invention relates to compounds of formula I

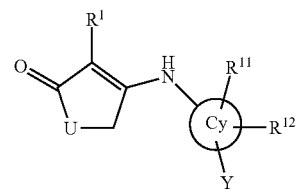

wherein:

U is $(CH_2)_n$, where n=1, 2 or 3;

$R^1$ is selected from the group consisting of: $(C_1-C_{10})$alkyl, substituted $(C_1-C_{10})$alkyl, and nitrile;

Cy is a carbocycle or heterocycle;

$R^{11}$ and $R^{12}$ are independently selected from the group consisting of: H, $(C_1-C_{10})$alkyl, $(C_1-C_{10})$perfluoroalkyl, halogen, nitrile, hydroxy, $(C_1-C_{10})$alkoxy, perfluoro$(C_1-C_{10})$alkoxy, $(C_1-C_{10})$alkylthio, amino, $(C_1-C_{10})$alkylamino, $(C_1-C_{10})$acylamino, aryl, heteroaryl, aminocarbonyl, carboxyl, and $(C_1-C_{10})$alkoxycarbonyl; or taken together, $R^{11}$ and $R^{12}$ may form a 5, 6, or 7-membered carbocycle or heterocycle wherein said carbocycle or heterocycle may be optionally substituted with $R^2$;

$R^2$ is selected from the group consisting of: halogen, $(C_1-C_4)$alkyl, halo$(C_1-C_4)$alkyl, hydroxy, $(C_1-C_4)$alkoxy, halo$(C_1-C_4)$alkoxy, carboxy, amino, $(C_1-C_4)$alkylamino and di$(C_1-C_4)$alkylamino;

Y is selected from H,

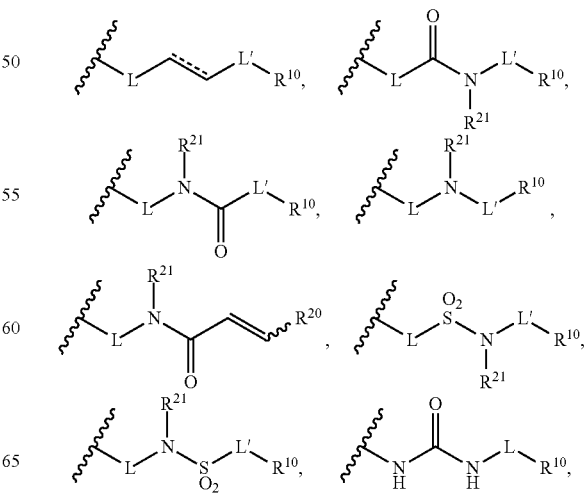

-continued

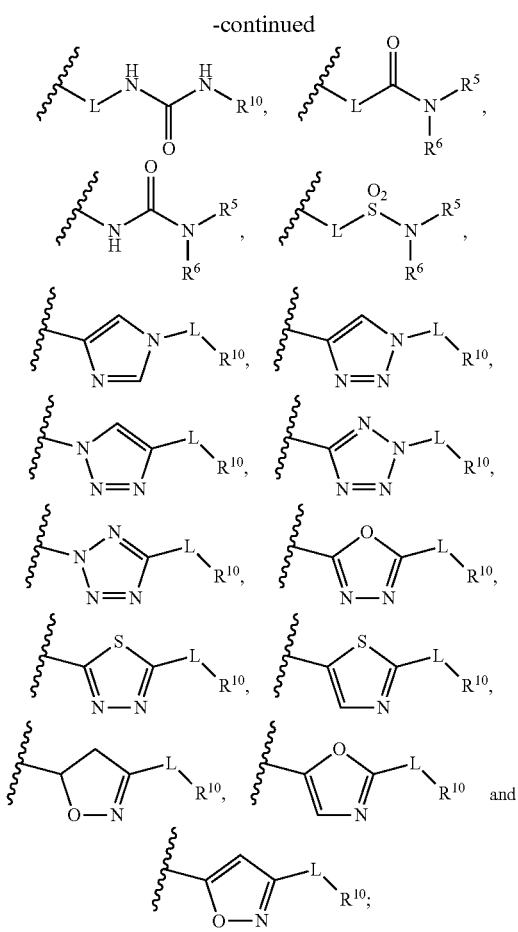

L and L' are independently a bond or $(CR^3R^4)_m$ where $R^3$ and $R^4$ are independently selected from the group consisting of H and $(C_1-C_4)$alkyl, and m is 1 or 2;

$R^{10}$ is chosen from alkyl, carbocycle and heterocycle, wherein said alkyl, carbocycle or heterocycle is optionally substituted with $R^7$ and/or $R^8$;

$R^{20}$ is —C(=O)OR$^{21}$;

$R^{21}$ is chosen from H and $(C_1-C_4)$alkyl;

$R^5$ and $R^6$ are independently selected from the group consisting of hydrogen, hydroxy, $(C_1-C_{10})$ hydrocarbyl, halo$(C_1-C_{10})$hydrocarbyl, and $(C_1-C_{10})$alkoxy;

$R^7$ and $R^8$ are independently selected from the group consisting of: hydroxy, halogen, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, $(C_1-C_4)$alkylthio, $(C_1-C_4)$alkylcarbonyl, aryl, heteroaryl, cycloalkyl, heterocycloalkyl, cyano, oxo, $(C_1-C_4)$alkylsulfonyl, amino, $(C_1-C_4)$alkylamino, di$(C_1-C_4)$alkylamino, $(C_1-C_4)$acylamino, aminocarbonyl, carboxyl, and $(C_1-C_4)$alkoxycarbonyl, where each said alkyl, aryl, heteroaryl, cycloalkyl, or heterocycloalkyl, may be further optionally substituted with hydroxy, oxo, carboxy, carboxy$(C_1-C_4)$alkyl, hydroxy$(C_1-C_4)$alkyl, $(C_1-C_4)$alkoxy, $(C_1-C_4)$alkoxycarbonyl, $(C_1-C_4)$alkoxycarbonyl$(C_1-C_4)$alkyl, amino, $(C_1-C_4)$alkylamino, di $(C_1-C_4)$alkylamino, amido, $(C_1-C_4)$alkylamido, di $(C_1-C_4)$alkylamido, halogen, $(C_1-C_4)$alkyl, halo$(C_1-C_4)$alkyl, aryl, heteroaryl, heterocycloalkyl, or cycloalkyl;

or, taken together, $R^5$ and $R^6$, or $R^7$ and $R^8$ may form a 5, 6, or 7-membered carbocycle or heterocycle, wherein said carbocycle or heterocycle is optionally substituted with $R^9$;

$R^9$ is selected from the group consisting of: halogen, $(C_1-C_4)$alkyl, halo$(C_1-C_4)$alkyl, hydroxy, $(C_1-C_4)$alkoxy, halo$(C_1-C_4)$alkoxy, amino, $(C_1-C_4)$alkylamino and di$(C_1-C_4)$alkylamino.

In a second aspect, the invention relates to pharmaceutical compositions comprising a pharmaceutically acceptable carrier and a compound described herein.

In a third aspect, the invention relates to method for treating a disease or disorder arising from inappropriate activity of proteins containing an acetyl-lysine residue. The method comprises administering to a patient in need thereof a therapeutically effective amount of a compound described herein.

In a fourth aspect, the invention relates to a method for inhibiting bromodomain in a cell. The method comprises contacting the cell with an inhibitory amount of a compound described herein.

DETAILED DESCRIPTION OF THE INVENTION

Figure 1:
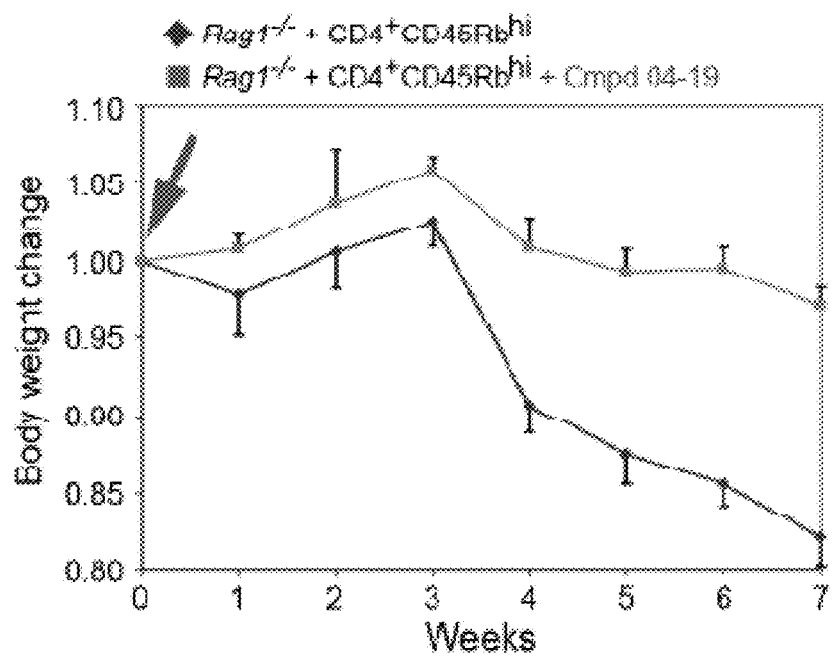
FIG. 1 is a graph of body weight as percent change from baseline vs time (in weeks) for treated and untreated mice in which inflammatory colitis has been induced.

In one aspect, the invention relates to compounds having general formula I:

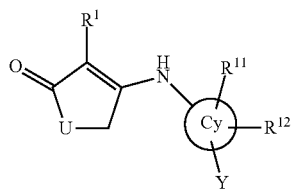

I

In some embodiments, Cy is aliphatic, for example cyclohexyl, or heteroaliphatic; in others it is aryl, for example phenyl or naphthyl, or heteroaryl, for example pyridinyl. When Cy is naphthyl, Y is often hydrogen. When Cy is phenyl, the compounds have the general formula:

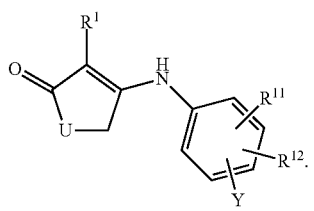

In some embodiments, U is —CH$_2$CH$_2$—, and the vinylogous amide is an N-substituted 3-aminocyclohex-2-enone. In other embodiments, U is —CH$_2$—, and the vinylogous amide is an N-substituted 3-aminocyclopent-2-enone. In both series, the cycloalkenone is substituted at the 2-position with a substituent $R^1$. In some embodiments, $R^1$ is nitrile. In other embodiments, $R^1$ is substituted or unsubstituted $(C_1$-$C_{10})$alkyl. In some embodiments, $R^1$ is preferably $(C_1$-$C_6)$ alkyl, most commonly methyl.

In some embodiments, $R^{11}$ and $R^{12}$ are independently selected from the group consisting of H, $(C_1$-$C_{10})$alkyl, $(C_1$-$C_{10})$perfluoroalkyl, halogen, nitrile, hydroxy, $(C_1$-$C_{10})$ alkoxy, perfluoro$(C_1$-$C_{10})$alkoxy, $(C_1$-$C_{10})$alkylthio, amino, $(C_1$-$C_{10})$alkylamino, $(C_1$-$C_{10})$acylamino, aryl, heteroaryl, aminocarbonyl, carboxyl, and $(C_1$-$C_{10})$alkoxycarbonyl. In some embodiments, at least one of $R^{11}$ and $R^{12}$ is hydrogen. In some embodiments, taken together, $R^{11}$ and $R^{12}$ may form a 5, 6, or 7-membered carbocycle or heterocycle. In these embodiments, the carbocycle or heterocycle may be optionally substituted with $R^2$. In some embodiments, $R^2$ is selected from halogen, $(C_1$-$C_4)$alkyl, halo$(C_1$-$C_4)$alkyl, hydroxy, $(C_1$-$C_4)$alkoxy, halo$(C_1$-$C_4)$alkoxy, carboxy, amino, $(C_1$-$C_4)$alkylamino or di$(C_1$-$C_4)$alkylamino.

In some embodiments, Y is a sulfonamide, such as

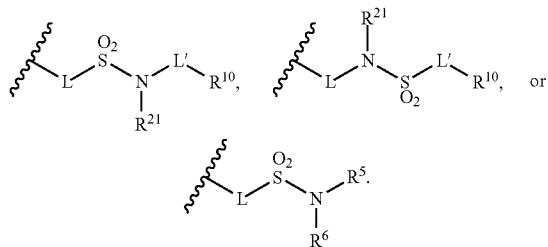

In some embodiments Y is a urea, such as

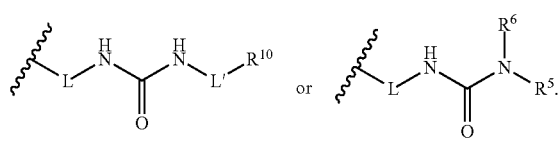

In some embodiments Y is a carboxamide, such as

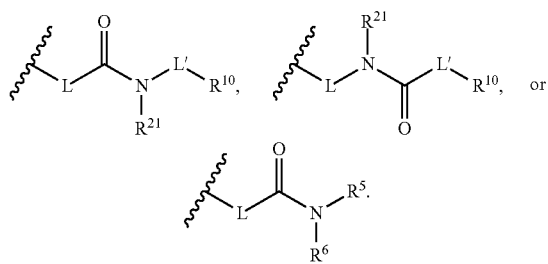

In such compounds, L may be a direct bond, L' may be a direct bond or both L and L' may be direct bonds. In one embodiment, Y is

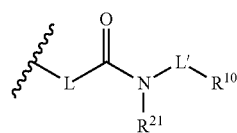

and both L and L' are direct bonds, i.e. Y is

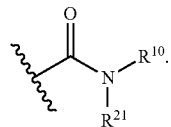

In some embodiments, Y is

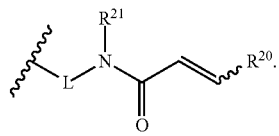

In these compounds, the wavy line indicates that a particular stereochemical configuration is not designated; thus a carbon-carbon double bond depicted arbitrarily herein as trans may be cis, trans, or a mixture of the two in any proportion. In some embodiments, $R^{20}$ is —C(═O)O$R^{21}$. In some of these embodiments, $R^{21}$ is hydrogen. In some of these embodiments, $R^{21}$ is $(C_1$-$C_4)$alkyl, particularly methyl. In some embodiments, Y is

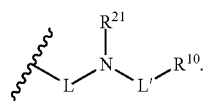

In some of these embodiments, $R^{21}$ is $(C_1$-$C_4)$alkyl. In other embodiments, $R^{21}$ is hydrogen. In some embodiments, L is a direct bond and $R^{21}$ is hydrogen. In some embodiments, Y is

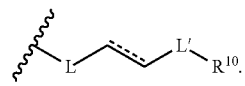

In these compounds the dotted line represents an optional double bond, which encompasses compounds in which Y is -L-CH$_2$CH$_2$—R$^{10}$ and -L-CH═CH—R$^{10}$. In other embodiments, Y may be a 5-membered heterocycle, particularly an aromatic 5-membered heterocycle, substituted with L-R$^{10}$. The 5-membered heterocycle will usually contain more than one heteroatom in the ring, and 1,2,3-triazoles are preferred. When Y is a substituted 5-membered heterocycle, L may be —(CR$^3$R$^4$)$_m$—, particularly —CH$_2$—.

In many embodiments in which Y is a sulfonamide, a urea, a carboxamide or a 5-membered heterocycle, R$^{10}$ may be cyclohexyl, cyclopentyl, phenyl, naphthyl, thiophenyl, pyrrolyl, pyridinyl, or pyrimidinyl, each optionally substituted with R$^7$ and/or R$^8$. Cyclohexyl, phenyl and naphthyl are preferred. When R$^{10}$ is phenyl, in some embodiments it may be only singly substituted with R$^7$, and, in those embodiments, the structure may be represented:

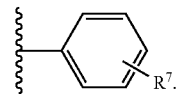

In these compounds, $R^7$ may be halogen, $(C_1-C_4)$alkyl, halo$(C_1-C_4)$alkyl, $(C_1-C_4)$alkoxy, halo$(C_1-C_4)$alkoxy or aminocarbonyl. Fluoro, chloro, methyl and methoxy are preferred. In some embodiments, $R^{10}$ is phenyl substituted with both $R^7$ and $R^8$. In these embodiments, $R^7$ and $R^8$ may each independently be halogen, $(C_1-C_4)$alkyl, halo$(C_1-C_4)$alkyl, $(C_1-C_4)$alkoxy, halo$(C_1-C_4)$alkoxy or aminocarbonyl. In some embodiments, $R^8$ is fluoro.

In a second aspect, the invention relates to pharmaceutical compositions comprising a pharmaceutically acceptable carrier and a compound described herein.

In a third aspect, the invention relates to method for treating a disease or disorder arising from inappropriate activity of proteins containing an acetyl-lysine residue. The method comprises administering to a patient in need thereof a therapeutically effective amount of a compound described herein. In some embodiments, the disease or disorder is chronic inflammation. In some embodiments, the disease or disorder is autoimmune disease. In some embodiments, the disease or disorder is cancer. In some embodiments, an additional therapeutic agent may be administered.

In a fourth aspect, the invention relates to a method for inhibiting bromodomain in a cell. The method comprises contacting the cell with an inhibitory amount of a compound described herein.

For convenience and clarity certain terms employed in the specification, examples and claims are described herein.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Alkoxy or alkoxyl refers to groups of from 1 to 20 carbon atoms, preferably 1 to 10 carbon atoms, more preferably 1 to 6 carbon atoms of a straight or branched configuration attached to the parent structure through an oxygen. Examples include methoxy, ethoxy, propoxy, isopropoxy and the like. Lower-alkoxy refers to groups containing one to four carbons. For the purpose of this application, alkoxy and lower alkoxy include methylenedioxy and ethylenedioxy.

The term "halogen" means fluorine, chlorine, bromine or iodine atoms. In one embodiment, halogen may be a fluorine or chlorine atom.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 2002 edition, ¶196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples of azaalkyl include ethylaminoethyl and aminohexyl.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In preferred embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy. Most preferred are halogen, $(C_1-C_4)$alkyl, halo$(C_1-C_4)$alkyl, $(C_1-C_4)$alkoxy, halo$(C_1-C_4)$alkoxy, and aminocarbonyl.

Substituents R″ are generally defined when introduced in a claim and retain that definition throughout the all the claims. Certain R″ in the detailed description have definitions that are associated only with a particular set of exemplary syntheses; the Rn in the exemplary syntheses do not necessarily correlate with the R″ in the claims or summary of the invention.

As used herein, and as would be understood by the person of skill in the art, the recitation of "a compound"—unless expressly further limited—is intended to include salts of that compound. Thus, for example, the recitation "a compound of formula I" as depicted above, which incorporates a substituent COOH, would include salts in which the substituent is COO⁻ M⁺, wherein M is any counterion. Examples 02-01 to 02-07 below are examples of such carboxylic acids that can undergo salt formation. Similarly, a compound of formula I as depicted above may include a substituent $NH_2$, such as in Example 05-25 below, and therefore would also include salts in which the substituent is $NH_3^+X^-$, wherein X is any counterion. In a particular embodiment, the term "compound of formula I" refers to the compound or a pharmaceutically acceptable salt thereof.

The term "pharmaceutically acceptable salt" refers to salts whose counter ion derives from pharmaceutically acceptable non-toxic acids and bases. Suitable pharmaceutically acceptable acids for salts of the amino-substituted compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Suitable pharmaceutically acceptable base addition salts for the carboxylate-substituted compounds of the present invention include, but are not limited to, metallic salts made from aluminum, calcium, lithium, magnesium, potassium, sodium and zinc or organic salts made from lysine, arginine, N,N′-dibenzylethylenediamine, chloroprocaine, choline, diethanolamine, ethylenediamine, meglumine (N-methylglucamine), and procaine. Further pharmaceutically acceptable salts include, when appropriate, nontoxic ammonium cations and carboxylate, sulfonate and phosphonate anions attached to alkyl having from 1 to 20 carbon atoms.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^2H$, $^3H$, $^{11}C$, $^{13}C$, $^{14}C$, $^{15}N$, $^{35}S$, $^{18}F$, $^{36}Cl$, $^{125}I$, $^{124}I$, and $^{131}I$ respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$, and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus I that are not already in the possession of the public.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical, or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous, and intraarticular), rectal and topical (including dermal, buccal, sublingual, and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refers to an approach for obtaining a therapeutic benefit in the form of eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. The compositions may be administered to a patient at risk of developing a particular disease, or to a patient reporting one or more of the physiological systems of a disease, even though a diagnosis of this disease may not have been made.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials are either commercially available, synthesized as described in the examples or may be obtained by the methods well known to persons of skill in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given; other process conditions can also be used unless otherwise stated. Optimum reaction conditions can vary with the particular reactants or solvent used. Those skilled in the art will recognize that the nature and order of the synthetic steps presented can be varied for the purpose of optimizing the formation of the compounds described.

The reactions or the processes described herein can be carried out in suitable solvents, which can be readily selected by one skilled in the art. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The description of this invention utilizes conventional American Chemical Society abbreviations well known to those skilled in the art, in addition to the following:

AcCl: acetyl chloride
$Ac_2O$: acetic anhydride
AcOH: acetic acid
Alk: alkyl
BINAP: 2,2'-bis(diphenylphosphino)-1,1'-binaphthyl
cat: catalytic
$CH_2Cl_2$: dichloromethane; methylenechloride
$CHCl_3$: chloroform
Δ: heat
DI $H_2O$: deionized water
DMA: dimethylacetamide
DMF-DMA: 1,1-dimethyoxy-N,N-dimethylmethanamine
DMF: N,N-dimethylformamide
EDCCl: 3-(ethyliminomethylene-amino)-N,N-dimethylpropan-1-amine hydrochloride
eq: equivalence
ESS: eluting solvent system
EtOAc: ethyl acetate
EtOH: ethanol
$H^+$: acid
HCl: hydrochloric acid
$HCO_2H$: formic acid
IBCF: isobutylchloroformate
LCMS: liquid chromatography mass spectra
MeOH: methanol
NaOH: sodium hydroxide
NMM: N-methylmorpholine
PG: protecting group
PS-CDI: polystyrene carbodiimidazole
pTSA: para-toluensulfonic acid
rt: room temperature
sat: saturated
TEA: triethylamine
TFA: trifluoroacetic acid
THF: tetrahydrofuran
TMS: tetramethylsilane $^1H$ Nuclear Magnetic Resonance (NMR) spectra were in all cases consistent with the proposed structures. $^{13}C$ NMR spectra were in relevant cases consistent with the proposed structures. NMR were acquired on a Bruker® DRX-600 spectrometer at 600 MHz for $^1H$ and 125 MHz for $^{13}C$. Characteristic chemical shifts (δ) are expressed in parts per million downfield from tetramethylsilane (TMS) using conventional abbreviations for designation of major peaks: s, singlet; d, doublet; t, triplet; q, quartet; m, multiplet; br, broad. The following abbreviations have been used for common solvents: CDCl₃, deuterochloroform; D6-DMSO, deuterodimethyl-sulfoxide; MeOD, deuteromethanol.

Mass Spectra were in all cases consistent with the proposed structures. Liquid chromatography mass spectra, LCMS, with retention time, t, in minutes, min, and with mass to charge ratio, m/z, were recorded using peak elution time and electrospray ionization, ESI. LCMS analysis was performed on an Agilent® 1200 HPLC equipped with a Zorbax® 300SB-C18 column held at 45° C., and a G1969A API-TOF in positive mode. Purity of all Examples was estimated at >95% by the DAD trace using the following LC method: solvent system (A)/(B) with 0.1% buffer=$H_2O$/acetonitrile with formic acid, flow rate=0.4 mL/min, and timed percentage of solvent B=0-1 min (1%), gradient 1-4 min (1-99%), 4-8 min (99%). Theoretical mass to charge ratios were calculated, Calcd, using ChemDraw® software. In relevant cases identifiable, radical cation of mass plus hydrogen, $[M+H]^+$; mass plus sodium, $[M+Na]^+$; two masses plus hydrogen, $[2M+H]^+$; and two masses plus sodium, $[2M+Na]^+$ data were recorded. In relevant Examples containing bromine atoms, the two stable isotopes $^{79}$Br and $^{81}$Br, for $[M+H]^+$ and $[M+Na]^+$ were recorded.

Melting points (mp) were determined on an automated Standford Research System OptiMelt MPA100 heating at a rate of 10° C./min.

Synthetic Procedures

In the tabulated experimental details that follow, the Examples and Intermediates were prepared according to the corresponding reference method (i.e. Example 01-01, Intermediate 03, and so on). The skilled person will appreciate that, in the synthesis of any specific Example or Intermediate, it may be necessary to make minor variations to the reaction conditions and purification procedures of the reference method (e.g. with regard to ratios, time, and so on).

Reagents used in the preparation of the compounds of this invention can be either obtained commercially or prepared by standard literature procedures. Unless otherwise stated, all reagents and solvents were obtained from commercial suppliers and used without further purification.

Certain compounds of the Examples and Preparations were continuously irradiated at 2.45 gigahertz, GHz in a sealed microwave vial contained in a single mode Biotage®-Initiator cavity.

Certain compounds of the Examples and Preparations were purified using automated chromatography. Isocratic, or stepwise gradient mobile phases were used on normal-phase KP-Sil™ silica-gel columns attached to a Biotage®-Isolera Four instrument, monitoring UV Trace at 254 nm and 365 nm. Solvent systems utilized one, two, or three solvents (acetone, hexanes, EtOAc, or MeOH) running from nonpolar to polar steps. Eluting Solvent System (ESS) is the solvent step which eluted the product and is indicated below in the following format ESS=H:E (X:X), or the percentage of MeOH (%) in EtOAc. Additional monitoring by analytical thin layer chromatography (TLC) was performed employing EMD Chemicals Inc. TLC Silica gel 60 F254 on aluminium, visualized either by exposure to UV light or, staining agents such as: iodine impregnated silica gel; 10% phosphomolybdic acid in EtOH and so on.

Schemes 1-4 present general synthetic approaches. The details of each example are described in the Examples. Compounds may be prepared according to the reactions in Scheme 1. $R^1$ can be present from commercial reagents, added through C-alkylation, or formed through ring opening chemistry. $R^2$ can be hydrogen, present from commercial reagents, or prepared as in Scheme 2, have appended acid, ester, nitro, or protected amine functionalities. $R^8$ can be from reagents bearing a halogen.

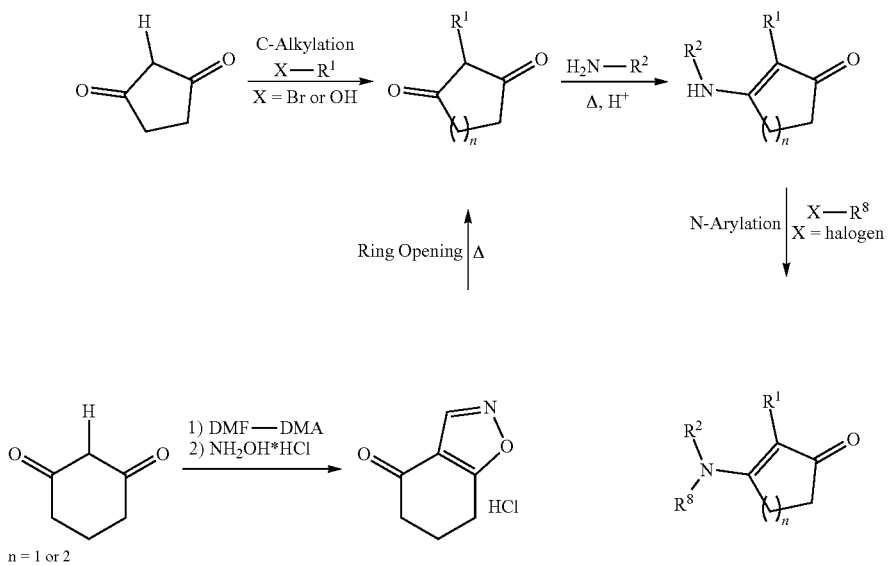

Appended acid, or ester, compounds can undergo reactions in Scheme 2. Compounds can be protected commercial reagents, or from Scheme 1. $R^3$ can be added with an appended ester functionality and undergo a second iteration of base hydrolysis and amide bond formation.

Scheme 2:
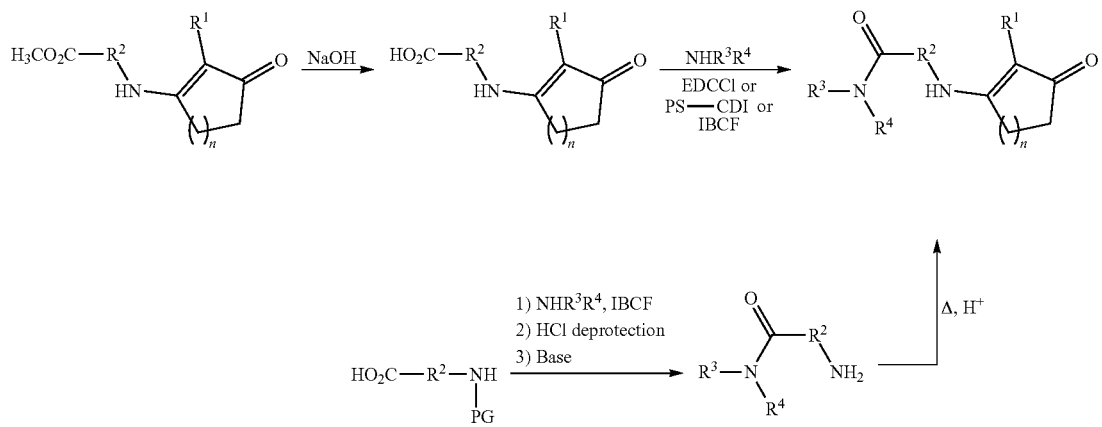
Amine compounds, deprotected or reduced from nitro, can undergo reactions in Scheme 3. $R^5$ can be from carboxylic acids, acid halides, anhydrides, cyclic anhydrides, or activated acids. $R^6$ can be from sulfonic acids, or sulfonyl chlorides. $R^7$ can be from aldehydes. $R^8$ can be from reagents bearing a halogen.
Scheme 3:
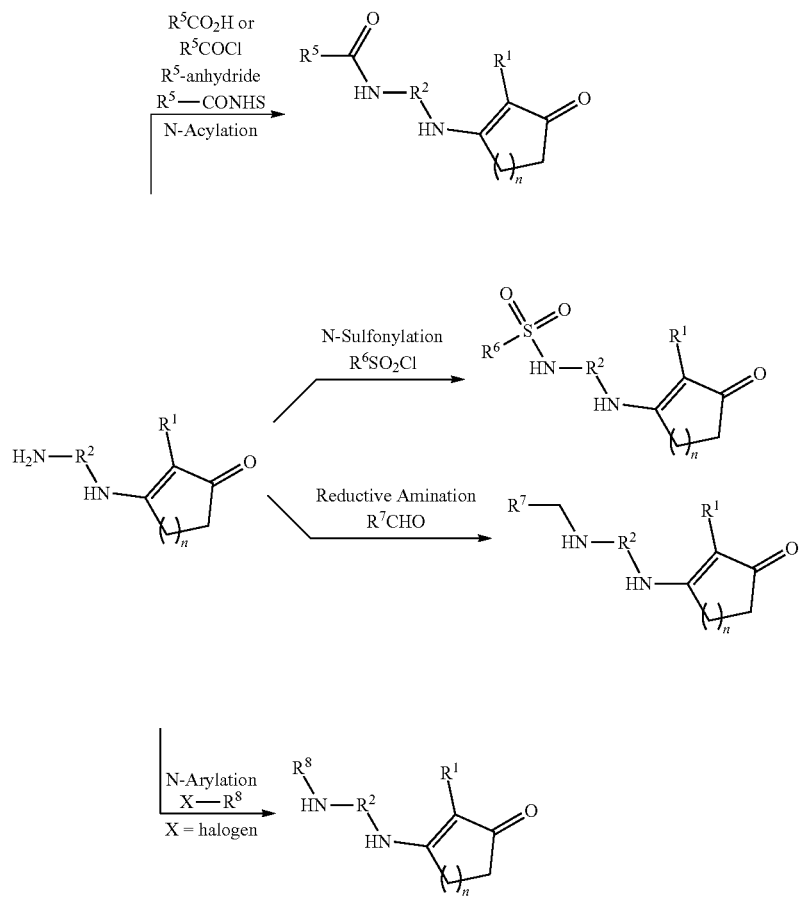

Alkynes can undergo reactions in Scheme 4. $R^9$ can be from azides or amines.

Scheme 4:

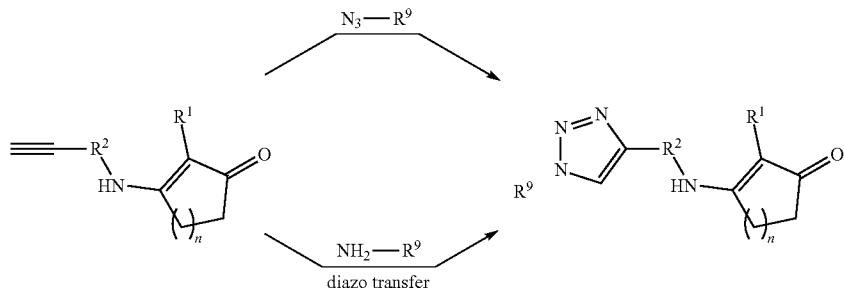

Specific Examples follow:

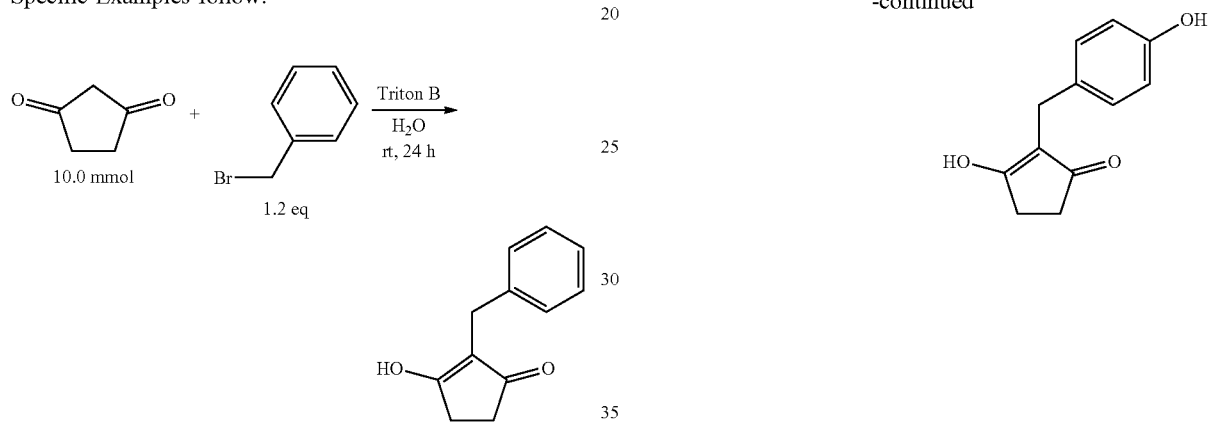

Intermediate 01

Preparation of 2-Benzylcyclopentane-1,3-dione (Intermediate 01)

1,3-Cyclopentandione (0.98 g, 10.0 mmol, 1.0 eq, Synth. Comm. 1993, 23(22), p. 3095-3108) was treated with 40% aq Triton B (3.95 mL<1.0 eq) in DI $H_2O$ (5.0 mL) followed by benzyl bromide (1.4 mL, 1.2 eq). The reaction mixture was stirred at rt for 24 h. The crude was extracted with EtOAc and dried over anhyd sodium sulfate. The reaction on a 10.0 mmol scale yielded 0.9 g of the title intermediate after recrystallization from EtOAc (48% yield). $^1$H NMR (D6-DMSO) δ 2.39 (br s, 4H), 3.36 (br s, 2H), 7.10-7.17 (m, 3H), 7.20-7.25 (m, 2H), 11.71 (br s, 1H). LCMS t=4.3 min, m/z Calcd for $C_{12}H_{13}O_2$; $C_{12}H_{12}NaO_2$; $C_{24}H_{25}O_4$; $C_{24}H_{24}NaO_4$ 189.09; 211.07; 377.16; 399.16 $[M+H]^+$; $[M+Na]^+$; $[2M+H]^+$; $[2M+Na]^+$, Found 189.18; 211.14; 377.16; 399.13.

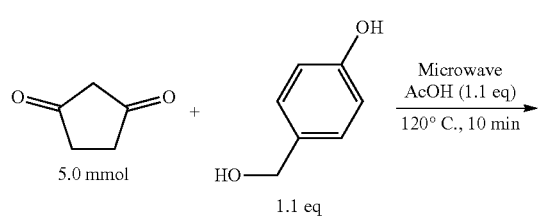

Intermediate 02

Preparation of 2-(4-Hydroxybenzyl)cyclopentane-1,3-dione (Intermediate 02)

1,3-Cyclopentandione (491 mg, 5.0 mmol, 1.0 eq, J. Org. Chem. 1988, 53, p. 891-893) was treated with AcOH (315 mL, 1.1 eq) followed by p-hydroxybenzyl alcohol (683 mg, 1.1 eq). Microwave irradiation was applied to a sealed microwave vial for 10 min in a single mode Biotage®-Initiator cavity, producing continuous irradiation to hold 120° C. at 2.45 GHz. The crude material was added directly to a KP-Sil™ column (10 g) in a small amount of $CH_2Cl_2$ with products separating from impurities using stepwise gradients on the Biotage®-Isolera Four instrument, monitoring UV Trace at 254/365 nm. The reaction on a 5.0 mmol scale yielded 0.55 g of the title intermediate after chromatography (ESS=H:E (1:3), 54% yield). $^1$H NMR (D6-DMSO) δ 2.37 (br s, 4H), 3.36 (br s, 2H), 6.60 (d, J=8.1 Hz, 2H), 6.93 (d, J=8.1 Hz, 2H), 9.06 (br s, 1H), 11.62 (br s, 1H). LCMS t=3.9 min, m/z Calcd for $C_{12}H_{13}O_3$; $C_{12}H_{12}NaO_3$; $C_{24}H_{25}O_6$; $C_{24}H_{24}NaO_6$ 205.09; 227.07; 409.17; 431.15 $[M+H]^+$; $[M+Na]^+$; $[2M+H]^+$; $[2M+Na]^+$, Found 205.16; 227.13; 409.14; 431.12.

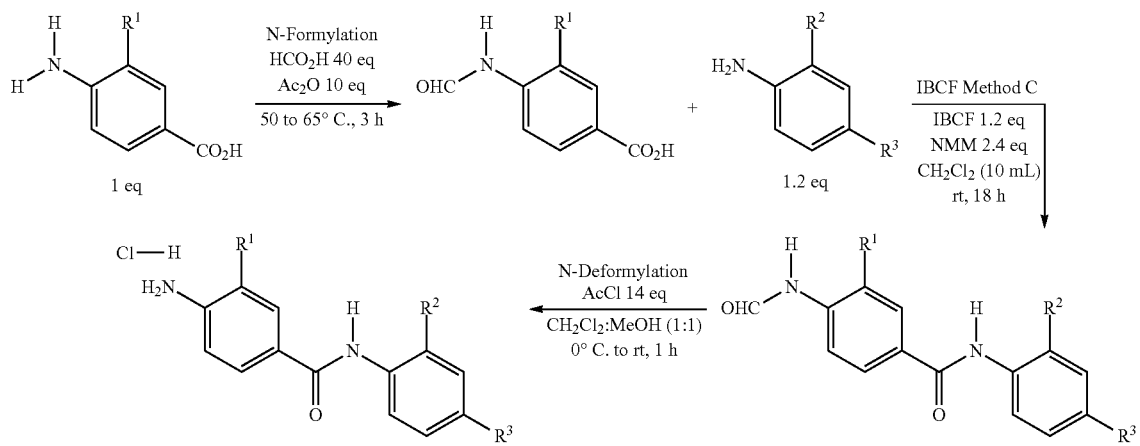

| INTER-MEDIATE # | TITLED INTERMEDIATE NAME | R¹ | R² | R³ |
|---|---|---|---|---|
| 03 | 2-Chloro-4-(o-tolylcar-bamoyl)benzenaminium Chloride | Cl | CH₃ | H |
| 04 | 2-Fluoro-4-((4-methoxyphenyl)car-bamoyl)benzenaminium Chloride | F | H | OCH₃ |
| 05 | 2-Bromo-4-((4-methoxyphenyl)car-bamoyl)benzenaminium Chloride | Br | H | OCH₃ |

Intermediate 03

Preparation of 2-Chloro-4-(o-tolylcarbamoyl)benzenaminium Chloride (Intermediate 03)

Step 1, N-Formylation: A mixture of formic acid (18.1 mL, 40 eq, Chem. Pharm. Bull. 2002, 50(7), p. 941-959) and acetic anhydride (11.3 mL, 10 eq) were heated to 50° C. for 1 h. After addition of 4-amino-3-chlorobenzoic acid (2.1 g, 12.0 mmol, 1.0 eq), the whole was heated to 65° C. for 2 h and cooled to rt. The reaction mixture was poured into cold H$_2$O and the precipitates were collected by filtration, washed with H$_2$O, and dried on the frit. The reaction on a 12.0 mmol scale yielded 2.2 g of 3-chloro-4-formamidobenzoic acid, white microcrystals (mp=227-229° C., 92% yield). LCMS t=4.0 min, m/z Calcd for C$_8$H$_7$ClNO$_3$; C$_8$H$_6$ClNNaO$_3$ 200.01; 221.99 [M+H]$^+$; [M+Na]$^+$, Found 200.09; 222.06.

Step 2, IBCF Method C: 3-Chloro-4-formamidobenzoic acid and o-toluidine were coupled according to the procedure of Example 04-13; 5.0 mmol scale yielded 1.0 g of 3-chloro-4-formamido-N-(o-tolyl)benzamide from precipitate (69% yield). LCMS t=5.1 min, m/z Calcd for C$_{15}$H$_{14}$ClN$_2$O$_2$; C$_{15}$H$_{13}$ClN$_2$NaO$_2$; C$_{30}$H$_{27}$Cl$_2$N$_4$O$_4$; C$_{30}$H$_{26}$Cl$_2$N$_4$NaO$_4$ 289.07; 311.06; 577.14; 599.12 [M+H]$^+$; [M+Na]$^+$; [2M+H]$^+$; [2M+Na]$^+$, Found 289.07; 311.05; 577.14; 599.12.

Step 3, N-Deformylation: Acetyl chloride (14 eq, Org. Lett. 2011, 13(12), p. 3028-3031) was added to a CH$_2$Cl$_2$:MeOH (20 mL, 1:1) mixture at 0° C., followed by the 3-chloro-4-formamido-N-(o-tolyl)benzamide (0.87 g, 3.0 mmol, 1.0 eq). After warming to rt, HCl salts were collected by filtration and dried on the frit. The reaction on a 3.0 mmol scale yielded 0.8 g of 2-chloro-4-(o-tolylcarbamoyl)benzenaminium chloride, the title intermediate (90% yield). $^1$H NMR (D6-DMSO) δ 2.20 (s, 3H), 4.60 (br s, 3H), 6.84 (d, J=8.4 Hz, 1H), 7.14 (t, J=7.3 Hz, 1H), 7.19 (t, J=7.3 Hz, 1H), 7.24 (d, J=7.3 Hz, 1H), 7.28 (d, J=7.7 Hz, 1H), 7.70 (d, J=8.4 Hz, 1H), 7.89 (s, 1H), 9.56 (s, 1H). $^{13}$C NMR (D6-DMSO) δ 18.0, 114.2, 122.2, 125.7, 125.9, 126.6, 127.8, 128.9, 130.2, 133.7, 136.7, 147.7, 164.0. LCMS t=5.0 min, m/z Calcd for C$_{14}$H$_{14}$ClN$_2$O; C$_{14}$H$_{13}$ClN$_2$NaO; C$_{28}$H$_{26}$Cl$_2$N$_4$NaO$_2$ 261.08; 283.06; 543.13 [M+H]$^+$; [M+Na]$^+$; [2M+Na]$^+$, Found 261.12; 283.09; 543.09.

Intermediate 04

Preparation of 2-Fluoro-4-((4-methoxyphenyl)carbamoyl)benzenaminium Chloride (Intermediate 04)

Step 1, N-Formylation: 4-Amino-3-fluorobenzoic acid (5.0 g, 32.3 mmol) was N-formylated according to the procedure of Intermediate 03; the reaction on a 32.3 mmol scale yielded 4.0 g of 3-fluoro-4-formamidobenzoic acid, white microcrystals (mp=238-240° C., 68% yield). LCMS t=3.0 min, m/z Calcd for C$_8$H$_7$FNO$_3$; C$_8$H$_6$FNNaO$_3$; C$_{16}$H$_{13}$F$_2$N$_2$O$_6$ 184.04; 206.02; 367.07 [M+H]$^+$; [M+Na]$^+$; [2M+H]$^+$, Found 184.04; 202.05; 367.07.

Step 2, IBCF Method C: 3-Fluoro-4-formamidobenzoic acid and p-anisidine were coupled according to the procedure of Example 04-13; 5.0 mmol scale yielded 1.0 g of 3-fluoro-4-formamido-N-(4-methoxyphenyl)benzamide from precipitate (69% yield). LCMS t=4.8 min, m/z Calcd for C$_{15}$H$_{14}$FN$_2$O$_3$; C$_{30}$H$_{27}$F$_2$N$_4$O$_6$; C$_{30}$H$_{26}$F$_2$N$_4$NaO$_6$ 289.10; 577.19; 599.17 [M+H]$^+$; [2M+H]$^+$; [2M+Na]$^+$, Found 289.10; 577.19; 599.17.

Step 3, N-Deformylation: The title intermediate was prepared from 3-fluoro-4-formamido-N-(4-methoxyphenyl)benzamide according to the procedure of Intermediate 03; 3.3 mmol scale, with solvent (20 mL), yielded 0.9 g of 2-fluoro-4-((4-methoxyphenyl)carbamoyl)-benzenaminium chloride (92% yield). LCMS t=4.6 min, m/z Calcd for C$_{14}$H$_{14}$FN$_2$O$_2$; C$_{14}$H$_{13}$FN$_2$NaO$_2$; C$_{28}$H$_{27}$F$_2$N$_4$O$_4$; C$_{28}$H$_{26}$F$_2$N$_4$NaO$_4$ 261.10; 283.09; 521.20; 543.18 [M+H]$^+$; [M+Na]$^+$; [2M+H]$^+$; [2M+Na]$^+$, Found 261.10; 283.07; 521.19; 543.17.

Intermediate 05

Preparation of 2-Bromo-4-((4-methoxyphenyl)carbamoyl)benzenaminium Chloride (Intermediate 05)

Step 1, N-Formylation: 4-Amino-3-bromobenzoic acid (5.0 g, 23.1 mmol) was N-formylated according to the procedure of Intermediate 03; the reaction on a 23.1 mmol scale yielded 3.0 g of 3-bromo-4-formamidobenzoic acid, white microcrystals (mp=232-234° C., 79% yield). LCMS t=4.1 min, m/z Calcd for $C_8H_7BrNO_3$; $C_{16}H_{13}Br_2N_2O_6$; $C_{16}H_{12}Br_2N_2NaO_6$ 243.96, 245.96; 488.91; 510.89 $[M+H]^+$; $[2M+H]^+$; $[2M+Na]^+$, Found 243.96, 245.96; 488.91; 510.90.

Step 2, IBCF Method C: 3-Bromo-4-formamidobenzoic acid and p-anisidine were coupled according to the procedure of Example 04-13; 5.0 mmol scale (exothermic) yielded 0.27 g of 3-bromo-4-formamido-N-(4-methoxyphenyl)benzamide from precipitate (15% yield). LCMS t=5.0 min, m/z Calcd for $C_{15}H_{14}BrN_2O_3$; $C_{15}H_{13}BrN_2NaO_3$; $C_{30}H_{27}Br_2N_4O_6$; $C_{30}H_{26}Br_2N_4NaO_6$ 349.02, 351.02; 371.00, 372.10; 699.03; 721.01 $[M+H]^+$; $[M+Na]^+$; $[2M+H]^+$; $[2M+Na]^+$, Found 349.01, 351.01; 370.99, 372.99; 699.01; 720.99.

Step 3, N-Deformylation: The title intermediate was prepared from 3-bromo-4-formamido-N-(4-methoxyphenyl)benzamide according to the procedure of Intermediate 03; 0.75 mmol scale, with solvent (10 mL), yielded 0.16 g of 2-bromo-4-((4-methoxyphenyl)carbamoyl)-benzenaminium chloride (66% yield). LCMS t=4.9 min, m/z Calcd for $C_{14}H_{14}BrN_2O_2$; $C_{14}H_{13}BrN_2NaO_2$; $C_{28}H_{27}Br_2N_4O_4$; $C_{28}H_{26}Br_2N_4NaO_4$ 321.02, 323.02; 343.01, 345.00; 643.04; 665.02 $[M+H]^+$; $[M+Na]^+$; $[2M+H]^+$; $[2M+Na]^+$, Found 321.04, 323.04; 343.02, 345.02; 643.07; 665.05.

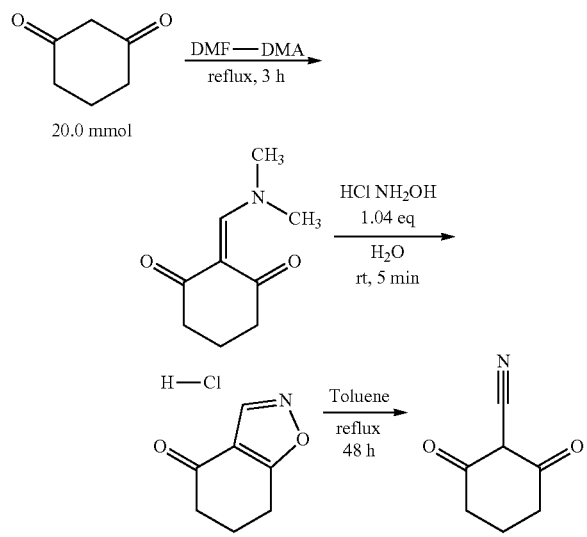

Intermediate 06

Preparation of 2,6-Dioxocyclohexanecarbonitrile (Intermediate 06)

Step 1: 1,3-Cyclohexandione (2.24 g, 20.0 mmol, J. Med. Chem. 2011, 54, p. 5070-5081) and 1,1-dimethyoxy-N,N-dimethylmethanamine (DMF-DMA, 26.5 mL, 200 mmol, 10 eq) were mixed and heated under reflux for 3 h. The solvent was removed on the rotovap to provide the product in suitable purity for the next step. The reaction on a 20.0 mmol scale yielded 3.25 g of 2-((dimethylamino)methylene)-cyclohexane-1,3-dione (97% yield). $^1$H NMR (CDCl$_3$) δ 1.85-1.90 (m, 2H), 2.38-2.41 (m, 4H), 3.11 (s, 3H), 3.33 (s, 3H), 7.98 (s, 1H). $^{13}$C NMR (CDCl$_3$) δ 19.4, 38.1, 44.5, 48.4, 109.2, 162.1, 196.1. LCMS t=1.4 min, m/z Calcd for $C_9H_{14}NO_2$; $C_9H_{13}NNaO_2$; $C_{18}H_{27}N_2O_4$; $C_{18}H_{26}N_2NaO_4$ 168.10; 190.08; 335.20; 357.18 $[M+H]^+$; $[M+Na]^+$; $[2M+H]^+$; $[2M+Na]^+$, Found 168.11; 190.09; 335.21; 357.19.

Step 2: 2-((Dimethylamino)-methylene)cyclohexane-1,3-dione (2.675 g, 16.0 mmol, Synthesis 2002, 12, p. 1669-1674) and hydroxylamine hydrochloride (1.15 g, 1.04 eq) were mixed in DI H$_2$O (1.5 mL) and agitated on a vortex shaker for 30 sec. After 5 min, the product was isolated by filtration. The reaction on a 16 mmol scale yielded 1.75 g of 6,7-dihydrobenzoisoxazol-4-one hydrochloride (mp=88-90° C., 63% yield). $^1$H NMR (CDCl$_3$) δ 1.70-1.90 (m, 2H), 2.20-2.60 (m, 4H), 8.10 (s, 1H), 11.25 (br s, 1H). LCMS t=1.2 min, m/z Calcd for $C_7H_8NO_2$; $C_7H_7NNaO_2$; $C_{14}H_{15}N_2O_4$; $C_{14}H_{14}N_2NaO_4$ 138.06; 160.04; 275.10; 297.09 $[M+H]^+$; $[M+Na]^+$; $[2M+H]^+$; $[2M+Na]^+$, Found 138.06; 160.04; 275.12; 297.10.

Step 3: 6,7-Dihydrobenzoisoxazol-4-one hydrochloride (2.88 mmol, J. Het. Chem. 1983, 20, p. 645-648) was added to toluene and heated under reflux, for 48 h. The product was filtered from toluene. The reaction on a 2.88 mmol scale yielded 0.3 g of the title intermediate, 2,6-dioxocyclohexanecarbonitrile (mp=208-210° C., 76% yield). $^1$H NMR (D6-DMSO) δ 1.85-1.91 (m, 2H), 2.44-2.50 (m, 4H). $^{13}$C NMR (D6-DMSO) δ 19.8, 33.0, 91.9, 115.1, 191.7. LCMS t=1.0 min, m/z Calcd for $C_7H_8NO_2$; $C_7H_7NNaO_2$; $C_{14}H_{15}N_2O_4$; $C_{14}H_{14}N_2NaO_4$ 138.06; 160.04; 275.10; 297.09 $[M+H]^+$; $[M+Na]^+$; $[2M+H]^+$; $[2M+Na]^+$, Found 138.06; 160.04; 275.11; 297.10.

Synthesis of Exemplary Species

Examples 01-01 to 01-39

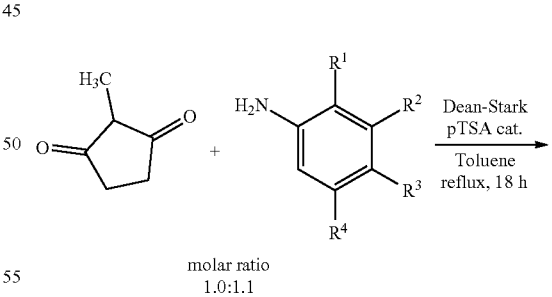

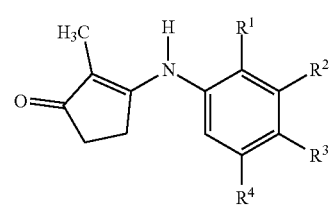

| Example 01-# | TITLE COMPOUND NAME | R¹ | R² | R³ | R⁴ |
|---|---|---|---|---|---|
| 01 | Methyl 4-((3-oxocyclopent-1-en-1-yl)amino)benzoate | H | H | CO$_2$CH$_3$ | H |
| 02 | 4-((3-Oxocyclopent-1-en-1-yl)amino)benzoamide | H | H | CONH$_2$ | H |
| 03 | 3-((2-Methyl-3-oxocyclopent-1-en-1-yl)amino)benzoic acid | H | CO$_2$H | H | H |
| 04 | Methyl 3-((2-methyl-3-oxocyclopent-1-en-1-yl)amino)benzoate | H | CO$_2$CH$_3$ | H | H |
| 05 | 3-((2-Methyl-3-oxocyclohex-1-en-1-yl)amino)benzamide | H | CONH$_2$ | H | H |
| 06 | 4-((2-Methyl-3-oxocyclopent-1-en-1-yl)amino)benzenesulfonamide | H | H | SO$_2$NH$_2$ | H |
| 07 | 4-((2-Methyl-3-oxocyclopent-1-en-1-yl)amino)benzonitrile | H | H | CN | H |
| 08 | 3-((3-Bromophenyl)amino)-2-methylcyclopent-2-enone | H | Br | H | H |
| 09 | 3-((4-Acetylphenyl)amino)-2-methylcyclopent-2-enone | H | H | COCH$_3$ | H |
| 10 | 2-Chloro-4-((2-methyl-3-oxocyclopent-1-en-1-yl)amino)benzoic acid | H | Cl | CO$_2$H | H |
| 11 | Methyl 3-chloro-4-((2-methyl-3-oxocyclopent-1-en-1-yl)amino)benzoate | Cl | H | CO$_2$CH$_3$ | H |
| 12 | 3-Methoxy-4-((2-methyl-3-oxocyclopent-1-en-1-yl)amino)benzoic acid | OCH$_3$ | H | CO$_2$H | H |
| 13 | Methyl 2-methoxy-4-((2-methyl-3-oxocyclopent-1-en-1-yl)amino)benzoate | H | OCH$_3$ | CO$_2$CH$_3$ | H |
| 14 | 3-Methyl-4-((2-methyl-3-oxocyclopent-1-en-1-yl)amino)benzoic acid | CH$_3$ | H | CO$_2$H | H |
| 15 | 2-Methoxy-3-((2-methyl-3-oxocyclopent-1-en-1-yl)amino)benzoic acid | OCH$_3$ | CO$_2$H | H | H |
| 16 | 2-Methyl-4-((2-methyl-3-oxocyclopent-1-en-1-yl)amino)benzoic acid | H | CH$_3$ | CO$_2$H | H |
| 17 | 2,5-Dichloro-4-((2-methyl-3-oxocyclopent-1-en-1-yl)amino)benzoic acid | Cl | H | CO$_2$H | Cl |
| 18 | 2-((2-Methyl-3-oxocyclopent-1-en-1-yl)amino)benzamide | CONH$_2$ | H | H | H |
| 19 | Methyl 2-((2-methyl-3-oxocyclopent-1-en-1-yl)amino)benzoate | CO$_2$CH$_3$ | H | H | H |
| 20 | Methyl 5-chloro-2-((2-methyl-3-oxocyclopent-1-en-1-yl)amino)benzoate | CO$_2$CH$_3$ | H | Cl | H |
| 21 | Methyl 3-fluoro-4-((2-methyl-3-oxocyclopent-1-en-1-yl)amino)benzoate | F | H | CO$_2$CH$_3$ | H |
| 22 | Methyl 3-bromo-4-((2-methyl-3-oxocyclopent-1-en-1-yl)amino)benzoate | Br | H | CO$_2$CH$_3$ | H |
| 23 | 2-Chloro-6-((2-methyl-3-oxocyclopent-1-en-1-yl)amino)benzoic acid | CO$_2$H | Cl | H | H |
| 24 | Methyl 4-chloro-2-((2-methyl-3-oxocyclopent-1-en-1-yl)amino)benzoate | CO$_2$CH$_3$ | H | H | Cl |
| 25 | 4-Chloro-3-((2-methyl-3-oxocyclopent-1-en-1-yl)amino)benzoic acid | Cl | H | H | CO$_2$H |

Example 01-01

Preparation of methyl 4-((3-oxocyclopent-1-en-1-yl)amino)benzoate (01-01)

2-methyl-1,3-cyclopentandione (5.0 g, 45.0 mmol) and methyl-4-aminobenzoate (7.5 g, 1.1 eq) were heated to reflux in toluene. Upon reflux the solution was removed from heating, and p-TSA (cat.) was added. The apparatus was equipped with a Dean-Stark condenser and returned to reflux for 18 h, unless more time was required. The solvent was removed on the rotovap and the subsequent crude material was recrystallized to give the title compound as product from the indicated solvent(s). The reaction on a 45.0 mmol scale yielded 10.0 g of gray microcrystals from MeOH/H$_2$O (mp=210-212° C., 91% yield). $^1$H NMR (D6-DMSO) δ 1.59 (s, 3H), 2.24-2.26 (m, 2H), 2.78-2.80 (m, 2H), 3.81 (s, 3H), 7.32 (d, J=8.1 Hz, 2H), 7.89 (d, J=8.3 Hz, 2H), 9.18 (s, 1H). $^{13}$C NMR (D6-DMSO) δ 8.0, 26.7, 33.4, 52.3, 112.9, 120.8, 123.9, 130.8, 145.2, 166.2, 168.2, 203.0. LCMS t=4.8 min, m/z Calcd for $C_{14}H_{16}NO_3$; $C_{14}H_{15}NNaO_3$; $C_{28}H_{31}N_2O_6$; $C_{28}H_{30}N_2NaO_6$ 246.11; 268.10; 491.22; 513.20 [M+H]$^+$; [M+Na]$^+$; [2M+H]$^+$; [2M+Na]$^+$, Found 246.12; 268.11; 491.24; 513.22.

Example 01-02

Preparation of 4-((3-oxocyclopent-1-en-1-yl)amino)benzamide (01-02)

The title compound was prepared from 2-methyl-1,3-cyclopentandione and 4-aminobenzamide according to the procedure of Example 01-01; 25.0 mmol scale yielded 5.0 g of yellow microcrystals from H$_2$O (mp=192-195° C., 87% yield). $^1$H NMR (D6-DMSO) δ 1.60 (s, 3H), 2.23-2.25 (m, 2H), 2.76 (s, 2H), 7.28 (d, J=7.8 Hz, 2H), 7.84 (d, J=8.3 Hz, 2H), 7.90 (s, 1H), 9.11 (s, 1H). LCMS t=2.8 min, m/z Calcd for $C_{13}H_{15}N_2O_2$; $C_{13}H_{14}N_2NaO_2$; $C_{26}H_{28}N_4NaO_4$ 231.11; 253.10; 483.20 [M+H]$^+$; [M+Na]$^+$; [2M+Na]$^+$, Found 231.12; 253.11; 483.22.

Example 01-03

Preparation of 3-((2-methyl-3-oxocyclopent-1-en-1-yl)amino)benzoic acid (01-03)

The title compound was prepared from 2-methyl-1,3-cyclopentandione and 3-aminobenzoic acid according to the procedure of Example 01-01; 30.0 mmol scale refluxed for 48 h yielded 5.0 g of white microcrystals from toluene (mp=236-238° C., 72% yield). $^1$H NMR (D6-DMSO) δ 1.58 (s, 3H), 2.23 (s, 2H), 2.70 (s, 2H), 7.46-7.50 (m, 2H), 7.66-7.67 (m, 1H), 7.78 (s, 1H), 9.11 (s, 1H), 13.11 (s, 1H). LCMS t=4.4 min, m/z Calcd for $C_{13}H_{14}NO_3$; $C_{13}H_{13}NNaO_3$; $C_{26}H_{27}N_2O_6$; $C_{26}H_{26}N_2NaO_6$ 232.10; 254.08; 463.19; 485.17 [M+H]$^+$; [M+Na]$^+$; [2M+H]$^+$; [2M+Na]$^+$, Found 232.11; 254.09; 463.21; 485.19.

Example 01-04

Preparation of methyl 3-((2-methyl-3-oxocyclopent-1-en-1-yl)amino)benzoate (01-04)

The title compound was prepared from 2-methyl-1,3-cyclopentandione and methyl 3-benzoate according to the procedure of Example 01-01; 30.0 mmol scale yielded 7.0 g of white microcrystals from EtOAc (mp=133-135° C., 95% yield). $^1$H NMR (D6-DMSO) δ 1.57 (s, 3H), 2.22-2.24 (m, 2H), 2.70 (s, 2H), 3.86 (s, 3H), 7.49-7.54 (m, 3H), 7.67 (d, J=7.5 Hz, 1H), 7.80 (s, 1H), 9.13 (s, 1H). LCMS t=5.0, m/z Calcd for $C_{14}H_{16}NO_3$; $C_{28}H_{31}N_2O_6$; $C_{28}H_{30}N_2NaO_6$ 246.11; 491.22; 513.20 [M+H]$^+$; [2M+H]$^+$; [2M+Na]$^+$, Found 246.13; 491.24; 513.22.

Example 01-05

Preparation of 3-((2-methyl-3-oxocyclohex-1-en-1-yl)amino)benzamide (01-05)

The title compound was prepared from 2-methyl-1,3-cyclopentandione and 3-aminobenzamide according to the procedure of Example 01-01; 30.0 mmol scale yielded 5.0 g of grey microcrystals from MeOH (mp=269-271° C., 72% yield). $^1$H NMR (D6-DMSO) δ 1.57 (s, 3H), 2.21-2.23 (m, 2H), 2.67 (s, 2H), 7.37-7.42 (m, 3H), 7.63 (d, J=7.5 Hz, 2H), 7.71 (s, 1H), 8.00 (s, 1H), 9.08 (s, 1H). LCMS t=3.1 min, m/z Calcd for $C_{13}H_{15}N_2O_2$; $C_{13}H_{14}N_2NaO_2$; $C_{26}H_{29}N_4O_4$; $C_{26}H_{28}N_4NaO_4$ 231.11; 253.10; 461.22; 483.20 [M+H]$^+$; [M+Na]$^+$; [2M+H]$^+$; [2M+Na]$^+$, Found 231.12; 253.11; 461.24; 483.22.

Example 01-06

Preparation of 4-((2-methyl-3-oxocyclopent-1-en-1-yl)amino)benzenesulfonamide (01-06)

The title compound was prepared from 2-methyl-1,3-cyclopentandione and sulfanilamide according to the procedure of Example 01-01; 30.0 mmol scale yielded 7.0 g of yellow microcrystals from THF/H$_2$O (mp=245-247° C., 88% yield). $^1$H NMR (D6-DMSO) δ 1.60 (s, 3H), 2.25-2.26 (m, 2H), 2.78 (s, 2H), 7.29 (s, 2H), 7.37 (d, J=8.4 Hz, 2H), 7.76 (d, J=8.4 Hz, 2H), 9.22 (s, 1H). LCMS t=2.9 min, m/z Calcd for $C_{12}H_{15}N_2O_3S$; $C_{24}H_{28}N_4NaO_6S_2$ 267.08; 555.13 [M+H]$^+$; [2M+Na]$^+$, Found 267.09; 555.16.

Example 01-07

Preparation of 4-((2-methyl-3-oxocyclopent-1-en-1-yl)amino)benzonitrile (01-07)

The title compound was prepared from 2-methyl-1,3-cyclopentandione and 4-aminobenzonitrile according to the procedure of Example 01-01; 30.0 mmol scale yielded 4.0 g of yellow microcrystals from H$_2$O (mp=204-206° C., 63% yield). $^1$H NMR (D6-DMSO) δ 1.61 (s, 3H), 2.26-2.27 (m, 2H), 2.82 (s, 2H), 7.38 (d, J=8.3 Hz, 2H), 7.76 (d, J=8.2 Hz, 2H), 9.27 (s, 1H). LCMS t=5.3 min, m/z Calcd for $C_{13}H_{13}N_2O$; $C_{13}H_{12}N_2NaO$; $C_{26}H_{24}N_4NaO_2$ 213.10; 235.08; 447.18 [M+H]$^+$; [M+Na]$^+$; [2M+Na]$^+$, Found 213.17; 235.14; 447.15.

Example 01-08

Preparation of 3-((3-bromophenyl)amino)-2-methyl-cyclopent-2-enone (01-08)

The title compound was prepared from 2-methyl-1,3-cyclopentandione and 3-bromoaniline according to the procedure of Example 01-01; 50.0 mmol scale yielded 6.1 g of brown microcrystals from EtOAc (mp=291-294° C., 46% yield). $^1$H NMR (D6-DMSO) δ 1.58 (s, 3H), 2.22 (s, 2H), 2.69 (s, 2H), 7.25-7.31 (m, 3H), 7.45 (s, 1H), 9.04 (s, 1H). LCMS t=5.8 min, m/z Calcd for $C_{12}H_{13}BrNO$; $C_{12}H_{12}BrNNaO$; $C_{24}H_{24}Br_2N_2NaO_2$ 266.02; 268.02; 288.00, 290.00; 555.01 [M+H]$^+$; [M+Na]$^+$; [2M+Na]$^+$, Found 266.07, 268.06; 288.04, 290.03; 554.98.

Example 01-09

Preparation of 3-((4-acetylphenyl)amino)-2-methyl-cyclopent-2-enone (01-09)

The title compound was prepared from 2-methyl-1,3-cyclopentandione and 4-aminoacetophenone according to the procedure of Example 01-01; 25.0 mmol scale yielded 0.5 g of orange microcrystals from toluene (mp=270-273° C., 9% yield). $^1$H NMR (D6-DMSO) δ 1.61 (s, 3H), 2.26 (s, 2H), 2.82 (s, 2H), 3.36 (s, 3H), 7.33 (d, J=8.5 Hz, 2H), 7.92 (d, J=8.5 Hz, 2H), 9.23 (s, 1H). LCMS t=5.2 min, m/z Calcd

Example 01-10

Preparation of 2-chloro-4-((2-methyl-3-oxocyclopent-1-en-1-yl)amino)benzoic acid (01-10)

The title compound was prepared from 2-methyl-1,3-cyclopentandione and 4-amino-2-chlorobenzoic acid according to the procedure of Example 01-01; 25.0 mmol scale yielded 4.3 g of yellow needles from acetone (mp=239-241° C., 65% yield). $^1$H NMR (D6-DMSO) δ 1.61 (s, 3H), 2.27 (s, 2H), 2.83 (s, 2H), 7.27 (d, J=6.8 Hz, 1H), 7.38 (s, 1H), 7.84 (d, J=8.6 Hz, 1H), 9.21 (s, 1H), 13.1 (s, 1H). LCMS t=5.1 min, m/z Calcd for $C_{13}H_{13}ClNO_3$; $C_{13}H_{12}ClNNaO_3$; $C_{26}H_{24}Cl_2N_2NaO_6$ 266.06; 288.04; 553.09 [M+H]$^+$; [M+Na]$^+$; [2M+Na]$^+$, Found 266.12; 288.09; 553.09.

Example 01-11

Preparation of methyl 3-chloro-4-((2-methyl-3-oxocyclopent-1-en-1-yl)amino)benzoate (01-11)

The title compound was prepared from 2-methyl-1,3-cyclopentandione and methyl 4-amino-3-chlorobenzoate according to the procedure of Example 01-01; 25.0 mmol scale yielded 3.4 g from EtOAc (49% yield). $^1$H NMR (D6-DMSO) δ 1.44 (s, 3H), 2.24-2.26 (m, 2H), 2.54-2.55 (m, 2H), 3.86 (s, 3H), 7.42 (d, J=8.3 Hz, 1H), 7.90 (d, J=8.3 Hz, 1H), 8.02 (s, 1H), 8.98 (s, 1H). LCMS t=5.7 min, m/z Calcd for $C_{14}H_{15}ClNO_3$; $C_{14}H_{14}ClNNaO_3$; $C_{28}H_{28}Cl_2N_2NaO_6$ 280.07; 302.06; 581.12 [M+H]$^+$; [M+Na]$^+$; [2M+Na]$^+$, Found 280.13; 302.10; 581.12.

Example 01-12

Preparation of 3-methoxy-4-((2-methyl-3-oxocyclopent-1-en-1-yl)amino)benzoic acid (01-12)

The title compound was prepared from 2-methyl-1,3-cyclopentandione and 4-amino-3-methoxybenzoic acid according to the procedure of Example 01-01; 25.0 mmol scale yielded 4.8 g of tan needles from EtOH (mp=231-234° C., 74% yield). $^1$H NMR (D6-DMSO) δ 1.51 (s, 3H), 2.19-2.21 (m, 2H), 2.55-2.56 (m, 2H), 3.89 (s, 3H), 7.28 (d, J=8.5 Hz, 1H), 7.55-7.57 (m, 2H), 8.56 (s, 1H), 12.96 (s, 1H). LCMS t=5.1 min, m/z Calcd for $C_{14}H_{16}NO_4$; $C_{14}H_{15}NNaO_4$; $C_{28}H_{30}N_2NaO_8$ 262.11; 284.09; 545.19 [M+H]$^+$; [M+Na]$^+$; [2M+Na]$^+$, Found 262.17; 284.14; 545.19.

Example 01-13

Preparation of methyl 2-methoxy-4-((2-methyl-3-oxocyclopent-1-en-1-yl)amino)benzoate (01-13)

The title compound was prepared from 2-methyl-1,3-cyclopentandione and methyl 4-amino-2-methoxybenzoate according to the procedure of Example 01-01; 25.0 mmol scale yielded 6.8 g of tan microcrystals from toluene (mp=193-196° C., 99% yield). $^1$H NMR (D6-DMSO) δ 1.62 (s, 3H), 2.25-2.26 (m, 2H), 2.84 (s, 2H), 3.75 (s, 3H), 3.82 (s, 3H), 6.88 (d, J=8.4 Hz, 1H), 6.97 (d, J=8.4 Hz, 1H), 7.68 (d, J=8.4 Hz, 1H), 9.15 (s, 1H). LCMS t=5.3 min, m/z Calcd for $C_{14}H_{16}NO_2$; $C_{14}H_{15}NNaO_2$; $C_{28}H_{30}N_2NaO_4$ 230.12; 252.10; 481.21 [M+H]$^+$; [M+Na]$^+$; [2M+Na]$^+$, Found 230.19; 252.16; 481.21.

Example 01-14

Preparation of 3-methyl-4-((2-methyl-3-oxocyclopent-1-en-1-yl)amino)benzoic acid (01-14)

The title compound was prepared from 2-methyl-1,3-cyclopentandione and 4-amino-3-methylbenzoic acid according to the procedure of Example 01-01; 25.0 mmol scale yielded 3.0 g of tan sheets from EtOH (mp=233-236° C., 49% yield). $^1$H NMR (D6-DMSO) δ 1.45 (s, 3H), 2.19-2.21 (m, 2H), 2.30 (s, 3H), 2.47 (s, 2H), 7.24 (d, J=8.2 Hz, 1H), 7.77 (d, J=8.0 Hz, 1H), 7.85 (s, 1H), 8.74 (s, 1H), 12.88 (s, 1H). LCMS t=5.1 min, m/z Calcd for $C_{14}H_{16}NO_3$; $C_{14}H_{15}NNaO_3$; $C_{26}H_{30}N_2NaO_6$ 246.11; 268.10; 513.20 [M+H]$^+$; [M+Na]$^+$; [2M+Na]$^+$, Found 246.19; 268.15; 513.20.

Example 01-15

Preparation of 2-methoxy-3-((2-methyl-3-oxocyclopent-1-en-1-yl)amino)benzoic acid (01-15)

The title compound was prepared from 2-methyl-1,3-cyclopentandione and 3-amino-2-methoxybenzoic acid according to the procedure of Example 01-01; 25.0 mmol scale yielded 4.0 g of grey microcrystals from EtOH (mp=220-223° C., 61% yield). $^1$H NMR (D6-DMSO) δ 1.53 (s, 3H), 2.16-2.19 (m, 2H), 2.44 (s, 2H), 3.72 (s, 3H), 7.19 (t, J=7.8 Hz, 1H), 7.42 (d, J=7.8 Hz, 1H), 7.54 (d, J=7.7 Hz, 1H), 8.72 (s, 1H), 13.03 (s, 1H). $^{13}$C NMR (D6-DMSO) δ 7.2, 25.3, 32.7, 61.3, 109.1, 123.7, 127.1, 127.7, 130.6, 133.7, 153.6, 167.0, 170.3, 202.0. LCMS t=1.2 min, m/z Calcd for $C_{14}H_{16}NO_4$; $C_{14}H_{15}NNaO_4$; $C_{28}H_{30}N_2NaO_8$ 262.11; 284.09; 545.19 [M+H]$^+$; [M+Na]$^+$; [2M+Na]$^+$, Found 262.21; 284.18; 545.27.

Example 01-16

Preparation of 2-methyl-4-((2-methyl-3-oxocyclopent-1-en-1-yl)amino)benzoic acid (01-16)

The title compound was prepared from 2-methyl-1,3-cyclopentandione and 4-amino-2-methylbenzoic acid according to the procedure of Example 01-01; 25.0 mmol scale yielded 3.0 g of black needles from EtOH (mp=213-216° C., 49% yield). $^1$H NMR (D6-DMSO) δ 1.59 (s, 3H), 2.23-2.25 (m, 2H), 2.52 (s, 3H), 2.78 (s, 2H), 7.11-7.13 (m, 2H), 7.83 (d, J=8.2 Hz, 1H), 9.07 (s, 1H), 12.58 (s, 1H). $^{13}$C NMR (D6-DMSO) δ 7.5, 21.7, 26.2, 33.0, 111.8, 118.1, 123.7, 124.4, 131.9, 141.0, 143.2, 168.0, 168.3, 202.4. LCMS t=5.1 min, m/z Calcd for $C_{14}H_{16}NO_3$; $C_{14}H_{15}NNaO_3$; $C_{26}H_{30}N_2NaO_6$ 246.11; 268.10; 513.20 [M+H]$^+$; [M+Na]$^+$; [2M+Na]$^+$, Found 246.22; 268.19; 513.27.

Example 01-17

Preparation of 2,5-dichloro-4-((2-methyl-3-oxocyclopent-1-en-1-yl)amino)benzoic acid (01-17)

The title compound was prepared from 2-methyl-1,3-cyclopentandione and 4-amino-2,5-dichlorobenzoic acid according to the procedure of Example 01-01; 20.0 mmol scale yielded 5.0 g of yellow needles from EtOH (mp=229-232° C., 82% yield). $^1$H NMR (D6-DMSO) δ 1.45 (s, 3H), 2.21 (s, 2H), 2.45 (s, 2H), 7.64-7.66 (m, 2H), 8.97 (s, 1H), 13.85 (s, 1H). $^{13}$C NMR (D6-DMSO) δ 7.5, 25.5, 32.7, 110.4, 126.6, 129.4, 131.5, 134.9, 139.1, 165.7, 168.9, 202.8. LCMS t=5.1 min, m/z Calcd for $C_{13}H_{12}Cl_2NO_3$; $C_{26}H_{22}Cl_4N_2NaO_6$ 300.02; 623.01 [M+H]$^+$; [2M+Na]$^+$, Found 300.10; 623.09.

Example 01-18

Preparation of 2-((2-methyl-3-oxocyclopent-1-en-1-yl)amino)benzamide (01-18)

The title compound was prepared from 2-methyl-1,3-cyclopentandione and anthranilamide according to the procedure of Example 01-01; 20.0 mmol scale yielded 3.0 g of yellow microcrystal from EtOH (mp=235-238° C., 65% yield). $^1$H NMR (D6-DMSO) δ 1.59 (s, 3H), 2.26-2.29 (m, 2H), 2.91 (s, 2H), 7.07-7.11 (m, 1H), 7.47-7.49 (m, 2H), 7.75 (s, 1H), 7.78 (d, J=7.9 Hz, 1H) 8.25 (s, 1H), 11.14 (s, 1H). $^{13}$C NMR (D6-DMSO) δ 6.6, 26.3, 33.3, 112.2, 119.8, 121.3, 121.8, 129.2, 132.3, 140.9, 168.4, 170.9, 201.6. LCMS t=4.3 min, m/z Calcd for $C_{13}H_{15}N_2O_2$; $C_{13}H_{14}N_2NaO_2$; $C_{26}H_{29}N_4O_4$; $C_{26}H_{28}N_4NaO_4$ 231.11; 253.10; 461.22; 483.20 [M+H]$^+$; [M+Na]$^+$; [2M+H]$^+$; [2M+Na]$^+$, Found 231.11; 253.10; 461.22; 483.20.

Example 01-19

Preparation of methyl 2-((2-methyl-3-oxocyclopent-1-en-1-yl)amino)benzoate (01-19)

The title compound was prepared from 2-methyl-1,3-cyclopentandione and methyl anthranilate according to the procedure of Example 01-01; 20.0 mmol scale yielded 4.0 g from EtOAc (82% yield). $^1$H NMR (D6-DMSO) δ 1.62 (s, 3H), 2.29-2.31 (m, 2H), 2.88 (s, 2H), 3.87 (s, 3H), 7.17 (t, J=7.5 Hz, 1H), 7.53 (d, J=8.3 Hz, 1H), 7.61 (t, J=7.6 Hz, 1H), 7.97 (d, J=7.9 Hz, 1H) 10.11 (s, 1H). $^{13}$C NMR (D6-DMSO) δ 6.7, 26.3, 33.2, 52.5, 112.7, 117.9, 120.9, 122.6, 131.3, 134.3, 141.6, 167.7, 168.3, 201.8. LCMS t=5.3 min, m/z Calcd for $C_{14}H_{16}NO_3$; $C_{14}H_{15}NNaO_3$; $C_{28}H_{31}N_2O_6$; $C_{28}H_{30}N_2NaO_6$ 246.11; 268.10; 491.22; 513.20 [M+H]$^+$; [M+Na]$^+$; [2M+H]$^+$; [2M+Na]$^+$, Found 246.11; 268.09; 491.22; 513.20.

Example 01-20

Preparation of methyl 5-chloro-2-((2-methyl-3-oxocyclopent-1-en-1-yl)amino)benzoate (01-20)

The title compound was prepared from 2-methyl-1,3-cyclopentandione and methyl 5-chloroanthranilate according to the procedure of Example 01-01; 5.0 mmol scale yielded 1.0 g of yellow microcrystals from EtOAc (mp=162-165° C., 82% yield). $^1$H NMR (D6-DMSO) δ 1.60 (s, 3H), 2.29-2.31 (m, 2H), 2.86 (s, 2H), 3.88 (s, 3H), 7.54 (d, J=8.9 Hz, 1H), 7.65 (dd, J=8.9, 2.3 Hz, 1H), 7.92 (d, J=2.3 Hz, 1H), 9.96 (s, 1H). $^{13}$C NMR (D6-DMSO) δ 6.8, 26.2, 33.2, 52.8, 113.2, 119.6, 122.9, 126.2, 130.4, 133.8, 140.5, 166.6, 167.7, 202.1. LCMS t=5.7 min, m/z Calcd for $C_{14}H_{15}ClNO_3$; $C_{14}H_{14}ClNNaO_3$; $C_{28}H_{28}Cl_2N_2NaO_6$ 280.07; 302.06; 581.12 [M+H]$^+$; [M+Na]$^+$; [2M+Na]$^+$, Found 280.07; 302.05; 581.12.

Example 01-21

Preparation of methyl 3-fluoro-4-((2-methyl-3-oxocyclopent-1-en-1-yl)amino)benzoate (01-21)

The title compound was prepared from 2-methyl-1,3-cyclopentandione and methyl 4-amino-3-fluorobenzoate according to the procedure of Example 01-01; 20.0 mmol scale yielded 4.5 g of beige microcrystals from EtOAc (mp=198-201° C., 85% yield). $^1$H NMR (D6-DMSO) δ 1.51 (s, 3H), 2.24-2.26 (m, 2H), 2.57 (s, 2H), 3.86 (s, 3H), 7.40-7.44 (m, 1H), 7.77-7.79 (m, 2H), 9.09 (s, 1H). LCMS t=5.0 min, m/z Calcd for $C_{14}H_{15}FNO_3$; $C_{14}H_{14}FNNaO_3$; $C_{28}H_{29}F_2N_2O_6$; $C_{28}H_{28}F_2N_2NaO_6$ 264.10; 286.09; 527.20; 549.18 [M+H]$^+$; [M+Na]$^+$; [2M+H]$^+$; [2M+Na]$^+$, Found 264.10; 286.08; 527.20; 549.18.

Example 01-22

Preparation of methyl 3-bromo-4-((2-methyl-3-oxocyclopent-1-en-1-yl)amino)benzoate (01-22)

The title compound was prepared from 2-methyl-1,3-cyclopentandione and methyl 4-amino-3-bromobenzoate according to the procedure of Example 01-01; 20.0 mmol scale yielded 4.0 g of white microcrystals from EtOAc (mp=155-158° C., 62% yield). $^1$H NMR (D6-DMSO) δ 1.43 (s, 3H), 2.23-2.25 (m, 2H), 2.50-2.53 (m, 2H), 3.86 (s, 3H), 7.44 (d, J=8.3 Hz, 1H), 7.94-7.95 (m, 1H), 8.17 (d, J=1.4 Hz, 1H), 8.91 (s, 1H). $^{13}$C NMR (D6-DMSO) δ 7.8, 25.9, 32.7, 52.4, 111.4, 119.1, 126.9, 127.6, 129.1, 133.5, 142.5, 164.6, 168.2, 203.0. LCMS t=5.2 min, m/z Calcd for $C_{14}H_{15}BrNO_3$; $C_{14}H_{14}BrNNaO_3$; $C_{28}H_{29}Br_2N_2O_6$; $C_{28}H_{28}Br_2N_2NaO_6$ 324.02, 326.02; 346.01, 348.00; 649.04; 671.02 [M+H]$^+$; [M+Na]$^+$; [2M+H]$^+$; [2M+Na]$^+$, Found 324.02, 326.02; 346.00, 348.00; 649.04; 671.02.

Example 01-23

Preparation of 2-chloro-6-((2-methyl-3-oxocyclopent-1-en-1-yl)amino)benzoic acid (01-23)

The title compound was prepared from 2-methyl-1,3-cyclopentandione and 6-chloroanthranilic acid according to the procedure of Example 01-01; 20.0 mmol scale yielded 3.0 g of white microcrystals from EtOH (mp=277-280° C., 56% yield). $^1$H NMR (D6-DMSO) δ 1.44 (s, 3H), 2.14-2.16 (m, 2H), 2.36-2.38 (m, 2H), 7.31 (dd, J=6.5, 2.1 Hz, 1H), 7.45-7.48 (m, 2H), 8.95 (s, 1H). $^{13}$C NMR (D6-DMSO) δ 7.1, 25.3, 32.6, 109.1, 127.0, 127.4, 129.6, 130.7, 132.9, 137.6, 166.3, 170.3, 202.2. LCMS t=4.5 min, m/z Calcd for $C_{13}H_{13}ClNO_3$; $C_{26}H_{25}Cl_2N_2O_6$ 266.06; 531.11 [M+H]$^+$; [2M+H]$^+$, Found 266.06; 531.11.

Example 01-24

Preparation of methyl 4-chloro-2-((2-methyl-3-oxocyclopent-1-en-1-yl)amino)benzoate (01-24)

The title compound was prepared from 2-methyl-1,3-cyclopentandione and methyl 4-chloroanthranilate according to the procedure of Example 01-01; 20.0 mmol scale yielded 4.6 g of yellow sheets from EtOAc (mp=167-170° C., 82% yield). $^1$H NMR (CDCl3) δ 1.82 (s, 3H), 2.53-2.55 (m, 2H), 3.02-3.03 (m, 2H), 3.95 (s, 3H), 6.98 (dd, J=8.6, 1.7 Hz, 1H), 7.37 (d, J=1.6 Hz, 1H), 8.00 (d, J=8.6 Hz, 1H), 10.67 (s, 1H). $^{13}$C NMR (CDCl3) δ 7.2, 27.8, 33.9, 52.8, 113.9, 117.2, 117.9, 121.4, 133.4, 140.7, 144.3, 166.8, 168.3, 204.0. LCMS t=5.7 min, m/z Calcd for $C_{14}H_{15}ClNO_3$; $C_{14}H_{14}ClNNaO_3$; $C_{28}H_{29}Cl_2N_2O_6$; $C_{28}H_{28}Cl_2N_2NaO_6$ 280.07; 302.06; 559.14; 581.12 $[M+H]^+$; $[M+Na]^+$; $[2M+H]^+$; $[2M+Na]^+$, Found 280.07; 302.05; 559.14; 581.12.

Example 01-25

Preparation of 4-chloro-3-((2-methyl-3-oxocyclopent-1-en-1-yl)amino)benzoic acid (01-25)

The title compound was prepared from 2-methyl-1,3-cyclopentandione and 3-amino-4-chlorobenzoic acid according to the procedure of Example 01-01; 20.0 mmol scale yielded 5.0 g of white microcrystals from EtOH (mp=272-275° C., 94% yield). $^1$H NMR (D6-DMSO) δ 1.42 (s, 3H), 2.20-2.22 (m, 2H), 2.41-2.43 (m, 2H), 7.69 (d, J=7.9 Hz, 1H), 7.79-7.81 (m, 2H), 8.97 (s, 1H), 13.31 (s, 1H). $^{13}$C NMR (D6-DMSO) δ 7.5, 25.7, 32.6, 109.7, 127.8, 128.7, 130.2, 134.5, 136.9, 166.1, 169.2, 202.6. LCMS t=4.3 min, m/z Calcd for $C_{13}H_{13}ClNO_3$; $C_{26}H_{25}Cl_2N_2O_6$ 266.06; 531.11 $[M+H]^+$; $[2M+H]^+$, Found 266.06; 531.07.

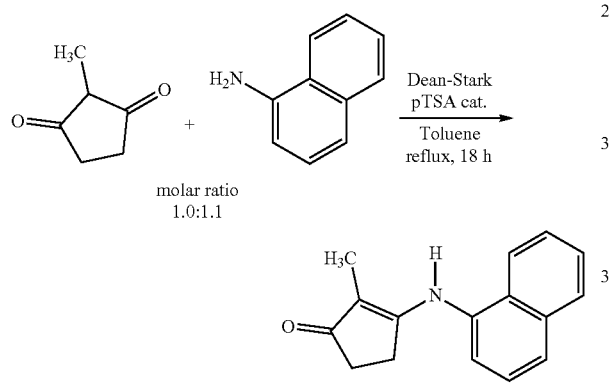

molar ratio
1.0:1.1

Example 01-26

Preparation of 2-methyl-3-(naphthalen-1-ylamino)cyclopent-2-enone (01-26)

The title compound was prepared from 2-methyl-1,3-cyclopentandione and 1-naphthylamine according to the procedure of Example 01-01; 12.5 mmol scale yielded 1.0 g of tan needles from EtOAc (mp=166-168° C., 34% yield). $^1$H NMR (D6-DMSO) δ 1.51 (s, 3H), 2.15-2.16 (m, 2H), 2.38 (s, 2H), 7.42 (d, J=7.1 Hz, 1H), 7.52-7.61 (m, 3H), 7.87 (d, J=8.1 Hz, 1H), 8.00 (t, J=8.6 Hz, 2H), 9.26 (s, 1H). LCMS t=5.4 min, m/z Calcd for $C_{16}H_{16}NO$; $C_{16}H_{15}NNaO$; $C_{32}H_{31}N_2O_2$; $C_{32}H_{30}N_2NaO_2$ 238.12; 260.11; 475.24; 497.22 $[M+H]^+$; $[M+Na]^+$; $[2M+H]^+$; $[2M+Na]^+$, Found 238.14; 260.12; 475.26; 497.24.

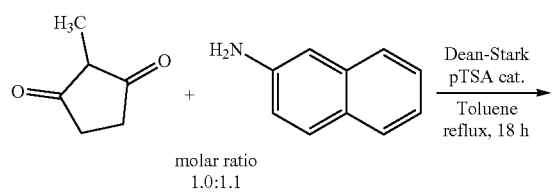

molar ratio
1.0:1.1

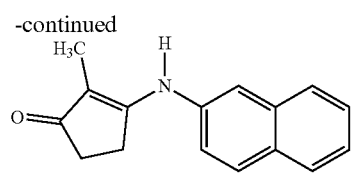

Example 01-27

Preparation of 2-methyl-3-(naphthalen-2-ylamino)cyclopent-2-enone (01-27)

The title compound was prepared from 2-methyl-1,3-cyclopentandione and 2-naphthylamine according to the procedure of Example 01-01; 6.0 mmol scale yielded 0.2 g of yellow needles from EtOAc (mp=248-250° C., 14% yield). $^1$H NMR (D6-DMSO) δ 1.62 (s, 3H), 2.23-2.25 (m, 2H), 2.77-2.78 (m, 2H), 7.42-7.51 (m, 3H), 7.71 (s, 1H), 7.85-7.90 (m, 3H), 9.16 (s, 1H). LCMS t=5.5 min, m/z Calcd for $C_{16}H_{16}NO$; $C_{16}H_{15}NNaO$; $C_{32}H_{31}N_2O_2$; $C_{32}H_{30}N_2NaO_2$ 238.12; 260.11; 475.24; 497.22 $[M+H]^+$; $[M+Na]^+$; $[2M+H]^+$; $[2M+Na]^+$, Found 238.13; 260.12; 475.26; 497.24.

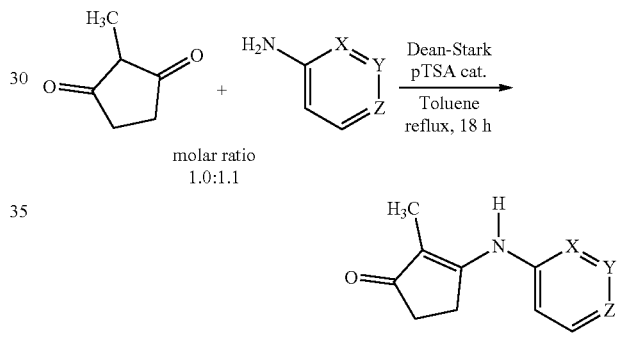

molar ratio
1.0:1.1

| Example 01-# | TITLE COMPOUND NAME | X | Y | Z |
|---|---|---|---|---|
| 28 | 2-Methyl-3-(pyridin-2-ylamino)cyclopent-2-enone | N | CH | CH |
| 29 | 2-Methyl-3-(pyridin-3-ylamino)cyclopent-2-enone | CH | N | CH |
| 30 | 2-Methyl-3-(pyridin-4-ylamino)cyclopent-2-enone | CH | CH | N |

Example 01-28

Preparation of 2-methyl-3-(pyridin-2-ylamino)cyclopent-2-enone (01-28)

The title compound was prepared from 2-methyl-1,3-cyclopentandione and 2-aminopyridine according to the procedure of Example 01-01; 30.0 mmol scale yielded 0.6 g of yellow sheets from EtOAc (mp=163-165° C., 11% yield). $^1$H NMR (D6-DMSO) δ 1.66 (s, 3H), 2.23 (s, 2H), 3.18 (s, 2H), 6.96 (d, J=5.0 Hz, 1H), 7.18 (d, J=8.0 Hz, 1H), 7.69-7.71 (m, 1H), 8.23 (s, 1H), 9.32 (s, 1H). LCMS t=4.4 min, m/z Calcd for $C_{11}H_{13}N_2O$; $C_{11}H_{12}N_2NaO$; $C_{22}H_{25}N_4O_2$; $C_{22}H_{24}N_4NaO_2$ 189.10; 211.08; 377.20;

399.18 [M+H]⁺; [M+Na]⁺; [2M+H]⁺; [2M+Na]⁺, Found 189.11; 211.09; 377.21; 399.20.

Example 01-29

Preparation of 2-methyl-3-(pyridin-3-ylamino)cyclopent-2-enone (01-29)

The title compound was prepared from 2-methyl-1,3-cyclopentandione and 3-aminopyridine according to the procedure of Example 01-01; 30.0 mmol scale yielded 1.6 g of grey microneedles from EtOAc (mp=133-135° C., 28% yield). $^1$H NMR (D6-DMSO) δ 1.59 (s, 3H), 2.22 (s, 2H), 2.66 (s, 2H), 7.38 (dd, J=7.7, 4.7 Hz, 1H), 7.67 (d, J=7.8 Hz, 1H), 8.32 (d, J=3.6 Hz, 1H), 8.51 (s, 1H), 9.07 (s, 1H). LCMS t=1.4 min, m/z Calcd for $C_{11}H_{13}N_2O$; $C_{11}H_{12}N_2NaO$; $C_{22}H_{25}N_4O_2$; $C_{22}H_{24}N_4NaO_2$ 189.10; 211.08; 377.20; 399.18 [M+H]⁺; [M+Na]⁺; [2M+H]⁺; [2M+Na]⁺, Found 189.11; 211.09; 377.22; 399.20.

Example 01-30

Preparation of 2-methyl-3-(pyridin-4-ylamino)cyclopent-2-enone (01-30)

The title compound was prepared from 2-methyl-1,3-cyclopentandione and 4-aminopyridine according to the procedure of Example 01-01; 20.0 mmol scale for 72 h yielded 0.02 g of yellow microcrystals from EtOAc (mp=203-205° C., 1% yield). $^1$H NMR (D6-DMSO) δ 1.63 (s, 3H), 2.28-2.29 (m, 2H), 2.90 (s, 2H), 7.20 (d, J=4.9 Hz, 2H), 8.38 (s, 2H), 9.15 (s, 1H). LCMS t=1.4 min, m/z Calcd for $C_{11}H_{13}N_2O$ 189.10 [M+H]⁺, Found 189.12.

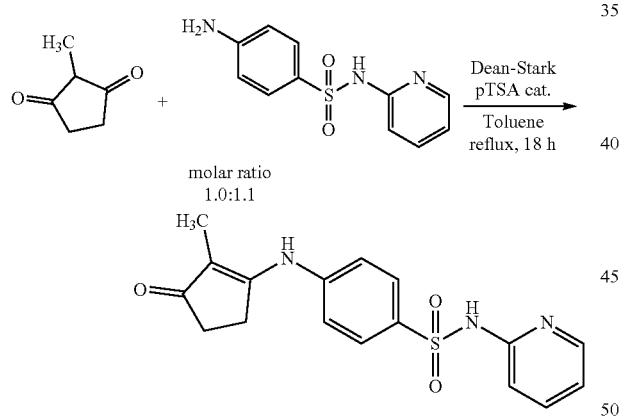

Example 01-31

Preparation of 4-((2-methyl-3-oxocyclopent-1-en-1-yl)amino)-N-(pyridin-2-yl)benzenesulfonamide (01-31)

The title compound was prepared from 2-methyl-1,3-cyclopentandione and 4-amino-N-(2-pyridinyl)benzenesulfonamide according to the procedure of Example 01-01; 10.0 mmol scale yielded 2.0 g of yellow microcrystals from H₂O (mp=230-233° C., 58% yield). $^1$H NMR (D6-DMSO) δ 1.58 (s, 3H), 2.23-2.25 (m, 2H), 2.77 (s, 2H), 6.88 (t, J=5.5 Hz, 1H), 7.15 (d, J=8.5 Hz, 1H), 7.34 (d, J=8.5 Hz, 2H), 7.72 (t, J=7.8 Hz, 1H), 7.80 (d, J=8.4 Hz, 1H), 9.18 (s, 1H). LCMS t=4.9 min, m/z Calcd for $C_{17}H_{18}N_3O_3S$; $C_{17}H_{17}N_3NaO_3S$; $C_{34}H_{34}N_6NaO_6S_2$ 344.11; 366.09; 709.19 [M+H]⁺; [M+Na]⁺; [2M+Na]⁺, Found 344.11; 366.08; 709.16.

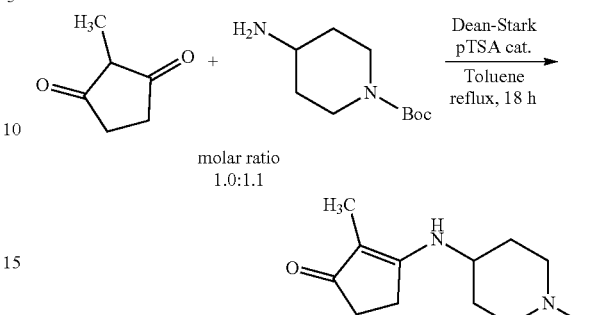

Example 01-32

Preparation of tert-Butyl 4-((2-methyl-3-oxocyclopent-1-en-1-yl)amino)piperidine-1-carboxylate (01-32)

The title compound was prepared from 2-methyl-1,3-cyclopentandione and tert-butyl 4-aminopiperidine-1-carboxylate according to the procedure of Example 01-01; 5.0 mmol scale yielded 0.6 g of grey microcrystals from H₂O (mp=189-191° C., 41% yield). $^1$H NMR (D6-DMSO) δ 1.40-1.46 (m, 14H), 1.76 (d, J=11.6 Hz, 2H), 2.10-2.11 (m, 2H), 2.51 (d, J=5.8 Hz, 2H), 2.73 (s, 2H), 2.65-2.90 (m, 2H), 3.52 (s, 1H), 3.94 (s, 2H), 6.88 (d, J=8.3 Hz, 1H). LCMS t=5.6 min, m/z Calcd for $C_{16}H_{27}N_2O_3$; $C_{16}H_{26}N_2NaO_3$; $C_{32}H_{52}N_4NaO_6$ 295.20; 317.18; 611.38 [M+H]⁺; [M+Na]⁺; [2M+Na]⁺, Found 295.26; 317.20; 611.35.

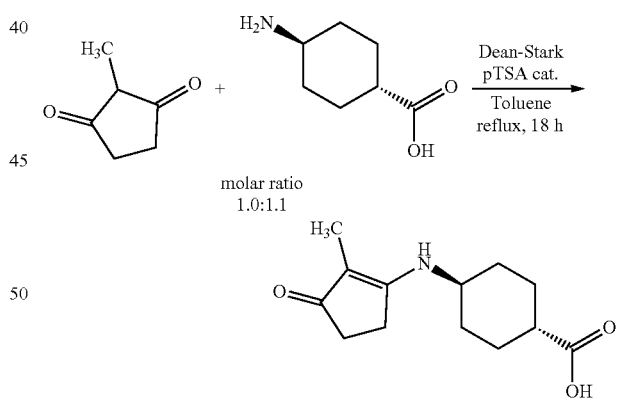

Example 01-33

Preparation of trans-(1R,4R)-4-((2-methyl-3-oxocyclopent-1-en-1-yl)amino)cyclohexanecarboxylic acid (01-33)

The title compound was prepared from 2-methyl-1,3-cyclopentandione and trans-(1R,4R)-4-aminocyclohexanecarboxylic acid according to the procedure of Example 01-01; 25.0 mmol scale yielded 4.0 g of white microneedles from H₂O (mp=236-238° C., 67% yield). $^1$H NMR (D6-

DMSO) δ 1.35-1.45 (m, 7H), 1.84 (d, J=9.3 Hz, 2H), 1.87-1.93 (m, 1H), 2.10 (s, 2H), 2.50 (s, 2H), 3.34 (br s, 2H), 6.88 (d, J=7.6 Hz, 1H), 12.1 (s, 1H). LCMS t=4.7 min, m/z Calcd for $C_{13}H_{20}NO_3$; $C_{13}H_{19}NNaO_3$; $C_{26}H_{39}N_2O_6$; $C_{26}H_{38}N_2NaO_6$ 238.14; 260.13; 475.28; 497.26 $[M+H]^+$; $[M+Na]^+$; $[2M+H]^{2+}$; $[2M+Na]^+$, Found 238.21; 260.18; 475.26; 497.24.

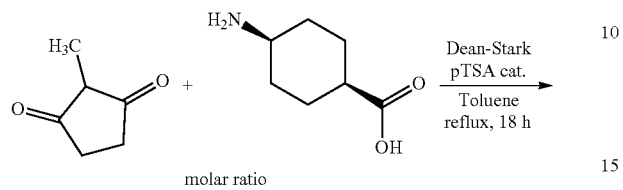

molar ratio
1.0:1.1

Example 01-34

Preparation of cis-(1S,4S)-4-((2-methyl-3-oxocyclopent-1-en-1-yl)amino)cyclohexanecarboxylic acid (01-34)

The title compound was prepared from 2-methyl-1,3-cyclopentandione and cis-(1S,4S)-4-aminocyclohexanecarboxylic acid according to the procedure of Example 01-01; 25.0 mmol scale yielded 2.6 g of tan microneedles from $H_2O$ (mp=233-235° C., 44% yield). $^1H$ NMR (D6-DMSO) δ 1.46-1.52 (m, 7H), 1.66 (d, J=8.8 Hz, 2H), 2.03-2.11 (m, 3H), 2.51 (s, 2H), 3.38 (br s, 2H), 6.94 (d, J=7.6 Hz, 1H), 12.25 (s, 1H). LCMS t=4.9 min, m/z Calcd for $C_{13}H_{20}NO_3$; $C_{13}H_{19}NNaO_3$; $C_{26}H_{39}N_2O_6$; $C_{26}H_{38}N_2NaO_6$ 238.14; 260.13; 475.28; 497.26 $[M+H]^+$; $[M+Na]^+$; $[2M+H]^+$; $[2M+Na]^+$, Found 238.21; 260.18; 475.26; 497.24.

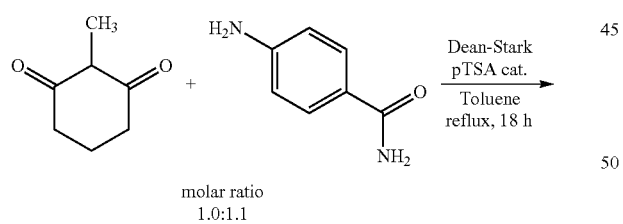

molar ratio
1.0:1.1

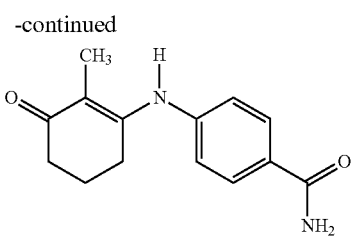

Example 01-35

Preparation of 4-((2-methyl-3-oxocyclohex-1-en-1-yl)amino)benzamide (01-35)

The title compound was prepared from 2-methyl-1,3-cyclohexandione and 4-aminobenzamide according to the procedure of Example 01-01; 12.5 mmol scale yielded 1.0 g of tan microsheets from $CH_2Cl_2$/hexanes (mp=221-223° C., 33% yield). $^1H$ NMR (D6-DMSO) δ 1.66 (s, 3H), 1.81 (t, J=5.7 Hz, 2H), 2.24 (t, J=5.8 Hz, 2H), 2.53 (s, 2H), 7.11 (d, J=8.1 Hz, 2H), 7.28 (s, 1H), 7.83 (d, J=8.1 Hz, 2H), 7.89 (s, 1H), 8.36 (s, 1H). LCMS t=3.9 min, m/z Calcd for $C_{14}H_{17}N_2O_2$; $C_{14}H_{16}N_2NaO_2$; $C_{28}H_{32}N_4NaO_4$ 245.13; 267.11; 511.23 $[M+H]^+$; $[M+Na]^+$; $[2M+Na]^+$, Found 245.15; 267.12; 511.26.

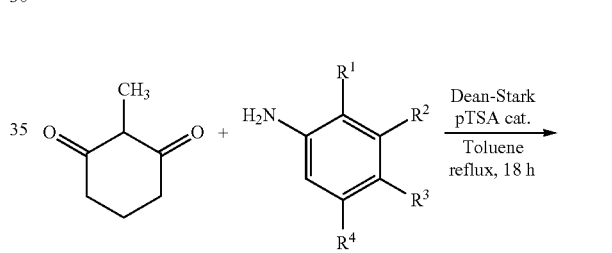

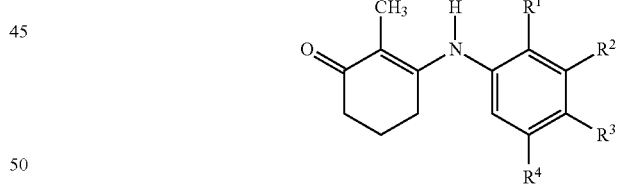

| Example 01-# | TITLE COMPOUND NAME | $R^1$ | $R^2$ | $R^3$ | $R^4$ |
|---|---|---|---|---|---|
| 36 | 4-Chloro-3-((2-methyl-3-oxocyclohex-1-en-1-yl)amino)benzoic acid | Cl | H | H | $CO_2H$ |
| 37 | 2-(3-((2-Methyl-3-oxocyclohex-1-en-1-yl)amino)phenyl)acetic acid | H | $CH_2CO_2H$ | H | H |
| 38 | 2-(4-((2-Methyl-3-oxocyclohex-1-en-1-yl)amino)phenyl)acetic acid | H | H | $CH_2CO_2H$ | H |
| 39 | 3-((2-Methyl-3-oxocyclohex-1-en-1-yl)amino)-4-(trifluoromethyl)benzoic acid | $CF_3$ | H | H | $CO_2H$ |
| 40 | 4-((2-Methyl-3-oxocyclohex-1-en-1-yl)amino)-4-(trifluoromethyl)benzoic acid | $CF_3$ | H | $CO_2H$ | H |

Example 01-36

Preparation of 4-chloro-3-((2-methyl-3-oxocyclo-hex-1-en-1-yl)amino)benzoic acid (01-36)

The title compound was prepared from 2-methyl-1,3-cyclohexandione and 3-amino-4-chlorobenzoic acid according to the procedure of Example 01-01; 20.0 mmol scale yielded 5.0 g of tan microcrystals from EtOH (mp=232-235° C., 89% yield). $^1$H NMR (D6-DMSO) δ 1.61 (s, 3H), 1.76-1.80 (m, 2H), 2.21 (t, J=6.2 Hz, 2H), 2.26 (t, J=5.6 Hz, 2H), 7.66 (dd, J=8.3, 1.0 Hz, 1H), 7.12 (s, 1H), 7.77 (d, J=8.3 Hz, 1H), 8.09 (s, 1H), 13.29 (br s, 1H). $^{13}$C NMR (D6-DMSO) δ 9.2, 21.0, 27.2, 36.3, 107.9, 127.4, 128.8, 130.1, 130.3, 134.8, 137.5, 158.2, 166.2, 194.9. LCMS t=4.7 min, m/z Calcd for $C_{14}H_{15}ClNO_3$; $C_{28}H_{28}Cl_2N_2NaO_6$ 280.07; 581.12 [M+H]$^+$; [2M+Na]$^+$, Found 280.06; 581.11.

Example 01-37

Preparation of 2-(3-((2-methyl-3-oxocyclohex-1-en-1-yl)amino)phenyl)acetic acid (01-37)

The title compound was prepared from 2-methyl-1,3-cyclohexandione and 3-aminophenylacetic acid according to the procedure of Example 01-01; 2.5 mmol scale yielded 0.25 g of orange microcrystals from EtOH (mp=203-207° C., 39% yield). $^1$H NMR (D6-DMSO) δ 1.67 (s, 3H), 2.20 (t, J=6.4 Hz, 2H), 2.43 (t, J=5.6 Hz, 2H), 3.56 (s, 2H), 6.99-7.02 (m, 3H), 7.27 (t, J=7.9 Hz, 1H), 8.18 (s, 1H), 12.38 (br s, 1H). $^{13}$C NMR (D6-DMSO) δ 9.6, 22.2, 27.8, 36.9, 41.01, 107.5, 123.00, 125.6, 125.7, 129.0, 136.2, 140.2, 158.6, 173.0, 194.8. LCMS t=4.4 min, m/z Calcd for $C_{15}H_{18}NO_3$; $C_{15}H_{17}NNaO_3$; $C_{30}H_{34}N_2NaO_6$ 260.13; 282.11; 541.23 [M+H]$^+$; [M+Na]$^+$; [2M+Na]$^+$, Found 260.11; 282.09; 541.19.

Example 01-38

Preparation of 2-(4-((2-methyl-3-oxocyclohex-1-en-1-yl)amino)phenyl)acetic acid (01-38)

The title compound was prepared from 2-methyl-1,3-cyclohexandione and 4-aminophenylacetic acid according to the procedure of Example 01-01; 20.0 mmol scale yielded 3.6 g of brown sheets from EtOH (mp=215-219° C., 69% yield). $^1$H NMR (D6-DMSO) δ 1.68 (s, 3H), 1.75-1.78 (m, 2H), 2.19 (t, J=6.4 Hz, 2H), 2.42 (t, J=5.7 Hz, 2H), 3.55 (s, 2H), 7.06 (d, J=8.3 Hz, 2H), 7.22 (d, J=8.3 Hz, 2H), 8.16 (s, 1H), 12.31 (br s, 1H). $^{13}$C NMR (D6-DMSO) δ 9.5, 22.1, 27.7, 36.8, 40.5, 107.0, 124.9, 130.2, 131.4, 138.8, 158.9, 173.2, 194.6. LCMS t=4.3 min, m/z Calcd for $C_{15}H_{18}NO_3$; $C_{15}H_{17}NNaO_3$; $C_{30}H_{34}N_2NaO_6$ 260.13; 282.11; 541.23 [M+H]$^+$; [M+Na]$^+$; [2M+Na]$^+$, Found 260.11; 282.09; 541.19.

Example 01-39

Preparation of 3-((2-methyl-3-oxocyclohex-1-en-1-yl)amino)-4-(trifluoromethyl)benzoic acid (01-39)

The title compound was prepared from 2-methyl-1,3-cyclohexandione and 3-amino-4-(trifluoromethyl)benzoic acid according to the procedure of Example 01-01; 2.5 mmol scale yielded 0.5 g of tan microcrystals from EtOH/EtOAc (mp=209-212° C., 64% yield). $^1$H NMR (D6-DMSO) δ 1.62 (s, 3H), 1.73-1.76 (m, 2H), 2.20-2.25 (m, 4H), 7.11 (d, J=7.7 Hz, 1H), 7.47 (d, J=7.8 Hz, 1H), 7.81 (s, 1H), 8.26 (s, 1H). LCMS t=4.6 min, m/z Calcd for $C_{15}H_{15}F_3NO_3$; $C_{30}H_{28}F_6N_2NaO_6$ 314.10; 649.17 [M+H]$^+$; [2M+Na]$^+$, Found 314.09; 649.12.

Example 01-40

Preparation of 4-((2-methyl-3-oxocyclohex-1-en-1-yl)amino)-4-(trifluoromethyl)benzoic acid (01-40)

The title compound was prepared from 2-methyl-1,3-cyclohexandione and 4-amino-3-(trifluoromethyl)benzoic acid according to the procedure of Example 01-01; 20.0 mmol scale yielded 2.5 g of tan microneedles from EtOH (mp=229-231° C., 40% yield). $^1$H NMR (D6-DMSO) δ 1.53 (s, 3H), 1.78-1.81 (m, 2H), 2.24 (t, J=6.2 Hz, 2H), 2.36-2.40 (m, 2H), 7.36 (d, J=8.3 Hz, 1H), 7.88 (s, 1H), 8.16 (d, J=8.5 Hz, 1H), 8.18 (s, 1H), 13.36 (br s, 1H). $^{13}$C NMR (D6-DMSO) δ 10.1, 21.3, 28.4, 36.9, 111.5, 123.7 ($J_{CF}$=28.6 Hz), 123.8 ($J_{CF}$=274.0 Hz), 127.5, 128.0, 128.6, 134.3, 143.3, 157.6, 166.2, 196.1. LCMS t=4.7 min, m/z Calcd for $C_{15}H_{15}F_3NO_3$; $C_{15}H_{14}F_3NNaO_3$; $C_{30}H_{28}F_6N_2NaO_6$ 314.10; 336.08; 649.17 [M+H]$^+$; [M+Na]$^+$; [2M+Na]$^+$, Found 314.08; 336.06; 649.13.

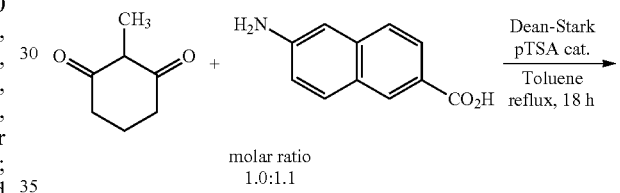

molar ratio 1.0:1.1

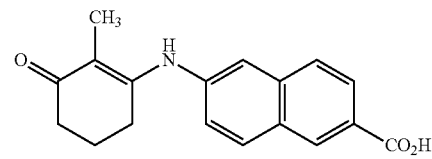

Example 01-41

Preparation of 6-((2-methyl-3-oxocyclohex-1-en-1-yl)amino)-2-naphthoic acid (01-41)

The title compound was prepared from 2-methyl-1,3-cyclohexandione and 6-amino-2-naphthoic acid according to the procedure of Example 01-01; 20.0 mmol scale yielded 2.7 g of brown microcrystals from EtOH (mp=259-263° C., 46% yield). $^1$H NMR (D6-DMSO) δ 1.73 (s, 3H), 1.83-1.86 (m, 2H), 2.27-2.30 (m, 2H), 2.61-2.63 (m, 2H), 7.42 (d, J=8.7 Hz, 1H), 7.56 (s, 1H), 7.90 (d, J=8.6 Hz, 1H), 7.95 (d, J=8.5 Hz, 1H), 8.06 (d, J=8.8 Hz, 1H), 8.52 (s, 1H), 8.55 (s, 1H), 12.97 (br s, 1H). $^{13}$C NMR (D6-DMSO) δ 10.1, 22.2, 28.2, 37.0, 109.9, 118.7, 124.6, 126.2, 127.0, 127.7, 129.1, 130.4, 130.7, 136.0, 140.5, 157.7, 167.9, 195.5. LCMS t=4.7 min, m/z Calcd for $C_{18}H_{18}NO_3$; $C_{36}H_{35}N_2O_6$; $C_{36}H_{34}N_2NaO_6$ 296.13; 591.25; 613.23 [M+H]$^+$; [2M+H]$^+$; [2M+Na]$^+$, Found 296.15; 591.27; 613.25.

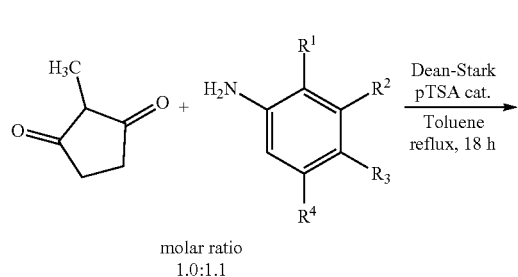

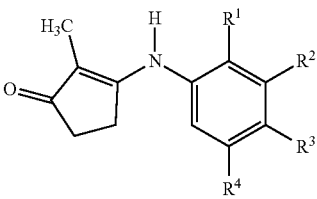

| Example 01-# | TITLE COMPOUND NAME | R¹ | R² | R³ | R⁴ |
|---|---|---|---|---|---|
| 42 | N-(4-Chloro-3-((2-methyl-3-oxocyclopent-1-en-1-yl)amino)phenyl)-acetamide | Cl | H | H | NAc |
| 43 | Methyl 3-iodo-4-((2-methyl-3-oxocyclopent-1-en-1-yl)amino)benzoate | I | H | $CO_2CH_3$ | H |
| 44 | 2-Chloro-3-((2-methyl-3-oxocyclopent-1-en-1-yl)amino)benzoic acid | Cl | $CO_2H$ | H | H |
| 45 | 3-((2-Methyl-3-oxocyclopent-1-en-1-yl)amino)benzenesulfonamide | H | $SO_2NH_2$ | H | H |
| 46 | 4-Chloro-3-((2-methyl-3-oxocyclopent-1-en-1-yl)amino)benzene-sulfonamide | Cl | H | $SO_2NH_2$ | H |

Example 01-42

Preparation of N-(4-chloro-3-((2-methyl-3-oxocyclopent-1-en-1-yl)amino)phenyl)-acetamide (01-42)

The title compound was prepared from 2-methyl-1,3-cyclopentandione and N-(3-amino-4-chlorophenyl)acetamide according to the procedure of Example 01-01; 20.0 mmol scale yielded 5.5 g (99% yield) of tan microcrystals. A portion was recrystallized from EtOH:EtOAc (1:1.1) (mp=265-268° C., 50% recovery). $^1$H NMR (D6-DMSO) δ 1.44 (s, 3H), 2.05 (s, 3H), 2.18-2.21 (m, 2H), 2.40-2.41 (m, 2H), 7.41 (dd, J=8.7, 2.3 Hz, 1H), 7.45 (d, J=8.8 Hz, 1H), 7.67 (d, J=2.2 Hz, 1H), 8.86 (s, 1H), 10.13 (s, 1H). $^{13}$C NMR (D6-DMSO) δ 7.4, 24.1, 25.6, 32.6, 109.3, 117.8, 118.4, 123.3, 129.7, 136.6, 138.7, 168.7, 169.5, 202.4. LCMS t=4.3 min, m/z Calcd for $C_{14}H_{16}ClN_2O_2$; $C_{14}H_{15}ClN_2NaO_2$; $C_{28}H_{31}Cl_2N_4O_4$; $C_{28}H_{30}Cl_2N_4NaO_4$ 279.09; 301.07; 557.17; 579.15 [M+H]⁺; [M+Na]⁺; [2M+H]⁺; [2M+Na]⁺, Found 279.11; 301.09; 557.13; 579.11.

Example 01-43

Preparation of methyl 3-iodo-4-((2-methyl-3-oxocyclopent-1-en-1-yl)amino)benzoate (01-43)

The title compound was prepared from 2-methyl-1,3-cyclopentandione and methyl 3-iodo-4-aminobenzoate according to the procedure of Example 01-01; 10 mmol scale yielded 1.7 g of white prisms from EtOAc (mp=178-180° C., 46% yield). $^1$H NMR (D6-DMSO) δ 1.43 (s, 3H), 2.21-2.23 (m, 2H), 2.44-2.47 (m, 2H), 3.86 (s, 3H), 7.41 (d, J=8.3 Hz, 1H), 7.96 (dd, J=8.3, 1.8 Hz, 1H), 8.40 (d, J=1.8 Hz, 1H), 8.86 (s, 1H). $^{13}$C NMR (D6-DMSO) δ 7.7, 25.9, 32.7, 52.4, 97.7, 110.5, 126.7, 128.1, 129.8, 139.6, 145.7, 164.5, 168.5, 202.6. LCMS t=4.6 min, m/z Calcd for $C_{14}H_{15}INO_3$; $C_{14}H_{14}INNaO_3$; $C_{28}H_{28}I_2N_2NaO_6$ 372.01; 393.99; 764.99 [M+H]⁺; [M+Na]⁺; [2M+Na]⁺, Found 372.04; 393.96; 764.95.

Example 01-44

Preparation of 2-chloro-3-((2-methyl-3-oxocyclopent-1-en-1-yl)amino)benzoic acid (01-44)

The title compound was prepared from 2-methyl-1,3-cyclopentandione and 3-amino-2-chlorobenzoic acid according to the procedure of Example 01-01; 2.5 mmol scale yielded 415 mg of white microneedles from EtOH (mp=230-232° C., 62% yield). $^1$H NMR (D6-DMSO) δ 1.46 (s, 3H), 2.18-2.02 (m, 2H), 2.37-2.40 (m, 2H), 7.44 (t, J=7.8 Hz, 1H), 7.54 (dd, J=7.9, 1.6 Hz, 1H), 7.62 (dd, J=7.7, 1.6 Hz, 1H), 8.93 (s, 1H), 13.53 (br s, 1H). $^{13}$C NMR (D6-DMSO) δ 7.3, 25.4, 32.6, 109.4, 127.4, 127.7, 128.3, 130.8, 133.5, 137.7, 166.9, 169.7, 202.3. LCMS t=1.8 min, m/z Calcd for $C_{13}H_{13}ClNO_3$; $C_{13}H_{12}ClNNaO_3$; $C_{26}H_{24}Cl_2N_2NaO_6$ 266.06; 288.04; 553.09 [M+H]⁺; [M+Na]⁺; [2M+Na]⁺, Found 266.09; 288.06; 553.03.

Example 01-45

Preparation of 3-((2-methyl-3-oxocyclopent-1-en-1-yl)amino)benzenesulfonamide (01-45)

The title compound was prepared from 2-methyl-1,3-cyclopentandione and 3-aminobenzenesulfonamide according to the procedure of Example 01-01; 5.0 mmol scale yielded 600 mg of light brown microcrystals from $H_2O$ (mp=223-225° C., 45% yield). $^1$H NMR (D6-DMSO) δ 1.58 (s, 3H), 2.22-2.27 (m, 2H), 2.68-2.75 (m, 2H), 7.40-7.47 (m, 3H), 7.53 (d, J=5.2 Hz, 2H), 7.65 (s, 1H), 9.22 (s, 1H). $^{13}$C NMR (D6-DMSO) δ 7.5, 25.8, 32.9, 111.1, 119.0, 120.4, 125.0, 129.8, 140.5, 144.9, 168.6, 202.3. LCMS t=2.6 min, m/z Calcd for $C_{12}H_{15}N_2O_3S$; $C_{12}H_{14}N_2NaO_3S$; $C_{24}H_{29}N_4O_6S_2$; $C_{24}H_{28}N_4NaO_6S_2$ 267.083; 289.062; 533.152; 555.135 [M+H]⁺; [2M+H]⁺; [2M+H]⁺; [2M+Na]⁺, Found 267.083; 289.061; 533.151; 555.133.

Example 01-46

Preparation of 4-chloro-3-((2-methyl-3-oxocyclopent-1-en-1-yl)amino)benzene-sulfonamide (01-46)

The title compound was prepared from 2-methyl-1,3-cyclopentandione and 3-amino-4-chlorobenzenesulfonamide according to the procedure of Example 01-01; 5.0 mmol scale yielded 800 mg of light brown microcrystals from H$_2$O (mp=223-225° C., 53% yield). $^1$H NMR (D6-DMSO) δ 1.42 (s, 3H), 2.20-2.28 (m, 2H), 2.45-2.49 (m, 2H), 7.55 (s, 2H), 7.66 (dd, J=8.2, 2.1 Hz, 1H), 7.68 (d, J=1.8 Hz, 1H), 7.77 (d, J=8.2 Hz, 1H), 9.07 (s, 1H). $^{13}$C NMR (D6-DMSO) δ 7.8, 25.8, 32.7, 110.4, 123.9, 124.8, 130.5, 132.8, 137.2, 143.4, 168.8, 202.9. LCMS t=3.4 min, m/z Calcd for C$_{12}$H$_{15}$ClN$_2$O$_3$S; C$_{12}$H$_{14}$ClN$_2$NaO$_3$S; C$_{24}$H$_{29}$Cl$_2$N$_4$O$_6$S$_2$; C$_{24}$H$_{28}$Cl$_2$N$_4$NaO$_6$S$_2$ 301.041; 323.023; 601.075; 623.057 [M+H]$^+$; [2M+H]$^+$; [2M+H]$^+$; [2M+Na]$^+$, Found 301.040; 323.021; 601.071; 623.056.

Example 01-48

Preparation of 4-bromo-3-((2-methyl-3-oxocyclo-hex-1-en-1-yl)amino)benzoic acid (01-48)

The title compound was prepared from 2-methyl-1,3-cyclohexandione and 3-amino-4-bromobenzoic acid according to the procedure of Example 01-01; 10.0 mmol scale yielded 2.9 g of white microneedles from EtOH (mp=265-267° C., 89% yield). $^1$H NMR (D6-DMSO) δ 1.62 (s, 3H), 1.75-1.80 (m, 2H), 2.18-2.23 (m, 4H), 7.69-7.72 (m, 2H), 7.84 (d, J=8.1 Hz, 1H), 8.07 (s, 1H), 13.31 (s, 1H). $^{13}$C NMR (D6-DMSO) δ 9.2, 21.1, 27.2, 36.4, 107.5, 126.9, 127.9, 129.2, 131.0, 133.3, 139.1, 158.1, 166.3, 194.8. LCMS t=4.2 min, m/z Calcd for C$_{14}$H$_{15}$BrNO$_3$; C$_{14}$H$_{14}$BrNNaO$_3$; C$_{28}$H$_{28}$Br$_2$N$_2$NaO$_6$ 324.02, 326.02; 346.01, 348.00; 671.02 [M+H]$^+$; [M+Na]$^+$; [2M+Na]$^+$, Found 324.03, 326.02; 345.99, 347.99; 670.96.

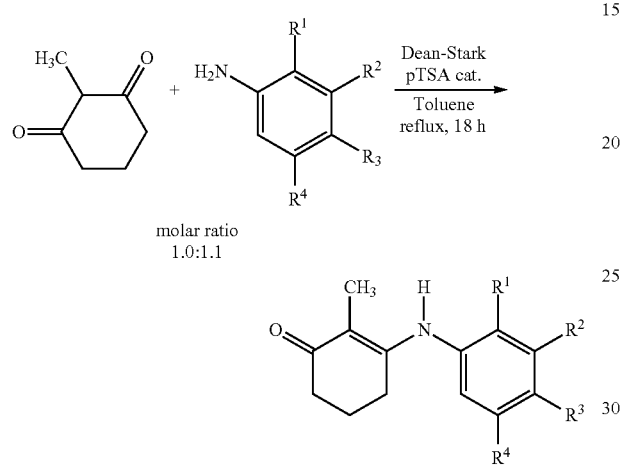

molar ratio 1.0:1.1

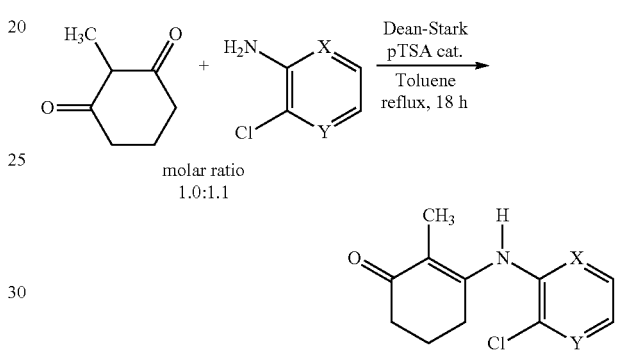

molar ratio 1.0:1.1

| Example 01-# | TITLE COMPOUND NAME | R$^1$ | R$^2$ | R$^3$ | R$^4$ |
|---|---|---|---|---|---|
| 47 | N-(4-Chloro-3-((2-methyl-3-oxocyclopent-1-en-1-yl)amino)phenyl)-acetamide | Cl | H | H | NAc |
| 48 | Methyl 3-iodo-4-((2-methyl-3-oxocyclopent-1-en-1-yl)amino)benzoate | Br | H | H | CO$_2$H |

| Example 01-# | TITLE COMPOUND NAME | X | Y |
|---|---|---|---|
| 49 | 3-[(3-Chloropyridin-2-yl)amino]-2-methylcyclohex-2-en-1-one | N | CH |
| 50 | 3-[(3-Chloropyrazin-2-yl)amino]-2-methylcyclohex-2-en-1-one | N | N |

Example 01-47

Preparation of N-(4-chloro-3-((2-methyl-3-oxocyclohex-1-en-1-yl)amino)phenyl)-acetamide (01-47)

The title compound was prepared from 2-methyl-1,3-cyclohexandione and N-(4-amino-3-chlorophenyl)acetamide according to the procedure of Example 01-01; 10.0 mmol scale yielded 2.9 g of pale orange microcrystals from EtOAc (mp=234-236° C., 99% yield). $^1$H NMR (D6-DMSO) δ 1.64 (s, 3H), 1.75-1.79 (m, 2H), 2.05 (s, 3H), 2.18-2.24 (m, 4H), 7.42-7.46 (m, 2H), 7.58 (d, J=1.9 Hz, 1H), 8.04 (s, 1H), 10.12 (s, 1H). $^{13}$C NMR (D6-DMSO) δ 9.0, 21.1, 24.0, 27.0, 36.3, 107.1, 117.7, 118.8, 123.9, 129.7, 137.1, 138.8, 158.8, 168.6, 194.4. LCMS t=4.5 min, m/z Calcd for C$_{15}$H$_{18}$ClN$_2$O$_2$; C$_{15}$H$_{17}$ClN$_2$NaO$_2$; C$_{30}$H$_{35}$Cl$_2$N$_4$O$_4$; C$_{30}$H$_{34}$Cl$_2$N$_2$NaO$_4$ 293.11; 315.09; 585.20; 607.19 [M+H]$^+$; [M+Na]$^+$; [2M+H]$^+$; [2M+Na]$^+$, Found 293.13; 315.10, 585.16; 607.15.

Example 01-49

Preparation of 3-[(3-chloropyridin-2-yl)amino]-2-methylcyclohex-2-en-1-one (01-49)

The title compound was prepared from 2-methyl-1,3-cyclohexandione and 3-chloropyridin-2-amine according to the procedure of Example 01-01 (mp=113-115° C.). $^1$H NMR (D6-DMSO) δ 1.63 (s, 3H), 1.84 (quin, J=6.4 Hz, 2H), 2.28 (t, J=6.1 Hz, 2H), 2.67-2.80 (m, 2H), 7.07 (dd, J=8.5, 4.9 Hz, 1H), 7.91 (s, 1H), 7.93 (d, J=6.1 Hz, 1H), 8.25 (d, J=4.9 Hz, 1H). $^{13}$C NMR (D6-DMSO) δ ppm 9.4, 21.3, 28.1, 36.7, 113.6, 119.2, 120.8, 138.2, 146.3, 149.7, 155.6, 196.2. LCMS t=4.3 min, m/z Calcd for C$_{12}$H$_{14}$ClN$_2$O; C$_{12}$H$_{13}$ClN$_2$NaO; C$_{24}$H$_{26}$Cl$_2$N$_4$NaO$_2$ 237.080; 259.061; 495.133 [M+H]$^+$; [M+Na]$^+$; [2M+Na]$^+$, Found 237.080; 259.060; 495.131.

Example 01-50

Preparation of 3-[(3-chloropyrazin-2-yl)amino]-2-methylcyclohex-2-en-1-one (01-50)

The title compound was prepared from 2-methyl-1,3-cyclohexandione and 3-chloropyrazin-2-amine according to the procedure of Example 01-01 (mp=116-118° C.). $^1$H NMR (D6-DMSO) δ 1.60 (s, 3H), 1.87 (quin, J=6.1 Hz, 2H), 2.32 (t, J=6.1 Hz, 2H), 2.71-2.76 (m, 2H), 8.00 (d, J=2.4 Hz, 1H), 8.18 (s, 1H), 8.28 (d, J=2.4 Hz, 1H). $^{13}$C NMR (D6-DMSO) δ 10.6, 21.6, 28.8, 37.2, 118.6, 135.9, 137.9, 141.3, 147.8, 154.3, 197.5. LCMS t=4.1 min, m/z Calcd for $C_{11}H_{13}ClN_3O$; $C_{11}H_{12}ClN_3NaO$; $C_{22}H_{24}Cl_2N_6NaO_2$ 238.075; 260.060; 497.120 [M+H]$^+$; [M+Na]$^+$; [2M+Na]$^+$, Found 238.075; 260.056; 497.122.

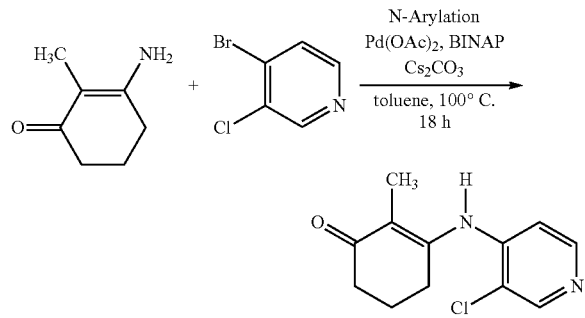

Example 01-51

Preparation of 3-[(3-chloropyridin-4-yl)amino]-2-methylcyclohex-2-en-1-one (01-51)

3-amino-2-methylcyclohex-2-enone (500 mg, 4 mmol), 4-bromo-3-chloropyridine (950 mg, 5 mmol), palladium acetate (90 mg, 0.4 mmol), BINAP (197 mg, 0.8 mmol), cesium carbonate (2.6 g, 8 mmol) and toluene (10 mL) were combined in a sealed flask and heated at 100° C., for 18 h. At rt, the mixture was filtered and the filtrate was diluted with EtOAc (30 mL), washed with brine (3×10 mL), dried with $Na_2SO_4$. The crude was purified by HPLC to afford the title compound (140 mg, 15% yield, white microcrystal, mp=135-138° C.). $^1$H NMR (D6-DMSO) δ 1.46 (s, 3H), 1.83-1.88 (m, 2H), 2.31 (t, J=6.7 Hz, 2H), 2.53-2.57 (m, 2H), 6.84 (d, J=6.1 Hz, 1H), 8.06 (s, 1H), 8.29 (d, J=6.1 Hz, 1H), 8.48 (s, 1H). $^{13}$C NMR (D6-DMSO) δ 10.9, 20.6, 28.7, 36.7, 115.7, 117.1, 121.2, 144.7, 148.3, 148.3, 149.2, 154.4, 197.0. LCMS t=1.9 min, m/z Calcd for $C_{12}H_{14}ClN_2O$; $C_{12}H_{13}ClN_2NaO$ 237.080; 259.061 [M+H]$^+$; [2M+H]$^+$, Found 237.080; 259.180.

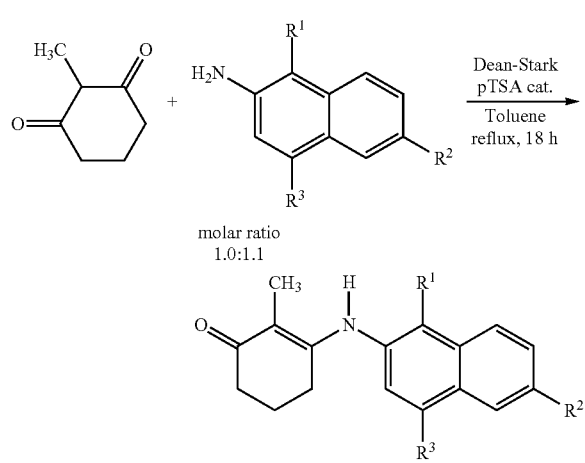

| Example 01-# | TITLE COMPOUND NAME | $R^1$ | $R^2$ | $R^3$ |
|---|---|---|---|---|
| 52 | 3-[(2-Methyl-3-oxocyclohex-1-en-1-yl)amino]naphthalene-1-carboxylic acid | H | H | $CO_2H$ |
| 53 | 5-Chloro-6-[(2-methyl-3-oxocyclohex-1-en-1-yl)amino]naphthalene-2-carboxylic acid | Cl | $CO_2H$ | H |

Example 01-52

Preparation of 3-[(2-methyl-3-oxocyclohex-1-en-1-yl)amino]naphthalene-1-carboxylic acid (01-52)

The title compound was prepared from 2-methyl-1,3-cyclohexandione and 3-amino-1-naphthoic acid according to the procedure of Example 01-01; 4.0 mmol scale refluxed for 48 h yielded 1.2 g of crude filtered from toluene (97% yield), brown microcrystals were obtained after acetone titration (mp=270-272° C.). $^1$H NMR (D6-DMSO) δ 1.71 (s, 3H), 1.81-1.85 (m, 2H), 2.25-2.28 (m, 2H), 2.57-2.50 (m, 2H), 7.52-7.57 (m, 2H), 7.76 (d, J=1.9 Hz, 1H), 7.92-7.95 (m, 1H), 7.98 (d, J=2.0 Hz, 1H), 8.48 (s, 1H), 8.77-8.79 (m, 1H), 13.23 (br s, 1H). $^{13}$C NMR (D6-DMSO) δ 9.5, 21.8, 27.6, 36.6, 108.6, 110.6, 124.1, 125.4, 126.3, 126.7, 127.5, 128.0, 128.4, 134.1, 136.7, 157.4, 169.2, 194.9. LCMS t=4.3 min, Calcd for $C_{18}H_{18}NO_3$; $C_{18}H_{17}NNaO_3$; $C_{36}H_{34}N_2NaO_6$ 296.13; 318.11; 613.23 [M+H]$^+$; [M+Na]$^+$; [2M+Na]$^+$, Found 296.15; 318.11; 613.17.

3-Amino-1-naphthoic acid: mp=179-181° C. $^1$H NMR (D6-DMSO) δ 5.57 (br s, 2H), 7.02 (d, J=2.1 Hz, 1H), 7.18-7.22 (m, 1H), 7.31-7.35 (m, 1H), 7.59 (d, J=8.1 Hz, 1H), 7.63 (d, J=2.4 Hz, 1H), 8.57 (d, J=8.5 Hz, 1H), 12.91 (br s, 1H). $^{13}$C NMR (D6-DMSO) δ 110.6, 122.0, 122.4, 124.0, 125.4, 125.9, 126.0, 128.4, 135.6, 145.5, 168.8. LCMS t=3.1 min, Calcd for $C_{11}H_{10}NO_2$; $C_{11}H_9NNaO_2$ 188.07; 210.05 [M+H]$^+$; [M+Na]$^+$, Found 188.16; 210.13.

Example 01-53

Preparation of 5-chloro-6-[(2-methyl-3-oxocyclohex-1-en-1-yl)amino]naphthalene-2-carboxylic acid (01-53)

The title compound was prepared from 2-methyl-1,3-cyclohexandione and 6-amino-5-chloro-2-naphthoic acid according to the procedure of Example 01-01; 0.54 mmol scale refluxed for 48 h yielded 17 mg of grey microneedles after recrystallization from EtOH (mp=272-275° C. decomp, 10% yield). $^1$H NMR (D6-DMSO) δ 1.63 (s, 3H), 1.78-1.83 (m, 2H), 2.23-2.26 (m, 2H), 2.37-2.40 (m, 2H), 7.49 (d, J=8.8 Hz, 1H), 8.12-8.15 (m, 2H), 8.24-8.27 (m, 2H), 8.66 (d, J=1.5 Hz, 1H), 13.21 (s, 1H). $^{13}$C NMR (D6-DMSO) δ 9.6, 21.1, 27.8, 36.6, 109.4, 124.0, 124.1, 126.4, 127.3, 128.1, 128.9, 130.7, 130.9, 132.7, 137.7, 157.6, 167.0, 195.3. LCMS t=4.8 min, m/z Calcd for $C_{18}H_{17}ClNO_3$; $C_{18}H_{16}ClNNaO_3$; $C_{36}H_{32}Cl_2N_2NaO_6$ 330.09; 352.07; 681.15 [M+H]$^+$; [M+Na]$^+$; [2M+Na]$^+$, Found 330.08; 352.06; 681.14.

6-Amino-5-chloro-2-naphthoic acid: 6-Amino-2-naphthoic acid (0.17 g, 0.9 mmol), N-chlorosuccinimide (0.12 g, 1 eq), and carbon tetrachloride (25 mL) were combined in a round bottom flask, and heated under reflux for 1 h. After cooling to rt, the solid was filtered. The subsequent crude materials were added directly to KP-Sil™ columns (10 g) with products separating from impurities using an isocratic solvent system $CH_2Cl_2$:MeOH (1:19), on the Biotage®-Isolera Four instrument, monitoring UV Trace at 254/365 nm. The 0.9 mmol scale yielded 120 mg of white microcrystals after chromatography (mp=274-276° C. decomp, 60% yield). $^1$H NMR (D6-DMSO) δ 6.14 (s, 2H), 7.19 (d, J=8.8 Hz, 1H), 7.85 (dd, J=42.2, 8.8 Hz, 1H), 7.94 (d, J=1.7 Hz, 1H), 7.96 (d, J=1.7 Hz, 1H), 8.39 (d, J=1.7 Hz, 1H), 12.78 (s, 1H). $^{13}$C NMR (D6-DMSO) 107.5, 118.9, 121.1, 123.5, 125.8, 126.9, 129.3, 130.9, 133.8, 145.0, 167.5. LCMS t=4.2 min, Calcd for $C_{11}H_9ClNO_2$; $C_{11}H_8ClNNaO_2$ 222.03; 244.01 [M+H]+; [M+Na]+, Found 222.09; 244.06.

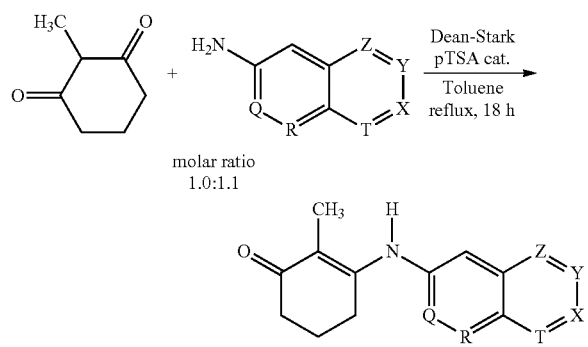

| Example 01-# | TITLE COMPOUND NAME | Q | R | T | X | Y | Z |
|---|---|---|---|---|---|---|---|
| 54 | 2-Methyl-3-[(quinolin-6-yl)amino]cyclohex-2-en-1-one | CH | CH | N | CH | CH | CH |
| 55 | 3-[(Isoquinolin-6-yl)amino]-2-methylcyclohex-2-en-1-one | CH | CH | CH | N | CH | CH |
| 56 | 3-[(Isoquinolin-7-yl)amino]-2-methylcyclohex-2-en-1-one | CH | CH | CH | CH | N | CH |
| 57 | 2-Methyl-3-[(quinolin-7-yl)amino]cyclohex-2-en-1-one | CH | CH | CH | CH | CH | N |
| 58 | 3-[(isoquinolin-3-yl)amino]-2-methylcyclohex-2-en-1-one | N | CH | CH | CH | CH | CH |
| 59 | 2-Methyl-3-[(quinolin-3-yl)amino]cyclohex-2-en-1-one | CH | N | CH | CH | CH | CH |
| 60 | 2-Methyl-3-[(quinoxalin-6-yl)amino]cyclohex-2-en-1-one | CH | CH | N | CH | CH | N |
| 61 | 2-Methyl-3-[(quinazolin-6-yl)amino]cyclohex-2-en-1-one | CH | CH | N | CH | N | CH |

Example 01-54

Preparation of 2-methyl-3-[(quinolin-6-yl)amino]cyclohex-2-en-1-one (01-54)

The title compound was prepared from 2-methyl-1,3-cyclohexandione and quinolin-6-amine according to the procedure of Example 01-01 (brown microcrystals, mp=208-210° C.). $^1$H NMR (D6-DMSO) δ 1.71 (s, 3H), 1.77-1.88 (m, 2H), 2.26 (t, J=6.7 Hz, 2H), 2.58 (t, J=5.5 Hz, 2H), 7.46-7.52 (m, 1H), 7.54-7.62 (m, 2H), 7.96 (d, J=9.8 Hz, 1H), 8.28 (d, J=7.3 Hz, 1H), 8.48 (s, 1H), 8.80 (d, J=6.1 Hz, 1H). $^{13}$C NMR (D6-DMSO) δ 9.6, 21.8, 27.7, 36.6, 108.7, 119.2, 121.8, 127.2, 128.2, 129.4, 135.2, 138.1, 144.8, 149.2, 157.5, 194.9. LCMS t=3.6 min, m/z Calcd for $C_{16}H_{17}N_2O$; $C_{16}H_{16}N_2NaO$; $C_{32}H_{32}N_4NaO_2$ 253.134; 275.116; 527.242 [M+H]+; [M+Na]+; [2M+Na]+, Found 253.131; 275.112; 527.231.

Example 01-55

Preparation of 3-[(isoquinolin-6-yl)amino]-2-methylcyclohex-2-en-1-one (01-55)

The title compound was prepared from 2-methyl-1,3-cyclohexandione and isoquinolin-6-amine according to the procedure of Example 01-01 (brown microcrystals, mp=163-165° C.). $^1$H NMR (D6-DMSO) δ 1.67 (s, 3H), 1.81-1.89 (m, 2H), 2.29 (t, J=6.1 Hz, 2H), 2.63 (t, J=6.1 Hz, 2H), 7.40 (s, 1H), 7.45 (dd, J=8.5, 2.4 Hz, 1H), 7.70 (d, J=4.9 Hz, 1H), 8.03 (d, J=8.5 Hz, 1H), 8.40 (d, J=4.9 Hz, 1H), 8.58 (s, 1H), 9.17 (s, 1H). $^{13}$C NMR (D6-DMSO) δ 10.1, 21.7, 28.1, 36.7, 111.0, 115.2, 119.6, 124.1, 124.6, 128.4, 136.1, 142.1, 143.3, 156.5, 195.6. LCMS t=2.9 min, m/z Calcd for $C_{16}H_{17}N_2O$; $C_{16}H_{16}N_2NaO$ 253.134; 275.116; [M+H]+; [M+Na]+, Found 253.129; 275.112.

Example 01-56

Preparation of 3-[(isoquinolin-7-yl)amino]-2-methylcyclohex-2-en-1-one (01-56)

The title compound was prepared from 2-methyl-1,3-cyclohexandione and isoquinolin-7-amine according to the procedure of Example 01-01 (yellow microcrystals, mp=145-147° C.). $^1$H NMR (D6-DMSO) δ 1.70 (s, 3H), 1.84 (quin, J=6.1 Hz, 2H), 2.27 (t, J=6.1 Hz, 2H), 2.59 (t, J=6.1 Hz, 2H), 7.61 (dd, J=8.5, 2.4 Hz, 1H), 7.69 (d, J=2.4 Hz, 1H), 7.80 (d, J=6.1 Hz, 1H), 7.94 (d, J=8.5 Hz, 1H), 8.42 (d, J=6.1 Hz, 1H), 8.54 (s, 1H), 9.25 (s, 1H). $^{13}$C NMR (D6-DMSO) δ 9.7, 21.7, 27.7, 36.6, 109.2, 118.3, 120.3, 127.2, 128.4, 128.7, 131.9, 139.2, 141.3, 151.2, 157.2, 195.1. LCMS t=2.8 min, m/z Calcd for $C_{16}H_{17}N_2O$; $C_{16}H_{16}N_2NaO$; $C_{32}H_{32}N_4NaO_2$ 253.134; 275.116; 527.242 [M+H]+; [M+Na]+; [2M+Na]+, Found 253.128; 275.108; 527.227.

Example 01-57

Preparation of 2-methyl-3-[(quinolin-7-yl)amino]cyclohex-2-en-1-one (01-57)

The title compound was prepared from 2-methyl-1,3-cyclohexandione and quinolin-7-amine according to the procedure of Example 01-01 (yellow microcrystals, mp=133-135° C.). $^1$H NMR (D6-DMSO) δ 1.70 (s, 3H), 1.84 (quin, J=6.1 Hz, 2H), 2.28 (t, J=6.7 Hz, 2H), 2.62 (t, J=5.5 Hz, 2H), 7.39-7.45 (m, 2H), 7.54 (d, J=2.4 Hz, 1H), 7.92 (d, J=8.5 Hz, 1H), 8.29 (d, J=6.1 Hz, 1H), 8.53 (s, 1H), 8.82-8.85 (m, 1H). $^{13}$C NMR (D6-DMSO) δ 9.8, 21.8, 27.9, 36.6, 109.7, 119.2, 120.1, 123.8, 124.3, 128.4, 135.6, 141.3, 148.3, 151.0, 157.1, 195.3. LCMS t=3.4 min, m/z Calcd for $C_{16}H_{17}N_2O$; $C_{16}H_{16}N_2NaO$; $C_{32}H_{32}N_4NaO_2$ 253.134; 275.116; 527.242 [M+H]+; [M+Na]+; [2M+Na]+, Found 253.127; 275.109; 527.228.

Example 01-58

Preparation of 3-[(isoquinolin-3-yl)amino]-2-methylcyclohex-2-en-1-one (01-58)

The title compound was prepared from 2-methyl-1,3-cyclohexandione and isoquinolin-3-amine according to the procedure of Example 01-01 (grey microneedles, mp=205-208° C.). $^1$H NMR (D6-DMSO) δ 1.72 (s, 3H), 1.84 (quin, J=6.1 Hz, 2H), 2.27 (t, J=6.7 Hz, 2H), 2.80 (t, J=5.5 Hz, 2H), 7.41 (s, 1H), 7.50 (t, J=7.3 Hz, 1H), 7.65-7.73 (m, 1H), 7.84 (d, J=8.5 Hz, 1H), 8.04 (d, J=8.5 Hz, 1H), 8.20-8.20 (m, 1H), 8.70 (s, 1H), 9.12 (s, 1H). $^{13}$C NMR (D6-DMSO) δ 9.5, 21.8, 28.1, 36.7, 108.7, 110.2, 125.0, 125.4, 125.7, 127.7, 130.9, 137.3, 148.9, 151.1, 157.0, 195.4. LCMS t=4.8 min, m/z Calcd for $C_{16}H_{17}N_2O$; $C_{16}H_{16}N_2NaO$; $C_{32}H_{32}N_4NaO_2$ 253.134; 275.116; 527.242 [M+H]$^+$; [M+Na]$^+$; [2M+Na]$^+$, Found 253.131; 275.108; 527.227.

Example 01-59

Preparation of 2-methyl-3-[(quinolin-3-yl)amino] cyclohex-2-en-1-one (01-59)

The title compound was prepared from 2-methyl-1,3-cyclohexandione and quinolin-3-amine according to the procedure of Example 01-01 (tan microcrystals, mp=172-175° C.). $^1$H NMR (D6-DMSO) δ 1.73 (s, 3H), 1.83 (quin, J=6.1 Hz, 2H), 2.26 (t, J=6.1 Hz, 2H), 2.58 (t, J=6.1 Hz, 2H), 7.57-7.61 (m, 1H), 7.64-7.69 (m, 1H), 7.92 (d, J=7.3 Hz, 1H), 7.95-8.01 (m, 2H), 8.51 (s, 1H), 8.78 (d, J=2.4 Hz, 1H). $^{13}$C NMR (D6-DMSO) δ 9.4, 21.7, 27.2, 36.5, 108.8, 126.4, 127.1, 127.5, 127.7, 128.1, 128.6, 133.8, 144.2, 148.3, 157.4, 194.9. LCMS t=4.5 min, m/z Calcd for $C_{16}H_{17}N_2O$; $C_{16}H_{16}N_2NaO$; $C_{32}H_{32}N_4NaO_2$ 253.134; 275.116; 527.242 [M+H]$^+$; [M+Na]$^+$; [2M+Na]$^+$, Found 253.130; 275.106; 527.227.

Example 01-60

Preparation of 2-methyl-3-[(quinoxalin-6-yl)amino] cyclohex-2-en-1-one (01-60)

The title compound was prepared from 2-methyl-1,3-cyclohexandione and quinolin-6-amine according to the procedure of Example 01-01 (yellow microcrystals, mp=110-112° C.). $^1$H NMR (D6-DMSO) δ 1.69 (s, 3H), 1.83-1.90 (m, 2H), 2.30 (t, J=6.7 Hz, 2H), 2.63-2.70 (m, 2H), 7.52 (d, J=2.4 Hz, 1H), 7.66 (dd, J=8.5, 2.4 Hz, 1H), 8.01 (d, J=9.8 Hz, 1H), 8.66 (s, 1H), 8.79 (d, J=2.4 Hz, 1H), 8.86 (s, 1H). $^{13}$C NMR (D6-DMSO) δ 10.1, 21.7, 28.0, 36.7, 111.3, 117.4, 126.8, 129.4, 138.9, 142.0, 143.0, 143.6, 145.9, 156.4, 195.7. LCMS t=4.2 min, m/z Calcd for $C_{15}H_{16}N_3O$; $C_{15}H_5N_3NaO$; $C_{30}H_{31}N_6NaO_2$ 254.129; 276.111; 529.233 [M+H]$^+$; [M+Na]$^+$; [2M+Na]$^+$, Found 254.121; 276.102; 529.219.

Example 01-61

Preparation of 2-methyl-3-[(quinazolin-6-yl)amino] cyclohex-2-en-1-one (01-61)

The title compound was prepared from 2-methyl-1,3-cyclohexandione and quinazolin-6-amine according to the procedure of Example 01-01 (tan microcrystals, mp=215-216° C.). $^1$H NMR (D6-DMSO) δ 1.69 (s, 3H), 1.83-1.88 (m, 2H), 2.29 (t, J=6.1 Hz, 2H), 2.61-2.64 (m, 2H), 7.63 (d, J=2.4 Hz, 1H), 7.79-7.85 (m, 1H), 7.96 (d, J=8.5 Hz, 1H), 8.61 (s, 1H), 9.18 (s, 1H), 9.51 (s, 1H). $^{13}$C NMR (D6-DMSO) δ ppm 10.0, 21.7, 27.8, 36.7, 110.4, 116.7, 125.2, 128.3, 131.5, 139.7, 146.0, 153.7, 156.6, 159.5, 195.4. LCMS t=3.8 min, m/z Calcd for $C_{15}H_{16}N_3O$; $C_{15}H_{15}N_3NaO$; $C_{30}H_{31}N_6NaO_2$ 254.129; 276.111; 529.233 [M+H]$^+$; [M+Na]$^+$; [2M+Na]$^+$, Found 254.120; 276.102; 529.218.

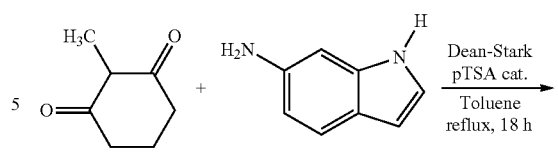

Example 01-62

Preparation of 3-[(1H-indol-6-yl)amino]-2-methyl-cyclohex-2-en-1-one (01-62)

The title compound was prepared from 2-methyl-1,3-cyclohexandione and 1H-indol-6-amine according to the procedure of Example 01-01 (white microneedles, mp=227-230° C.). $^1$H NMR (D6-DMSO) δ 1.71 (s, 3H), 1.72-1.77 (m, 2H), 2.17 (t, J=6.7 Hz, 2H), 2.36-2.40 (m, 2H), 6.41 (br s, 1H), 6.79-6.83 (m, 1H), 7.15 (s, 1H), 7.33 (t, J=2.4 Hz, 1H), 7.49 (d, J=8.5 Hz, 1H), 8.20 (s, 1H), 11.09 (br s, 1H). $^{13}$C NMR (D6-DMSO) δ 8.9, 21.7, 27.2, 36.4, 101.0, 104.9, 108.5, 118.1, 119.8, 125.3, 125.8, 133.3, 135.8, 159.7, 193.6. LCMS t=4.6 min, m/z Calcd for $C_{15}H_{17}N_2O$; $C_{15}H_{16}N_2NaO$; $C_{30}H_{32}N_4NaO_2$ 241.134; 263.116; 503.242 [M+H]$^+$; [M+Na]$^+$; [2M+Na]$^+$, Found 241.141; 263.106; 503.224.

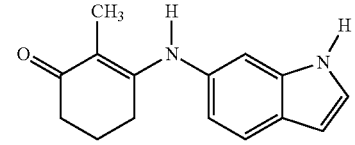

Example 01-63

Preparation of 5-[(2-methyl-3-oxocyclohex-1-en-1-yl)amino]-2,3-dihydro-1H-1,3-benzodiazol-2-one (01-63)

The title compound was prepared from 2-methyl-1,3-cyclohexandione and 5-amino-1H-benzo[d]imidazol-2(3H)-one according to the procedure of Example 01-01 (brown microcrystals, mp=233-235° C.). $^1$H NMR (D6-DMSO) δ 1.67 (s, 3H), 1.70-1.77 (m, 2H), 2.16 (t, J=6.1 Hz, 2H), 2.29-2.36 (m, 2H), 6.71 (s, 1H), 6.73 (d, J=2.4 Hz, 1H), 6.87 (d, J=8.5 Hz, 1H), 8.08 (s, 1H), 10.63 (d, J=13.4 Hz, 2H).

$^{13}$C NMR (D6-DMSO) δ 8.8, 21.6, 27.0, 36.4, 105.1, 106.6, 108.2, 118.5, 127.2, 129.9, 132.7, 155.5, 159.4, 193.7. LCMS t=3.2 min, m/z Calcd for $C_{14}H_{16}N_3O_2$; $C_{14}H_{15}N_3NaO_2$; $C_{28}H_{30}N_6NaO_4$ 258.124; 280.106; 537.222 [M+H]$^+$; [M+Na]$^+$; [2M+Na]$^+$, Found 258.123; 280.096; 537.206.

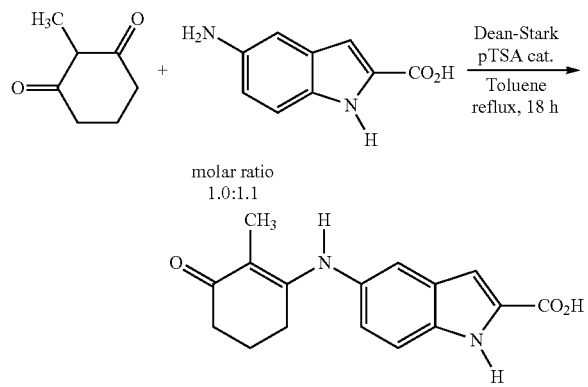

Example 01-64

Preparation of 5-((2-methyl-3-oxocyclohex-1-en-1-yl)amino)-1H-indole-2-carboxylic acid (01-64)

The title compound was prepared from 2-methyl-1,3-cyclohexandione and 5-amino-1H-indole-2-carboxylic acid according to the procedure of Example 01-01 (brown microcrystals, mp=310-315° C.). $^1$H NMR (D6-DMSO) δ 1.69-1.77 (m, 5H), 2.17 (t, J=6.3 Hz, 2H), 2.32-2.37 (m, 2H), 6.98-7.17 (m, 2H), 7.33-7.50 (m, 2H), 8.21 (s, 1H), 11.84 (s, 1H), 13.05 (br s, 1H). $^{13}$C NMR (D6-DMSO) δ 8.8, 21.6, 27.1, 36.4, 104.8, 107.3, 112.6, 118.6, 124.0, 126.9, 129.4, 132.2, 135.2, 159.8, 162.7, 193.7. LCMS t=3.8 min, m/z Calcd for $C_{16}H_{17}N_2O_3$; $C_{32}H_{33}N_4O_6$; $C_{32}H_{32}N_4NaO_6$ 285.124; 569.240; 591.221 [M+H]$^+$; [2M+H]$^+$; [2M+Na]$^+$, Found 285.123; 569.239; 591.220.

Examples 02-01 to 02-07

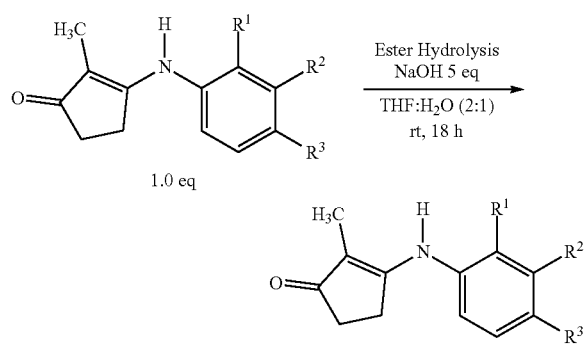

| EXAMPLE 02-# | TITLE COMPOUND NAME | R$^1$ | R$^2$ | R$^3$ |
|---|---|---|---|---|
| 01 | 4-((2-Methyl-3-oxocyclopent-1-en-1-yl)amino)benzoic acid | H | H | CO$_2$H |
| 02 | 3-Chloro-4-((2-methyl-3-oxocyclopent-1-en-1-yl)amino)benzoic acid | Cl | H | CO$_2$H |
| 03 | 2-Methoxy-4-((2-methyl-3-oxocyclopent-1-en-1-yl)amino)benzoic acid | H | OCH$_3$ | CO$_2$H |
| 04 | 2-((2-Methyl-3-oxocyclopent-1-en-1-yl)amino)benzoic acid | CO$_2$H | H | H |
| 05 | 5-Chloro-2-((2-methyl-3-oxocyclopent-1-en-1-yl)amino)benzoic acid | CO$_2$H | H | Cl |
| 06 | 3-Fluoro-4-((2-methyl-3-oxocyclopent-1-en-1-yl)amino)benzoic acid | F | H | CO$_2$H |
| 07 | 3-Bromo-4-((2-methyl-3-oxocyclopent-1-en-1-yl)amino)benzoic acid | Br | H | CO$_2$H |

Example 02-01

Preparation of 4-((2-methyl-3-oxocyclopent-1-en-1-yl)amino)benzoic acid (02-01)

Example 01-01 (1.0 g, 4.1 mmol) was stirred in a THF:H$_2$O (70 mL, 2:1) solution with sodium hydroxide (0.8 g, ~5 eq), for 18 h. Aqueous hydrochloric acid was added until pH paper read at, or below, 3. Additional THF was added forming one layer and precipitating the hydrolyzed product, which was collected by filtration. The reaction on a 4.1 mmol scale yielded 0.36 g of the title compound, yellow microneedles (mp=228-230° C., 43% yield). $^1$H NMR (D6-DMSO) δ 1.61 (s, 3H), 2.26 (s, 2H), 2.80 (s, 2H), 7.31 (d, J=8.1 Hz, 2H), 7.89 (d, J=8.2 Hz, 2H), 9.19 (s, 1H). LCMS t=4.7 min, m/z Calcd for $C_{13}H_{14}NO_3$; $C_{13}H_{13}NNaO_3$; $C_{26}H_{27}N_2O_6$; $C_{26}H_{26}N_2NaO_6$ 232.10; 254.08; 463.19; 485.17 [M+H]$^+$; [M+Na]$^+$; [2M+H]$^+$; [2M+Na]$^+$, Found 232.11; 254.09; 463.21; 485.19.

Example 02-02

Preparation of 3-chloro-4-((2-methyl-3-oxocyclopent-1-en-1-yl)amino)benzoic acid (02-02)

The title compound was prepared from Example 01-11 according to the procedure of Example 02-01; 6.0 mmol scale yielded 1.2 g of yellow microcrystals (mp=226-230° C., 86% yield). $^1$H NMR (D6-DMSO) δ 1.45 (s, 3H), 2.23-2.25 (m, 2H), 2.52-2.54 (m, 2H), 7.42 (d, J=8.3 Hz, 1H), 7.88 (d, J=8.2 Hz, 1H), 7.99 (s, 1H), 8.97 (s, 1H), 13.21 (br s, 1H). LCMS t=5.2 min, m/z Calcd for $C_{13}H_{13}ClNO_3$; $C_{13}H_{12}ClNNaO_3$; $C_{26}H_{24}Cl_2N_2NaO_6$ 266.06; 288.04; 553.09 [M+H]$^+$; [M+Na]$^+$; [2M+Na]$^+$, Found 266.11; 288.09; 553.08.

Example 02-03

Preparation of 2-methoxy-4-((2-methyl-3-oxocyclopent-1-en-1-yl)amino)benzoic acid (02-03)

The title compound was prepared from Example 01-13 according to the procedure of Example 02-01; 18.0 mmol scale yielded 3.6 g of yellow microcrystals (mp=240-243° C., 87% yield). $^1$H NMR (D6-DMSO) δ 1.62 (s, 3H), 2.25-2.27 (m, 2H), 2.82-2.84 (m, 2H), 3.85 (s, 3H), 6.86 (d, J=8.4 Hz, 1H), 6.95 (s, 1H), 7.68 (d, J=8.4 Hz, 1H), 9.16 (s, 1H). LCMS t=4.9 min, m/z Calcd for $C_{14}H_{16}NO_4$; $C_{14}H_{15}NNaO_4$; $C_{28}H_{30}N_2NaO_8$ 262.11; 284.09; 545.19 [M+H]$^+$; [M+Na]$^+$; [2M+Na]$^+$, Found 262.17; 284.14; 545.20.

Example 02-04

Preparation of 2-((2-methyl-3-oxocyclopent-1-en-1-yl)amino)benzoic acid (02-04)

The title compound was prepared from Example 01-19 according to the procedure of Example 02-01; 13.7 mmol scale yielded 3.0 g of yellow microcrystals (mp=245-248° C., 95% yield). $^1$H NMR (D6-DMSO) δ 1.62 (s, 3H), 2.30-2.32 (m, 2H), 2.96-2.98 (m, 2H), 7.11 (t, J=7.5 Hz, 1H), 7.53 (d, J=8.3 Hz, 1H), 7.56-7.60 (m, 1H), 7.99 (d, J=7.9 Hz, 1H), 10.68 (s, 1H). $^{13}$C NMR (D6-DMSO) δ 6.6, 26.6, 33.3, 113.1, 117.2, 119.3, 121.8, 131.8, 134.2, 142.4, 167.9, 169.8, 201.8. LCMS t=4.7 min, m/z Calcd for $C_{13}H_{14}NO_3$; $C_{13}H_{13}NNaO_3$; $C_{26}H_{27}N_2O_6$; $C_{26}H_{26}N_2NaO_6$ 232.10; 254.08; 463.19; 485.17 [M+H]$^+$; [M+Na]$^+$; [2M+H]$^+$; [2M+Na]$^+$, Found 232.10; 254.08; 463.19; 485.17.

Example 02-05

Preparation of 5-chloro-2-((2-methyl-3-oxocyclopent-1-en-1-yl)amino)benzoic acid (02-05)

The title compound was prepared from Example 01-20 according to the procedure of Example 02-01; 2.5 mmol scale yielded 0.54 g of yellow microcrystals (mp=242-245° C., 81% yield). $^1$H NMR (D6-DMSO) δ 1.62 (s, 3H), 2.32-2.34 (m, 2H), 2.93-2.95 (m, 2H), 7.55 (d, J=8.9 Hz, 1H), 7.62 (dd, J=8.9, 2.6 Hz, 1H), 7.93 (d, J=2.6 Hz, 1H), 10.60 (s, 1H). LCMS t=5.1 min, m/z Calcd for $C_{13}H_{13}ClNO_3$; $C_{13}H_{12}ClNNaO_3$; $C_{26}H_{25}Cl_2N_2O_6$; $C_{26}H_{24}Cl_2N_2NaO_6$ 266.06; 288.04; 531.11; 553.09 [M+H]$^+$; [M+Na]$^+$; [2M+H]$^+$; [2M+Na]$^+$, Found 266.06; 288.04; 531.10; 553.09.

Example 02-06

Preparation of 3-fluoro-4-((2-methyl-3-oxocyclopent-1-en-1-yl)amino)benzoic acid (02-06)

The title compound was prepared from Example 01-21 according to the procedure of Example 02-01; 15.0 mmol scale yielded 2.9 g of yellow microcrystals (mp=210-213° C., 77% yield). $^1$H NMR (D6-DMSO) δ 1.52 (s, 3H), 2.23-2.25 (m, 2H), 2.54-2.56 (m, 2H), 7.41 (d, J=8.3 Hz, 1H), 7.73-7.78 (m, 2H), 9.07 (s, 1H). LCMS t=4.4 min, m/z Calcd for $C_{13}H_{13}FNO_3$; $C_{13}H_{12}FNNaO_3$; $C_{26}H_{25}F_2N_2O_6$; $C_{26}H_{24}F_2N_2NaO_6$ 250.09; 272.07; 499.17; 521.15 [M+H]$^+$; [M+Na]$^+$; [2M+H]$^+$; [2M+Na]$^+$, Found 250.09; 272.07; 499.17; 521.15.

Example 02-07

Preparation of 3-bromo-4-((2-methyl-3-oxocyclopent-1-en-1-yl)amino)benzoic acid (02-07)

The title compound was prepared from Example 01-22 according to the procedure of Example 02-01; 9.5 mmol scale yielded 1.7 g of yellow microcrystals (mp=246-248° C., 58% yield). $^1$H NMR (D6-DMSO) δ 1.47 (s, 3H), 2.26-2.28 (m, 2H), 2.50-2.52 (m, 2H), 7.45 (d, J=8.3 Hz, 1H), 7.94 (dd, J=8.2, 1.8 Hz, 1H), 8.16 (d, J=1.8 Hz, 1H), 9.13 (s, 1H). $^{13}$C NMR (D6-DMSO) δ 7.63, 25.9, 32.5, 110.9, 119.4, 127.3, 129.3, 133.6, 141.9, 165.6, 169.7, 202.5. LCMS t=4.6 min, m/z Calcd for $C_{13}H_{13}BrNO_3$; $C_{13}H_{12}BrNNaO_3$; $C_{26}H_{25}Br_2N_2O_6$; $C_{26}H_{24}Br_2N_2NaO_6$ 310.01, 312.01; 331.99, 333.99; 621.01; 642.99 [M+H]$^+$; [M+Na]$^+$; [2M+H]$^+$; [2M+Na]$^+$, Found 310.01, 312.01; 331.99, 333.99; 621.00; 642.99.

Example 02-08

Preparation of 3-iodo-4-((2-methyl-3-oxocyclopent-1-en-1-yl)amino)benzoic acid (02-08)

The title compound was prepared from Example 01-43 according to the procedure of Example 02-01; 5.5 mmol scale yielded 1.7 g of yellow precipitate (87% yield), pale yellow microcrystals from EtOH (mp=263-264° C.). $^1$H NMR (D6-DMSO) δ 1.44 (s, 3H), 2.20-2.23 (m, 2H), 2.42-2.44 (m, 2H), 7.40 (d, J=8.2 Hz, 1H), 7.94 (dd, J=8.2, 1.7 Hz, 1H), 8.38 (d, J=1.7 Hz, 1H), 8.86 (s, 1H), 13.22 (s, 1H). $^{13}$C NMR (D6-DMSO) δ 7.6, 25.8, 32.7, 97.9, 110.2, 126.9, 129.5, 129.9, 139.8, 145.3, 165.5, 168.7, 202.5. LCMS t=4.4 min, m/z Calcd for $C_{13}H_{13}INO_3$; $C_{13}H_{12}INNaO_3$; $C_{26}H_{24}I_2N_2NaO_6$ 357.994; 379.976; 736.962 [M+H]+; [M+Na]+; [2M+Na]+, Found 357.995; 379.965; 736.944.

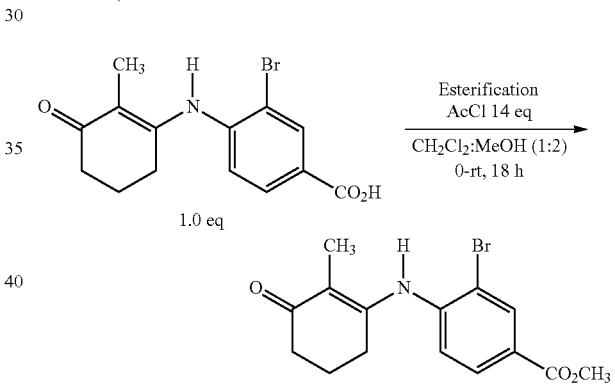

Example 02-09

Preparation of methyl 4-bromo-3-((2-methyl-3-oxocyclohex-1-en-1-yl)amino)benzoate (02-09)

Acetyl chloride (14 eq) was added to a CH$_2$Cl$_2$:MeOH (60 mL, 1:2) mixture at 0° C., followed by Example 01-48 (1.6 g, 5.0 mmol). After warming to rt, the mixture was stirred overnight. The solvent was removed on the rotovap to provide the crude material. 5.0 mmol scale yielded 1.23 g of brown microcrystals slowly from EtOAc (mp=211-213° C., 76% yield). $^1$H NMR (D6-DMSO) δ 1.74 (s, 3H), 1.78-1.81 (m, 2H), 2.25-2.29 (m, 2H), 2.38-2.41 (m, 2H), 3.88 (s, 3H), 7.81 (dd, J=8.4, 2.0 Hz, 1H), 7.87 (d, J=2.0 Hz, 1H), 7.93 (d, J=8.4 Hz, 1H), 9.30 (s, 1H). $^{13}$C NMR (D6-DMSO) δ 8.9, 20.7, 27.2, 34.0, 52.6, 106.8, 127.2, 128.9, 129.3, 130.0, 133.7, 138.2, 165.1, 192.3. LCMS t=5.0 min, m/z Calcd for $C_{15}H_{17}BrNO_3$; $C_{15}H_{16}BrNNaO_3$; $C_{30}H_{33}Br_2N_2NaO_6$ 338.04, 340.04; 360.02, 362.02; 699.05 [M+H]+; [M+Na]+; [2M+Na]+, Found 324.03, 326.02; 345.99, 347.99; 670.96.

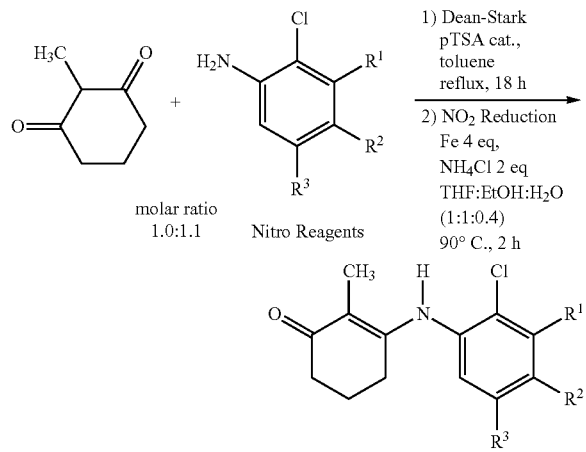

| EXAMPLE 02-# | TITLE COMPOUND NAME | $R^1$ | $R^2$ | $R^3$ |
|---|---|---|---|---|
| 10 | 3-((5-Amino-2-chlorophenyl)amino)-2-methylcyclohex-2-enone | H | H | $NH_2$ |
| 11 | 3-((3-Amino-2-chlorophenyl)amino)-2-methylcyclohex-2-enone | $NH_2$ | H | H |
| 12 | 3-((4-Amino-2-chlorophenyl)amino)-2-methylcyclohex-2-enone | H | $NH_2$ | H |

Example 02-10

Preparation of 3-((5-amino-2-chlorophenyl)amino)-2-methylcyclohex-2-enone (02-10)

3-((2-Chloro-5-nitrophenyl)amino)-2-methylcyclohex-2-enone (2 g, 7 mmol), Fe (1.6 g, 28 mmol), and $NH_4Cl$ (0.76 g, 14 mmol) were stirred in $THF:EtOH:H_2O$ (48 mL, 1:1:0.4) at 90° C., for 2 h. The mixture was filtered. The filtrate was diluted with EtOAc (50 mL), washed with brine (2×30 mL), dried with $Na_2SO_4$, and filtered. The second filtrate was concentrated to provide the title compound (1.5 g, 84% yield, mp=182-184° C.). $^1$H NMR (D6-DMSO) δ 1.64 (s, 3H), 1.71-1.82 (m, 2H), 2.15 (t, J=6.1 Hz, 2H), 2.18-2.22 (m, 2H), 5.37 (s, 2H), 6.45 (d, J=2.4 Hz, 1H), 6.47 (dd, J=8.5, 2.4 Hz, 1H), 7.11 (d, J=8.5 Hz, 1H), 7.84 (s, 1H). $^{13}$C NMR (D6-DMSO) δ 8.8, 21.2, 26.7, 36.4, 105.8, 113.2. 114.1, 116.6, 129.6, 137.0, 148.5, 159.2, 194.1. LCMS t=3.8 min, m/z Calcd for $C_{13}H_{16}ClN_2O$; $C_{13}H_{15}ClN_2NaO$; $C_{26}H_{30}Cl_2N_4NaO_2$ 251.095; 273.077; 523.164 [M+H]+; [M+Na]+; [2M+Na]+, Found 251.095; 273.076; 523.163.

3-((2-Chloro-5-nitrophenyl)amino)-2-methylcyclohex-2-enone (5.6 g of yellow solid, 50% yield) was prepared from 2-methyl-1,3-cyclohexandione (40 mmol) and 2-chloro-5-nitroaniline according to the procedure of Example 01-01.

Example 02-11

Preparation of 3-((3-amino-2-chlorophenyl)amino)-2-methylcyclohex-2-enone (02-11)

The title compound was prepared from 3-((2-chloro-3-nitrophenyl)amino)-2-methylcyclohex-2-enone according to the procedure of Example 02-10. $^1$H NMR (D6-DMSO) δ 1.66 (s, 3H), 1.73 (quin, J=6.1 Hz, 2H), 2.15 (t, J=6.1 Hz, 2H), 2.19 (t, J=6.1 Hz, 2H), 5.49 (br s, 2H), 6.47 (d, J=7.3 Hz, 1H), 6.70 (d, J=9.8 Hz, 1H), 7.01 (t, J=7.9 Hz, 1H), 7.87 (s, 1H). $^{13}$C NMR (D6-DMSO) δ 8.7, 21.3, 26.6, 36.3, 105.7, 105.7, 113.0, 115.3, 116.1, 126.9, 137.3, 145.8, 159.4, 194.0. LCMS t=4.0 min, m/z Calcd for $C_{13}H_{16}ClN_2O$; $C_{13}H_{15}ClN_2NaO$; $C_{26}H_{30}Cl_2N_4NaO_2$ 251.095; 273.077; 523.164 [M+H]+; [M+Na]+; [2M+Na]+, Found 251.095; 273.076; 523.163.

3-((2-Chloro-3-nitrophenyl)amino)-2-methylcyclohex-2-enone was prepared from 2-methyl-1,3-cyclohexandione and 2-chloro-3-nitroaniline according to the procedure of Example 01-01.

Example 02-12

Preparation of 3-((4-amino-2-chlorophenyl)amino)-2-methylcyclohex-2-enone (02-12)

The title compound was prepared from 3-((2-chloro-4-nitrophenyl)amino)-2-methylcyclohex-2-enone according to the procedure of Example 02-10 (mp=156-158° C.). $^1$H NMR (D6-DMSO) δ 1.66 (s, 3H), 1.71 (quin, J=6.1 Hz, 2H), 2.07 (t, J=5.5 Hz, 2H), 2.12 (t, J=6.1 Hz, 2H), 5.47 (s, 2H), 6.51 (dd, J=8.5, 2.4 Hz, 1H), 6.68 (d, J=2.4 Hz, 1H), 6.96 (d, J=8.5 Hz, 1H), 7.77 (s, 1H). $^{13}$C NMR (D6-DMSO) δ 8.4, 21.2, 26.2, 36.2, 104.2, 112.8, 113.4, 124.2, 130.9, 132.6, 149.0, 160.8, 193.5. LCMS t=3.7 min, m/z Calcd for $C_{13}H_{16}ClN_2O$; $C_{13}H_{15}ClN_2NaO$; $C_{26}H_{30}Cl_2N_4NaO_2$ 251.095; 273.077; 523.164 [M+H]+; [M+Na]+; [2M+Na]+, Found 251.095; 273.077; 523.164.

3-((2-Chloro-4-nitrophenyl)amino)-2-methylcyclohex-2-enone was prepared from 2-methyl-1,3-cyclohexandione and 2-chloro-4-nitroaniline according to the procedure of Example 01-01.

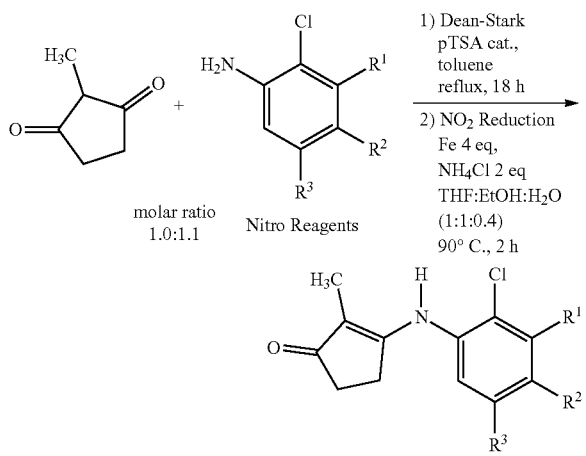

| EXAMPLE 02-# | TITLE COMPOUND NAME | $R^1$ | $R^2$ | $R^3$ |
|---|---|---|---|---|
| 13 | 3-((3-Amino-2-chlorophenyl)amino)-2-methylcyclopent-2-enone | $NH_2$ | H | H |
| 14 | 3-((4-Amino-2-chlorophenyl)amino)-2-methylcyclopent-2-enone | H | $NH_2$ | H |

| EXAMPLE 02-# | TITLE COMPOUND NAME | R¹ | R² | R³ |
|---|---|---|---|---|
| 15 | 3-((5-Amino-2-chlorophenyl)amino)-2-methylcyclopent-2-en-1-one | H | H | NH₂ |

Example 02-13

Preparation of 3-((3-amino-2-chlorophenyl)amino)-2-methylcyclopent-2-enone (02-13)

The title compound was prepared from 3-((2-chloro-3-nitrophenyl)amino)-2-methylcyclopent-2-enone according to the procedure of Example 02-10 (mp=223-225° C.). $^1$H NMR (D6-DMSO) δ 1.46 (s, 3H), 2.12-2.17 (m, 2H), 2.32-2.39 (m, 2H), 5.49 (br s, 2H), 6.53 (d, J=7.3 Hz, 1H), 6.71 (d, J=6.1 Hz, 1H), 6.99-7.03 (m, 1H), 8.72 (s, 1H). $^{13}$C NMR (D6-DMSO) δ 7.1, 25.3, 32.6, 108.2, 113.1, 114.6, 115.5, 127.0, 136.9, 145.8, 170.3, 201.8. LCMS t=3.7 min, m/z Calcd for $C_{12}H_{14}ClN_2O$; $C_{12}H_{13}ClN_2NaO$; $C_{24}H_{27}Cl_2N_4O_2$; $C_{24}H_{26}Cl_2N_4NaO_2$ 237.080; 259.061; 473.151; 495.133 [M+H]+; [M+Na]+; [2M+H]+; [2M+Na]+, Found 237.080; 259.060; 473.150 495.132.

3-((2-Chloro-3-nitrophenyl)amino)-2-methylcyclopent-2-enone was prepared from 2-methyl-1,3-cyclopentandione and 2-chloro-3-nitroaniline according to the procedure of Example 01-01.

Example 02-14

Preparation of 3-((4-amino-2-chlorophenyl)amino)-2-methylcyclopent-2-enone (02-14)

The title compound was prepared from 3-((2-chloro-4-nitrophenyl)amino)-2-methylcyclopent-2-enone according to the procedure of Example 02-10. $^1$H NMR (D6-DMSO) δ 1.44 (s, 3H), 2.09-2.13 (m, 2H), 2.18-2.27 (m, 2H), 5.47 (br s, 2H), 6.50 (dd, J=8.5, 2.4 Hz, 1H), 6.68 (d, J=2.4 Hz, 1H), 7.01 (d, J=8.5 Hz, 1H), 8.58 (s, 1H). $^{13}$C NMR (D6-DMSO) δ 6.9, 25.1, 32.5, 107.0, 112.7, 113.4, 123.9, 130.4, 131.9, 149.0, 171.9, 201.4. LCMS t=3.5 min, m/z Calcd for $C_{12}H_{14}ClN_2O$; $C_{12}H_{13}ClN_2NaO$; $C_{24}H_{27}Cl_2N_4O_2$; $C_{24}H_{26}Cl_2N_4NaO_2$ 237.080; 259.061; 473.151; 495.133 [M+H]+; [M+Na]+; [2M+H]+; [2M+Na]+, Found 237.080; 259.061; 473.151 495.132.

3-((2-Chloro-4-nitrophenyl)amino)-2-methylcyclopent-2-enone was prepared from 2-methyl-1,3-cyclopentandione and 2-chloro-4-nitroaniline according to the procedure of Example 01-01.

Example 02-15

Preparation of 3-((5-amino-2-chlorophenyl)amino)-2-methylcyclopent-2-en-1-one (02-15)

The title compound was prepared from 3-((2-chloro-5-nitrophenyl)amino)-2-methylcyclopent-2-enone according to the procedure of Example 02-10 (mp=166-168° C.). $^1$H NMR (D6-DMSO) δ 1.45 (s, 3H), 2.13-2.21 (m, 2H), 2.34-2.40 (m, 2H), 5.38 (s, 2H), 6.47 (dd, J=8.5, 2.4 Hz, 1H), 6.51 (d, J=2.4 Hz, 1H), 7.12 (d, J=8.5 Hz, 1H), 8.69 (s, 1H). $^{13}$C NMR (D6-DMSO) δ 7.2, 25.4, 32.6, 108.4, 113.2, 113.4, 115.8, 129.6, 136.5, 148.4, 170.1, 202.0. LCMS t=3.6 min, m/z Calcd for $C_{12}H_{14}ClN_2O$; $C_{12}H_{13}ClN_2NaO$; $C_{24}H_{26}Cl_2N_4NaO_2$ 237.080; 259.061; 495.133 [M+H]+; [M+Na]+; [2M+Na]+, Found 237.080; 259.061; 495.133.

3-((2-Chloro-5-nitrophenyl)amino)-2-methylcyclopent-2-enone was prepared from 2-methyl-1,3-cyclopentandione and 2-chloro-5-nitroaniline according to the procedure of Example 01-01.

Examples 03-01 to 03-23

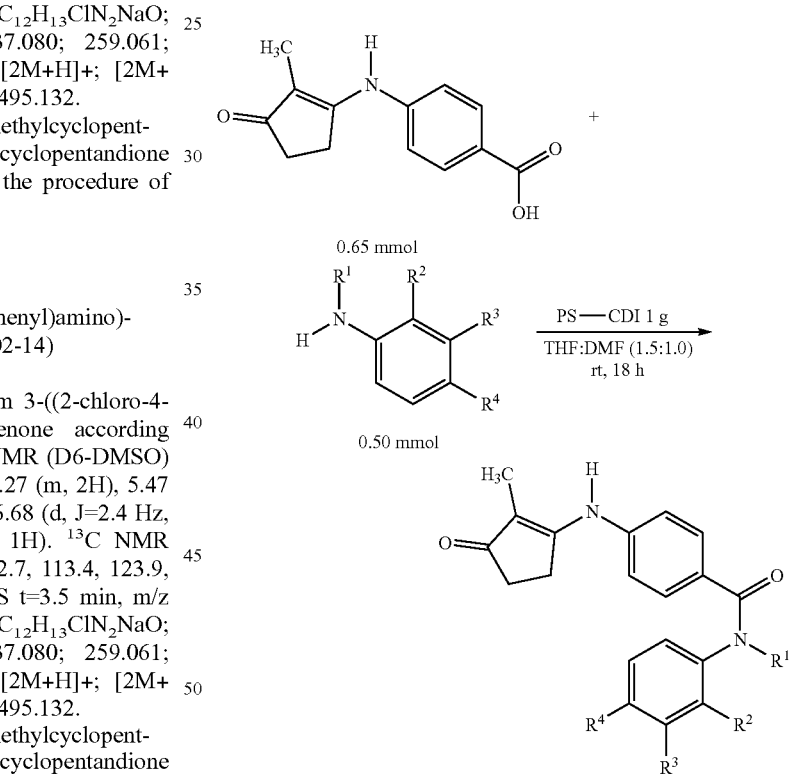

| EXAMPLE 03-# | TITLE COMPOUND NAME | R¹ | R² | R³ | R⁴ |
|---|---|---|---|---|---|
| 01 | 4-((2-Methyl-3-oxocyclopent-1-en-1-yl)amino)-N-phenylbenzamide | H | H | H | H |
| 02 | N-Methyl-4-((2-methyl-3-oxocyclopent-1-en-1-yl)amino)-N-phenylbenzamide | CH₃ | H | H | H |
| 03 | N-(2-Fluorophenyl)-4-((2-methyl-3-oxocyclopent-1-en-1-yl)amino)benzamide | H | F | H | H |
| 04 | N-(3-Fluorophenyl)-4-((2-methyl-3-oxocyclopent-1-en-1-yl)amino)benzamide | H | H | F | H |
| 05 | N-(4-Chlorophenyl)-4-((2-methyl-3-oxocyclopent-1-en-1-yl)amino)benzamide | H | H | H | Cl |

-continued

| EXAMPLE 03-# | TITLE COMPOUND NAME | $R^1$ | $R^2$ | $R^3$ | $R^4$ |
|---|---|---|---|---|---|
| 06 | N-(4-Methoxyphenyl)-4-((2-methyl-3-oxocyclopent-1-en-1-yl)amino)benzamide | H | H | H | $OCH_3$ |
| 07 | 4-((2-Methyl-3-oxocyclopent-1-en-1-yl)amino)-N-(p-tolyl)benzamide | H | H | H | $CH_3$ |
| 08 | 4-((2-Methyl-3-oxocyclopent-1-en-1-yl)amino)-N-(o-tolyl)benzamide | H | $CH_3$ | H | H |
| 09 | 4-((2-Methyl-3-oxocyclopent-1-en-1-yl)amino)-N-(m-tolyl)benzamide | H | H | $CH_3$ | H |
| 10 | N-(2-Methoxyphenyl)-4-((2-methyl-3-oxocyclopent-1-en-1-yl)amino)benzamide | H | $OCH_3$ | H | H |
| 11 | N-(3-Methoxyphenyl)-4-((2-methyl-3-oxocyclopent-1-en-1-yl)amino)benzamide | H | H | $OCH_3$ | H |
| 12 | 4-((2-Methyl-3-oxocyclopent-1-en-1-yl)amino)-N-(3-(trifluoromethyl)phenyl)benzamide | H | H | $CF_3$ | H |
| 13 | N-(4-(tert-Butyl)phenyl)-4-((2-methyl-3-oxocyclopent-1-en-1-yl)amino)benzamide | H | H | H | $C(CH_3)_3$ |
| 14 | N-(3-Bromophenyl)-4-((2-methyl-3-oxocyclopent-1-en-1-yl)amino)benzamide | H | H | Br | H |
| 15 | N-(4-Bromophenyl)-4-((2-methyl-3-oxocyclopent-1-en-1-yl)amino)benzamide | H | H | H | Br |

Example 03-01

Preparation of 4-((2-methyl-3-oxocyclopent-1-en-1-yl)amino)-N-phenylbenzamide (03-01)

Example 02-01 (150 mg, 0.65 mmol, 1.3 eq) was dissolved in THF:DMF (1.5:1.0, 7.5 mL) and added to aniline (0.046 mL, 0.5 mmol) and PS-CDI (1.0 g, loading=1.33 mmol/g) in a dry reaction vessel. The reaction vessel was sealed and shaken for 18 h at rt. Resin was filtered from the solvent, washed with 1 vol of the reaction solvent, and THF (3×8 mL). Isolute™ HM-N was added to the crude solution and dried on the rotovap. The crude material absorbed to Isolute™ was packed into an empty samplet (1 g) and placed into the receiving KP-Sil™ column (10 g). Products were separated from impurities using an isocratic solvent system, EtOAc:acetone (17:3), on Biotage®-Isolera Four instrument, monitoring UV Trace at 254/365 nm. The reaction on a 0.5 mmol scale yielded 15 mg of the title compound (10% yield). $^1$H NMR (D6-DMSO) δ 1.62 (s, 3H), 2.25-2.27 (m, 2H), 2.80-2.81 (m, 2H), 7.09 (t, J=7.3 Hz, 1H), 7.33-7.37 (m, 4H), 7.77 (d, J=7.7 Hz, 2H), 7.85 (d, J=8.4 Hz, 2H), 9.18 (s, 1H), 10.16 (s, 1H). LCMS t=5.4 min, m/z Calcd for $C_{19}H_{19}N_2O_2$; $C_{19}H_8N_2NaO_2$; $C_{38}H_{37}N_4O_4$; $C_{38}H_{36}N_4NaO_4$ 307.14; 329.13; 613.28; 635.26 [M+H]$^+$; [M+Na]$^+$; [2M+H]$^+$; [2M+Na]$^+$, Found 307.16; 329.14; 613.31; 635.29.

Example 03-02

Preparation of N-methyl-4-((2-methyl-3-oxocyclopent-1-en-1-yl)amino)-N-phenylbenzamide (03-02)

The title compound was prepared from Example 02-01 and N-methylaniline according to the procedure of Example 03-01; 0.5 mmol scale yielded 30 mg (19% yield). $^1$H NMR (MeOD) δ 1.59 (s, 3H), 2.35-2.37 (m, 2H), 2.68-2.69 (m, 2H), 3.47 (s, 3H), 7.08 (d, J=8.2 Hz, 2H), 7.15 (d, J=7.6 Hz, 2H), 7.19 (t, J=7.3 Hz, 1H), 7.26-7.31 (m, 4H). LCMS t=5.4 min, m/z Calcd for $C_{20}H_{21}N_2O_2$; $C_{20}H_{20}N_2O_2$; $C_{40}H_{41}N_4O_4$; $C_{40}H_{40}N_4NaO_4$ 321.16; 343.14; 641.31; 663.29 [M+H]$^+$; [M+Na]$^+$; [2M+H]$^+$; [2M+Na]$^+$, Found 321.17; 343.16; 641.34; 663.32.

Example 03-03

Preparation of N-(2-fluorophenyl)-4-((2-methyl-3-oxocyclopent-1-en-1-yl)amino)benzamide (03-03)

The title compound was prepared from Example 02-01 and 2-fluoroaniline according to the procedure of Example 03-01; 0.5 mmol scale yielded 10 mg (6% yield). $^1$H NMR (CDCl$_3$) δ 1.60 (s, 3H), 2.76-2.78 (m, 2H), 3.34-3.36 (m, 2H), 6.68 (s, 1H), 7.10-7.28 (m, 5H), 7.92 (d, J=8.2 Hz, 2H), 8.04 (s, 1H), 8.45 (t, J=8.0 Hz, 1H). LCMS t=5.4 min, m/z Calcd for $C_{19}H_{18}FN_2O_2$; $C_{19}H_{17}FN_2NaO_2$; $C_{38}H_{35}F_2N_4O_4$; $C_{38}H_{34}F_2N_4NaO_4$ 325.14; 347.12; 649.26; 671.24 [M+H]$^+$; [M+Na]$^+$; [2M+H]$^+$; [2M+Na]$^+$, Found 325.15; 347.13; 649.29; 671.27.

Example 03-04

Preparation of N-(3-fluorophenyl)-4-((2-methyl-3-oxocyclopent-1-en-1-yl)amino)benzamide (03-04)

The title compound was prepared from Example 02-01 and 3-fluoroaniline according to the procedure of Example 03-01; 0.5 mmol scale yielded 18 mg (11% yield). $^1$H NMR (D6-DMSO) δ 1.62 (s, 3H), 2.25-2.28 (m, 2H), 2.80-2.82 (m, 2H), 6.91-6.93 (m, 1H), 7.36-7.39 (m, 3H), 7.56 (d, J=8.1 Hz, 1H), 7.76 (d, J=11.8 Hz, 1H), 7.94 (d, J=8.5 Hz, 2H), 9.19 (s, 1H), 10.34 (s, 1H). LCMS t=5.5 min, m/z Calcd for $C_{19}H_{18}FN_2O_2$; $C_{19}H_{17}FN_2NaO_2$; $C_{38}H_{35}F_2N_4O_4$; $C_{38}H_{34}F_2N_4NaO_4$ 325.14; 347.12; 649.26; 671.24 [M+H]$^+$; [M+Na]$^+$; [2M+H]$^+$; [2M+Na]$^+$, Found 325.15; 347.13; 649.29; 671.28.

Example 03-05

Preparation of N-(4-chlorophenyl)-4-((2-methyl-3-oxocyclopent-1-en-1-yl)amino)benzamide (03-05)

The title compound was prepared from Example 02-01 and 4-chloroaniline according to the procedure of Example 03-01; 0.5 mmol scale yielded 10 mg (6% yield). $^1$H NMR (D6-DMSO) δ 1.62 (s, 3H), 2.25-2.27 (m, 2H), 2.80-2.81 (m, 2H), 7.36 (d, J=8.4 Hz, 2H), 7.41 (d, J=8.7 Hz, 2H), 7.82 (d, J=8.8 Hz, 2H), 7.94 (d, J=8.5 Hz, 2H), 9.19 (s, 1H), 10.29

(s, 1H). LCMS t=5.7 min, m/z Calcd for $C_{19}H_{18}ClN_2O_2$; $C_{19}H_{17}ClN_2NaO_2$; $C_{38}H_{35}Cl_2N_4O_4$; $C_{38}H_{34}Cl_2N_4NaO_4$ 341.11; 363.09; 681.20; 703.19 $[M+H]^+$; $[M+Na]^+$; $[2M+H]^+$; $[2M+Na]^+$, Found 341.12; 363.09; 681.23; 703.21.

Example 03-06

Preparation of N-(4-methoxyphenyl)-4-((2-methyl-3-oxocyclopent-1-en-1-yl)amino)benzamide (03-06)

The title compound was prepared from Example 02-01 and 4-aminoanisole according to the procedure of Example 03-01; 0.5 mmol scale yielded 12 mg (7% yield). $^1$H NMR (D6-DMSO) δ 1.62 (s, 3H), 2.25-2.27 (m, 2H), 2.79-2.80 (m, 2H), 3.74 (s, 3H), 6.92 (d, J=8.8 Hz, 2H), 7.35 (d, J=8.4 Hz, 2H), 7.66 (d, J=8.7 Hz, 2H), 7.93 (d, J=8.4 Hz, 2H), 9.17 (s, 1H), 10.05 (s, 1H). LCMS t=5.2 min, m/z Calcd for $C_{20}H_{21}N_2O_3$; $C_{40}H_{41}N_4O_6$; $C_{40}H_{40}N_4NaO_6$ 337.16; 673.30; 695.28 $[M+H]^+$; $[2M+H]^+$; $[2M+Na]^+$, Found 337.17; 673.33; 695.31.

Example 03-07

Preparation of 4-((2-methyl-3-oxocyclopent-1-en-1-yl)amino)-N-(p-tolyl)benzamide (03-07)

The title compound was prepared from Example 02-01 and 4-aminotoluene according to the procedure of Example 03-01; 0.5 mmol scale yielded 25 mg (16% yield). $^1$H NMR (D6-DMSO) δ 1.62 (s, 3H), 2.25-2.28 (m, 5H), 2.79-2.81 (m, 2H), 7.15 (d, J=8.1 Hz, 2H), 7.35 (d, J=8.4 Hz, 2H), 7.65 (d, J=8.2 Hz, 2H), 7.94 (d, J=8.4 Hz, 2H), 9.17 (s, 1H), 10.08 (s, 1H). LCMS t=5.5 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 $[M+H]^+$; $[M+Na]^+$; $[2M+H]^+$; $[2M+Na]^+$, Found 321.17; 343.16; 641.34; 663.32.

Example 03-08

Preparation of 4-((2-methyl-3-oxocyclopent-1-en-1-yl)amino)-N-(o-tolyl)benzamide (03-08)

The title compound was prepared from Example 02-01 and o-toluidine according to the procedure of Example 03-01; 0.5 mmol scale yielded 1 mg (1% yield). $^1$H NMR (D6-DMSO) δ 1.62 (s, 3H), 2.26-2.28 (m, 2H), 2.31 (s, 3H), 2.80-2.82 (m, 2H), 6.91 (d, J=6.4 Hz, 1H), 7.22 (s, 1H), 7.36 (d, J=6.9 Hz, 2H), 7.56 (d, J=6.4 Hz, 1H), 7.62 (s, 1H), 7.94 (d, J=6.9 Hz, 2H), 9.18 (s, 1H), 10.08 (s, 1H). LCMS t=5.7 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 $[M+H]^+$; $[M+Na]^+$; $[2M+H]^+$; $[2M+Na]^+$, Found 321.18; 343.16; 641.29; 663.28.

Example 03-09

Preparation of 4-((2-methyl-3-oxocyclopent-1-en-1-yl)amino)-N-(m-tolyl)benzamide (03-09)

The title compound was prepared from Example 02-01 and m-toluidine according to the procedure of Example 03-01; 0.5 mmol scale yielded 13 mg (8% yield). $^1$H NMR (D6-DMSO) δ 1.62 (s, 3H), 2.23 (s, 3H), 2.24-2.26 (m, 2H), 2.79-2.80 (m, 2H), 7.16 (t, J=7.3 Hz, 1H), 7.21 (t, J=7.3 Hz, 1H), 7.27 (d, J=7.3 Hz, 1H), 7.33 (d, J=7.6 Hz, 1H), 7.36 (d, J=8.4 Hz, 2H), 7.96 (d, J=8.4 Hz, 2H), 9.18 (s, 1H), 9.81 (s, 1H). LCMS t=5.5 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 $[M+H]^+$; $[M+Na]^+$; $[2M+H]^+$; $[2M+Na]^+$, Found 321.18; 343.16; 641.29; 663.28.

Example 03-10

Preparation of N-(2-methoxyphenyl)-4-((2-methyl-3-oxocyclopent-1-en-1-yl)amino)benzamide (03-10)

The title compound was prepared from Example 02-01 and o-anisidine according to the procedure of Example 03-01; 0.5 mmol scale yielded 8 mg (5% yield). $^1$H NMR (D6-DMSO) δ 1.62 (s, 3H), 2.26-2.27 (m, 2H), 2.79-2.81 (m, 2H), 3.84 (s, 3H), 6.97 (t, J=7.2 Hz, 1H), 7.09 (d, J=7.9 Hz, 1H), 7.17 (t, J=7.3 Hz, 1H), 7.35 (d, J=7.9 Hz, 2H), 7.77 (d, J=7.4 Hz, 1H), 7.94 (d, J=7.9 Hz, 2H), 9.18 (s, 1H), 9.34 (s, 1H). LCMS t=5.7 min, m/z Calcd for $C_{20}H_{21}N_2O_3$; $C_{20}H_{20}N_2NaO_3$; $C_{40}H_{40}N_4NaO_6$ 337.16; 359.14; 695.28 $[M+H]^+$; $[M+Na]^+$; $[2M+Na]^+$, Found 337.17; 359.14; 695.27.

Example 03-11

Preparation of N-(3-methoxyphenyl)-4-((2-methyl-3-oxocyclopent-1-en-1-yl)amino)benzamide (03-11)

The title compound was prepared from Example 02-01 and m-anisidine according to the procedure of Example 03-01; 0.5 mmol scale yielded 4 mg (2% yield). $^1$H NMR (D6-DMSO) δ 1.62 (s, 3H), 2.26-2.28 (m, 2H), 2.80-2.82 (m, 2H), 3.75 (s, 3H), 6.67 (d, J=7.3 Hz, 1H), 7.24 (t, J=7.5 Hz, 1H), 7.36 (d, J=8.0 Hz, 2H), 7.47 (s, 1H), 7.94 (d, J=8.3 Hz, 2H), 9.18 (s, 1H), 10.12 (s, 1H). LCMS t=5.6 min, m/z Calcd for $C_{20}H_{21}N_2O_3$; $C_{20}H_{20}N_2NaO_3$; $C_{40}H_{40}N_4NaO_6$ 337.16; 359.14; 695.28 $[M+H]^+$; $[M+Na]^+$; $[2M+Na]^+$, Found 337.17; 359.14; 695.28.

Example 03-12

Preparation of 4-((2-methyl-3-oxocyclopent-1-en-1-yl)amino)-N-(3-(trifluoromethyl)phenyl)benzamide (03-12)

The title compound was prepared from Example 02-01 and 3-(trifluoromethyl)aniline according to the procedure of Example 03-01; 0.5 mmol scale yielded 3 mg (2% yield). $^1$H NMR (D6-DMSO) δ 1.62 (s, 3H), 2.26-2.28 (m, 2H), 2.81-2.83 (m, 2H), 7.38 (d, J=7.9 Hz, 2H), 7.45 (d, J=7.2 Hz, 1H), 7.60 (t, J=7.6 Hz, 1H), 7.97 (d, J=7.9 Hz, 2H), 8.05 (d, J=7.6 Hz, 1H), 8.26 (s, 1H), 9.21 (s, 1H), 10.47 (s, 1H). LCMS t=5.9 min, m/z Calcd for $C_{20}H_{18}F_3N_2O_2$; $C_{20}H_{17}F_3N_2NaO_2$; $C_{40}H_{34}F_6N_4NaO_6$ 375.13; 397.11; 771.24 $[M+H]^+$; $[M+Na]^+$; $[2M+Na]^+$, Found 375.13; 397.11; 771.24.

Example 03-13

Preparation of N-(4-(tert-butyl)phenyl)-4-((2-methyl-3-oxocyclopent-1-en-1-yl)amino)-benzamide (03-13)

The title compound was prepared from Example 02-01 and 4-tert-butylaniline according to the procedure of Example 03-01; 0.5 mmol scale yielded 4 mg (2% yield). $^1$H NMR (D6-DMSO) δ 1.28 (s, 9H), 1.62 (s, 3H), 2.26-2.28 (m, 2H), 2.79-2.81 (m, 2H), 7.36 (d, J=8.0 Hz, 4H), 7.68 (d, J=8.2 Hz, 2H), 7.94 (d, J=8.1 Hz, 2H), 9.18 (s, 1H), 10.10

(s, 1H). LCMS t=6.1 min, m/z Calcd for $C_{23}H_{27}N_2O_2$; $C_{23}H_{26}N_2NaO_2$; $C_{46}H_{53}N_4O_4$; $C_{46}H_{52}N_4NaO_4$ 363.21; 385.19; 725.41; 747.39 [M+H]$^+$; [M+Na]$^+$; [2M+H]$^+$; [2M+Na]$^+$, Found 363.21; 385.19; 725.41; 747.39.

Example 03-14

Preparation of N-(3-bromophenyl)-4-((2-methyl-3-oxocyclopent-1-en-1-yl)amino)benzamide (03-14)

The title compound was prepared from Example 02-01 and 3-bromoaniline according to the procedure of Example 03-01; 0.5 mmol scale yielded 4 mg (2% yield). $^1$H NMR (D6-DMSO) δ 1.62 (s, 3H), 2.26-2.28 (m, 2H), 2.81-2.83 (m, 2H), 7.29-7.34 (m, 2H), 7.37 (d, J=8.4 Hz, 2H), 7.75 (d, J=7.9 Hz, 1H), 7.95 (d, J=8.4 Hz, 2H), 8.11 (s, 1H), 9.20 (s, 1H), 10.31 (s, 1H). LCMS t=5.9 min, m/z Calcd for $C_{19}H_{18}BrN_2O_2$; $C_{19}H_{17}BrN_2NaO_2$; $C_{38}H_{34}BrN_4NaO_6$ 385.06, 387.05; 407.04, 409.04; 793.08 [M+H]$^+$; [M+Na]$^+$; [2M+Na]$^+$, Found 385.05, 387.05; 407.03, 409.03; 793.09.

Example 03-15

Preparation of N-(4-bromophenyl)-4-((2-methyl-3-oxocyclopent-1-en-1-yl)amino)benzamide (03-15)

The title compound was prepared from Example 02-01 and 4-bromoaniline according to the procedure of Example 03-01; 0.5 mmol scale yielded 3 mg (2% yield). $^1$H NMR (D6-DMSO) δ 1.62 (s, 3H), 2.26-2.28 (m, 2H), 2.80-2.82 (m, 2H), 7.36 (d, J=8.4 Hz, 2H), 7.53 (d, J=8.6 Hz, 2H), 7.76 (d, J=8.6 Hz, 2H), 7.94 (d, J=8.4 Hz, 2H), 9.19 (s, 1H), 10.28 (s, 1H). LCMS t=5.9 min, m/z Calcd for $C_{19}H_{18}BrN_2O_2$; $C_{19}H_{17}BrN_2NaO_2$; $C_{38}H_{34}BrN_4NaO_6$ 385.06, 387.05; 407.04, 409.04; 793.08 [M+H]$^+$; [M+Na]$^+$; [2M+Na]$^+$, Found 385.05, 387.05; 407.03, 409.03; 793.09.

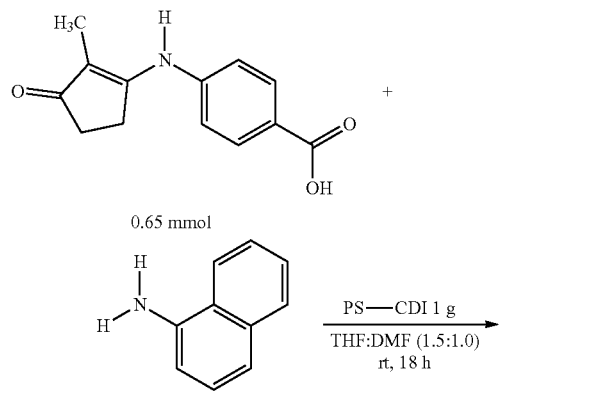

Example 03-16

Preparation of 4-((2-methyl-3-oxocyclopent-1-en-1-yl)amino)-N-(naphthalen-1-yl)benzamide (03-16)

The title compound was prepared from Example 02-01 and 1-aminonaphthalene according to the procedure of Example 03-01; 0.5 mmol scale yielded 11 mg (6% yield). $^1$H NMR (D6-DMSO) δ 1.64 (s, 3H), 2.27-2.29 (m, 2H), 2.82-2.84 (m, 2H), 7.40 (d, J=8.3 Hz, 2H), 7.54-7.60 (m, 4H), 7.81-7.87 (m, 2H), 7.98-8.00 (m, 2H), 8.08 (d, J=8.3 Hz, 2H), 9.21 (s, 1H), 10.36 (s, 1H). LCMS t=5.6 min, m/z Calcd for $C_{23}H_{21}N_2O_2$; $C_{23}H_{20}N_2NaO_2$; $C_{46}H_{41}N_4O_4$; $C_{46}H_{40}N_4NaO_4$ 357.16; 379.14; 713.31; 735.29 [M+H]$^+$; [M+Na]$^+$; [2M+H]$^+$; [2M+Na]$^+$, Found 357.18; 379.18; 713.34; 735.33.

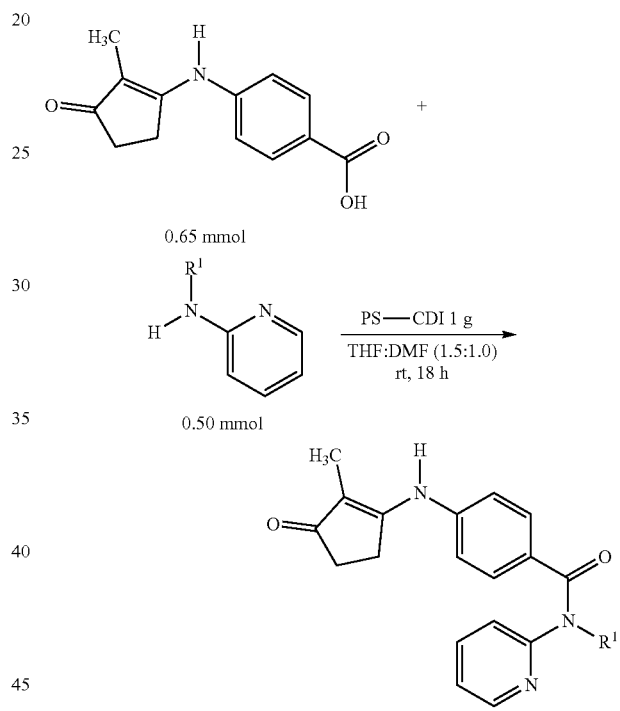

Example 03-17

Preparation of 4-((2-methyl-3-oxocyclopent-1-en-1-yl)amino)-N-(pyridin-2-yl)benzamide (03-17)

The title compound was prepared from Example 02-01 and 2-aminopyridine according to the procedure of Example 03-01; 0.5 mmol scale yielded 2 mg (1% yield). $^1$H NMR (D6-DMSO) δ 1.62 (s, 3H), 2.26-2.28 (m, 2H), 2.81-2.82 (m, 2H), 7.16 (s, 1H), 7.34 (d, J=7.8 Hz, 2H), 7.83-7.84 (m, 1H), 8.03 (d, J=7.7 Hz, 2H), 8.18 (d, J=8.0 Hz, 2H), 8.39 (s, 1H), 9.18 (s, 1H), 10.68 (s, 1H). LCMS t=5.1 min, m/z Calcd for $C_{18}H_{18}N_3O_2$; $C_{18}H_{17}N_3NaO_2$; $C_{36}H_{34}N_6NaO_4$ 308.14; 330.12; 637.25 [M+H]$^+$; [M+Na]$^+$; [2M+Na]$^+$, Found 308.16; 330.13; 637.22.

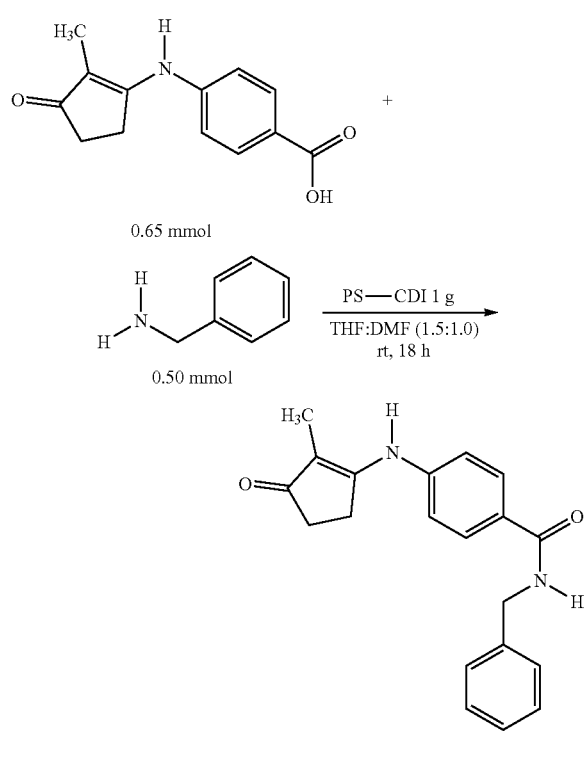

Example 03-18

Preparation of N-benzyl-4-((2-methyl-3-oxocyclo-pent-1-en-1-yl)amino)benzamide (03-18)

The title compound was prepared from Example 02-01 and benzylamine according to the procedure of Example 03-01; 0.5 mmol scale yielded 20 mg (13% yield). $^1$H NMR (D6-DMSO) δ 1.60 (s, 3H), 2.23-2.25 (m, 2H), 2.76-2.78 (m, 2H), 4.47 (d, J=5.7 Hz, 2H), 7.23-7.30 (m, 7H), 7.87 (d, J=8.2 Hz, 2H), 8.98 (s, 1H), 9.12 (s, 1H). LCMS t=5.3 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 [M+H]$^+$; [M+Na]$^+$; [2M+H]$^+$; [2M+Na]$^+$, Found 321.17; 343.16; 641.24; 663.32.

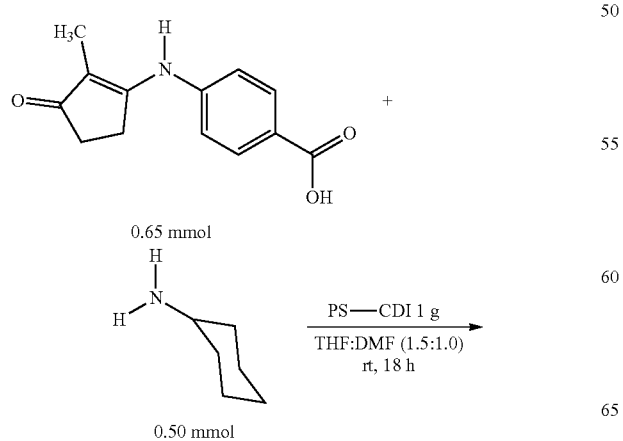

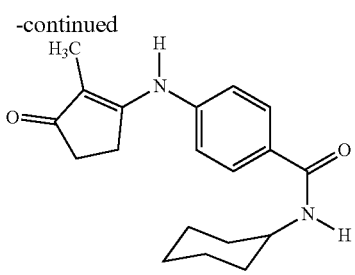

Example 03-19

Preparation of N-cyclohexyl-4-((2-methyl-3-oxocyclopent-1-en-1-yl)amino)benzamide (03-19)

The title compound was prepared from Example 02-01 and cyclohexylamine according to the procedure of Example 03-01; 0.5 mmol scale yielded 11 mg (7% yield). $^1$H NMR (MeOD) δ 1.21-1.25 (m, 2H), 1.34-1.42 (m, 4H), 1.69 (s, 3H), 1.80-1.83 (m, 2H), 1.94-1.96 (m, 2H), 2.40-2.43 (m, 2H), 2.82-2.83 (m, 2H), 3.85-3.86 (m, 1H), 7.32 (d, J=8.5 Hz, 2H), 7.83 (d, J=8.5 Hz, 2H). LCMS t=5.4 min, m/z Calcd for $C_{19}H_{25}N_2O_2$; $C_{19}H_{24}N_2NaO_2$; $C_{38}H_{49}N_4O_4$; $C_{38}H_{48}N_4NaO_4$ 313.19; 335.17; 625.38; 647.38 [M+H]$^+$; [M+Na]$^+$; [2M+H]$^+$; [2M+Na]$^+$, Found 313.21; 335.19; 625.40; 647.39.

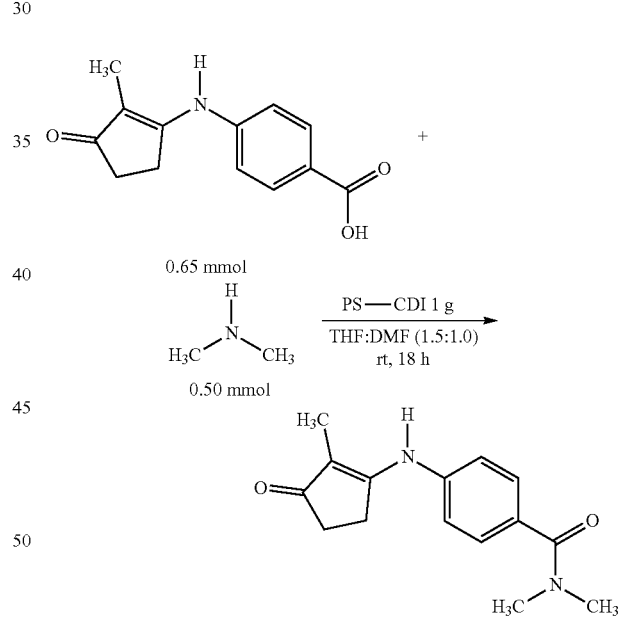

Example 03-20

Preparation of N,N-dimethyl-4-((2-methyl-3-oxocyclopent-1-en-1-yl)amino)benzamide (03-20)

The title compound was prepared from Example 02-01 and dimethylamine according to the procedure of Example 03-01; 0.5 mmol scale yielded 55 mg (43% yield). $^1$H NMR (D6-DMSO) δ 1.59 (s, 3H), 2.21-2.23 (m, 2H), 2.73-2.74 (m, 2H), 2.96 (s, 6H), 7.27 (d, J=8.3 Hz, 2H), 7.39 (d, J=8.3 Hz, 2H), 9.07 (s, 1H). LCMS t=5.0 min, m/z Calcd for $C_{15}H_{19}N_2O_2$; $C_{15}H_{18}N_2NaO_2$; $C_{30}H_{37}N_4O_4$;

$C_{30}H_{36}N_4NaO_4$ 259.14; 281.13; 517.28; 539.26 [M+H]$^+$; [M+Na]$^+$; [2M+H]$^+$; [2M+Na]$^+$, Found 259.19; 281.16; 517.25; 539.23.

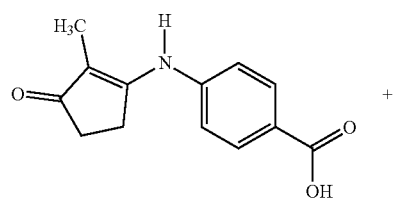

0.65 mmol

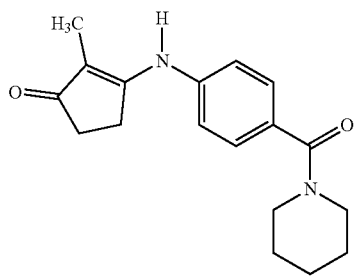

Example 03-21

Preparation of 2-methyl-3-((4-(piperidine-1-carbonyl)phenyl)amino)cyclopent-2-enone (03-21)

The title compound was prepared from Example 02-01 and piperidine according to the procedure of Example 03-01; 0.5 mmol scale yielded 33 mg (22% yield). $^1$H NMR (D6-DMSO) δ 1.50 (br s, 8H), 1.59 (s, 3H), 2.22-2.24 (m, 2H), 2.72-2.24 (m, 2H), 3.53 (br s, 2H), 7.27 (d, J=8.0 Hz, 2H), 7.35 (d, J=8.0 Hz, 2H), 9.06 (s, 1H). LCMS t=5.4 min, m/z Calcd for $C_{18}H_{23}N_2O_2$; $C_{18}H_{22}N_2NaO_2$; $C_{36}H_{45}N_4O_4$; 299.18; 321.16; 619.33 [M+H]$^+$; [M+Na]$^+$; [2M+Na]$^+$, Found 299.20; 321.17; 619.29.

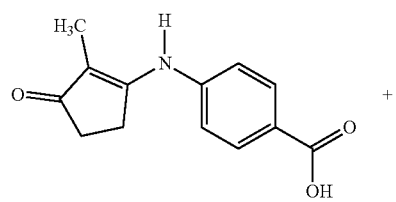

0.65 mmol

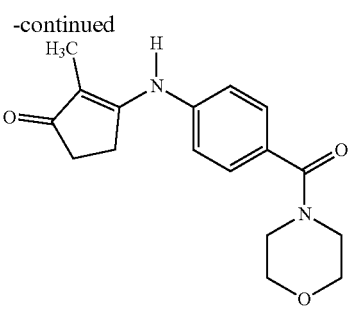

Example 03-22

Preparation of 2-methyl-3-((4-(morpholine-4-carbonyl)phenyl)amino)cyclopent-2-enone (03-22)

The title compound was prepared from Example 02-01 and morpholine according to the procedure of Example 03-01; 0.5 mmol scale yielded 59 mg (39% yield). $^1$H NMR (D6-DMSO) δ 1.60 (s, 3H), 2.22-2.24 (m, 2H), 2.73-2.75 (m, 2H), 3.40-3.70 (m, 8H), 7.28 (d, J=8.1 Hz, 2H), 7.40 (d, J=8.1 Hz, 2H), 9.08 (s, 1H). LCMS t=4.9 min, m/z Calcd for $C_{17}H_{21}N_2O_3$; $C_{17}H_{20}N_2NaO_3$; $C_{34}H_{40}N_4NaO_6$ 301.16; 323.14; 623.28 [M+H]$^+$; [M+Na]$^+$; [2M+Na]$^+$, Found 301.18; 323.15; 623.25.

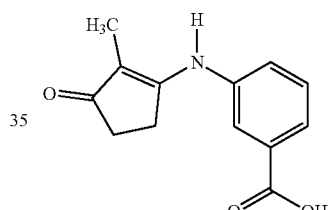

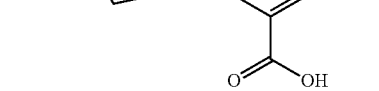

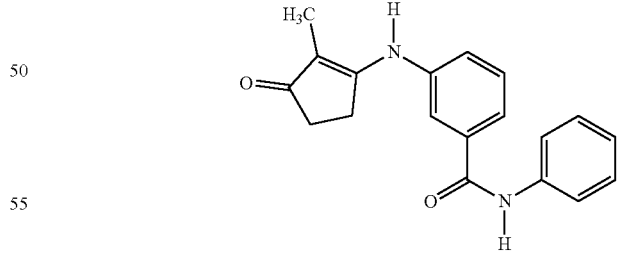

Example 03-23

Preparation of 3-((2-methyl-3-oxocyclopent-1-en-1-yl)amino)-N-phenylbenzamide (03-23)

The title compound was prepared from Example 01-03 and aniline according to the procedure of Example 03-01; 0.5 mmol scale yielded 8 mg (5% yield). $^1$H NMR (D6-

DMSO) δ 1.60 (s, 3H), 2.23-2.25 (m, 2H), 2.71-2.74 (m, 2H), 7.11 (t, J=7.1 Hz, 1H), 7.36 (t, J=7.5 Hz, 2H), 7.46 (d, J=7.6 Hz, 1H), 7.51 (t, J=7.7 Hz, 1H), 7.71 (d, J=7.3 Hz, 1H), 7.77 (d, J=7.8 Hz, 2H), 7.79 (s, 1H), 9.15 (s, 1H), 10.26 (s, 1H). LCMS t=5.6 min, m/z Calcd for $C_{19}H_{19}N_2O_2$; $C_{19}H_{18}N_2NaO_2$; $C_{38}H_{37}N_4O_4$; $C_{38}H_{36}N_4NaO_4$ 307.14; 329.13; 613.28; 635.26 $[M+H]^+$; $[M+Na]^+$; $[2M+H]^+$; $[2M+Na]^+$, Found 307.17; 329.15; 613.26; 635.24.

Examples 04-01 to 04-103

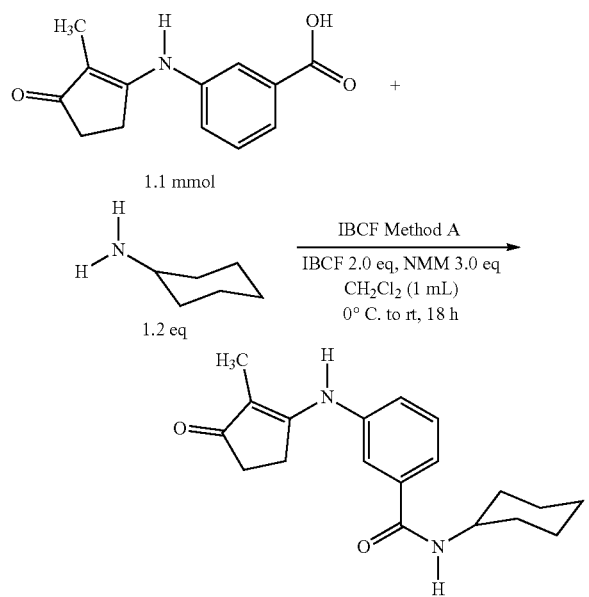

Example 04-01

Preparation of N-cyclohexyl-3-((2-methyl-3-oxocyclopent-1-en-1-yl)amino)benzamide (04-01)

Method A; Isobutylchloroformate (IBCF, 0.285 mL, 2.0 eq) was added to Example 01-03 (250 mg, 1.1 mmol, 1.0 eq) stirring in $CH_2Cl_2$ (1.0 mL), in a screw-capped vial. N-Methylmorpholine (NMM, 0.36 mL, 3.0 eq) was added at 0° C. in 3 portions. After stirring for 1 h, cyclohexylamine (0.15 mL, 1.2 eq) was added, sealed, and stirred for 18 h at rt. Crude materials were purified by recrystallization. The reaction on a 1.1 mmol scale yielded 140 mg of the title compound after recrystallization from $CHCl_3$ (41% yield). $^1$H NMR (D6-DMSO) δ 1.10-1.16 (m, 1H), 1.30-1.36 (m, 4H), 1.57 (s, 3H), 1.61 (d, J=9.7 Hz, 1H), 1.73-1.74 (m, 2H), 1.80-1.82 (m, 2H), 2.20-2.23 (m, 2H), 2.64-2.66 (m, 2H), 3.75-3.77 (m, 1H), 7.37 (d, J=8.1 Hz, 1H), 7.42 (t, J=7.7 Hz, 1H), 7.60 (d, J=7.7 Hz, 1H), 7.69 (s, 1H), 8.22 (d, J=7.9 Hz, 1H), 9.08 (s, 1H). LCMS t=5.8 min, m/z Calcd for $C_{19}H_{25}N_2O_2$; $C_{19}H_{24}N_2NaO_2$; $C_{38}H_{49}N_4O_4$; $C_{38}H_{49}N_4NaO_4$ 313.19; 335.17; 625.38; 647.36 $[M+H]^+$; $[M+Na]^+$; $[2M+H]^+$; $[2M+Na]^+$, Found 313.23; 335.20; 625.37; 647.37.

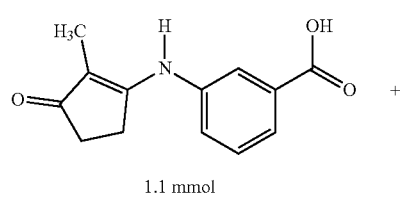

1.1 mmol

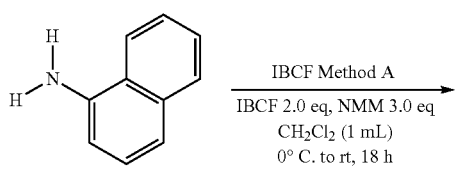

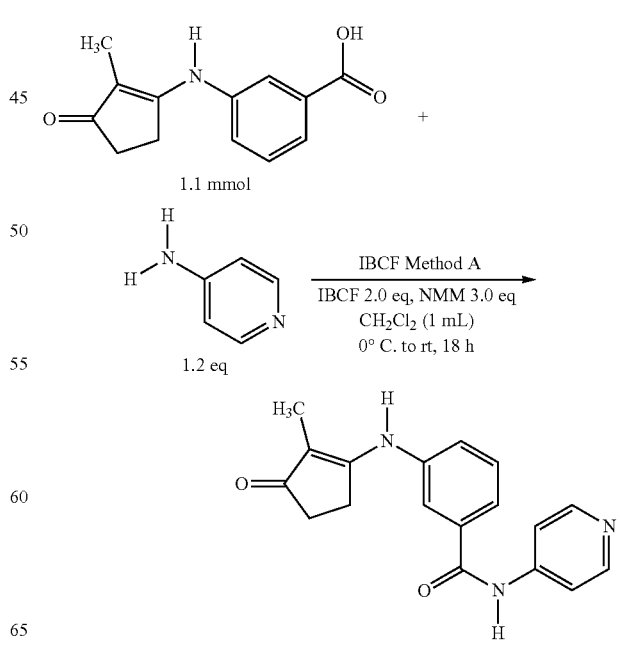

Example 04-02

Preparation of 3-((2-methyl-3-oxocyclopent-1-en-1-yl)amino)-N-(naphthalen-1-yl)benzamide (04-02)

The title compound was prepared from Example 01-03 and 1-aminonaphthalene according to the procedure of Example 04-01; 1.1 mmol scale yielded 100 mg after recrystallization from $CHCl_3$ (26% yield). $^1$H NMR (D6-DMSO) δ 1.61 (s, 3H), 2.23-2.25 (m, 2H), 2.74-2.76 (m, 2H), 7.50 (d, J=7.9 Hz, 2H), 7.53-7.58 (m, 4H), 7.60 (d, J=7.2 Hz, 2H), 7.87 (t, J=8.9 Hz, 2H), 7.91 (s, 1H), 7.96-8.00 (m, 2H), 9.17 (s, 1H), 10.46 (s, 1H). LCMS t=5.9 min, m/z Calcd for $C_{23}H_{21}N_2O_2$; $C_{23}H_{20}N_2NaO_2$; $C_{46}H_{41}N_4O_4$; $C_{46}H_{40}N_4NaO_4$ 357.16; 379.14; 713.31; 735.29 $[M+H]^+$; $[M+Na]^+$; $[2M+H]^+$; $[2M+Na]^+$, Found 357.18; 379.15; 713.32; 735.31.

Example 04-03

Preparation of 3-((2-methyl-3-oxocyclopent-1-en-1-yl)amino)-N-(pyridin-4-yl)benzamide (04-03)

The title compound was prepared from Example 01-03 and 4-aminopyridine according to the procedure of Example 04-01; 1.1 mmol scale yielded 60 mg after recrystallization from MeOH (18% yield). $^1$H NMR (D6-DMSO) δ 1.60 (s, 3H), 2.23-2.25 (m, 2H), 2.71-2.73 (m, 2H), 7.49-7.54 (m, 2H), 7.72 (d, J=7.1 Hz, 1H), 7.80 (s, 3H), 8.49 (d, J=4.7 Hz, 2H), 9.17 (s, 1H), 10.62 (s, 1H). LCMS t=3.0 min, m/z Calcd for $C_{18}H_{18}N_3O_2$; $C_{18}H_{17}N_3NaO_2$; $C_{36}H_{34}N_6NaO_4$ 308.14; 330.12; 637.25 [M+H]$^+$; [M+Na]$^+$; [2M+Na]$^+$, Found 308.17; 330.14; 637.24.

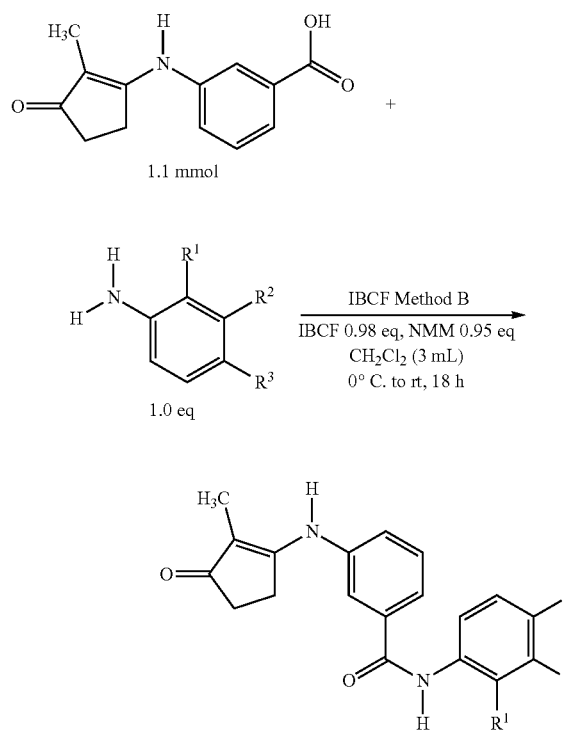

Example 04-04

Preparation of N-(4-methoxyphenyl)-3-((2-methyl-3-oxocyclopent-1-en-1-yl)amino)benzamide (04-04)

Method B; IBCF (0.98 eq) was added to Example 01-03 (250 mg, 1.1 mmol, 1.0 eq) stirring in $CH_2Cl_2$ (3.0 mL), in a screw-capped vial. NMM (0.95 eq) was added at 0° C. After stirring for 1 h, 4-aminoanisole (163 mg, 1.0 eq) was added, sealed, and stirred for 18 h at rt. Crude materials were added directly to KP-Sil™ columns (10 g) with products separating from impurities using stepwise gradients on the Biotage®-Isolera Four instrument, monitoring UV Trace at 254/365 nm. The stepwise gradient utilized two, or three, solvents (acetone, hexanes, EtOAc, or MeOH) running from non-polar to polar steps. Typical increments used were hexanes:EtOAc (H:E) steps 1:1-1:3-1:19-100% EtOAc, then when necessary 2-5% increments of MeOH were applied. Eluting Solvent System (ESS) is the solvent step which eluted the product and is indicated below in the following format ESS=H:E (X:X), or the percentage of MeOH (%) in EtOAc. Subsequent triturations or recrystallizations were performed from suitable solvents. The reaction on a 1.1 mmol scale yielded 30 mg of the title compound after chromatography (ESS=EtOAc:acetone (1:3)) and recrystallization from EtOAc (8% yield). $^1$H NMR (D6-DMSO) δ 1.59 (s, 3H), 2.23-2.25 (m, 2H), 2.70-2.72 (m, 2H), 3.75 (s, 3H), 6.93 (d, J=8.7 Hz, 2H), 7.44 (d, J=7.6 Hz, 1H), 7.49 (t, J=7.6 Hz, 1H), 7.67 (d, J=8.7 Hz, 2H), 7.70 (d, J=7.5 Hz, 1H), 7.78 (s, 1H), 9.14 (s, 1H), 10.14 (s, 1H). LCMS t=5.6 min, m/z Calcd for $C_{20}H_{21}N_2O_3$; $C_{20}H_{20}N_2NaO_3$; $C_{40}H_{41}N_4O_6$; $C_{40}H_{40}N_4NaO_6$ 337.16; 359.14; 673.30; 695.28 [M+H]$^+$; [M+Na]$^+$; [2M+H]$^+$; [2M+Na]$^+$, Found 337.19; 359.17; 673.33; 695.32.

Example 04-05

Preparation of 3-((2-methyl-3-oxocyclopent-1-en-1-yl)amino)-N-(o-tolyl)benzamide (04-05)

The title compound was prepared from Example 01-03 and o-toluidine according to the procedure of Example 04-04; 1.1 mmol scale yielded 10 mg after chromatography (ESS=H:E (1:1)) and recrystallization from MeOH (3% yield). $^1$H NMR (D6-DMSO) δ 1.59 (s, 3H), 2.23-2.25 (m, 5H), 2.71-2.73 (m, 2H), 7.18 (t, J=7.2 Hz, 1H), 7.22 (t, J=7.0 Hz, 1H), 7.28 (d, J=7.2 Hz, 1H), 7.33 (d, J=7.5 Hz, 1H), 7.36

| EXAMPLE 04-# | TITLE COMPOUND NAME | R$^1$ | R$^2$ | R$^3$ |
|---|---|---|---|---|
| 04 | N-(4-Methoxyphenyl)-3-((2-methyl-3-oxocyclopent-1-en-1-yl)amino)benzamide | H | H | OCH$_3$ |
| 05 | 3-((2-Methyl-3-oxocyclopent-1-en-1-yl)amino)-N-(o-tolyl)benzamide | CH$_3$ | H | H |
| 06 | 3-((2-Methyl-3-oxocyclopent-1-en-1-yl)amino)-N-(m-tolyl)benzamide | H | CH$_3$ | H |
| 07 | 3-((2-Methyl-3-oxocyclopent-1-en-1-yl)amino)-N-(p-tolyl)benzamide | H | H | CH$_3$ |
| 08 | N-(2-Fluorophenyl)-3-((2-methyl-3-oxocyclopent-1-en-1-yl)amino)benzamide | F | H | H |
| 09 | N-(3-Bromophenyl)-3-((2-methyl-3-oxocyclopent-1-en-1-yl)amino)benzamide | H | Br | H |
| 10 | N-(4-Bromophenyl)-3-((2-methyl-3-oxocyclopent-1-en-1-yl)amino)benzamide | H | H | Br |
| 11 | 3-((2-Methyl-3-oxocyclopent-1-en-1-yl)amino)-N-(3-(trifluoromethyl)phenyl)benzamide | H | CF$_3$ | H |
| 12 | 3-((2-Methyl-3-oxocyclopent-1-en-1-yl)amino)-N-(4-(trifluoromethyl)phenyl)benzamide | H | H | CF$_3$ |

(d, J=7.4 Hz, 1H), 7.50 (t, J=7.7 Hz, 1H), 7.74 (d, J=7.2 Hz, 1H), 7.81 (s, 1H), 9.13 (s, 1H), 9.90 (s, 1H). LCMS t=5.6 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 [M+H]$^+$; [M+Na]$^+$; [2M+H]$^+$; [2M+Na]$^+$, Found 321.19; 343.16; 641.31; 663.32.

Example 04-06

Preparation of 3-((2-methyl-3-oxocyclopent-1-en-1-yl)amino)-N-(m-tolyl)benzamide (04-06)

The title compound was prepared from Example 01-03 and m-toluidine according to the procedure of Example 04-04; 1.1 mmol scale yielded 30 mg after chromatography (ESS=EtOAc) and recrystallization from MeOH (9% yield). $^1$H NMR (D6-DMSO) δ 1.60 (s, 3H), 2.22-2.25 (m, 2H), 2.31 (s, 3H), 2.70-2.72 (m, 2H), 6.93 (d, J=7.5 Hz, 1H), 7.23 (t, J=7.7 Hz, 1H), 7.46 (d, J=8.2 Hz, 1H), 7.50 (t, J=7.8 Hz, 1H), 7.57 (d, J=8.1 Hz, 1H), 7.62 (s, 1H), 7.71 (d, J=7.6 Hz, 1H), 7.79 (s, 1H), 9.15 (s, 1H), 10.18 (s, 1H). LCMS t=5.8 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 [M+H]$^+$; [M+Na]$^+$; [2M+H]$^+$; [2M+Na]$^+$, Found 321.19; 343.16; 641.31; 663.29.

Example 04-07

Preparation of 3-((2-methyl-3-oxocyclopent-1-en-1-yl)amino)-N-(p-tolyl)benzamide (04-07)

The title compound was prepared from Example 01-03 and p-toluidine according to the procedure of Example 04-04; 1.1 mmol scale yielded 10 mg after chromatography (ESS=EtOAc) and recrystallization from CHCl$_3$ (3% yield). $^1$H NMR (D6-DMSO) δ 1.59 (s, 3H), 2.22-2.25 (m, 2H), 2.28 (s, 3H), 2.70-2.72 (m, 2H), 7.16 (d, J=8.2 Hz, 2H), 7.45 (d, J=8.1 Hz, 1H), 7.50 (t, J=7.8 Hz, 1H), 7.65 (d, J=8.3 Hz, 2H), 7.70 (d, J=7.6 Hz, 1H), 7.79 (s, 1H), 9.14 (s, 1H), 10.18 (s, 1H). LCMS t=5.8 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 [M+H]$^+$; [M+Na]$^+$; [2M+H]$^+$; [2M+Na]$^+$, Found 321.19; 343.16; 641.31; 663.30.

Example 04-08

Preparation of N-(2-fluorophenyl)-3-((2-methyl-3-oxocyclopent-1-en-1-yl)amino)benzamide (04-08)

The title compound was prepared from Example 01-03 and 2-fluoroaniline according to the procedure of Example 04-04; 1.1 mmol scale yielded 40 mg after chromatography (ESS=EtOAc) and recrystallization from MeOH (11% yield). $^1$H NMR (D6-DMSO) δ 1.59 (s, 3H), 2.22-2.25 (m, 2H), 2.70-2.72 (m, 2H), 7.21-7.25 (m, 1H), 7.29-7.33 (m, 2H), 7.48-7.52 (m, 2H), 7.59 (t, J=7.2 Hz, 1H), 7.74 (d, J=7.4 Hz, 1H), 7.82 (s, 1H), 9.15 (s, 1H), 10.14 (s, 1H). LCMS t=5.6 min, m/z Calcd for $C_{19}H_{18}FN_2O_2$; $C_{19}H_{17}FN_2NaO_2$; $C_{38}H_{35}F_2N_4O_4$; $C_{38}H_{34}F_2N_4NaO_4$ 325.14; 347.12; 649.26; 671.24 [M+H]$^+$; [M+Na]$^+$; [2M+H]$^+$; [2M+Na]$^+$, Found 325.16; 347.14; 649.26; 671.26.

Example 04-09

Preparation of N-(3-bromophenyl)-3-((2-methyl-3-oxocyclopent-1-en-1-yl)amino)benzamide (04-09)

The title compound was prepared from Example 01-03 and 3-bromoaniline according to the procedure of Example 04-04; 1.1 mmol scale yielded 40 mg after chromatography (ESS=EtOAc) and recrystallization from MeOH (9% yield). $^1$H NMR (D6-DMSO) δ 1.60 (s, 3H), 2.23-2.25 (m, 2H), 2.71-2.73 (m, 2H), 7.31-7.34 (m, 2H), 7.48 (d, J=8.1 Hz, 1H), 7.52 (t, J=7.8 Hz, 1H), 7.71 (d, J=7.5 Hz, 1H), 7.76 (d, J=7.8 Hz, 1H), 7.79 (s, 1H), 8.11 (s, 1H), 9.16 (s, 1H), 10.40 (s, 1H). LCMS t=5.9 min, m/z Calcd for $C_{19}H_{18}BrN_2O_2$; $C_{19}H_{17}BrN_2NaO_2$; $C_{38}H_{35}BrN_4O_4$; $C_{38}H_{34}BrN_4NaO_6$ 385.06, 387.05; 407.04, 409.04; 771.10; 793.08 [M+H]$^+$; [M+Na]$^+$; [2M+H]$^+$; [2M+Na]$^+$, Found 385.06, 387.06; 407.04, 409.04; 771.12; 793.11.

Example 04-10

Preparation of N-(4-bromophenyl)-3-((2-methyl-3-oxocyclopent-1-en-1-yl)amino)benzamide (04-10)

The title compound was prepared from Example 01-03 and 4-bromoaniline according to the procedure of Example 04-04; 1.1 mmol scale yielded 10 mg after chromatography (ESS=EtOAc) and recrystallization from CHCl$_3$ (2% yield). $^1$H NMR (D6-DMSO) δ 1.60 (s, 3H), 2.23-2.26 (m, 2H), 2.71-2.73 (m, 2H), 7.47-7.48 (m, 1H), 7.51 (t, J=7.7 Hz, 1H), 7.55 (d, J=8.8 Hz, 2H), 7.70 (d, J=7.7 Hz, 1H), 7.76 (d, J=8.8 Hz, 2H), 7.79 (s, 1H), 9.14 (s, 1H), 10.38 (s, 1H). LCMS t=5.9 min, m/z Calcd for $C_{19}H_{18}BrN_2O_2$; $C_{19}H_{17}BrN_2NaO_2$; $C_{38}H_{35}BrN_4O_4$; $C_{38}H_{34}BrN_4NaO_6$ 385.06, 387.05; 407.04, 409.04; 771.10; 793.08 [M+H]$^+$; [M+Na]$^+$; [2M+H]$^+$; [2M+Na]$^+$, Found 385.06, 387.06; 407.04, 409.03; 771.12; 793.11.

Example 04-11

Preparation of 3-((2-methyl-3-oxocyclopent-1-en-1-yl)amino)-N-(3-(trifluoromethyl)phenyl)-benzamide (04-11)

The title compound was prepared from Example 01-03 and 3-(trifluoromethyl)aniline according to the procedure of Example 04-04; 1.1 mmol scale yielded 30 mg after chromatography (ESS=EtOAc) and recrystallization from CHCl$_3$ (7% yield). $^1$H NMR (D6-DMSO) δ 1.60 (s, 3H), 2.23-2.25 (m, 2H), 2.71-2.73 (m, 2H), 7.46-7.50 (m, 2H), 7.53 (t, J=7.8 Hz, 1H), 7.61 (t, J=8.0 Hz, 1H), 7.74 (d, J=7.6 Hz, 1H), 7.82 (s, 1H), 8.06 (d, J=8.2 Hz, 1H), 8.25 (s, 1H), 9.16 (s, 1H), 10.56 (s, 1H). LCMS t=6.1 min, m/z Calcd for $C_{20}H_{18}F_3N_2O_2$; $C_{20}H_{17}F_3N_2NaO_2$; $C_{40}H_{35}F_6N_4O_4$; $C_{40}H_{34}F_6N_4NaO_6$ 375.13; 397.11; 749.26; 771.24 [M+H]$^+$; [M+Na]$^+$; [2M+H]$^+$; [2M+Na]$^+$, Found 375.14; 397.12; 749.27; 771.26.

Example 04-12

Preparation of 3-((2-methyl-3-oxocyclopent-1-en-1-yl)amino)-N-(4-(trifluoromethyl)phenyl)-benzamide (04-12)

The title compound was prepared from Example 01-03 and 3-(trifluoromethyl)aniline according to the procedure of Example 04-04; 1.1 mmol scale yielded 10 mg after chromatography (ESS=EtOAc) and recrystallization from CHCl$_3$ (2% yield). $^1$H NMR (D6-DMSO) δ 1.60 (s, 3H), 2.23-2.25 (m, 2H), 2.71-2.73 (m, 1H), 7.49-7.50 (m, 1H), 7.53 (t, J=7.7 Hz, 1H), 7.72-7.75 (m, 3H), 7.81 (s, 1H), 8.01 (d, J=8.5 Hz, 2H), 9.16 (s, 1H), 10.59 (s, 1H). LCMS t=6.1 min, m/z Calcd for $C_{20}H_{18}F_3N_2O_2$; $C_{20}H_{17}F_3N_2NaO_2$;

$C_{40}H_{34}F_6N_4NaO_6$ 375.13; 397.11; 771.24 [M+H]$^+$; [M+Na]$^+$; [2M+Na]$^+$, Found 375.16; 397.12; 771.26.

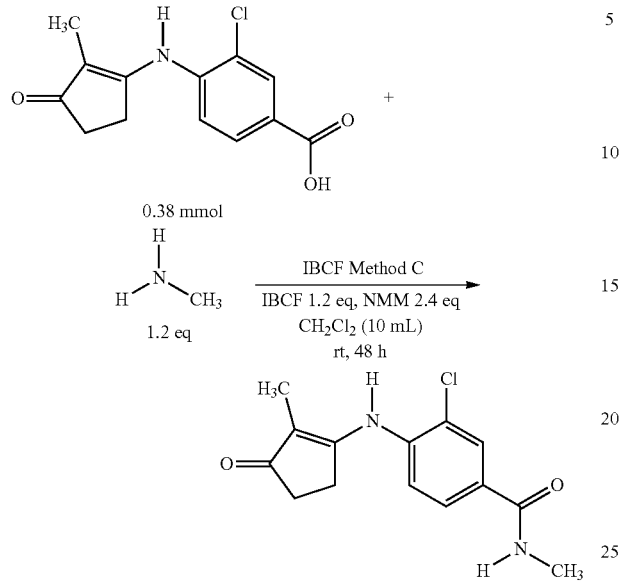

Example 04-13

Preparation of 3-chloro-N-methyl-4-((2-methyl-3-oxocyclopent-1-en-1-yl)amino)benzamide (04-13)

Method C; NMM (1.2 eq) and IBCF (1.2 eq) were added to Example 02-02 (100 mg, 0.38 mmol, 1.0 eq), stirring in CH$_2$Cl$_2$ (10 mL), in a screw-capped vial. After stirring for 30 min amine, methylamine (2M, 225 mL, 0.45 mmol, 1.2 eq), and a second aliquot of NMM (1.2 eq) were added, sealed, and stirred at rt for 48 h. Crude materials were added directly to KP-Sil™ columns (10 g) with products separating from impurities using stepwise gradients (see Example 04-04 Method B) on the Biotage®-Isolera Four instrument, monitoring UV Trace at 254/365 nm. Some reactions performed at higher concentrations allowed the crude solid product to precipitate. In these cases the purification was filtration with CH$_2$Cl$_2$, H2O, and diethyl ether rinsing. The reaction on a 0.38 mmol scale yielded 35 mg of the title compound after chromatography (ESS=MeOH (6%)) and EtOAc trituration (33% yield). $^1$H NMR (D6-DMSO) δ 1.45 (s, 3H), 2.21-2.23 (m, 2H), 2.47-2.49 (m, 2H), 2.78 (s, 3H), 7.44 (d, J=8.3 Hz, 1H), 7.80 (d, J=8.2 Hz, 1H), 7.98 (s, 1H), 8.56-8.58 (m, 1H), 8.93 (s, 1H). LCMS t=5.1 min, m/z Calcd for $C_{14}H_{16}ClN_2O_2$; $C_{14}H_{15}ClN_2NaO_2$; $C_{28}H_{31}Cl_2N_4O_4$; $C_{28}H_{30}Cl_2N_4NaO_4$ 279.09; 301.07; 557.17; 579.15 [M+H]$^+$; [M+Na]$^+$; [2M+H]$^+$; [2M+Na]$^+$, Found 279.14; 301.11; 557.16; 579.15.

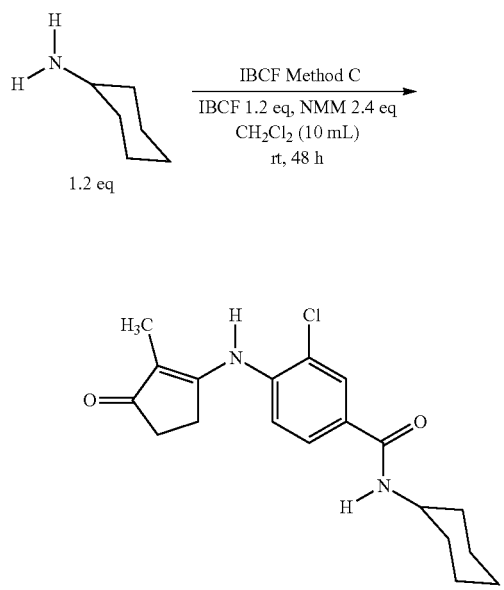

Example 04-14

Preparation of 3-chloro-N-cyclohexyl-4-((2-methyl-3-oxocyclopent-1-en-1-yl)amino)benzamide (04-14)

The title compound was prepared from Example 02-02 and cyclohexylamine according to the procedure of Example 04-13; 0.38 mmol scale yielded 56 mg after chromatography (ESS=EtOAc) and EtOAc trituration (43% yield). $^1$H NMR (D6-DMSO) δ 1.10-1.18 (m, 1H), 1.23-1.34 (m, 4H), 1.45 (s, 3H), 1.61 (d, J=12.1 Hz, 1H), 1.73 (s, 2H), 1.81 (s, 2H), 2.20-2.23 (m, 2H), 2.46-2.48 (m, 2H), 3.75 (s, 1H), 7.42 (d, J=8.3 Hz, 1H), 7.82 (d, J=8.2 Hz, 1H), 8.00 (d, J=1.3 Hz, 1H), 8.34 (d, J=7.8 Hz, 1H), 8.95 (s, 1H). LCMS t=6.0 min, m/z Calcd for $C_{19}H_{24}ClN_2O_2$; $C_{19}H_{23}ClN_2NaO_2$; $C_{36}H_{47}Cl_2N_4O_4$; $C_{36}H_{47}Cl_2N_4NaO_4$ 347.15; 369.13; 693.30; 715.28 [M+H]$^+$; [M+Na]$^+$; [2M+H]$^+$; [2M+Na]$^+$, Found 347.17; 369.15; 693.32; 715.30.

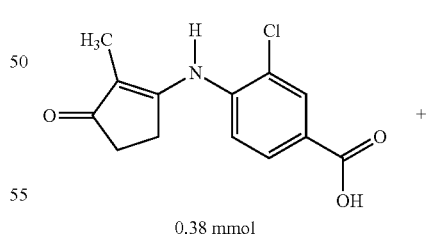

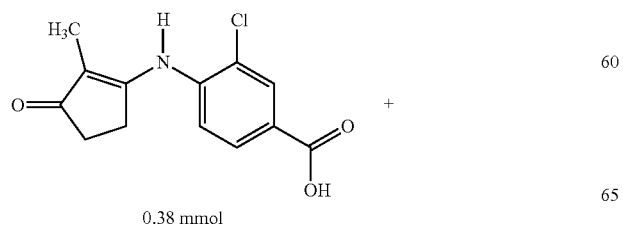

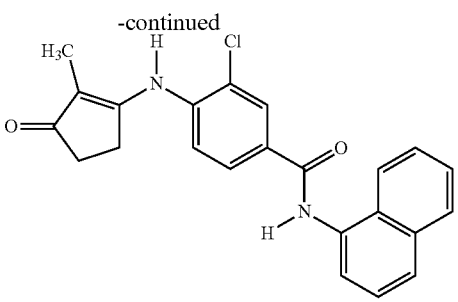

Example 04-15

Preparation of 3-chloro-4-((2-methyl-3-oxocyclopent-1-en-1-yl)amino)-N-(naphthalen-1-yl)-benzamide (04-15)

The title compound was prepared from Example 02-02 and 1-aminonaphthalene according to the procedure of Example 04-13; 0.38 mmol scale yielded 25 mg after chromatography (ESS=H:E (1:19)) and EtOAc trituration (17% yield). $^1$H NMR (D6-DMSO) δ 1.51 (s, 3H), 2.24-2.26 (m, 2H), 2.54-2.56 (m, 2H), 7.52-7.61 (m, 4H), 7.89 (d, J=8.0 Hz, 1H), 7.98-8.01 (m, 3H), 8.06 (d, J=7.7 Hz, 1H), 8.27 (s, 1H), 9.03 (s, 1H), 10.55 (s, 1H). LCMS t=5.9 min, m/z Calcd for $C_{23}H_{20}ClN_2O_2$; $C_{23}H_{19}ClN_2NaO_2$; $C_{46}H_{39}Cl_2N_4O_4$; $C_{46}H_{38}Cl_2N_4NaO_4$ 391.12; 413.10; 781.23; 803.22 [M+H]$^+$; [M+Na]$^+$; [2M+H]$^+$; [2M+Na]$^+$, Found 391.22; 413.11; 781.26; 803.25.

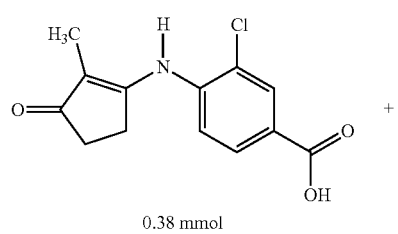

0.38 mmol

+

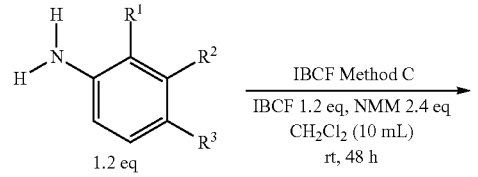

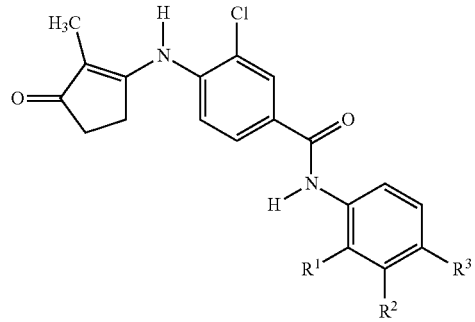

| EXAMPLE 04-# | TITLE COMPOUND NAME | R$^1$ | R$^2$ | R$^3$ |
|---|---|---|---|---|
| 16 | 3-Chloro-4-((2-methyl-3-oxocyclopent-1-en-1-yl)amino)-N-phenylbenzamide | H | H | H |
| 17 | 3-Chloro-N-(2-methoxyphenyl)-4-((2-methyl-3-oxocyclopent-1-en-1-yl)amino)benzamide | OCH$_3$ | H | H |
| 18 | 3-Chloro-N-(3-methoxyphenyl)-4-((2-methyl-3-oxocyclopent-1-en-1-yl)amino)benzamide | H | OCH$_3$ | H |
| 19 | 3-Chloro-N-(4-methoxyphenyl)-4-((2-methyl-3-oxocyclopent-1-en-1-yl)amino)benzamide | H | H | OCH$_3$ |
| 20 | 3-Chloro-4-((2-methyl-3-oxocyclopent-1-en-1-yl)amino)-N-(o-tolyl)benzamide | CH$_3$ | H | H |
| 21 | 3-Chloro-4-((2-methyl-3-oxocyclopent-1-en-1-yl)amino)-N-(m-tolyl)benzamide | H | CH$_3$ | H |
| 22 | 3-Chloro-4-((2-methyl-3-oxocyclopent-1-en-1-yl)amino)-N-(p-tolyl)benzamide | H | H | CH$_3$ |

Example 04-16

Preparation of 3-chloro-4-((2-methyl-3-oxocyclopent-1-en-1-yl)amino)-N-phenylbenzamide (04-16)

The title compound was prepared from Example 02-02 and aniline according to the procedure of Example 04-13; 0.38 mmol scale yielded 20 mg after chromatography (ESS=H:E (1:19)) and EtOAc trituration (16% yield). $^1$H NMR (D6-DMSO) δ 1.48 (s, 3H), 2.23-2.25 (m, 2H), 2.50-2.51 (m, 2H), 7.12 (t, J=7.3 Hz, 1H), 7.37 (t, J=7.8 Hz, 2H), 7.50 (d, J=8.3 Hz, 1H), 7.77 (d, J=7.9 Hz, 2H), 7.94 (dd, J=8.2, 1.4 Hz, 1H), 8.14 (d, J=1.4 Hz, 1H), 9.00 (s, 1H), 10.34 (s, 1H). LCMS t=5.8 min, m/z Calcd for $C_{19}H_{18}ClN_2O_2$; $C_{19}H_{17}ClN_2NaO_2$; $C_{38}H_{34}Cl_2N_4NaO_4$ 341.11; 363.09; 703.19 [M+H]$^+$; [M+Na]$^+$; [2M+Na]$^+$, Found 341.13; 363.10; 703.20.

Example 04-17

Preparation of 3-chloro-N-(2-methoxyphenyl)-4-((2-methyl-3-oxocyclopent-1-en-1-yl)amino)benzamide (04-17)

The title compound was prepared from Example 02-02 and o-anisidine according to the procedure of Example 04-13; 0.38 mmol scale yielded 55 mg after chromatography (ESS=H:E (1:19)) and EtOAc trituration (39% yield). $^1$H NMR (D6-DMSO) δ 1.48 (s, 3H), 2.22-2.25 (m, 2H), 2.50-2.52 (m, 2H), 3.83 (s, 3H), 6.97 (t, J=7.6 Hz, 1H), 7.10 (d, J=8.1 Hz, 1H), 7.21 (t, J=7.6 Hz, 1H), 7.48 (d, J=8.3 Hz, 1H), 7.65 (d, J=7.6 Hz, 1H), 7.94 (d, J=8.1 Hz, 1H), 8.13 (s, 1H), 9.00 (s, 1H), 9.67 (s, 1H). LCMS t=5.9 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.11; 393.10; 741.22; 763.21 [M+H]$^+$; [M+Na]$^+$; [2M+H]$^+$; [2M+Na]$^+$, Found 371.13; 393.11; 741.26; 763.24.

Example 04-18

Preparation of 3-chloro-N-(3-methoxyphenyl)-4-((2-methyl-3-oxocyclopent-1-en-1-yl)amino)benzamide (04-18)

The title compound was prepared from Example 02-02 and m-anisidine according to the procedure of Example 04-13; 0.38 mmol scale yielded 3 mg after chromatography (ESS=H:E (1:19)) and EtOAc trituration (2% yield). $^1$H NMR (D6-DMSO) δ 1.48 (s, 3H), 2.23-2.25 (m, 2H), 2.50-2.52 (m, 2H), 3.76 (s, 3H), 6.70 (d, J=8.3 Hz, 1H), 7.26 (t, J=8.3 Hz, 1H), 7.37 (d, J=8.3 Hz, 1H), 7.45 (s, 1H), 7.49 (d, J=8.3 Hz, 1H), 7.93 (dd, J=8.3, 1.6 Hz, 1H), 8.13 (d, J=1.6 Hz, 1H), 9.00 (s, 1H), 10.30 (s, 1H). LCMS t=5.8 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.11; 393.10; 741.22; 763.21 [M+H]$^+$; [M+Na]$^+$; [2M+H]$^+$; [2M+Na]$^+$, Found 371.13; 393.11; 741.26; 763.23.

Example 04-19

Preparation of 3-chloro-N-(4-methoxyphenyl)-4-((2-methyl-3-oxocyclopent-1-en-1-yl)amino)benzamide (04-19)

The title compound was prepared from Example 02-02 and 4-aminoanisole according to the procedure of Example 04-13; 0.38 mmol scale yielded 5 mg after chromatography (ESS=H:E (1:19)) and EtOAc trituration (4% yield). $^1$H NMR (D6-DMSO) δ 1.48 (s, 3H), 2.22-2.25 (m, 2H), 2.50-2.51 (m, 2H), 3.75 (s, 3H), 6.94 (d, J=8.9 Hz, 2H), 7.49 (d, J=8.3 Hz, 1H), 7.66 (d, J=8.9 Hz, 2H), 7.93 (dd, J=8.3, 1.2 Hz, 1H), 8.12 (s, 1H), 8.98 (s, 1H), 10.22 (s, 1H). LCMS t=5.7 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.11; 393.10; 741.22; 763.21 [M+H]$^+$; [M+Na]$^+$; [2M+H]$^+$; [2M+Na]$^+$, Found 371.13; 393.10; 741.24; 763.23.

Example 04-20

Preparation of 3-chloro-4-((2-methyl-3-oxocyclopent-1-en-1-yl)amino)-N-(o-tolyl)benzamide (04-20)

The title compound was prepared from Example 02-02 and o-toluidine according to the procedure of Example 04-13; 0.38 mmol scale yielded 45 mg after chromatography (ESS=H:E (1:19)) and EtOAc trituration (32% yield). $^1$H NMR (D6-DMSO) δ 1.48 (s, 3H), 2.23-2.25 (m, 5H), 2.50-2.51 (m, 2H), 7.18-7.23 (m, 2H), 7.28 (d, J=7.3 Hz, 1H), 7.32 (d, J=7.5 Hz, 1H), 7.50 (d, J=8.3 Hz, 1H), 7.96 (d, J=8.1 Hz, 1H), 8.14 (s, 1H), 8.99 (s, 1H), 10.02 (s, 1H). LCMS t=5.7 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]$^+$; [M+Na]$^+$; [2M+H]$^+$; [2M+Na]$^+$, Found 355.14; 377.12; 709.25; 731.24.

Example 04-21

Preparation of 3-chloro-4-((2-methyl-3-oxocyclopent-1-en-1-yl)amino)-N-(m-tolyl)benzamide (04-21)

The title compound was prepared from Example 02-02 and m-toluidine according to the procedure of Example 04-13; 0.38 mmol scale yielded 42 mg after chromatography (ESS=H:E (1:19)) and EtOAc trituration (30% yield). $^1$H NMR (D6-DMSO) δ 1.48 (s, 3H), 2.22-2.25 (m, 2H), 2.31 (s, 3H), 2.50-2.51 (m, 2H), 6.94 (d, J=7.4 Hz, 1H), 7.24 (t, J=7.8 Hz, 1H), 7.49 (d, J=8.3 Hz, 1H), 7.56 (d, J=8.0 Hz, 1H), 7.61 (s, 1H), 7.93 (d, J=8.3 Hz, 1H), 8.13 (d, J=1.2 Hz, 1H), 8.98 (s, 1H), 10.26 (s, 1H). LCMS t=5.9 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]$^+$; [M+Na]$^+$; [2M+H]$^+$; [2M+Na]$^+$, Found 355.14; 377.12; 709.25; 731.24.

Example 04-22

Preparation of 3-chloro-4-((2-methyl-3-oxocyclopent-1-en-1-yl)amino)-N-(p-tolyl)benzamide (04-22)

The title compound was prepared from Example 02-02 and p-toluidine according to the procedure of Example 04-13; 0.38 mmol scale yielded 25 mg after chromatography (ESS=H:E (1:19)) and EtOAc trituration (18% yield). $^1$H NMR (D6-DMSO) δ 1.48 (s, 3H), 2.23-2.24 (m, 2H), 2.29 (s, 3H), 2.50-2.51 (m, 2H), 7.17 (d, J=8.1 Hz, 2H), 7.49 (d, J=8.3 Hz, 1H), 7.64 (d, J=8.1 Hz, 2H), 7.93 (d, J=8.2 Hz, 1H), 8.13 (s, 1H), 8.96 (s, 1H), 10.25 (s, 1H). $^{13}$C NMR (D6-DMSO) δ 7.7, 20.5, 25.7, 32.7, 110.8, 120.5, 127.2, 128.8, 128.9, 129.0, 132.9, 136.4, 139.4, 163.3, 168.7, 202.7. LCMS t=5.9 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]$^+$; [M+Na]$^+$; [2M+H]$^+$; [2M+Na]$^+$, Found 355.12; 377.10; 709.21; 731.20.

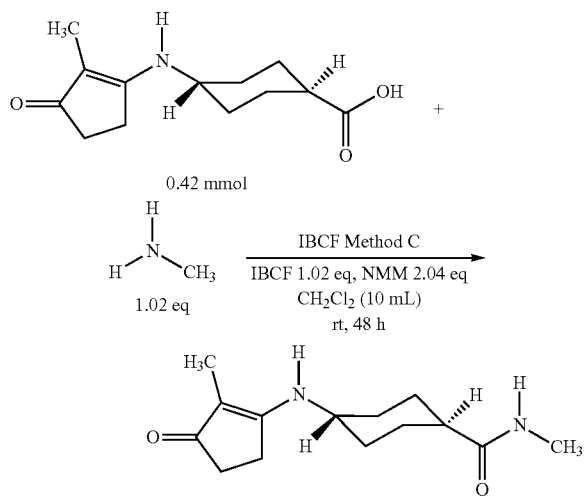

Example 04-23

Preparation of (1R,4R)—N-methyl-4-((2-methyl-3-oxocyclopent-1-en-1-yl)amino)cyclohexanecarboxamide (04-23)

The title compound was prepared from Example 01-33 and methylamine according to the procedure of Example 04-13; 0.42 mmol scale yielded 40 mg after chromatography (ESS=MeOH (15%)) and EtOAc trituration (38% yield). $^1$H NMR (D6-DMSO) δ 1.33-1.50 (m, 9H), 1.73 (d, J=12.0 Hz, 2H), 1.84 (d, J=10.6 Hz, 2H), 2.04-2.09 (m, 1H), 2.09-2.11 (2H), 2.54 (d, J=4.5 Hz, 2H), 3.25-3.30 (m, 1H), 6.84-6.87 (m, 1H), 7.70 (d, J=4.3 Hz, 1H). LCMS t=1.2 min, m/z Calcd for $C_{14}H_{23}N_2O_2$; $C_{14}H_{22}N_2NaO_2$; $C_{28}H_{45}N_4O_4$; $C_{28}H_{44}N_4NaO_4$ 251.18; 273.16; 501.34; 523.33 [M+H]$^+$; [M+Na]$^+$; [2M+H]$^+$; [2M+Na]$^+$, Found 251.28; 273.25; 501.41; 523.40.

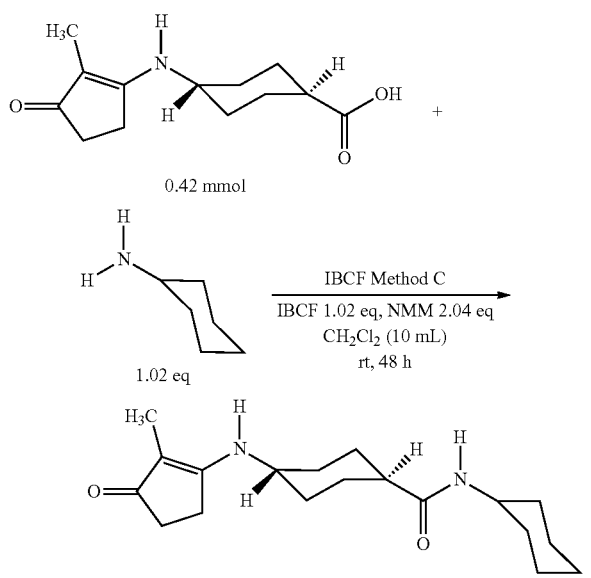

Example 04-24

Preparation of (1R,4R)—N-cyclohexyl-4-((2-methyl-3-oxocyclopent-1-en-1-yl)amino)-cyclohexanecarboxamide (04-24)

The title compound was prepared from Example 01-33 and cyclohexylamine according to the procedure of Example 04-13; 0.42 mmol scale yielded 75 mg after chromatography (ESS=MeOH (8%)) and EtOAc trituration (56% yield). $^1$H NMR (D6-DMSO) δ 1.10-1.18 (m, 4H), 1.20-1.28 (m, 2H), 1.30-1.40 (m, 2H), 1.40-1.50 (5H), 1.54 (d, J=10.8 Hz, 1H), 1.62-1.75 (m, 7H), 1.83 (d, J=10.4 Hz, 1H), 2.00-2.08 (m, 1H), 2.10-2.13 (m, 2H), 3.46-3.53 (m, 1H), 6.85-6.67 (m, 1H), 7.57 (d, J=7.4 Hz, 1H). LCMS t=5.4 min, m/z Calcd for $C_{19}H_{31}N_2O_2$; $C_{19}H_{30}N_2NaO_2$; $C_{38}H_{61}N_4NaO_4$; $C_{38}H_{60}N_4NaO_4$ 319.24; 341.22; 637.47; 659.45 [M+H]$^+$; [M+Na]$^+$; [2M+H]$^+$; [2M+Na]$^+$, Found 319.32; 341.29; 637.57; 659.60.

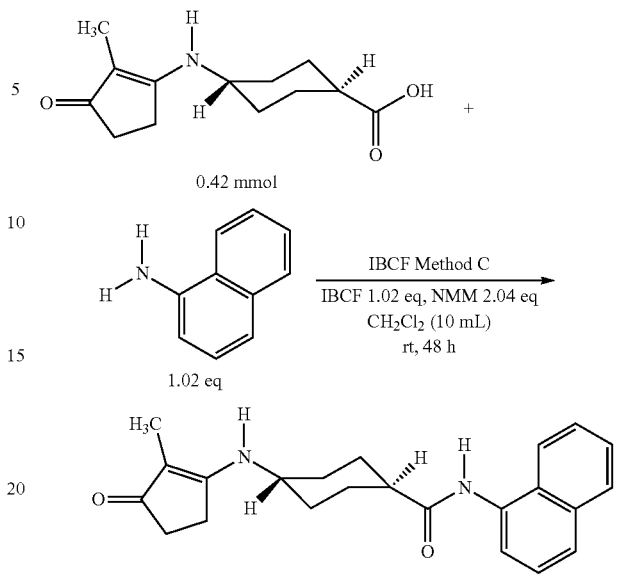

Example 04-25

Preparation of (1R,4R)-4-((2-methyl-3-oxocyclopent-1-en-1-yl)amino)-N-(naphthalen-1-yl)cyclohexanecarboxamide (04-25)

The title compound was prepared from Example 01-33 and 1-aminonaphthalene according to the procedure of Example 04-13; 0.42 mmol scale yielded 23 mg after chromatography (ESS=MeOH (8%)) and EtOAc trituration (15% yield). $^1$H NMR (D6-DMSO) δ 1.45-1.55 (m, 5H), 1.62 (q, J=12.1 Hz, 2H), 1.94 (d, J=10.8 Hz, 2H), 2.01 (d, J=12.7 Hz, 2H), 2.11-2.13 (m, 2H), 2.51-2.55 (m, 3H), 3.35-3.45 (m, 1H), 6.92 (d, J=7.7 Hz, 1H), 7.48 (t, J=7.8 Hz, 1H), 7.52-7.57 (m, 2H), 7.65 (d, J=7.3 Hz, 1H), 7.76 (d, J=8.1 Hz, 1H), 7.94 (d, J=7.1 Hz, 1H), 8.04 (d, J=7.7 Hz, 1H), 9.85 (s, 1H). LCMS t=5.6 min, m/z Calcd for $C_{23}H_{27}N_2O_2$; $C_{23}H_{26}N_2NaO_2$; $C_{46}H_{53}N_4O_4$; $C_{46}H_{52}N_4NaO_4$ 363.21; 385.18; 725.41; 747.39 [M+H]$^+$; [M+Na]$^+$; [2M+H]$^+$; [2M+Na]$^+$, Found 363.34; 385.25; 725.53; 747.52.

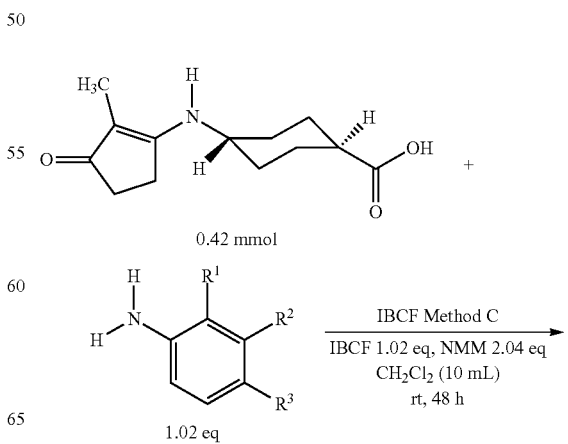

-continued

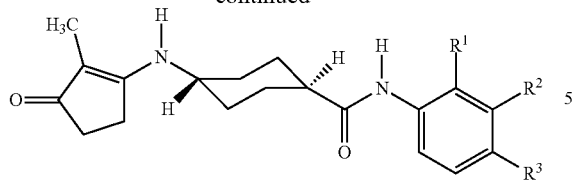

| EXAMPLE 04-# | TITLE COMPOUND NAME | R$^1$ | R$^2$ | R$^3$ |
|---|---|---|---|---|
| 26 | (1R,4R)-4-((2-Methyl-3-oxocyclopent-1-en-1-yl)amino)-N-phenylcyclohexanecarboxamide | H | H | H |
| 27 | (1R,4R)-N-(2-Methoxyphenyl)-4-((2-methyl-3-oxocyclopent-1-en-1-yl)amino)cyclohexanecarboxamide | OCH$_3$ | H | H |
| 28 | (1R,4R)-N-(3-Methoxyphenyl)-4-((2-methyl-3-oxocyclopent-1-en-1-yl)amino)cyclohexanecarboxamide | H | OCH$_3$ | H |
| 29 | (1R,4R)-N-(4-Methoxyphenyl)-4-((2-methyl-3-oxocyclopent-1-en-1-yl)amino)cyclohexanecarboxamide | H | H | OCH$_3$ |
| 30 | (1R,4R)-4-((2-Methyl-3-oxocyclopent-1-en-1-yl)amino)-N-(o-tolyl)cyclohexanecarboxamide | CH$_3$ | H | H |
| 31 | (1R,4R)-4-((2-Methyl-3-oxocyclopent-1-en-1-yl)amino)-N-(m-tolyl)cyclohexanecarboxamide | H | CH$_3$ | H |
| 32 | (1R,4R)-4-((2-Methyl-3-oxocyclopent-1-en-1-yl)amino)-N-(p-tolyl)cyclohexanecarboxamide | H | H | CH$_3$ |
| 33 | (1R,4R)-N-(3-Fluorophenyl)-4-((2-methyl-3-oxocyclopent-1-en-1-yl)amino)cyclohexanecarboxamide | H | F | H |
| 34 | (1R,4R)-N-(4-Chlorophenyl)-4-((2-methyl-3-oxocyclopent-1-en-1-yl)amino)cyclohexanecarboxamide | H | H | Cl |

Example 04-26

Preparation of (1R,4R)-4-((2-methyl-3-oxocyclopent-1-en-1-yl)amino)-N-phenylcyclohexane-carboxamide (04-26)

The title compound was prepared from Example 01-33 and aniline according to the procedure of Example 04-13; 0.42 mmol scale yielded 65 mg after chromatography (ESS=MeOH (10%)) and EtOAc trituration (50% yield). $^1$H NMR (D6-DMSO) δ 1.38-1.60 (m, 8H), 1.83-1.98 (m, 5H), 2.08-2.18 (m, 2H), 2.28-2.39 (m, 1H), 3.28-3.30 (m, 1H), 6.89 (s, 1H), 7.01 (s, 1H), 7.28 (s, 2H), 7.60 (s, 2H), 9.85 (s, 1H). LCMS t=5.4 min, m/z Calcd for C$_{19}$H$_{25}$N$_2$O$_2$; C$_{19}$H$_{24}$N$_2$NaO$_2$; C$_{38}$H$_{49}$N$_4$O$_4$; C$_{38}$H$_{48}$N$_4$NaO$_4$ 313.19; 335.17; 625.37; 647.36 [M+H]$^+$; [M+Na]$^+$; [2M+H]$^+$; [2M+Na]$^+$, Found 313.27; 335.25; 625.47; 647.46.

Example 04-27

Preparation of (1R,4R)—N-(2-methoxyphenyl)-4-((2-methyl-3-oxocyclopent-1-en-1-yl)amino)cyclohexanecarboxamide (04-27)

The title compound was prepared from Example 01-33 and o-anisidine according to the procedure of Example 04-13; 0.42 mmol scale yielded 75 mg after chromatography (ESS=MeOH (8%)) and EtOAc trituration (52% yield). $^1$H NMR (D6-DMSO) δ 1.40-1.56 (m, 8H) 1.84-1.89 (m, 5H), 2.10-2.12 (m, 2H), 2.47-2.52 (m, 2H), 3.83 (s, 3H), 6.86-6.91 (m, 2H), 7.01-7.07 (m, 2H), 7.94 (d, J=7.8 Hz, 1H), 9.02 (s, 1H). LCMS t=5.5 min, m/z Calcd for C$_{20}$H$_{27}$N$_2$O$_3$; C$_{20}$H$_{26}$N$_2$NaO$_3$; C$_{40}$H$_{53}$N$_4$O$_6$; C$_{40}$H$_{52}$N$_4$NaO$_6$ 343.20; 365.18; 685.40; 707.38 [M+H]$^+$; [M+Na]$^+$; [2M+H]$^+$; [2M+Na]$^+$, Found 343.30; 365.25; 685.51; 707.57.

Example 04-28

Preparation of (1R,4R)—N-(3-methoxyphenyl)-4-((2-methyl-3-oxocyclopent-1-en-1-yl)amino)cyclohexanecarboxamide (04-28)

The title compound was prepared from Example 01-33 and m-anisidine according to the procedure of Example 04-13; 0.42 mmol scale yielded 70 mg after chromatography (ESS=MeOH (8%)) and EtOAc trituration (49% yield). $^1$H NMR (D6-DMSO) δ 1.40-1.57 (m, 7H), 1.85-1.91 (m, 5H), 2.11-2.13 (m, 2H), 2.28 (t, J=11.6 Hz, 1H), 2.52-2.54 (m, 2H), 3.71 (s, 3H), 6.60 (d, J=7.6 Hz, 1H), 6.89 (d, J=7.9 Hz, 1H), 7.13 (d, J=7.8 Hz, 1H), 7.18 (d, J=8.0 Hz, 1H), 7.32 (s, 1H), 9.84 (s, 1H). LCMS t=5.4 min, m/z Calcd for C$_{20}$H$_{27}$N$_2$O$_3$; C$_{20}$H$_{26}$N$_2$NaO$_3$; C$_{40}$H$_{53}$N$_4$O$_6$; C$_{40}$H$_{52}$N$_4$NaO$_6$ 343.20; 365.18; 685.40; 707.38 [M+H]$^+$; [M+Na]$^+$; [2M+H]$^+$; [2M+Na]$^+$, Found 343.27; 365.25; 685.51; 707.50.

Example 04-29

Preparation of (1R,4R)—N-(4-methoxyphenyl)-4-((2-methyl-3-oxocyclopent-1-en-1-yl)amino)cyclohexanecarboxamide (04-29)

The title compound was prepared from Example 01-33 and p-anisidine according to the procedure of Example 04-13; 0.42 mmol scale yielded 35 mg after chromatography (ESS=MeOH (8%)) and EtOAc trituration (24% yield). $^1$H NMR (D6-DMSO) δ 1.38-1.58 (m, 7H), 1.84-1.90 (m, 5H), 2.10-2.12 (m, 2H), 2.25 (t, J=11.7 Hz, 1H), 2.51-2.54 (m, 2H), 3.71 (s, 3H), 6.84-6.89 (m, 3H), 7.50 (d, J=8.7 Hz, 2H), 9.71 (s, 1H). LCMS t=5.3 min, m/z Calcd for C$_{20}$H$_{27}$N$_2$O$_3$; C$_{20}$H$_{26}$N$_2$NaO$_3$; C$_{40}$H$_{53}$N$_4$O$_6$; C$_{40}$H$_{52}$N$_4$NaO$_6$ 343.20; 365.18; 685.40; 707.38 [M+H]$^+$; [M+Na]$^+$; [2M+H]$^+$; [2M+Na]$^+$, Found 343.27; 365.25; 685.50; 707.49.

Example 04-30

Preparation of (1R,4R)-4-((2-methyl-3-oxocyclopent-1-en-1-yl)amino)-N-(o-tolyl)cyclohexanecarboxamide (04-30)

The title compound was prepared from Example 01-33 and o-toluidine according to the procedure of Example 04-13; 0.42 mmol scale yielded 22 mg after chromatography (ESS=MeOH (7%)) and EtOAc trituration (16% yield). $^1$H NMR (D6-DMSO) δ 1.41-1.59 (m, 7H), 1.89-1.92 (m, 4H), 2.11-2.13 (m, 2H), 2.18 (s, 3H), 2.37 (t, J=10.9 Hz, 1H), 2.51-2.53 (m, 2H), 6.88-6.93 (m, 1H), 7.07 (t, J=6.9 Hz, 1H), 7.14 (t, J=7.1 Hz, 1H), 7.19 (d, J=7.1 Hz, 1H), 7.33 (d, J=7.5 Hz, 1H), 9.22 (s, 1H). LCMS t=5.3 min, m/z Calcd for $C_{20}H_{27}N_2O_2$; $C_{20}H_{26}N_2NaO_2$; $C_{40}H_{53}N_4O_4$; $C_{40}H_{52}N_4NaO_4$ 327.21; 349.19; 653.41; 675.39 [M+H]$^+$; [M+Na]$^+$; [2M+H]$^+$; [2M+Na]$^+$, Found 327.28; 349.26; 653.50; 675.49.

Example 04-31

Preparation of (1R,4R)-4-((2-methyl-3-oxocyclopent-1-en-1-yl)amino)-N-(m-tolyl)cyclohexanecarboxamide (04-31)

The title compound was prepared from Example 01-33 and m-toluidine according to the procedure of Example 04-13; 0.42 mmol scale yielded 70 mg after chromatography (ESS=MeOH (7%)) and EtOAc trituration (51% yield). $^1$H NMR (D6-DMSO) δ 1.38-1.58 (m, 7H), 1.84-1.91 (m, 4H), 2.10-2.12 (m, 2H), 2.26-2.31 (m, 4H), 2.51-2.53 (m, 2H), 3.33-3.35 (m, 1H), 6.83 (d, J=7.4 Hz, 1H), 6.88 (d, J=8.3 Hz, 1H), 7.5 (d, J=7.8 Hz, 1H), 7.36 (d, J=8.0 Hz, 1H), 7.46 (s, 1H), 9.77 (s, 1H). LCMS t=5.5 min, m/z Calcd for $C_{20}H_{27}N_2O_2$; $C_{20}H_{26}N_2NaO_2$; $C_{40}H_{53}N_4O_4$; $C_{40}H_{52}N_4NaO_4$ 327.21; 349.19; 653.41; 675.39 [M+H]$^+$; [M+Na]$^+$; [2M+H]$^+$; [2M+Na]$^+$, Found 327.28; 349.26; 653.50; 675.49.

Example 04-32

Preparation of (1R,4R)-4-((2-methyl-3-oxocyclopent-1-en-1-yl)amino)-N-(p-tolyl)-cyclohexanecarboxamide (04-32)

The title compound was prepared from Example 01-33 and p-toluidine according to the procedure of Example 04-13; 0.42 mmol scale yielded 60 mg after chromatography (ESS=MeOH (7%)) and EtOAc trituration (44% yield). $^1$H NMR (D6-DMSO) δ 1.28-1.58 (m, 7H), 1.84-1.90 (m, 4H), 2.10-2.12 (m, 2H), 2.23-2.30 (m, 4H), 2.51-2.53 (m, 2H), 3.30-3.35 (m, 1H), 6.89 (d, J=8.4 Hz, 1H), 7.08 (d, J=8.1 Hz, 2H), 7.48 (d, J=8.2 Hz, 2H), 9.76 (s, 1H). $^{13}$C NMR (D6-DMSO) δ 6.8, 20.4, 23.8, 28.1, 32.5, 32.7, 43.8, 51.6, 105.0, 119.0, 129.0, 131.8, 136.9, 172.1, 173.6, 200.0. LCMS t=5.6 min, m/z Calcd for $C_{20}H_{27}N_2O_2$; $C_{20}H_{26}N_2NaO_2$; $C_{40}H_{53}N_4O_4$; $C_{40}H_{52}N_4NaO_4$ 327.21; 349.19; 653.41; 675.39 [M+H]$^+$; [M+Na]$^+$; [2M+H]$^+$; [2M+Na]$^+$, Found 327.28; 349.26; 653.50; 675.49.

Example 04-33

Preparation of (1R,4R)-N-(3-fluorophenyl)-4-((2-methyl-3-oxocyclopent-1-en-1-yl)amino)-cyclohexanecarboxamide (04-33)

The title compound was prepared from Example 01-33 and m-fluoroaniline according to the procedure of Example 04-13; 0.42 mmol scale yielded 72 mg after chromatography (ESS=MeOH (7%)) and EtOAc trituration (52% yield). $^1$H NMR (D6-DMSO) δ 1.38-1.57 (m, 7H), 1.86-1.91 (m, 4H), 2.10-2.12 (m, 2H), 2.29 (t, J=11.9 Hz, 1H), 2.51-2.53 (m, 2H), 3.33-2.35 (m, 1H), 6.83-6.90 (m, 2H), 7.29-7.33 (m, 2H), 7.61 (d, J=11.9 Hz, 1H), 10.08 (s, 1H). LCMS t=5.5 min, m/z Calcd for $C_{19}H_{24}FN_2O_2$; $C_{19}H_{23}FN_2NaO_2$; $C_{38}H_{47}F_2N_4O_4$; $C_{38}H_{46}F_2N_4NaO_4$ 331.18; 353.16; 661.36; 683.34 [M+H]$^+$; [M+Na]$^+$; [2M+H]$^+$; [2M+Na]$^+$, Found 331.27; 353.23; 661.45; 683.44.

Example 04-34

Preparation of (1R,4R)-N-(4-chlorophenyl)-4-((2-methyl-3-oxocyclopent-1-en-1-yl)amino)-cyclohexanecarboxamide (04-34)

The title compound was prepared from Example 01-33 and p-chloroaniline according to the procedure of Example 04-13; 0.42 mmol scale yielded 30 mg after chromatography (ESS=MeOH (7%)) and EtOAc trituration (21% yield). $^1$H NMR (D6-DMSO) δ 1.38-1.58 (m, 7H), 1.86-1.91 (m, 4H), 2.10-2.12 (m, 2H), 2.28 (t, J=11.9 Hz, 1H), 2.51-2.53 (m, 2H), 3.33-3.35 (m, 1H), 6.88 (d, J=8.3 Hz, 1H), 7.34 (d, J=8.8 Hz, 2H), 7.63 (d, J=8.7 Hz, 2H), 10.01 (s, 1H). LCMS t=5.7 min, m/z Calcd for $C_{19}H_{24}ClN_2O_2$; $C_{19}H_{23}ClN_2NaO_2$; $C_{38}H_{47}Cl_2N_4O_4$; $C_{38}H_{46}Cl_2N_4NaO_4$ 347.15; 369.13; 693.30; 715.28 [M+H]$^+$; [M+Na]$^+$; [2M+H]$^+$; [2M+Na]$^+$, Found 347.22; 369.20; 693.40; 715.39.

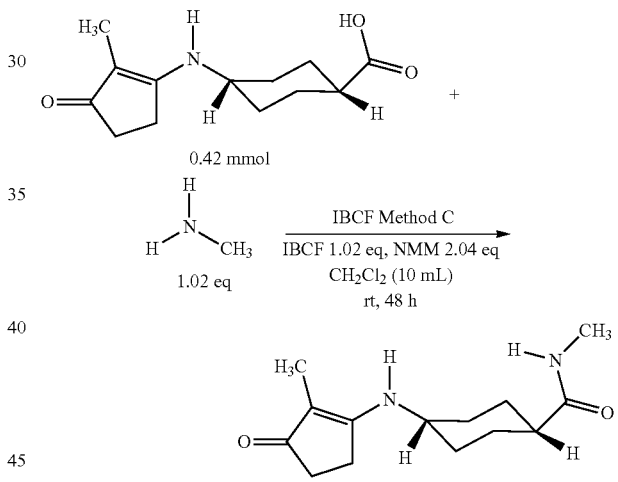

Example 04-35

Preparation of (1S,4S)-N-methyl-4-((2-methyl-3-oxocyclopent-1-en-1-yl)amino)cyclohexanecarboxamide (04-35)

The title compound was prepared from Example 01-34 and methylamine according to the procedure of Example 04-13; 0.42 mmol scale yielded 11 mg after chromatography (ESS=MeOH (12%)) and EtOAc trituration (10% yield). $^1$H NMR (D6-DMSO) δ 1.45-1.52 (m, 5H), 1.58-1.65 (m, 4H), 1.93-2.00 (m, 2H), 2.09-2.13 (m, 2H), 2.26-2.30 (m, 1H), 2.49-2.51 (m, 2H), 2.58 (d, J=3.9 Hz, 3H), 3.33-3.35 (m, 1H), 6.80-6.86 (m, 1H), 7.60-7.66 (m, 1H). LCMS t=1.4 min, m/z Calcd for $C_{14}H_{23}N_2O_2$; $C_{14}H_{22}N_2NaO_2$; $C_{28}H_{44}N_4NaO_4$ 251.18; 273.16; 523.33 [M+H]$^+$; [M+Na]$^+$; [2M+Na]$^+$, Found 251.28; 273.25; 523.40.

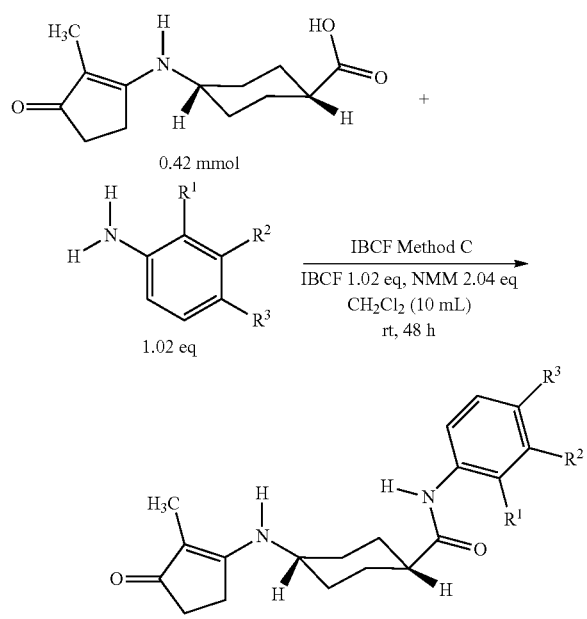

Example 04-36

Preparation of (1S,4S)-4-((2-methyl-3-oxocyclopent-1-en-1-yl)amino)-N-phenylcyclohexane-carboxamide (04-36)

The title compound was prepared from Example 01-34 and aniline according to the procedure of Example 04-13; 0.42 mmol scale yielded 16 mg after chromatography (ESS=MeOH (7%)) and EtOAc trituration (12% yield). $^1$H NMR (D6-DMSO) δ 1.45-1.55 (m, 3H), 1.61-1.68 (m, 5H), 1.74-1.81 (m, 2H), 2.00-2.18 (m, 2H), 2.09-2.12 (m, 2H), 2.53-2.55 (m, 2H), 3.40-3.60 (m, 1H), 6.88 (s, 1H), 7.02 (t, J=7.4 Hz, 1H), 7.28 (t, J=7.9 Hz, 2H), 7.62 (d, J=7.9 Hz, 2H), 9.74 (s, 1H). LCMS t=5.5 min, m/z Calcd for $C_{19}H_{25}N_2O_2$; $C_{19}H_{24}N_2NaO_2$; $C_{38}H_{48}N_4NaO_4$ 313.19; 335.17; 647.36 [M+H]$^+$; [M+Na]$^+$; [2M+Na]$^+$, Found 313.28; 335.25; 647.46.

Example 04-37

Preparation of (1S,4S)-N-(2-methoxyphenyl)-4-((2-methyl-3-oxocyclopent-1-en-1-yl)amino)-cyclohexanecarboxamide (04-37)

The title compound was prepared from Example 01-34 and o-anisidine according to the procedure of Example 04-13; 0.42 mmol scale yielded 60 mg after chromatography (ESS=MeOH (8%)) and EtOAc trituration (42% yield). $^1$H NMR (D6-DMSO) δ 1.45-1.54 (m, 3H), 1.60-1.69 (m, 5H), 1.71-1.77 (m, 2H), 1.98-2.05 (m, 2H), 2.08-2.12 (m, 2H), 2.51-2.53 (m, 1H), 2.68-2.72 (m, 1H), 3.42-3.58 (m, 1H), 3.83 (s, 3H), 6.85-6.92 (m, 2H), 7.02-7.08 (m, 2H), 7.95 (d, J=7.8 Hz, 1H), 8.87 (s, 1H). LCMS t=5.6 min, m/z Calcd for $C_{20}H_{27}N_2O_3$; $C_{20}H_{26}N_2NaO_3$; $C_{40}H_{52}N_4NaO_6$ 343.20; 365.18; 707.38 [M+H]$^+$; [M+Na]$^+$; [2M+Na]$^+$, Found 343.28; 365.26; 707.52.

Example 04-38

Preparation of (1S,4S)-N-(3-methoxyphenyl)-4-((2-methyl-3-oxocyclopent-1-en-1-yl)amino)-cyclohexanecarboxamide (04-38)

The title compound was prepared from Example 01-34 and m-anisidine according to the procedure of Example 04-13; 0.42 mmol scale yielded 3 mg after chromatography (ESS=MeOH (8%)) and EtOAc trituration (2% yield). $^1$H NMR (D6-DMSO) δ 1.45-1.53 (m, 3H), 1.59-1.69 (m, 5H), 1.73-1.78 (m, 2H), 1.99-2.08 (m, 2H), 2.09-2.12 (m, 2H), 2.49-2.51 (m, 2H), 3.45-3.55 (m, 1H), 3.72 (s, 3H), 6.60 (d, J=6.8 Hz, 1H), 6.88-6.92 (m, 1H), 7.14-7.20 (m, 2H), 7.37 (s, 1H), 9.74 (s, 1H). LCMS t=5.6 min, m/z Calcd for $C_{20}H_{27}N_2O_3$; $C_{20}H_{26}N_2NaO_3$; $C_{40}H_{52}N_4NaO_6$ 343.20; 365.18; 707.38 [M+H]$^+$; [M+Na]$^+$; [2M+Na]$^+$, Found 343.20; 365.18; 707.35.

Example 04-39

Preparation of (1S,4S)-4-((2-methyl-3-oxocyclopent-1-en-1-yl)amino)-N-(m-tolyl)-cyclohexanecarboxamide (04-39)

The title compound was prepared from Example 01-34 and m-toluidine according to the procedure of Example 04-13; 0.42 mmol scale yielded 1 mg after chromatography (ESS=MeOH (7%)) and EtOAc trituration (1% yield). $^1$H

| EXAMPLE 04-# | TITLE COMPOUND NAME | $R^1$ | $R^2$ | $R^3$ |
|---|---|---|---|---|
| 36 | (1S,4S)-4-((2-Methyl-3-oxocyclopent-1-en-1-yl)amino)-N-phenylcyclohexanecarboxamide | H | H | H |
| 37 | (1S,4S)-N-(2-Methoxyphenyl)-4-((2-methyl-3-oxocyclopent-1-en-1-yl)amino)cyclohexanecarboxamide | OCH$_3$ | H | H |
| 38 | (1S,4S)-N-(3-Methoxyphenyl)-4-((2-methyl-3-oxocyclopent-1-en-1-yl)amino)cyclohexanecarboxamide | H | OCH$_3$ | H |
| 39 | (1S,4S)-4-((2-Methyl-3-oxocyclopent-1-en-1-yl)amino)-N-(m-tolyl)cyclohexanecarboxamide | H | CH$_3$ | H |
| 40 | (1S,4S)-4-((2-Methyl-3-oxocyclopent-1-en-1-yl)amino)-N-(p-tolyl)cyclohexanecarboxamide | H | H | CH$_3$ |
| 41 | (1S,4S)-N-(3-Fluorophenyl)-4-((2-methyl-3-oxocyclopent-1-en-1-yl)amino)cyclohexanecarboxamide | H | F | H |
| 42 | (1S,4S)-N-(4-Chlorophenyl)-4-((2-methyl-3-oxocyclopent-1-en-1-yl)amino)cyclohexanecarboxamide | H | H | Cl |

NMR (D6-DMSO) δ 1.46-1.53 (m, 3H), 1.59-1.69 (m, 5H), 1.73-1.81 (m, 2H), 2.00-2.07 (m, 2H), 2.09-2.14 (m, 2H), 2.26 (s, 3H), 2.50-2.53 (m, 2H), 3.40-3.53 (m, 1H), 6.84 (d, J=7.4 Hz, 1H), 6.85-6.90 (m, 1H), 7.16 (t, J=7.8 Hz, 1H), 7.39 (d, J=8.0 Hz, 1H), 7.48 (s, 1H), 9.66 (s, 1H). LCMS t=5.6 min, m/z Calcd for $C_{20}H_{27}N_2O_2$; $C_{20}H_{26}N_2NaO_2$; $C_{40}H_{52}N_4NaO_4$ 327.21; 349.19; 675.39 [M+H]$^+$; [M+Na]$^+$; [2M+Na]$^+$, Found 327.29; 349.25; 675.52.

Example 04-40

Preparation of (1S,4S)-4-((2-methyl-3-oxocyclopent-1-en-1-yl)amino)-N-(p-tolyl)-cyclohexanecarboxamide (04-40)

The title compound was prepared from Example 01-34 and p-toluidine according to the procedure of Example 04-13; 0.42 mmol scale yielded 1 mg after chromatography (ESS=MeOH (7%)) and EtOAc trituration (1% yield). $^1$H NMR (D6-DMSO) δ 1.46-1.53 (m, 3H), 1.58-1.68 (m, 5H), 1.73-1.80 (m, 2H), 2.00-2.07 (m, 2H), 2.09-2.13 (m, 2H), 2.24 (s, 3H), 2.50-2.53 (m, 2H), 3.40-3.53 (m, 1H), 6.87-6.92 (m, 1H), 7.08 (d, J=7.9 Hz, 2H), 7.49 (d, J=8.0 Hz, 2H), 9.65 (s, 1H). LCMS t=5.7 min, m/z Calcd for $C_{20}H_{27}N_2O_2$; $C_{20}H_{26}N_2NaO_2$; $C_{40}H_{53}N_4O_4$; $C_{40}H_{52}N_4NaO_4$ 327.21; 349.19; 653.41; 675.39 [M+H]$^+$; [M+Na]$^+$; [2M+H]$^+$; [2M+Na]$^+$, Found 327.29; 349.26; 653.50; 675.49.

Example 04-41

Preparation of (1S,4S)—N-(3-fluorophenyl)-4-((2-methyl-3-oxocyclopent-1-en-1-yl)amino)-cyclohexanecarboxamide (04-41)

The title compound was prepared from Example 01-34 and m-fluoroaniline according to the procedure of Example 04-13; 0.42 mmol scale yielded 16 mg after chromatography (ESS=MeOH (7%)) and EtOAc trituration (12% yield). $^1$H NMR (D6-DMSO) δ 1.46-1.53 (m, 3H), 1.60-1.70 (m, 5H), 1.72-1.79 (m, 2H), 1.90-2.07 (m, 2H), 2.09-2.13 (m, 2H), 2.50-2.58 (m, 2H), 3.45-3.60 (m, 1H), 6.83-6.93 (m, 2H), 7.30-7.36 (m, 2H), 7.64 (d, J=12.0 Hz, 1H), 9.98 (s, 1H). LCMS t=5.7 min, m/z Calcd for $C_{19}H_{24}FN_2O_2$; $C_{19}H_{23}FN_2NaO_2$; $C_{38}H_{47}F_2N_4O_4$; $C_{38}H_{46}F_2N_4NaO_4$ 331.18; 353.16; 661.36; 683.34 [M+H]$^+$; [M+Na]$^+$; [2M+H]$^+$; [2M+Na]$^+$, Found 331.26; 353.23; 661.45; 683.44.

Example 04-42

Preparation of (1S,4S)—N-(4-chlorophenyl)-4-((2-methyl-3-oxocyclopent-1-en-1-yl)amino)-cyclohexanecarboxamide (04-42)

The title compound was prepared from Example 01-34 and p-chloroaniline according to the procedure of Example 04-13; 0.42 mmol scale yielded 13 mg after chromatography (ESS=MeOH (7%)) and EtOAc trituration (9% yield). $^1$H NMR (D6-DMSO) δ 1.46-1.54 (m, 3H), 1.59-1.69 (m, 5H), 1.72-1.79 (m, 2H), 2.00-2.07 (m, 2H), 2.09-2.13 (m, 2H), 2.50-2.54 (m, 2H), 3.40-3.58 (m, 1H), 6.83-6.92 (m, 1H), 7.34 (d, J=8.6 Hz, 2H), 7.65 (d, J=8.6 Hz, 2H), 9.90 (s, 1H). LCMS t=5.7 min, m/z Calcd for $C_{19}H_{24}ClN_2O_2$; $C_{19}H_{23}ClN_2NaO_2$; $C_{38}H_{46}Cl_2N_4NaO_4$ 347.15; 369.13; 715.28 [M+H]$^+$; [M+Na]$^+$; [2M+Na]$^+$, Found 347.22; 369.20; 715.39.

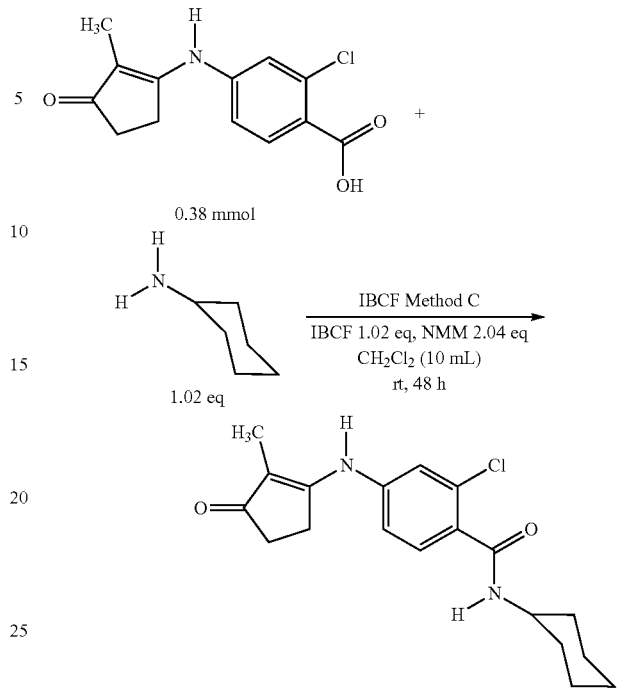

Example 04-43

Preparation of 2-chloro-N-cyclohexyl-4-((2-methyl-3-oxocyclopent-1-en-1-yl)amino)benzamide (04-43)

The title compound was prepared from Example 01-10 and cyclohexylamine according to the procedure of Example 04-13; 0.38 mmol scale yielded 1 mg after chromatography (ESS=H:E (1:19)) and EtOAc trituration (1% yield). $^1$H NMR (D6-DMSO) δ 1.10-1.18 (m, 2H), 1.27-1.33 (m, 4H), 1.58 (s, 3H), 1.70-1.73 (m, 2H), 1.81-1.83 (m, 2H), 2.23-2.25 (m, 2H), 2.72-2.75 (m, 2H), 3.32-3.70 (m, 1H), 7.22 (dd, J=8.2, 1.7 Hz, 1H), 7.32 (d, J=1.7 Hz, 1H), 7.34 (d, J=8.2 Hz, 1H), 8.24 (d, J=7.8 Hz, 1H), 8.95 (s, 1H). LCMS t=5.7 min, m/z Calcd for $C_{19}H_{24}ClN_2O_2$; $C_{19}H_{23}ClN_2NaO_2$; $C_{36}H_{47}Cl_2N_4O_4$; $C_{36}H_{47}Cl_2N_4NaO_4$ 347.15; 369.13; 693.30; 715.28 [M+H]$^+$; [M+Na]$^+$; [2M+H]$^+$; [2M+Na]$^+$, Found 347.23; 369.20; 693.41; 715.41.

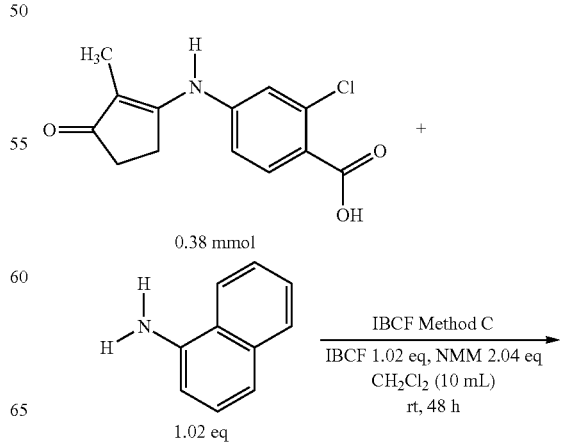

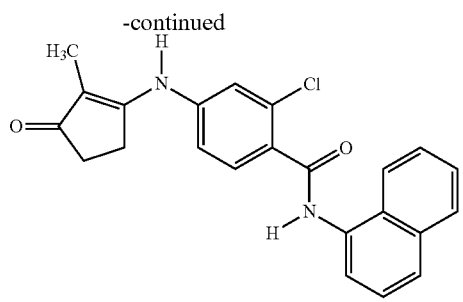

Example 04-44

Preparation of 2-chloro-4-((2-methyl-3-oxocyclopent-1-en-1-yl)amino)-N-(naphthalen-1-yl)-benzamide (04-44)

The title compound was prepared from Example 01-10 and 1-aminonaphthalene according to the procedure of Example 04-13; 0.38 mmol scale yielded 40 mg after

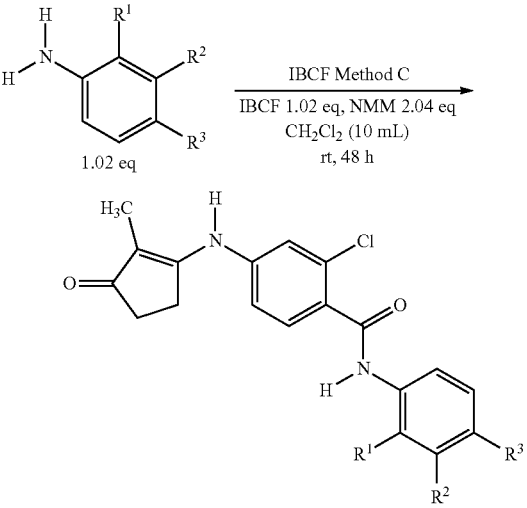

| EXAMPLE 04-# | TITLE COMPOUND NAME | $R^1$ | $R^2$ | $R^3$ |
|---|---|---|---|---|
| 45 | 2-Chloro-4-((2-methyl-3-oxocyclopent-1-en-1-yl)amino)-N-phenylbenzamide | H | H | H |
| 46 | 2-Chloro-N-(2-methoxyphenyl)-4-((2-methyl-3-oxocyclopent-1-en-1-yl)amino)benzamide | $OCH_3$ | H | H |
| 47 | 2-Chloro-N-(3-methoxyphenyl)-4-((2-methyl-3-oxocyclopent-1-en-1-yl)amino)benzamide | H | $OCH_3$ | H |
| 48 | 2-Chloro-N-(4-methoxyphenyl)-4-((2-methyl-3-oxocyclopent-1-en-1-yl)amino)benzamide | H | H | $OCH_3$ |
| 49 | 2-Chloro-4-((2-methyl-3-oxocyclopent-1-en-1-yl)amino)-N-(o-tolyl)benzamide | $CH_3$ | H | H |
| 50 | 2-Chloro-4-((2-methyl-3-oxocyclopent-1-en-1-yl)amino)-N-(m-tolyl)benzamide | H | $CH_3$ | H |
| 51 | 2-Chloro-4-((2-methyl-3-oxocyclopent-1-en-1-yl)amino)-N-(p-tolyl)benzamide | H | H | $CH_3$ |
| 52 | 2-Chloro-N-(3-fluorophenyl)-4-((2-methyl-3-oxocyclopent-1-en-1-yl)amino)benzamide | H | F | H | chromatography (ESS=H:E (1:19)) and EtOAc trituration (27% yield). $^1$H NMR (D6-DMSO) δ 1.63 (s, 3H), 2.27-2.29 (m, 2H), 2.80-2.82 (m, 2H), 7.35 (d, J=7.6 Hz, 1H), 7.45 (s, 1H), 7.54-7.59 (m, 3H), 7.70-7.74 (m, 2H), 7.85 (d, J=8.1 Hz, 1H), 7.97 (d, J=8.6 Hz, 1H), 8.16 (d, J=9.0 Hz, 1H), 9.19 (s, 1H), 10.50 (s, 1H). LCMS t=5.8 min, m/z Calcd for $C_{23}H_{20}ClN_2O_2$; $C_{23}H_{19}ClN_2NaO_2$; $C_{46}H_{39}Cl_2N_4O_4$; $C_{46}H_{38}Cl_2N_4NaO_4$ 391.12; 413.10; 781.23; 803.22 [M+H]$^+$; [M+Na]$^+$; [2M+H]$^+$; [2M+Na]$^+$, Found 391.19; 413.17; 781.39; 803.38.

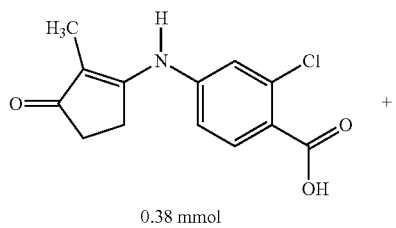

Example 04-45

Preparation of 2-chloro-4-((2-methyl-3-oxocyclopent-1-en-1-yl)amino)-N-phenylbenzamide (04-45)

The title compound was prepared from Example 01-10 and aniline according to the procedure of Example 04-13; 0.38 mmol scale yielded 17 mg after chromatography (ESS=EtOAc) and EtOAc trituration (13% yield). $^1$H NMR (D6-DMSO) δ 1.61 (s, 3H), 2.25-2.28 (m, 2H), 2.78-2.80 (m, 2H), 7.10 (t, J=7.4 Hz, 1H), 7.30 (dd, J=8.3, 1.6 Hz, 1H), 7.35 (t, J=7.8 Hz, 2H), 7.41 (s, 1H), 7.55 (d, J=8.3 Hz, 1H), 7.72 (d, J=7.9 Hz, 2H), 9.16 (s, 1H), 10.43 (s, 1H). LCMS t=5.6 min, m/z Calcd for $C_{19}H_{18}ClN_2O_2$; $C_{19}H_{17}ClN_2NaO_2$; $C_{38}H_{35}Cl_2N_4O_4$; $C_{38}H_{34}Cl_2N_4NaO_4$ 341.11; 363.09; 681.20; 703.19 [M+H]$^+$; [M+Na]$^+$; [2M+H]$^+$; [2M+Na]$^+$, Found 341.18; 363.16; 681.31; 703.31.

Example 04-46

Preparation of 2-chloro-N-(2-methoxyphenyl)-4-((2-methyl-3-oxocyclopent-1-en-1-yl)amino)benzamide (04-46)

The title compound was prepared from Example 01-10 and o-anisidine according to the procedure of Example 04-13; 0.38 mmol scale yielded 45 mg after chromatography (ESS=H:E (1:19)) and EtOAc trituration (30% yield). $^1$H NMR (D6-DMSO) δ 1.61 (s, 3H), 2.26-2.28 (m, 2H), 2.79-2.80 (m, 2H), 3.83 (s, 3H), 6.97 (t, J=6.9 Hz, 1H), 7.08 (d, J=7.6 Hz, 1H), 7.16 (t, J=7.5 Hz, 1H), 7.29 (d, J=7.4 Hz, 1H), 7.39 (s, 1H), 7.59 (d, J=7.6 Hz, 1H), 7.96 (d, J=6.6 Hz, 1H), 9.16 (s, 1H), 9.51 (s, 1H). LCMS t=5.8 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.11; 393.10; 741.22; 763.21 [M+H]$^+$; [M+Na]$^+$; [2M+H]$^+$; [2M+Na]$^+$, Found 371.18; 393.16; 741.36; 763.35.

Example 04-47

Preparation of 2-chloro-N-(3-methoxyphenyl)-4-((2-methyl-3-oxocyclopent-1-en-1-yl)amino)benzamide (04-47)

The title compound was prepared from Example 01-10 and m-anisidine according to the procedure of Example 04-13; 0.38 mmol scale yielded 47 mg after chromatography (ESS=H:E (1:19)) and EtOAc trituration (34% yield). $^1$H NMR (D6-DMSO) δ 1.61 (s, 3H), 2.25-2.28 (m, 2H), 2.78-2.79 (m, 2H), 3.75 (s, 3H), 6.69 (d, J=7.0 Hz, 1H), 7.22-7.31 (m, 3H), 7.40-7.42 (m, 2H), 7.54 (d, J=8.3 Hz, 1H), 9.16 (s, 1H), 10.41 (s, 1H). LCMS t=5.7 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.11; 393.10; 741.22; 763.21 [M+H]$^+$; [M+Na]$^+$; [2M+H]$^+$; [2M+Na]$^+$, Found 371.18; 393.16; 741.36; 763.35.

Example 04-48

Preparation of 2-chloro-N-(4-methoxyphenyl)-4-((2-methyl-3-oxocyclopent-1-en-1-yl)amino)-benzamide (04-48)

The title compound was prepared from Example 01-10 and p-anisidine according to the procedure of Example 04-13; 0.38 mmol scale yielded 17 mg after chromatography (ESS=H:E (1:19)) and EtOAc trituration (12% yield). $^1$H NMR (D6-DMSO) δ 1.61 (s, 3H), 2.26-2.28 (m, 2H), 2.77-2.79 (m, 2H), 3.74 (s, 3H), 6.92 (d, J=8.8 Hz, 2H), 7.29 (d, J=8.2 Hz, 1H), 7.40 (s, 1H), 7.53 (d, J=8.3 Hz, 1H), 7.62 (d, J=8.8 Hz, 2H), 9.15 (s, 1H), 10.29 (s, 1H). LCMS t=5.6 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.11; 393.10; 741.22; 763.21 [M+H]$^+$; [M+Na]$^+$; [2M+H]$^+$; [2M+Na]$^+$, Found 371.18; 393.16; 741.35; 763.34.

Example 04-49

Preparation of 2-chloro-4-((2-methyl-3-oxocyclopent-1-en-1-yl)amino)-N-(o-tolyl)benzamide (04-49)

The title compound was prepared from Example 01-10 and o-toluidine according to the procedure of Example 04-13; 0.38 mmol scale yielded 25 mg after chromatography (ESS=H:E (1:19)) and EtOAc trituration (19% yield). $^1$H NMR (D6-DMSO) δ 1.61 (s, 3H), 2.26-2.29 (m, 5H), 2.78-2.80 (m, 2H), 7.15 (t, J=7.1 Hz, 1H), 7.21-7.23 (m, 1H), 7.26 (d, J=7.1 Hz, 1H), 7.31 (d, J=7.9 Hz, 1H), 7.40-7.43 (m, 2H), 7.59 (d, J=8.1 Hz, 1H), 9.16 (s, 1H), 9.91 (s, 1H). LCMS t=5.7 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]$^+$; [M+Na]$^+$; [2M+H]$^+$; [2M+Na]$^+$, Found 355.19; 377.17; 709.34; 731.34.

Example 04-50

Preparation of 2-chloro-4-((2-methyl-3-oxocyclopent-1-en-1-yl)amino)-N-(m-tolyl)benzamide (04-50)

The title compound was prepared from Example 01-10 and m-toluidine according to the procedure of Example 04-13; 0.38 mmol scale yielded 36 mg after chromatography (ESS=H:E (1:19)) and EtOAc trituration (27% yield). $^1$H NMR (D6-DMSO) δ 1.61 (s, 3H), 2.26-2.28 (m, 2H), 2.30 (s, 3H), 2.78-2.79 (m, 2H), 6.92 (d, J=7.3 Hz, 1H), 7.22 (t, J=7.7 Hz, 1H), 7.30 (d, J=8.2 Hz, 1H), 7.40 (s, 1H), 7.48 (d, J=7.7 Hz, 1H), 7.53 (d, J=8.2 Hz, 1H), 9.16 (s, 1H), 10.36 (s, 1H). LCMS t=5.8 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]$^+$; [M+Na]$^+$; [2M+H]$^+$; [2M+Na]$^+$, Found 355.19; 377.17; 709.35; 731.34.

Example 04-51

Preparation of 2-chloro-4-((2-methyl-3-oxocyclopent-1-en-1-yl)amino)-N-(p-tolyl)benzamide (04-51)

The title compound was prepared from Example 01-10 and p-toluidine according to the procedure of Example 04-13; 0.38 mmol scale yielded 21 mg after chromatography (ESS=H:E (1:19)) and EtOAc trituration (16% yield). $^1$H NMR (D6-DMSO) δ 1.61 (2, 3H), 2.27-2.29 (m, 5H), 2.77-2.78 (m, 2H), 7.15 (d, J=7.8 Hz, 2H), 7.29 (d, J=8.2 Hz, 1H), 7.40 (s, 1H), 7.53 (d, J=8.3 Hz, 1H), 7.60 (d, J=7.9 Hz, 2H), 9.16 (s, 1H), 10.34 (s, 1H). LCMS t=5.8 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]$^+$; [M+Na]$^+$; [2M+H]$^+$; [2M+Na]$^+$, Found 355.19; 377.17; 709.34; 731.33.

Example 04-52

Preparation of 2-chloro-N-(3-fluorophenyl)-4-((2-methyl-3-oxocyclopent-1-en-1-yl)amino)-benzamide (04-52)

The title compound was prepared from Example 01-10 and m-fluoroaniline according to the procedure of Example 04-13; 0.38 mmol scale yielded 25 mg after chromatography (ESS=H:E (1:19)) and EtOAc trituration (18% yield). $^1$H NMR (D6-DMSO) δ 1.61 (s, 3H), 2.26-2.28 (m, 2H), 2.78-2.80 (m, 2H), 6.94 (d, J=8.2 Hz, 1H), 7.31 (d, J=8.3 Hz, 1H), 7.36-7.42 (m, 2H), 7.46 (d, J=7.7 Hz, 1H), 7.56 (d, J=8.3 Hz, 1H), 7.68 (d, J=11.3 Hz, 1H), 9.17 (s, 1H), 10.65 (s, 1H). LCMS t=5.8 min, m/z Calcd for $C_{19}H_{17}ClFN_2O_2$; $C_{19}H_{16}ClFN_2NaO_2$; $C_{38}H_{33}Cl_2F_2N_4O_4$; $C_{38}H_{32}Cl_2F_2N_4NaO_4$ 359.10; 381.08; 717.18; 739.17 [M+H]$^+$; [M+Na]$^+$; [2M+H]$^+$; [2M+Na]$^+$, Found 359.16; 381.14; 717.30; 739.29.

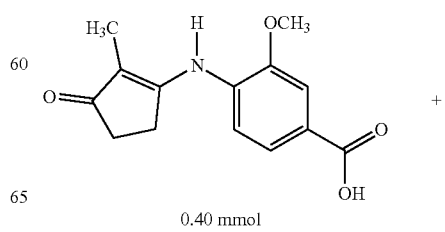

0.40 mmol

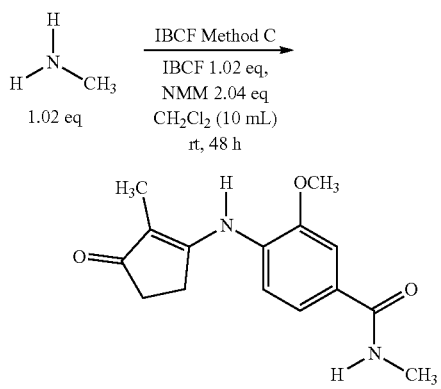

Example 04-53

Preparation of 3-methoxy-N-methyl-4-((2-methyl-3-oxocyclopent-1-en-1-yl)amino)benzamide (04-53)

The title compound was prepared from Example 01-12 and methylamine according to the procedure of Example 04-13; 0.40 mmol scale yielded 25 mg after chromatography (ESS=MeOH (7%)) and EtOAc trituration (23% yield). $^1$H NMR (D6-DMSO) δ 1.51 (s, 3H), 2.16-2.19 (m, 2H), 2.48-2.51 (m, 2H), 2.79 (d, J=4.5 Hz, 1H), 3.87 (s, 3H), 7.25 (d, J=8.1 Hz, 1H), 7.43 (dd, J=8.1, 1.4 Hz, 1H), 7.52 (d, J=1.2 Hz, 1H), 8.42-8.44 (m, 1H), 8.51 (s, 1H). LCMS t=4.9 min, m/z Calcd for $C_{15}H_{19}N_2O_3$; $C_{15}H_8N_2NaO_3$; $C_{30}H_{36}N_4NaO_6$ 275.14; 297.12; 571.25 [M+H]$^+$; [M+Na]$^+$; [2M+Na]$^+$, Found 275.23; 297.21; 571.42.

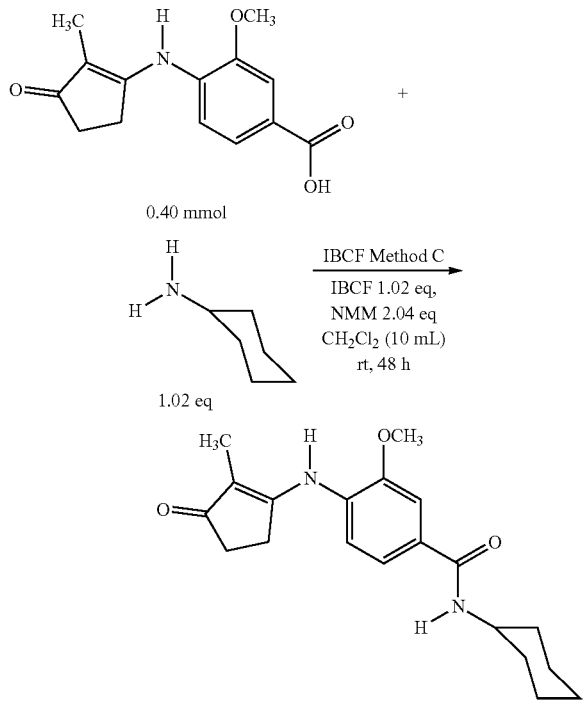

Example 04-54

Preparation of N-cyclohexyl-3-methoxy-4-((2-methyl-3-oxocyclopent-1-en-1-yl)amino)-benzamide (04-54)

The title compound was prepared from Example 01-12 and cyclohexylamine according to the procedure of Example 04-13; 0.40 mmol scale yielded 52 mg after chromatography (ESS=H:E (1:19)) and EtOAc trituration (38% yield). $^1$H NMR (D6-DMSO) δ 1.20-1.28 (m, 1H), 1.32-1.35 (m, 4H), 1.51 (s, 3H), 1.62 (d, J=11.9 Hz, 1H), 1.75 (s, 2H), 1.82 (s, 2H), 2.16-2.19 (m, 2H), 2.47-2.50 (m, 2H), 3.75-3.78 (m, 1H), 3.88 (s, 3H), 7.24 (d, J=8.1 Hz, 1H), 7.46 (d, J=8.1 Hz, 1H), 7.50 (s, 1H), 8.19 (d, J=7.9 Hz, 1H), 8.53 (s, 1H). LCMS t=5.7 min, m/z Calcd for $C_{20}H_{27}N_2O_3$; $C_{20}H_{26}N_2NaO_3$; $C_{40}H_{52}N_4NaO_6$ 343.20; 365.18; 707.38 [M+H]$^+$; [M+Na]$^+$; [2M+Na]$^+$, Found 343.27; 365.25; 707.55.

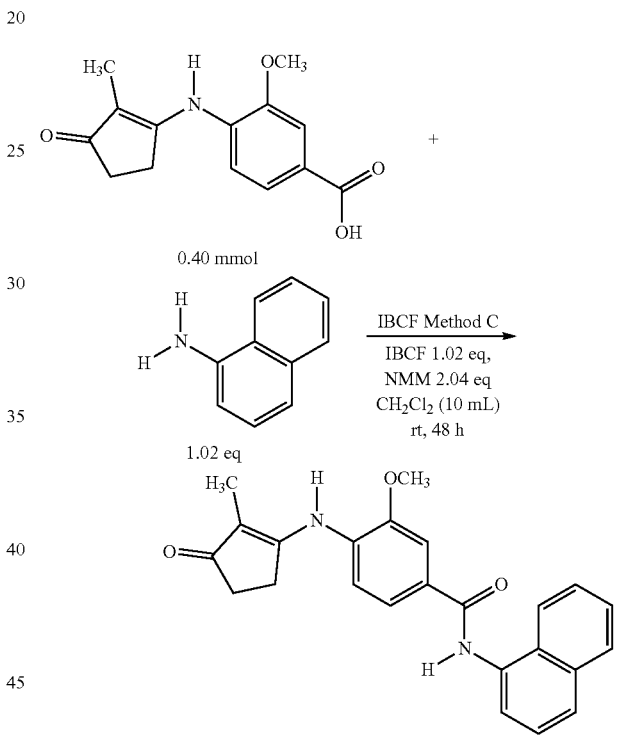

Example 04-55

Preparation of 3-methoxy-4-((2-methyl-3-oxocyclopent-1-en-1-yl)amino)-N-(naphthalen-1-yl)-benzamide (04-55)

The title compound was prepared from Example 01-12 and 1-aminonaphthalene according to the procedure of Example 04-13; 0.40 mmol scale yielded 41 mg after chromatography (ESS=H:E (1:19)) and EtOAc trituration (27% yield). $^1$H NMR (D6-DMSO) δ 1.55 (s, 3H), 2.21-2.23 (m, 2H), 2.56-2.58 (m, 2H), 3.95 (s, 3H), 7.36 (d, J=8.1 Hz, 1H), 7.55-7.60 (m, 4H), 7.73 (d, J=8.0 Hz, 1H), 7.77 (s, 1H), 7.88 (d, J=7.7 Hz, 1H), 7.98-8.00 (m, 2H), 8.60 (s, 1H), 10.43 (s, 1H). LCMS t=5.8 min, m/z Calcd for $C_{24}H_{23}N_2O_3$; $C_{24}H_{22}N_2NaO_3$; $C_{48}H_{45}N_4O_6$; $C_{48}H_{44}N_4NaO_6$ 387.17; 409.15; 773.33; 795.32 [M+H]$^+$; [M+Na]$^+$; [2M+H]$^+$; [2M+Na]$^+$, Found 387.24; 409.22; 773.48; 795.47.

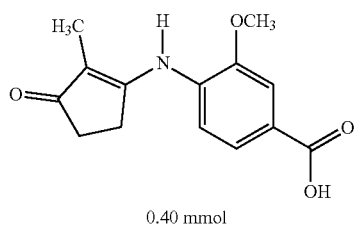

0.40 mmol

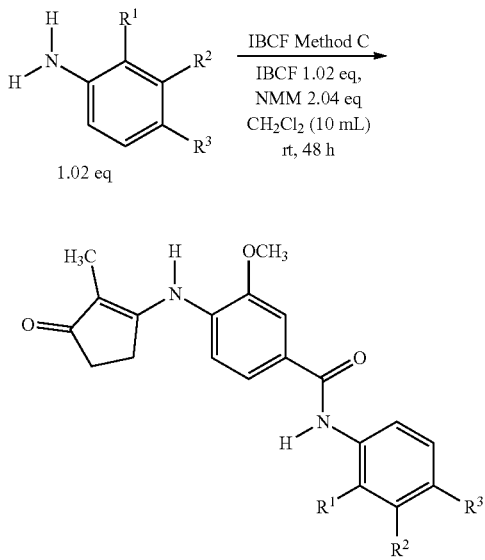

1H), 10.21 (s, 1H). LCMS t=5.6 min, m/z Calcd for $C_{20}H_{21}N_2O_3$; $C_{20}H_{20}N_2NaO_3$; $C_{40}H_{41}N_4O_6$; $C_{40}H_{40}N_4NaO_6$ 337.16; 359.14; 673.30; 695.28 $[M+H]^+$; $[M+Na]^+$; $[2M+H]^+$; $[2M+Na]^+$, Found 337.23; 359.21; 673.41; 695.41.

Example 04-57

Preparation of 3-methoxy-N-(2-methoxyphenyl)-4-((2-methyl-3-oxocyclopent-1-en-1-yl)amino)-benzamide (04-57)

The title compound was prepared from Example 01-12 and o-anisidine according to the procedure of Example 04-13; 0.40 mmol scale yielded 30 mg after chromatography (ESS=H:E (1:19)) and EtOAc trituration (20% yield). $^1$H NMR (D6-DMSO) δ 1.53 (s, 3H), 2.20-2.22 (m, 2H), 2.53-2.55 (m, 2H), 3.84 (s, 3H), 3.92 (s, 3H), 6.98 (t, J=7.5 Hz, 1H), 7.10 (d, J=8.1 Hz, 1H), 7.20 (t, J=7.8 Hz, 1H), 7.31 (d, J=8.1 Hz, 1H), 7.58 (d, J=7.9 Hz, 1H), 7.64 (s, 1H), 7.69 (d, J=7.6 Hz, 1H), 8.55 (s, 1H), 9.46 (s, 1H). LCMS t=5.9 min, m/z Calcd for $C_{21}H_{23}N_2O_4$; $C_{21}H_{22}N_2NaO_4$; $C_{42}H_{45}N_4O_8$; $C_{42}H_{44}N_4NaO_8$ 367.17; 389.15; 733.32; 755.31 $[M+H]^+$; $[M+Na]^+$; $[2M+H]^+$; $[2M+Na]^+$, Found 367.24; 389.22; 733.46; 755.46.

Example 04-58

Preparation of 3-methoxy-N-(3-methoxyphenyl)-4-((2-methyl-3-oxocyclopent-1-en-1-yl)amino)-benzamide (04-58)

The title compound was prepared from Example 01-12 and m-anisidine according to the procedure of Example

| EXAMPLE 04-# | TITLE COMPOUND NAME | $R^1$ | $R^2$ | $R^3$ |
|---|---|---|---|---|
| 56 | 3-Methoxy-4-((2-methyl-3-oxocyclopent-1-en-1-yl)amino)-N-phenylbenzamide | H | H | H |
| 57 | 3-Methoxy-N-(2-methoxyphenyl)-4-((2-methyl-3-oxocyclopent-1-en-1-yl)amino)benzamide | $OCH_3$ | H | H |
| 58 | 3-Methoxy-N-(3-methoxyphenyl)-4-((2-methyl-3-oxocyclopent-1-en-1-yl)amino)benzamide | H | $OCH_3$ | H |
| 59 | 3-Methoxy-N-(4-methoxyphenyl)-4-((2-methyl-3-oxocyclopent-1-en-1-yl)amino)benzamide | H | H | $OCH_3$ |
| 60 | 3-Methoxy-4-((2-methyl-3-oxocyclopent-1-en-1-yl)amino)-N-(o-tolyl)benzamide | $CH_3$ | H | H |
| 61 | 3-Methoxy-4-((2-methyl-3-oxocyclopent-1-en-1-yl)amino)-N-(m-tolyl)benzamide | H | $CH_3$ | H |
| 62 | 3-Methoxy-4-((2-methyl-3-oxocyclopent-1-en-1-yl)amino)-N-(p-tolyl)benzamide | H | H | $CH_3$ |
| 63 | N-(3-Fluorophenyl)-3-methoxy-4-((2-methyl-3-oxocyclopent-1-en-1-yl)amino)benzamide | H | F | H |
| 64 | N-(4-Chlorophenyl)-3-methoxy-4-((2-methyl-3-oxocyclopent-1-en-1-yl)amino)benzamide | H | H | Cl |

Example 04-56

Preparation of 3-methoxy-4-((2-methyl-3-oxocyclopent-1-en-1-yl)amino)-N-phenylbenzamide (04-56)

The title compound was prepared from Example 01-12 and aniline according to the procedure of Example 04-13; 0.40 mmol scale yielded 35 mg after chromatography (ESS=H:E (1:19)) and EtOAc trituration (26% yield). $^1$H NMR (D6-DMSO) δ 1.53 (s, 3H), 2.19-2.22 (m, 2H), 2.53-2.55 (m, 2H), 3.93 (s, 3H), 7.11 (t, J=8.1 Hz, 1H), 7.33 (d, J=8.1 Hz, 1H), 7.36 (t, J=7.8 Hz, 2H), 7.59 (d, J=8.1 Hz, 1H), 7.62 (d, J=1.2 Hz, 1H), 7.76 (d, J=7.8 Hz, 2H), 8.57 (s, 04-13; 0.40 mmol scale yielded 53 mg after chromatography (ESS=EtOAc) and EtOAc trituration (36% yield). $^1$H NMR (D6-DMSO) δ 1.53 (s, 3H), 2.19-2.22 (m, 2H), 2.53-2.55 (m, 2H), 3.76 (s, 3H), 3.93 (s, 3H), 6.69 (dd, J=8.1, 2.0 Hz, 1H), 7.26 (t, J=8.1 Hz, 1H), 7.32 (d, J=8.1 Hz, 1H), 7.36 (d, J=8.1 Hz, 1H), 7.47 (s, 1H), 7.58-7.61 (m, 2H), 8.57 (s, 1H), 10.18 (s, 1H). LCMS t=5.7 min, m/z Calcd for $C_{21}H_{23}N_2O_4$; $C_{21}H_{22}N_2NaO_4$; $C_{42}H_{45}N_4O_8$; $C_{42}H_{44}N_4NaO_8$ 367.17; 389.15; 733.32; 755.31 $[M+H]^+$; $[M+Na]^+$; $[2M+H]^+$; $[2M+Na]^+$, Found 367.24; 389.22; 733.46; 755.45.

Example 04-59

Preparation of 3-methoxy-N-(4-methoxyphenyl)-4-((2-methyl-3-oxocyclopent-1-en-1-yl)amino)-benzamide (04-59)

The title compound was prepared from Example 01-12 and p-anisidine according to the procedure of Example 04-13; 0.40 mmol scale yielded 55 mg after chromatography (ESS=H:E (1:19)) and EtOAc trituration (38% yield). $^1$H NMR (D6-DMSO) δ1.53 (s, 3H), 2.20-2.22 (m, 2H), 2.52-2.53 (m, 2H), 3.75 (s, 3H), 3.92 (s, 2H), 6.94 (d, J=8.7 Hz, 2H), 7.32 (d, J=8.0 Hz, 1H), 7.58 (d, J=8.0 Hz, 1H), 7.61 (s, 1H), 7.66 (d, J=8.7 Hz, 2H), 8.56 (s, 1H), 10.10 (s, 1H). $^{13}$C NMR (D6-DMSO) δ 7.3, 25.5, 32.8, 55.2, 55.9, 109.8, 110.9, 113.7, 119.9, 122.2, 124.7, 131.1, 132.1, 132.3, 152.4, 155.6, 164.4, 169.6, 202.1. LCMS t=5.6 min, m/z Calcd for $C_{21}H_{23}N_2O_4$; $C_{21}H_{22}N_2NaO_4$; $C_{42}H_{45}N_4O_8$; $C_{42}H_{44}N_4NaO_8$ 367.17; 389.15; 733.32; 755.31 [M+H]$^+$; [M+Na]$^+$; [2M+H]$^+$; [2M+Na]$^+$, Found 367.23; 389.21; 733.44; 755.43.

Example 04-60

Preparation of 3-methoxy-4-((2-methyl-3-oxocyclopent-1-en-1-yl)amino)-N-(o-tolyl)benzamide (04-60)

The title compound was prepared from Example 01-12 and o-toluidine according to the procedure of Example 04-13; 0.40 mmol scale yielded 60 mg after chromatography (ESS=H:E (1:19)) and EtOAc trituration (43% yield). $^1$H NMR (D6-DMSO) δ 1.54 (s, 3H), 2.20-2.22 (m, 2H), 2.24 (s, 3H), 2.53-2.55 (m, 2H), 3.92 (s, 3H), 7.18 (t, J=7.1 Hz, 1H), 7.23 (t, J=7.2 Hz, 1H), 7.29 (d, J=7.1 Hz, 1H), 7.32 (d, J=8.0 Hz, 2H), 7.61 (d, J=8.0 Hz, 1H), 7.66 (s, 1H), 8.58 (s, 1H), 9.89 (s, 1H). LCMS t=5.7 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.45; 723.44.

Example 04-61

Preparation of 3-methoxy-4-((2-methyl-3-oxocyclopent-1-en-1-yl)amino)-N-(m-tolyl)benzamide (04-61)

The title compound was prepared from Example 01-12 and m-toluidine according to the procedure of Example 04-13; 0.40 mmol scale yielded 47 mg after chromatography (ESS=H:E (1:19)) and EtOAc trituration (34% yield). $^1$H NMR (D6-DMSO) δ 1.53 (s, 3H), 2.20-2.22 (m, 2H), 2.32, (s, 3H), 2.53-2.55 (m, 2H), 3.93 (m, 3H), 6.93 (d, J=7.3 Hz, 1H), 7.24 (t, J=7.7 Hz, 1H), 7.32 (d, J=8.0 Hz, 1H), 7.56-7.62 (m, 4H), 8.57 (s, 1H), 10.13 (s, 1H). $^{13}$C NMR (D6-DMSO) δ 7.3, 21.2, 25.5, 32.8, 55.9, 109.9, 110.93, 117.7, 120.1, 121.1, 124.4, 124.6, 128.4, 131.2, 132.2, 137.7, 139.0, 152.4, 164.7, 169.6, 202.1. LCMS t=5.8 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.44; 723.43.

Example 04-62

Preparation of 3-methoxy-4-((2-methyl-3-oxocyclopent-1-en-1-yl)amino)-N-(p-tolyl)benzamide (04-62)

The title compound was prepared from Example 01-12 and p-toluidine according to the procedure of Example 04-13; 0.40 mmol scale yielded 45 mg after chromatography (ESS=H:E (1:19)) and EtOAc trituration (32% yield). $^1$H NMR (D6-DMSO) δ 1.53 (s, 3H), 2.20-2.22 (m, 2H), 2.29 (s, 3H), 2.53-2.55 (m, 2H), 3.92 (s, 3H), 7.16 (d, J=8.0 Hz, 2H), 7.32 (d, J=8.0 Hz, 1H), 7.58 (d, J=8.0 Hz, 1H), 7.61 (s, 1H), 7.64 (d, J=8.0 Hz, 2H), 8.57 (s, 1H), 10.14 (s, 1H). $^{13}$C NMR (D6-DMSO) δ 7.3, 20.5, 25.5, 32.8, 55.9, 109.9, 110.9, 120.0, 120.6, 124.7, 129.0, 131.2, 132.3, 132.7, 136.6, 152.4, 164.6, 169.6, 202.1. LCMS t=5.8 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.44; 723.43.

Example 04-63

Preparation of N-(3-fluorophenyl)-3-methoxy-4-((2-methyl-3-oxocyclopent-1-en-1-yl)amino)benzamide (04-63)

The title compound was prepared from Example 01-12 and m-fluoroaniline according to the procedure of Example 04-13; 0.40 mmol scale yielded 51 mg after chromatography (ESS=H:E (1:19)) and EtOAc trituration (36% yield). $^1$H NMR (D6-DMSO) δ 1.53 (s, 3H), 2.20-2.22 (m, 2H), 2.40-2.56 (m, 2H), 3.93 (s, 3H), 6.94 (t, J=7.7 Hz, 1H), 7.34 (d, J=8.0 Hz, 1H), 7.40 (dd, J=15.2, 7.9 Hz, 1H), 7.56 (d, J=8.1 Hz, 1H), 7.59 (d, J=11.7 Hz, 1H), 8.58 (s, 1H), 10.39 (s, 1H). $^{13}$C NMR (D6-DMSO) δ 7.4, 25.6, 32.8, 55.9, 107.0 ($J_{CF}$=26.2 Hz), 110.1 ($J_{CF}$=15.7 Hz), 111.0, 116.1, 120.1, 124.5, 130.2 ($J_{CF}$=9.1 Hz), 131.6 ($J_{CF}$=19.6 Hz), 141.0, 152.2, 162.1 ($J_{CF}$=241.2 Hz), 165.1, 169.4, 202.2. LCMS t=5.8 min, m/z Calcd for $C_{20}H_{20}FN_2O_3$; $C_{20}H_{19}FN_2NaO_3$; $C_{40}H_{39}F_2N_4O_6$; $C_{40}H_{38}F_2N_4NaO_6$ 355.15; 377.13; 709.28; 731.27 [M+H]$^+$; [M+Na]$^+$; [2M+H]$^+$; [2M+Na]$^+$, Found 355.21; 377.19; 709.39; 731.38.

Example 04-64

Preparation of N-(4-chlorophenyl)-3-methoxy-4-((2-methyl-3-oxocyclopent-1-en-1-yl)amino)-benzamide (04-64)

The title compound was prepared from Example 01-12 and p-chloroaniline according to the procedure of Example 04-13; 0.40 mmol scale yielded 52 mg after chromatography (ESS=H:E (1:19)) and EtOAc trituration (35% yield). $^1$H NMR (D6-DMSO) δ 1.53 (s, 3H), 2.20-2.22 (m, 2H), 2.53-2.55 (m, 2H), 3.93 (s, 3H), 7.33 (d, J=8.0 Hz, 1H), 7.42 (d, J=8.6 Hz, 2H), 7.58-7.61 (m, 3H), 7.81 (d, J=8.6 Hz, 2H), 8.57 (s, 1H), 10.33 (s, 1H). $^{13}$C NMR (D6-DMSO) δ 7.4, 25.6, 32.8, 55.9, 110.0, 111.1, 120.1, 122.0, 124.5, 127.3, 128.5, 131.5, 131.8, 138.1, 152.3, 164.9, 169.5, 202.1. LCMS t=5.9 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.12; 393.10; 741.22; 763.21 [M+H]$^+$; [M+Na]$^+$; [2M+H]$^+$; [2M+Na]$^+$, Found 371.18; 393.16; 741.35; 763.34.

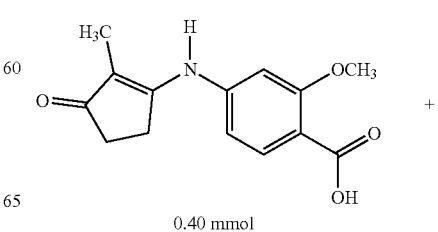

0.40 mmol

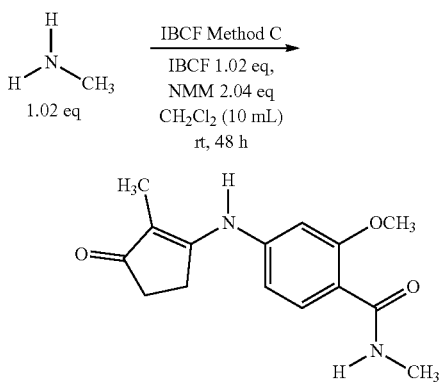

Example 04-65

Preparation of 2-methoxy-N-methyl-4-((2-methyl-3-oxocyclopent-1-en-1-yl)amino)benzamide (04-65)

The title compound was prepared from Example 02-03 and methylamine according to the procedure of Example 04-13; 0.40 mmol scale yielded 25 mg after chromatography (ESS=MeOH (8%)) and EtOAc trituration (22% yield). $^1$H NMR (D6-DMSO) δ 1.61 (s, 3H), 2.23-2.26 (m, 2H), 2.78-2.80 (m, 5H), 3.89 (s, 3H), 6.89 (dd, J=8.4, 1.7 Hz, 1H), 6.96 (d, J=1.6 Hz, 1H), 7.78 (d, J=8.4 Hz, 1H), 8.03-8.05 (m, 2H), 9.08 (s, 1H). LCMS t=4.6 min, m/z Calcd for $C_{15}H_{19}N_2O_3$; $C_{15}H_{18}N_2NaO_3$; $C_{30}H_{36}N_4NaO_6$ 275.14; 297.12; 571.25 [M+H]$^+$; [M+Na]$^+$; [2M+Na]$^+$, Found 275.23; 297.21; 571.34.

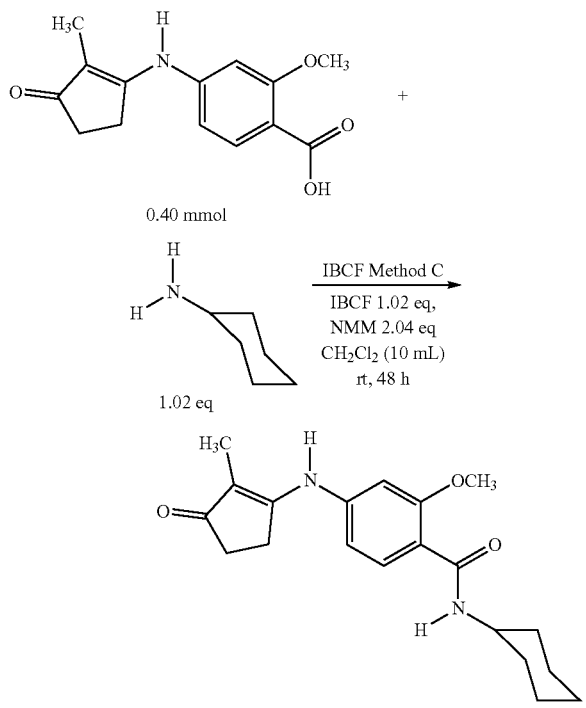

Example 04-66

Preparation of N-cyclohexyl-2-methoxy-4-((2-methyl-3-oxocyclopent-1-en-1-yl)amino)-benzamide (04-66)

The title compound was prepared from Example 02-03 and cyclohexylamine according to the procedure of Example 04-13; 0.40 mmol scale yielded 90 mg after chromatography (ESS=EtOAc) and EtOAc trituration (66% yield). $^1$H NMR (D6-DMSO) δ 1.18-1.28 (m, 1H), 1.30-1.35 (m, 4H), 1.56 (d, J=12.9 Hz, 1H), 1.61 (s, 3H), 1.66-1.69 (m, 2H), 1.81-1.84 (m, 2H), 2.24-2.26 (m, 2H), 2.78-2.80 (m, 2H), 3.77-3.79 (m, 1H), 3.90 (s, 3H), 6.90 (dd, J=8.4, 1.6 Hz, 1H), 6.97 (d, J=1.4 Hz, 1H), 7.74 (d, J=8.4 Hz, 1H), 7.85 (d, J=7.8 Hz, 1H), 8.53 (s, 1H). LCMS t=5.8 min, m/z Calcd for $C_{20}H_{27}N_2O_3$; $C_{20}H_{26}N_2NaO_3$; $C_{40}H_{53}N_4O_6$; $C_{40}H_{52}N_4NaO_6$ 343.20; 365.18; 685.40; 707.38 [M+H]$^+$; [M+Na]$^+$; [2M+H]$^+$; [2M+Na]$^+$, Found 343.28; 365.26; 685.50; 707.52.

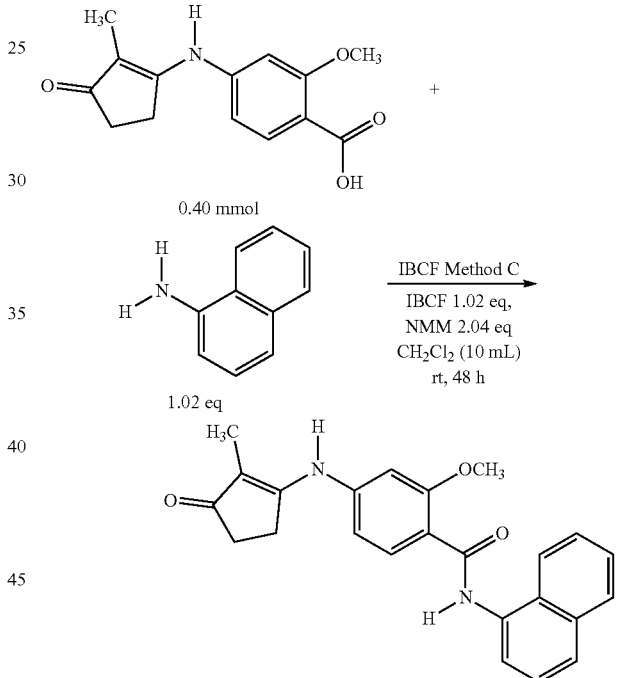

Example 04-67

Preparation of 2-methoxy-4-((2-methyl-3-oxocyclopent-1-en-1-yl)amino)-N-(naphthalen-1-yl)benzamide (04-67)

The title compound was prepared from Example 02-03 and 1-aminonaphthalene according to the procedure of Example 04-13; 0.40 mmol scale yielded 13 mg after chromatography (ESS=EtOAc) and EtOAc trituration (8% yield). $^1$H NMR (D6-DMSO) δ 1.65 (s, 3H), 2.28-2.30 (m, 2H), 2.87-2.89 (m, 2H), 4.10 (s, 3H), 7.02 (d, J=8.1 Hz, 1H), 7.12 (s, 1H), 7.55-7.60 (m, 2H), 7.64 (t, J=7.5 Hz, 1H), 7.79 (d, J=8.1 Hz, 1H), 7.92 (d, J=8.5 Hz, 1H), 7.99 (d, J=8.0 Hz, 1H), 8.04 (d, J=8.4 Hz, 2H), 9.19 (s, 1H), 10.31 (s, 1H). LCMS t=6.0 min, m/z Calcd for $C_{24}H_{23}N_2O_3$;

$C_{24}H_{22}N_2NaO_3$; $C_{48}H_{45}N_4O_6$; $C_{48}H_{44}N_4NaO_6$ 387.17; 409.15; 773.33 795.32 [M+H; M+Na]; [2M+H]; [2M+Na]$^+$, Found 387.24 409.22 773.49 795.47.

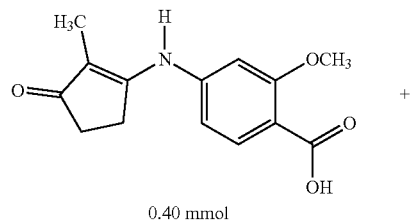

0.40 mmol

+

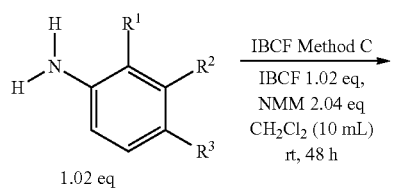

1.02 eq

IBCF Method C
IBCF 1.02 eq,
NMM 2.04 eq
$CH_2Cl_2$ (10 mL)
rt, 48 h

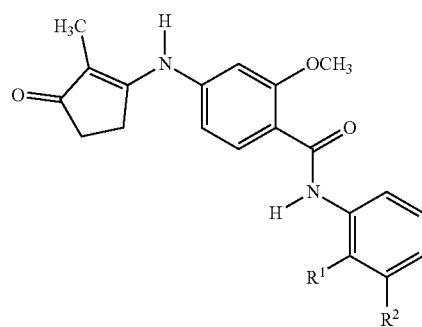

| EXAMPLE 04-# | TITLE COMPOUND NAME | $R^1$ | $R^2$ | $R^3$ |
|---|---|---|---|---|
| 68 | 2-Methoxy-4-((2-methyl-3-oxocyclopent-1-en-1-yl)amino)-N-phenylbenzamide | H | H | H |
| 69 | 2-Methoxy-N-(2-methoxyphenyl)-4-((2-methyl-3-oxocyclopent-1-en-1-yl)amino)benzamide | $OCH_3$ | H | H |
| 70 | 2-Methoxy-N-(3-methoxyphenyl)-4-((2-methyl-3-oxocyclopent-1-en-1-yl)amino)benzamide | H | $OCH_3$ | H |
| 71 | 2-Methoxy-N-(4-methoxyphenyl)-4-((2-methyl-3-oxocyclopent-1-en-1-yl)amino)benzamide | H | H | $OCH_3$ |
| 72 | 2-Methoxy-4-((2-methyl-3-oxocyclopent-1-en-1-yl)amino)-N-(o-tolyl)benzamide | $CH_3$ | H | H |
| 73 | 2-Methoxy-4-((2-methyl-3-oxocyclopent-1-en-1-yl)amino)-N-(m-tolyl)benzamide | H | $CH_3$ | H |
| 74 | 2-Methoxy-4-((2-methyl-3-oxocyclopent-1-en-1-yl)amino)-N-(p-tolyl)benzamide | H | H | $CH_3$ |
| 75 | N-(3-Fluorophenyl)-2-methoxy-4-((2-methyl-3-oxocyclopent-1-en-1-yl)amino)benzamide | H | F | H |
| 76 | N-(4-Chlorophenyl)-2-methoxy-4-((2-methyl-3-oxocyclopent-1-en-1-yl)amino)benzamide | H | H | Cl |

Example 04-68

Preparation of 2-methoxy-4-((2-methyl-3-oxocyclopent-1-en-1-yl)amino)-N-phenylbenzamide (04-68)

The title compound was prepared from Example 02-03 and aniline according to the procedure of Example 04-13; 0.40 mmol scale yielded 52 mg after chromatography (ESS=EtOAc) and EtOAc trituration (39% yield). $^1$H NMR (D6-DMSO) δ 1.63 (s, 3H), 2.25-2.28 (m, 2H), 2.82-2.83 (m, 2H), 3.95 (s, 3H), 6.95 (dd, J=8.4, 1.6 Hz, 1H), 7.03 (s, 1H), 7.08 (t, J=8.4 Hz, 1H), 7.34 (t, J=7.8 Hz, 2H), 7.70-7.74 (m, 3H), 9.14 (s, 1H), 9.99 (s, 1H). LCMS t=5.8 min, m/z Calcd for $C_{20}H_{21}N_2O_3$; $C_{20}H_{20}N_2NaO_3$; $C_{40}H_{41}N_4O_6$; $C_{40}H_{40}N_4NaO_6$ 337.16; 359.14; 673.30; 695.28 [M+H]$^+$; [M+Na]$^+$; [2M+H]$^+$; [2M+Na]$^+$, Found 337.23; 359.21; 673.42; 695.40.

Example 04-69

Preparation of 2-methoxy-N-(2-methoxyphenyl)-4-((2-methyl-3-oxocyclopent-1-en-1-yl)amino)-benzamide (04-69)

The title compound was prepared from Example 02-03 and o-anisidine according to the procedure of Example 04-13; 0.40 mmol scale yielded 60 mg after chromatography (ESS=MeOH (2%)) and EtOAc trituration (41% yield). $^1$H NMR (D6-DMSO) δ 1.64 (s, 3H), 2.27-2.29 (m, 2H), 2.88-2.90 (m, 2H), 3.96 (s, 3H), 4.08 (s, 3H), 6.96 (d, J=8.0 Hz, 1H), 7.02 (dd, J=8.6, 1.6 Hz, 1H), 7.06-7.10 (m, 3H), 8.04 (d, J=8.6 Hz, 1H), 8.47 (d, J=7.8 Hz, 1H), 9.19 (s, 1H), 10.57 (s, 1H). LCMS t=5.9 min, m/z Calcd for $C_{21}H_{23}N_2O_4$; $C_{21}H_{22}N_2NaO_4$; $C_{42}H_{45}N_4O_8$; $C_{42}H_{44}N_4NaO_8$ 367.17; 389.15; 733.32; 755.31 [M+H]$^+$; [M+Na]$^+$; [2M+H]$^+$; [2M+Na]$^+$, Found 367.24; 389.21; 733.45; 755.45.

Example 04-70

Preparation of 2-methoxy-N-(3-methoxyphenyl)-4-((2-methyl-3-oxocyclopent-1-en-1-yl)amino)-benzamide (04-70)

The title compound was prepared from Example 02-03 and m-anisidine according to the procedure of Example 04-13; 0.40 mmol scale yielded 55 mg after chromatography (ESS=EtOAc) and EtOAc trituration (38% yield). $^1$H NMR (D6-DMSO) δ 1.63 (s, 3H), 2.26-2.28 (m, 2H), 2.82-2.84 (m, 2H), 3.75 (s, 3H), 3.94 (s, 3H), 6.67 (d, J=8.3 Hz, 1H), 6.95 (d, J=8.3 Hz, 1H), 7.02 (s, 1H), 7.21-7.28 (m, 2H), 7.45 (s, 1H), 7.69 (d, J=8.3 Hz, 1H), 9.14 (s, 1H), 9.97 (s, 1H). LCMS t=5.8 min, m/z Calcd for $C_{21}H_{23}N_2O_4$; $C_{21}H_{22}N_2NaO_4$; $C_{42}H_{45}N_4O_8$; $C_{42}H_{44}N_4NaO_8$ 367.17; 389.15; 733.32; 755.31 [M+H]$^+$; [M+Na]$^+$; [2M+H]$^+$; [2M+Na]$^+$, Found 367.24; 389.22; 733.45; 755.45.

Example 04-71

Preparation of 2-methoxy-N-(4-methoxyphenyl)-4-((2-methyl-3-oxocyclopent-1-en-1-yl)amino)-benzamide (04-71)

The title compound was prepared from Example 02-03 and p-anisidine according to the procedure of Example 04-13; 0.40 mmol scale yielded 29 mg after chromatography (ESS=EtOAc) and EtOAc trituration (20% yield). $^1$H NMR (D6-DMSO) δ 1.63 (s, 3H), 2.26-2.28 (m, 2H), 2.82-2.84 (m, 2H), 3.74 (s, 3H), 3.94 (s, 3H), 6.91 (d, J=8.6 Hz, 2H), 6.94 (d, J=8.3 Hz, 1H), 7.02 (s, 1H), 7.64 (d, J=8.6 Hz, 2H), 7.71 (d, J=8.3 Hz, 1H), 9.13 (s, 1H), 9.85 (s, 1H). $^{13}$C NMR (D6-DMSO) δ 7.4, 26.1, 33.1, 55.2, 56.1, 105.0, 111.7, 113.1, 113.8, 118.5, 121.4, 131.1, 132.2, 143.9, 155.4, 157.4, 163.1, 168.3, 202.2. LCMS t=5.8 min, m/z Calcd for $C_{21}H_{23}N_2O_4$; $C_{21}H_{22}N_2NaO_4$; $C_{42}H_{45}N_4O_8$; $C_{42}H_{44}N_4NaO_8$ 367.17; 389.15; 733.32; 755.31 [M+H]$^+$; [M+Na]$^+$; [2M+H]$^+$; [2M+Na]$^+$, Found 367.23; 389.21; 733.53; 755.44.

Example 04-72

Preparation of 2-methoxy-4-((2-methyl-3-oxocyclopent-1-en-1-yl)amino)-N-(o-tolyl)benzamide (04-72)

The title compound was prepared from Example 02-03 and o-toluidine according to the procedure of Example 04-13; 0.40 mmol scale yielded 70 mg after chromatography (ESS=H:E (1:19)) and EtOAc trituration (50% yield). $^1$H NMR (D6-DMSO) δ 1.64 (s, 3H), 2.27-2.29 (m, 2H), 2.32 (s, 3H), 2.86-2.88 (m, 2H), 4.03 (s, 3H), 7.00 (d, J=8.4 Hz, 1H), 7.04-7.09 (m, 2H), 7.21 (t, J=7.4 Hz, 1H), 7.26 (d, J=7.2 Hz, 1H), 7.95 (d, J=8.4 Hz, 1H), 8.04 (d, J=7.8 Hz, 1H), 9.18 (s, 1H), 9.78 (s, 1H). $^{13}$C NMR (D6-DMSO) δ 7.5, 17.7, 26.2, 33.1, 56.5, 104.7, 112.2, 113.2, 116.4, 122.2, 124.1, 126.3, 128.6, 130.3, 132.2, 136.9, 144.7, 157.7, 162.4, 168.1, 202.4. LCMS t=5.9 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.44; 723.43.

Example 04-73

Preparation of 2-methoxy-4-((2-methyl-3-oxocyclopent-1-en-1-yl)amino)-N-(m-tolyl)benzamide (04-73)

The title compound was prepared from Example 02-03 and m-toluidine according to the procedure of Example 04-13; 0.40 mmol scale yielded 55 mg after chromatography (ESS=H:E (1:19)) and EtOAc trituration (39% yield). $^1$H NMR (D6-DMSO) δ 1.63 (s, 3H), 2.26-2.28 (m, 2H), 2.30 (s, 3H), 2.82-2.84 (m, 2H), 3.95 (s, 3H), 6.90 (d, J=6.9 Hz, 1H), 6.95 (d, J=8.1 Hz, 1H), 7.02 (s, 1H), 7.21 (t, J=7.4 Hz, 1H), 7.53 (d, J=7.4 Hz, 1H), 7.57 (s, 1H), 7.71 (d, J=8.1 Hz, 1H), 9.14 (s, 1H), 9.91 (s, 1H). $^{13}$C NMR (D6-DMSO) δ 7.5, 21.2, 26.1, 33.1, 56.1, 105.0, 112.0, 113.1, 117.0, 118.4, 120.3, 124.2, 128.5, 131.2, 137.9, 138.9, 144.1, 157.4, 163.8, 168.3, 202.3. LCMS t=5.9 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.45; 723.44.

Example 04-74

Preparation of 2-methoxy-4-((2-methyl-3-oxocyclopent-1-en-1-yl)amino)-N-(p-tolyl)benzamide (04-74)

The title compound was prepared from Example 02-03 and p-toluidine according to the procedure of Example 04-13; 0.40 mmol scale yielded 30 mg after chromatography (ESS=EtOAc) and EtOAc trituration (21% yield). $^1$H NMR (D6-DMSO) δ 1.63 (s, 3H), 2.27-2.29 (m, 5H), 2.82-2.85 (m, 2H), 3.94 (s, 3H), 6.95 (d, J=7.8 Hz, 1H), 7.02 (s, 1H), 7.14 (d, J=8.0 Hz, 2H), 7.62 (d, J=8.0 Hz, 2H), 7.71 (d, J=8.3 Hz, 1H), 9.13 (s, 1H), 9.90 (s, 1H). $^{13}$C NMR (D6-DMSO) δ 7.4, 20.5, 26.1, 33.1, 56.1, 105.0, 111.7, 113.1, 118.5, 119.8, 129.1, 131.2, 132.4, 136.5, 144.0, 157.4, 163.23, 168.2, 202.3. LCMS t=5.9 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.45; 723.44.

Example 04-75

Preparation of N-(3-fluorophenyl)-2-methoxy-4-((2-methyl-3-oxocyclopent-1-en-1-yl)amino)-benzamide (04-75)

The title compound was prepared from Example 02-03 and m-fluoroaniline according to the procedure of Example 04-13; 0.40 mmol scale yielded 75 mg after chromatography (ESS=EtOAc) and EtOAc trituration (53% yield). $^1$H NMR (D6-DMSO) δ 1.63 (s, 3H), 2.26-2.28 (m, 2H), 2.82-2.84 (m, 2H), 2.94 (s, 3H), 6.91 (d, J=7.7 Hz, 1H), 6.95 (d, J=8.3 Hz, 1H), 7.03 (s, 1H), 7.37 (dd, J=15.3, 7.8 Hz, 1H), 7.48 (d, J=8.0 Hz, 1H), 7.69 (d, J=8.3 Hz, 1H), 7.74 (d, J=11.5 Hz, 1H), 9.15 (s, 1H), 10.16 (s, 1H). $^{13}$C NMR (D6-DMSO) δ 7.5, 26.1, 33.1, 56.1, 104.9, 106.5 ($J_{CF}$=26.2 Hz), 109.8 ($J_{CF}$=20.8 Hz), 111.9, 113.0, 115.6, 118.3, 130.3 ($J_{CF}$=9.2 Hz), 131.1, 140.7 ($J_{CF}$=11.4 Hz), 144.3, 157.5, 163.5 ($J_{CF}$=241.3 Hz), 164.0, 168.2, 202.3. LCMS t=5.9 min, m/z Calcd for $C_{20}H_{20}FN_2O_3$; $C_{20}H_{19}FN_2NaO_3$; $C_{40}H_{39}F_2N_4O_6$; $C_{40}H_{38}F_2N_4NaO_6$ 355.15; 377.13; 709.28; 731.27 [M+H]$^+$; [M+Na]$^+$; [2M+H]$^+$; [2M+Na]$^+$, Found 355.22; 358.22; 709.40; 731.39.

Example 04-76

Preparation of N-(4-chlorophenyl)-2-methoxy-4-((2-methyl-3-oxocyclopent-1-en-1-yl)amino)-benzamide (04-76)

The title compound was prepared from Example 02-03 and p-chloroaniline according to the procedure of Example 04-13; 0.40 mmol scale yielded 70 mg after chromatography (ESS=EtOAc) and EtOAc trituration (47% yield). $^1$H NMR (D6-DMSO) δ 1.63 (s, 3H), 2.26-2.28 (m, 2H), 2.82-2.84 (m, 2H), 3.93 (s, 3H), 6.95 (d, J=8.3 Hz, 1H), 7.02 (s, 1H), 7.39 (d, J=8.5 Hz, 2H), 7.68 (d, J=8.3 Hz, 1H), 7.78 (d, J=8.4 Hz, 2H), 9.14 (s, 1H), 10.10 (s, 1H). $^{13}$C NMR (D6-DMSO) δ 7.5, 26.1, 33.1, 56.1, 104.9, 111.9, 113.1, 118.4, 121.4, 127.0, 128.6, 131.1, 138.0, 144.2, 157.4, 163.8, 168.3, 202.3. LCMS t=6.0 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_4NaO_6$ 371.12; 393.10; 741.22; 763.21 [M+H]$^+$; [M+Na]$^+$; [2M+H]$^+$; [2M+Na]$^+$, Found 371.18; 393.16; 741.35; 763.34.

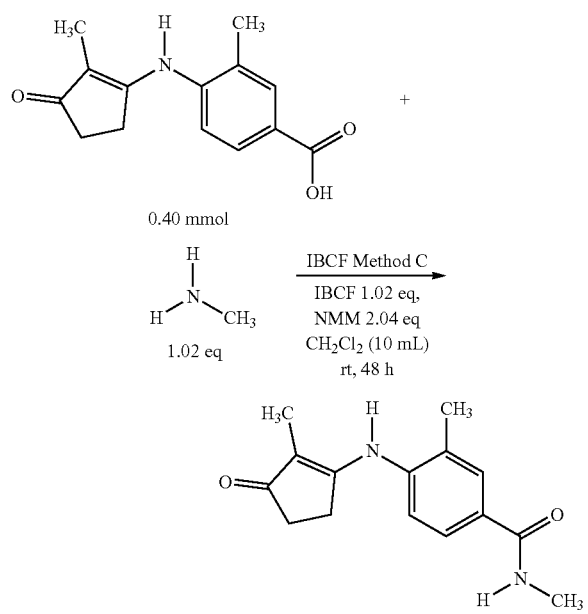

Example 04-77

Preparation of N,3-dimethyl-4-((2-methyl-3-oxocyclopent-1-en-1-yl)amino)benzamide (04-77)

The title compound was prepared from Example 01-14 and methylamine according to the procedure of Example 04-13; 0.40 mmol scale yielded 35 mg after chromatography (ESS=MeOH (8%)) and EtOAc trituration (34% yield). $^1$H NMR (D6-DMSO) δ 1.44 (s, 3H), 2.16-2.19 (m, 2H), 2.28 (s, 3H), 2.41-2.43 (m, 2H), 2.77 (d, J=4.4 Hz, 3H), 7.23 (d, J=8.1 Hz, 1H), 7.66 (d, J=8.1 Hz, 1H), 7.74 (s, 1H), 8.38-8.39 (m, 1H), 8.69 (s, 1H). LCMS t=4.9 min, m/z Calcd for $C_{15}H_{19}N_2O_2$; $C_{15}H_{18}N_2NaO_2$; $C_{30}H_{37}N_4O_4$; $C_{30}H_{36}N_4NaO_4$ 259.14; 281.13; 517.28; 539.26 [M+H]$^+$; [M+Na]$^+$; [2M+H]$^+$; [2M+Na]$^+$, Found 259.24; 281.22; 517.35; 539.42.

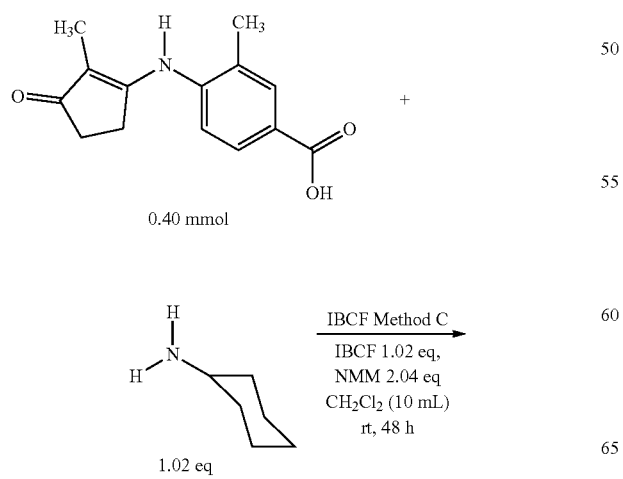

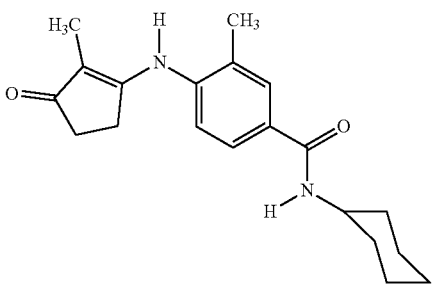

Example 04-78

Preparation of N-cyclohexyl-3-methyl-4-((2-methyl-3-oxocyclopent-1-en-1-yl)amino)benzamide (04-78)

The title compound was prepared from Example 01-14 and cyclohexylamine according to the procedure of Example 04-13; 0.40 mmol scale yielded 25 mg after chromatography (ESS=H:E (1:19)) and EtOAc trituration (19% yield). $^1$H NMR (D6-DMSO) δ 1.10-1.18 (m, 1H), 1.23-1.34 (m, 4H), 1.44 (s, 3H), 1.61 (d, J=12.4 Hz, 1H), 1.73 (s, 2H), 1.80 (s, 2H), 2.16-2.19 (m, 2H), 2.28 (s, 3H), 2.40-2.42 (m, 2H), 3.75 (s, 1H), 7.21 (d, J=8.2 Hz, 1H), 7.67 (d, J=8.0 Hz, 1H), 7.74 (s, 1H), 8.15 (d, J=7.8 Hz, 1H), 8.70 (s, 1H). LCMS t=5.7 min, m/z Calcd for $C_{20}H_{27}N_2O_2$; $C_{20}H_{26}N_2NaO_2$; $C_{40}H_{53}N_4O_4$; $C_{40}H_{52}N_4NaO_4$ 327.21; 349.19; 653.41; 675.39 [M+H]$^+$; [M+Na]$^+$; [2M+H]$^+$; [2M+Na]$^+$, Found 327.28; 349.26; 653.50; 675.54.

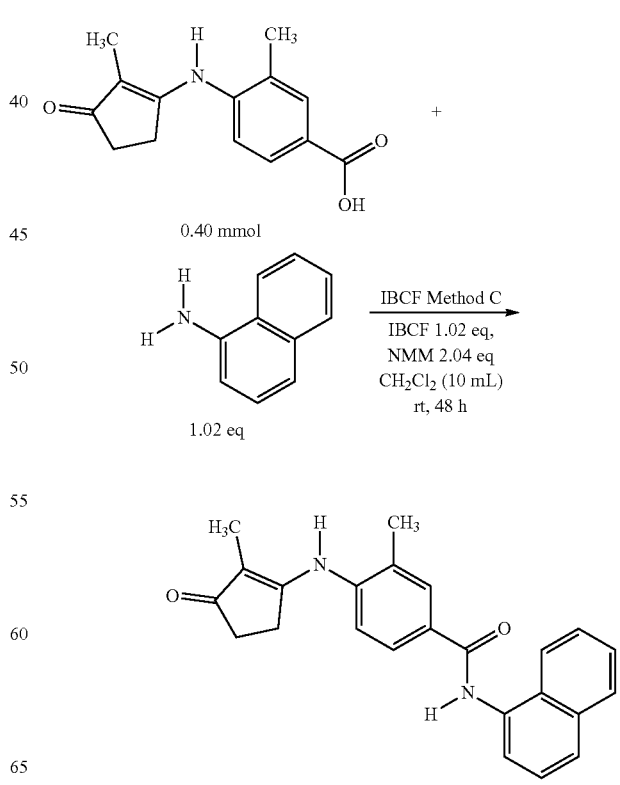

Example 04-79

Preparation of 3-methyl-4-((2-methyl-3-oxocyclopent-1-en-1-yl)amino)-N-(naphthalen-1-yl)benzamide (04-79)

The title compound was prepared from Example 01-14 and 1-aminonaphthalene according to the procedure of Example 04-13; 0.40 mmol scale yielded 35 mg after chromatography (ESS=H:E (1:19)) and EtOAc trituration (24% yield). $^1$H NMR (D6-DMSO) δ 1.50 (s, 3H), 2.21-2.23 (m, 3H), 2.36 (s, 3H), 2.48-2.50 (m, 2H), 7.33 (d, J=8.1 Hz, 1H), 7.54-7.60 (m, 4H), 7.87 (d, J=7.9 Hz, 1H), 7.94 (d, J=7.9 Hz, 1H), 7.97-8.02 (m, 3H), 8.78 (s, 1H), 10.40 (s, 1H). LCMS t=5.8 min, m/z Calcd for $C_{24}H_{23}N_2O_2$; $C_{24}H_{22}N_2NaO_2$; $C_{48}H_{45}N_4O_4$; $C_{48}H_{44}N_4NaO_4$ 371.18; 393.16; 741.34; 763.33 [M+H]$^+$; [M+Na]$^+$; [2M+H]$^+$; [2M+Na]$^+$, Found 371.24; 393.22; 741.47; 763.46.

Example 04-80

Preparation of 3-methyl-4-((2-methyl-3-oxocyclopent-1-en-1-yl)amino)-N-phenylbenzamide (04-80)

The title compound was prepared from Example 01-14 and aniline according to the procedure of Example 04-13; 0.40 mmol scale yielded 35 mg after chromatography (ESS=H:E (1:19)) and EtOAc trituration (27% yield). $^1$H NMR (D6-DMSO) δ 1.47 (s, 3H), 2.19-2.21 (m, 2H), 2.33 (s, 3H), 2.45-2.47 (m, 2H), 7.10 (t, J=7.3 Hz, 1H), 7.30 (d, J=8.1 Hz, 1H), 7.35 (t, J=7.7 Hz, 2H), 7.77 (d, J=8.0 Hz, 2H), 7.80 (d, J=8.1 Hz, 1H), 7.87 (s, 1H), 8.74 (s, 1H), 10.20 (s, 1H). LCMS t=5.7 min, m/z Calcd for $C_{20}H_{21}N_2O_2$; $C_{20}H_{20}N_2NaO_2$; $C_{40}H_{41}N_4O_4$; $C_{40}H_{40}N_4NaO_4$ 321.16; 343.14; 641.31; 663.29 [M+H]$^+$; [M+Na]$^+$; [2M+H]$^+$; [2M+Na]$^+$, Found 321.24; 343.21; 641.41; 663.41.

Example 04-81

Preparation of N-(2-methoxyphenyl)-3-methyl-4-((2-methyl-3-oxocyclopent-1-en-1-yl)amino)-benzamide (04-81)

The title compound was prepared from Example 01-14 and o-anisidine according to the procedure of Example 04-13; 0.40 mmol scale yielded 30 mg after chromatography (ESS=EtOAc) and EtOAc trituration (21% yield). $^1$H NMR (D6-DMSO) δ 1.47 (s, 3H), 2.20-2.22 (m, 2H), 2.33 (s, 3H), 2.45-2.47 (m, 2H), 3.84 (s, 3H), 6.97 (t, J=7.6 Hz, 1H), 7.10 (d, J=8.1 Hz, 1H), 7.18 (t, J=7.7 Hz, 1H), 7.28 (d, J=8.1 Hz, 1H), 7.74 (d, J=7.7 Hz, 1H), 7.80 (d, J=7.9 Hz, 1H), 7.89 (s, 1H), 8.74 (s, 1H), 9.40 (s, 1H). LCMS t=5.8 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.45; 723.48.

Example 04-82

Preparation of N-(3-methoxyphenyl)-3-methyl-4-((2-methyl-3-oxocyclopent-1-en-1-yl)amino)-benzamide (04-82)

The title compound was prepared from Example 01-14 and m-anisidine according to the procedure of Example 04-13; 0.40 mmol scale yielded 31 mg after chromatography

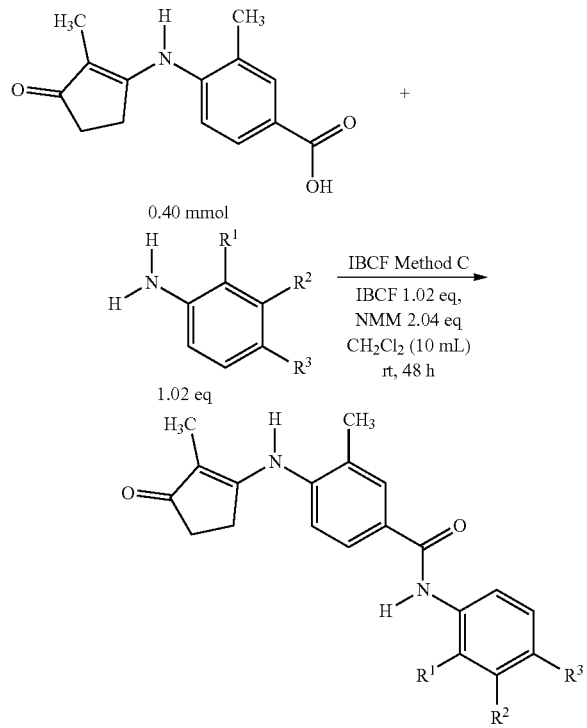

| EXAMPLE 04-# | TITLE COMPOUND NAME | R$^1$ | R$^2$ | R$^3$ |
|---|---|---|---|---|
| 80 | 3-Methyl-4-((2-methyl-3-oxocyclopent-1-en-1-yl)amino)-N-phenylbenzamide | H | H | H |
| 81 | N-(2-Methoxyphenyl)-3-methyl-4-((2-methyl-3-oxocyclopent-1-en-1-yl)amino)benzamide | OCH$_3$ | H | H |
| 82 | N-(3-Methoxyphenyl)-3-methyl-4-((2-methyl-3-oxocyclopent-1-en-1-yl)amino)benzamide | H | OCH$_3$ | H |
| 83 | N-(4-Methoxyphenyl)-3-methyl-4-((2-methyl-3-oxocyclopent-1-en-1-yl)amino)benzamide | H | H | OCH$_3$ |
| 84 | 3-Methyl-4-((2-methyl-3-oxocyclopent-1-en-1-yl)amino)-N-(o-tolyl)benzamide | CH$_3$ | H | H |
| 85 | 3-Methyl-4-((2-methyl-3-oxocyclopent-1-en-1-yl)amino)-N-(m-tolyl)benzamide | H | CH$_3$ | H |
| 86 | 3-Methyl-4-((2-methyl-3-oxocyclopent-1-en-1-yl)amino)-N-(p-tolyl)benzamide | H | H | CH$_3$ |
| 87 | N-(3-Fluorophenyl)-3-methyl-4-((2-methyl-3-oxocyclopent-1-en-1-yl)amino)benzamide | H | F | H |
| 88 | N-(4-Chlorophenyl)-3-methyl-4-((2-methyl-3-oxocyclopent-1-en-1-yl)amino)benzamide | H | H | Cl |

(ESS=H:E (1:19)) and EtOAc trituration (22% yield). $^1$H NMR (D6-DMSO) δ 1.47 (s, 3H), 2.19-2.22 (m, 2H), 2.33 (s, 3H), 2.45-2.47 (m, 2H), 3.76 (s, 3H), 6.68 (d, J=8.2 Hz, 1H), 7.25 (t, J=8.1 Hz, 1H), 7.30 (d, J=8.1 Hz, 1H), 7.37 (d, J=8.0 Hz, 1H), 7.46 (s, 1H), 7.79 (d, J=8.1 Hz, 1H), 7.86 (s, 1H), 8.74 (s, 1H), 10.17 (s, 1H). LCMS t=5.7 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.45; 723.44.

Example 04-83

Preparation of N-(4-methoxyphenyl)-3-methyl-4-((2-methyl-3-oxocyclopent-1-en-1-yl)amino)-benzamide (04-83)

The title compound was prepared from Example 01-14 and p-anisidine according to the procedure of Example 04-13; 0.40 mmol scale yielded 20 mg after chromatography (ESS=H:E (1:19)) and EtOAc trituration (14% yield). $^1$H NMR (D6-DMSO) δ 1.47 (s, 3H), 2.20-2.22 (m, 2H), 2.33 (s, 3H), 2.44-2.46 (m, 2H), 2.75 (s, 3H), 6.93 (d, J=8.7 Hz, 2H), 7.29 (d, J=8.1 Hz, 1H), 7.67 (d, J=8.6 Hz, 2H), 7.79 (d, J=8.1 Hz, 1H), 7.86 (s, 1H), 8.74 (s, 1H), 10.09 (s, 1H). $^{13}$C NMR (D6-DMSO) δ 7.6, 17.7, 25.6, 32.7, 55.2, 108.9, 113.7, 121.9, 125.7, 126.1, 129.8, 132.1, 132.3, 133.5, 140.9, 155.5, 164.6, 169.7, 202.2. LCMS t=5.6 min, m/z Calcd for $C_{21}H_{23}N_2O_3$; $C_{21}H_{22}N_2NaO_3$; $C_{42}H_{45}N_4O_6$; $C_{42}H_{44}N_4NaO_6$ 351.17; 373.15; 701.33; 723.32 [M+H]$^+$; [M+Na]$^+$; [2M+H]$^+$; [2M+Na]$^+$, Found 351.24; 373.22; 701.45; 723.43.

Example 04-84

Preparation of 3-methyl-4-((2-methyl-3-oxocyclopent-1-en-1-yl)amino)-N-(o-tolyl)benzamide (04-84)

The title compound was prepared from Example 01-14 and o-toluidine according to the procedure of Example 04-13; 0.40 mmol scale yielded 28 mg after chromatography (ESS=H:E (1:19)) and EtOAc trituration (21% yield). $^1$H NMR (D6-DMSO) δ 1.48 (s, 3H), 2.19-2.21 (m, 2H), 2.24 (s, 3H), 2.33 (s, 3H), 2.45-2.47 (m, 2H), 7.17 (d, J=7.3 Hz, 1H), 7.22 (d, J=7.4 Hz, 1H), 7.26-7.34 (m, 3H), 7.83 (d, J=8.1 Hz, 1H), 7.90 (s, 1H), 8.75 (s, 1H), 9.85 (s, 1H). $^{13}$C NMR (D6-DMSO) δ 7.6, 17.8, 18.0, 25.6, 32.7, 109.0, 125.8, 126.0, 126.2, 126.6, 130.0, 130.3, 131.6, 133.6, 133.8, 136.5, 141.0, 164.8, 169.7, 202.2. LCMS t=5.6 min, m/z Calcd for $C_{21}H_{23}N_2O_2$; $C_{21}H_{22}N_2NaO_2$; $C_{42}H_{45}N_4O_4$; $C_{42}H_{44}N_4NaO_4$ 335.18; 357.16; 669.34; 691.33 [M+H]$^+$; [M+Na]$^+$; [2M+H]$^+$; [2M+Na]$^+$, Found 335.28; 357.23; 669.45; 691.43.

Example 04-85

Preparation of 3-methyl-4-((2-methyl-3-oxocyclopent-1-en-1-yl)amino)-N-(m-tolyl)benzamide (04-85)

The title compound was prepared from Example 01-14 and m-toluidine according to the procedure of Example 04-13; 0.40 mmol scale yielded 22 mg after chromatography (ESS=H:E (1:19)) and EtOAc trituration (16% yield). $^1$H NMR (D6-DMSO) δ 1.47 (s, 3H), 2.19-2.21 (m, 2H), 2.31 (s, 3H), 2.33 (s, 3H), 2.45-2.47 (m, 2H), 6.92 (d, J=7.4 Hz, 1H), 7.22 (d, J=7.8 Hz, 1H), 7.29 (d, J=8.1 Hz, 1H), 7.56 (d, J=8.2 Hz, 1H), 7.61 (s, 1H), 7.79 (d, J=8.1 Hz, 1H), 7.87 (s, 1H), 8.74 (s, 1H), 10.12 (s, 1H). LCMS t=5.8 min, m/z Calcd for $C_{21}H_{23}N_2O_2$; $C_{21}H_{22}N_2NaO_2$; $C_{42}H_{45}N_4O_4$; $C_{42}H_{44}N_4NaO_4$ 335.18; 357.16; 669.34; 691.33 [M+H]$^+$; [M+Na]$^+$; [2M+H]$^+$; [2M+Na]$^+$, Found 335.26; 357.23; 669.44; 691.43.

Example 04-86

Preparation of 3-methyl-4-((2-methyl-3-oxocyclopent-1-en-1-yl)amino)-N-(p-tolyl)benzamide (04-86)

The title compound was prepared from Example 01-14 and p-toluidine according to the procedure of Example 04-13; 0.40 mmol scale yielded 35 mg after chromatography (ESS=H:E (1:19)) and EtOAc trituration (26% yield). $^1$H NMR (D6-DMSO) δ 1.47 (s, 3H), 2.19-2.21 (m, 2H), 2.28 (s, 3H), 2.33 (s, 3H), 2.44-2.46 (m, 2H), 7.15 (d, J=8.1 Hz, 2H), 7.29 (d, J=8.1 Hz, 1H), 7.65 (d, J=8.1 Hz, 2H), 7.79 (d, J=8.1 Hz, 1H), 7.86 (s, 1H), 8.74 (s, 1H), 10.12 (s, 1H). LCMS t=5.8 min, m/z Calcd for $C_{21}H_{23}N_2O_2$; $C_{21}H_{22}N_2NaO_2$; $C_{42}H_{45}N_4O_4$; $C_{42}H_{44}N_4NaO_4$ 335.18; 357.16; 669.34; 691.33 [M+H]$^+$; [M+Na]$^+$; [2M+H]$^+$; [2M+Na]$^+$, Found 335.25; 357.23; 669.44; 691.43.

Example 04-87

Preparation of N-(3-fluorophenyl)-3-methyl-4-((2-methyl-3-oxocyclopent-1-en-1-yl)amino)-benzamide (04-87)

The title compound was prepared from Example 01-14 and m-fluoroaniline according to the procedure of Example 04-13; 0.40 mmol scale yielded 30 mg after chromatography (ESS=H:E (1:19)) and EtOAc trituration (22% yield). $^1$H NMR (D6-DMSO) δ 1.47 (s, 3H), 2.19-2.22 (m, 2H), 2.34 (s, 3H), 2.46-2.48 (m, 2H), 6.93 (t, J=8.3 Hz, 1H), 7.31 (d, J=8.1 Hz, 1H), 7.39 (dd, J=15.4, 7.8 Hz, 1H), 7.56 (d, J=8.1 Hz, 1H), 7.75 (d, J=11.7 Hz, 1H), 7.80 (d, J=8.1 Hz, 1H), 7.87 (s, 1H), 8.75 (s, 1H), 10.39 (s, 1H). $^{13}$C NMR (D6-DMSO) δ 7.6, 17.7, 25.6, 32.7, 106.9 ($J_{CF}$=26.2 Hz), 109.2, 110.0 ($J_{CF}$=20.8 Hz), 115.9, 125.9 ($J_{CF}$=25.8 Hz), 130.1 ($J_{CF}$=38.9 Hz), 131.6, 133.5, 141.0, 141.3, 162.1 ($J_{CF}$=240.7.3 Hz), 165.3, 169.6, 202.2. LCMS t=5.7 min, m/z Calcd for $C_{20}H_{20}FN_2O_2$; $C_{20}H_{19}FN_2NaO_2$; $C_{40}H_{39}F_2N_4O_4$; $C_{40}H_{38}F_2N_4NaO_4$ 339.15; 361.13; 677.29; 699.28 [M+H]$^+$; [M+Na]$^+$; [2M+H]$^+$; [2M+Na]$^+$, Found 339.25; 361.20; 677.40; 600.39.

Example 04-88

Preparation of N-(4-chlorophenyl)-3-methyl-4-((2-methyl-3-oxocyclopent-1-en-1-yl)amino)-benzamide (04-88)

The title compound was prepared from Example 01-14 and p-chloroaniline according to the procedure of Example 04-13; 0.40 mmol scale yielded 25 mg after chromatography (ESS=H:E (1:19)) and EtOAc trituration (18% yield). $^1$H NMR (D6-DMSO) δ 1.47 (s, 3H), 2.19-2.22 (m, 3H), 2.33 (s, 3H), 2.45-2.47 (m, 2H), 7.30 (d, J=8.2 Hz, 1H), 7.41 (d, J=8.7 Hz, 2H), 7.79-7.82 (m, 3H), 7.86 (s, 1H), 8.75 (s, 1H), 10.33 (s, 1H). $^{13}$C NMR (D6-DMSO) δ 7.6, 17.7 25.6, 32.7, 109.1, 121.8, 125.9, 126.1, 127.2, 128.5, 130.0, 131.7, 133.5, 138.2, 141.3, 165.1, 169.6, 202.2. LCMS t=5.9 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10;

709.23; 731.22 [M+H]⁺; [M+Na]⁺; [2M+H]⁺; [2M+Na]⁺, Found 355.19; 377.17; 709.35; 731.34.

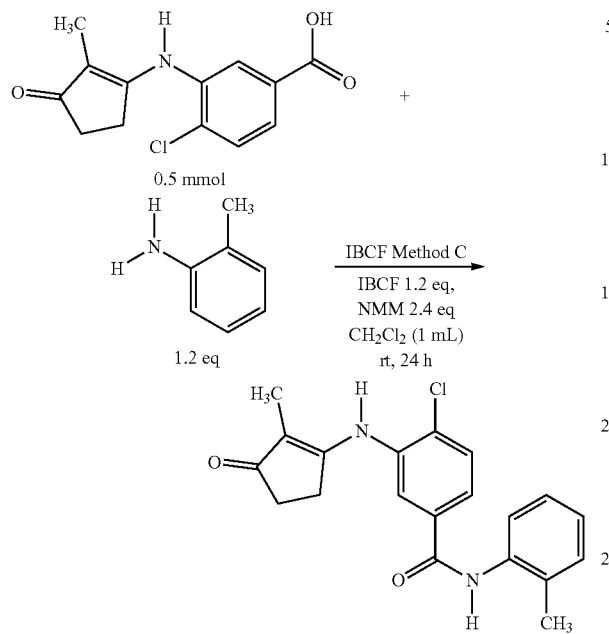

Example 04-89

Preparation of 4-chloro-3-((2-methyl-3-oxocyclopent-1-en-1-yl)amino)-N-(o-tolyl)benzamide (04-89)

The title compound was prepared from Example 01-25 and o-toluidine according to the procedure of Example 04-13; 0.50 mmol scale yielded 50 mg after chromatography (ESS=H:E (1:3)) and EtOAc trituration (28% yield). $^1$H NMR (D6-DMSO) δ 1.47 (s, 3H), 2.20-2.23 (m, 5H), 2.45-2.47 (m, 2H), 7.17-7.24 (m, 2H), 7.28 (d, J=7.3 Hz, 1H), 7.31 (d, J=7.6 Hz, 1H), 7.74 (d, J=8.3 Hz, 1H), 7.90 (d, J=8.3 Hz, 1H), 7.95 (s, 1H), 9.03 (s, 1H), 10.01 (s, 1H). $^{13}$C NMR (D6-DMSO) δ 7.9, 18.3, 26.0, 33.1, 110.0, 126.5, 126.7, 127.2, 128.0, 130.4, 130.8, 133.9, 134.2, 134.3, 136.5, 137.2, 140.1, 160.5, 170.0, 202.9. LCMS t=4.8 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.12; 377.10; 709.23; 731.22 [M+H]⁺; [M+Na]⁺; [2M+H]⁺; [2M+Na]⁺, Found 355.12; 377.11; 709.24; 731.22.

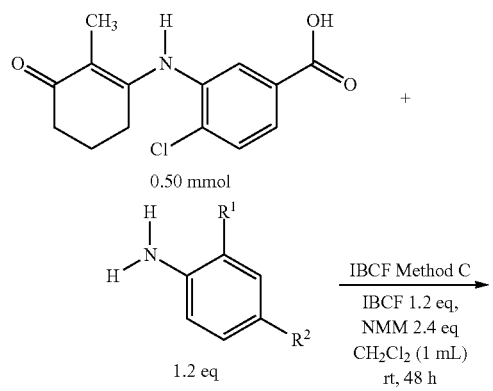

| EXAMPLE 04-# | TITLE COMPOUND NAME | R¹ | R² |
|---|---|---|---|
| 90 | 4-Chloro-N-(4-methoxyphenyl)-3-((2-methyl-3-oxocyclohex-1-en-1-yl)amino)benzamide | H | OCH₃ |
| 91 | 4-Chloro-3-((2-methyl-3-oxocyclohex-1-en-1-yl)amino)-N-(o-tolyl)benzamide | CH₃ | H |

Example 04-90

Preparation of 4-chloro-N-(4-methoxyphenyl)-3-((2-methyl-3-oxocyclohex-1-en-1-yl)amino)benzamide (04-90)

The title compound was prepared from Example 01-36 and p-anisidine according to the procedure of Example 04-13; 0.50 mmol scale yielded 90 mg from solid precipitate (47% yield). $^1$H NMR (D6-DMSO) δ 1.67 (s, 3H), 1.77-1.80 (m, 2H), 2.19-2.22 (m, 2H), 2.24-2.27 (m, 2H), 3.75 (s, 3H), 6.93 (d, J=9.0 Hz, 2H), 7.66 (d, J=8.9 Hz, 2H), 7.71 (d, J=8.1 Hz, 1H), 7.86-7.89 (m, 2H), 8.11 (s, 1H), 10.19 (s, 1H). $^{13}$C NMR (D6-DMSO) δ 9.5, 21.6, 27.4, 36.8, 55.6, 107.7, 114.2, 122.6, 126.8, 128.4, 130.2, 132.3, 134.4, 134.7, 137.7, 156.2, 158.8, 163.7, 195.1. LCMS t=5.0 min, m/z Calcd for $C_{21}H_{22}ClN_2O_3$; $C_{21}H_{21}ClN_2NaO_3$; $C_{42}H_{43}Cl_2N_4O_6$; $C_{42}H_{42}Cl_2N_4NaO_6$ 385.13; 407.11; 769.26; 791.24 [M+H]⁺; [M+Na]⁺; [2M+H]⁺; [2M+Na]⁺, Found 385.12; 407.10; 769.23; 791.21.

Example 04-91

Preparation of 4-chloro-3-((2-methyl-3-oxocyclohex-1-en-1-yl)amino)-N-(o-tolyl)benzamide (04-91)

The title compound was prepared from Example 01-36 and o-toluidine according to the procedure of Example 04-13; 0.50 mmol scale yielded 55 mg after chromatography (ESS=H:E (1:3)) and EtOAc trituration (30% yield). $^1$H NMR (D6-DMSO) δ 1.66 (s, 3H), 1.77-1.80 (m, 2H), 2.19-2.23 (m, 5H), 2.26-2.28 (m, 2H), 7.17-7.24 (m, 2H), 7.28 (d, J=7.3 Hz, 1H), 7.31 (d, J=7.5 Hz, 1H), 7.72 (d, J=8.1 Hz, 1H), 7.87-7.89 (m, 2H), 8.13 (s, 1H), 10.00 (s, 1H). $^{13}$C NMR (D6-DMSO) δ 9.5, 18.3, 21.6, 27.5, 36.8, 107.9, 126.5, 126.7, 127.2, 128.3, 130.3, 130.8, 134.2, 134.3, 136.5, 137.8, 158.8, 164.1, 195.2. LCMS t=5.0 min, m/z Calcd for $C_{21}H_{22}ClN_2O_2$; $C_{21}H_{21}ClN_2NaO_2$; $C_{42}H_{43}Cl_2N_4O_4$; $C_{42}H_{43}Cl_2N_4NaO_4$ 369.14; 391.12; 737.27; 759.25 [M+H]⁺; [M+Na]⁺; [2M+H]⁺; [2M+Na]⁺, Found 369.14; 391.12; 737.27; 759.25.

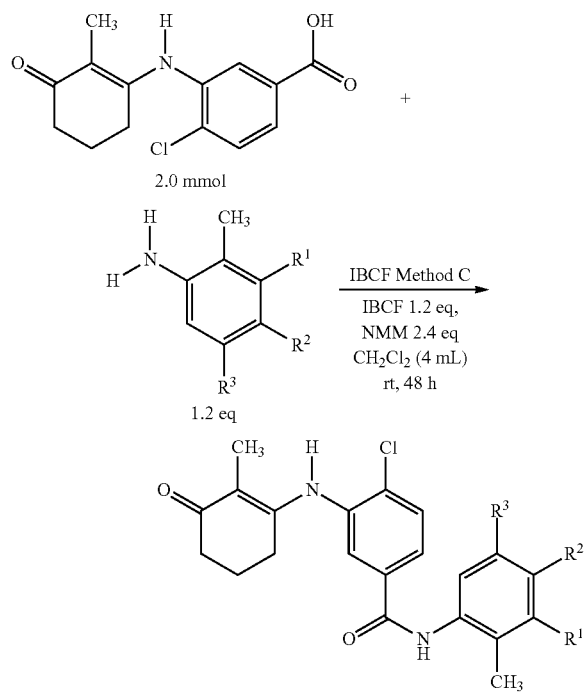

| EXAMPLE 04-# | TITLE COMPOUND NAME | R¹ | R² | R³ |
|---|---|---|---|---|
| 92 | Methyl 3-(4-chloro-3-((2-methyl-3-oxocyclohex-1-en-1-yl)amino)benzamido)-2-methylbenzoate | CO₂CH₃ | H | H |
| 93 | Methyl 3-(4-chloro-3-((2-methyl-3-oxocyclohex-1-en-1-yl)amino)benzamido)-4-methylbenzoate | H | H | CO₂CH₃ |
| 94 | Methyl 4-(4-chloro-3-((2-methyl-3-oxocyclohex-1-en-1-yl)amino)benzamido)-3-methylbenzoate | H | CO₂CH₃ | H |

Preparation of methyl 3-(4-chloro-3-((2-methyl-3-oxocyclohex-1-en-1-yl)amino)benzamido)-2-methylbenzoate (04-92)

The title compound was prepared from Example 01-36 and methyl 3-amino-2-methylbenzoate according to the procedure of Example 04-13; 2.0 mmol scale yielded 340 mg from precipitate (40% yield). $^1$H NMR (D6-DMSO) δ 1.67 (s, 3H), 1.78-1.81 (m, 2H), 2.19-2.22 (m, 2H), 2.27-2.29 (m, 2H), 2.34 (s, 3H), 3.85 (s, 3H), 7.35 (t, J=7.8 Hz, 1H), 7.51 (d, J=7.7 Hz, 1H), 7.68 (d, J=7.7 Hz, 1H), 7.73 (d, J=8.1 Hz, 1H), 7.88-7.90 (m, 2H), 8.14 (s, 1H), 10.20 (s, 1H). $^{13}$C NMR (D6-DMSO) δ 9.5, 15.7, 21.6, 27.4, 36.8, 52.6, 107.9, 126.3, 126.8, 128.2, 128.4, 130.4, 131.2, 132.0, 133.9, 134.5, 135.3, 137.7, 137.8, 158.7, 164.4, 168.1, 195.2. LCMS t=5.1 min, m/z Calcd for $C_{23}H_{24}ClN_2O_4$; $C_{23}H_{23}ClN_2NaO_4$; $C_{46}H_{47}Cl_2N_4O_8$; $C_{46}H_{46}Cl_2N_4NaO_8$ 427.14; 449.12; 853.28; 875.26 [M+H]⁺; [M+Na]⁺; [2M+H]⁺; [2M+Na]⁺, Found 427.16; 449.14; 853.31; 875.29.

Example 04-93

Preparation of methyl 3-(4-chloro-3-((2-methyl-3-oxocyclohex-1-en-1-yl)amino)benzamido)-4-methylbenzoate (04-93)

The title compound was prepared from Example 01-36 and methyl 3-amino-4-methylbenzoate according to the procedure of Example 04-13; 2.0 mmol scale yielded 310 mg from precipitate (36% yield). $^1$H NMR (D6-DMSO) δ 1.67 (s, 3H), 1.78-1.81 (m, 2H), 2.19-2.22 (m, 2H), 2.27-2.29 (m, 2H), 2.31 (s, 3H), 3.85 (s, 3H), 7.45 (d, J=7.9 Hz, 1H), 7.74 (d, J=8.0 Hz, 1H), 7.77 (d, J=7.9 Hz, 1H), 7.87-7.90 (m, 2H), 7.97 (s, 1H), 8.14 (s, 1H), 10.14 (s, 1H). LCMS t=5.1 min, m/z Calcd for $C_{23}H_{24}ClN_2O_4$; $C_{23}H_{23}ClN_2NaO_4$; $C_{46}H_{47}Cl_2N_4O_8$; $C_{46}H_{46}Cl_2N_4NaO_8$ 427.14; 449.12; 853.28; 875.26 [M+H]⁺; [M+Na]⁺; [2M+H]⁺; [2M+Na]⁺, Found 427.16; 449.14; 853.32; 875.29.

Example 04-94

Preparation of methyl 4-(4-chloro-3-((2-methyl-3-oxocyclohex-1-en-1-yl)amino)benzamido)-3-methylbenzoate (04-94)

The title compound was prepared from Example 01-36 and methyl 4-amino-3-methylbenzoate according to the procedure of Example 04-13; 2.0 mmol scale yielded 175 mg from precipitate (21% yield). $^1$H NMR (D6-DMSO) δ 1.67 (s, 3H), 1.78-1.81 (m, 2H), 2.19-2.22 (m, 2H), 2.29-2.32 (m, 5H), 3.86 (s, 3H), 7.58 (d, J=8.3 Hz, 1H), 7.73 (d, J=8.1 Hz, 1H), 7.83 (d, J=8.2 Hz, 1H), 7.85-7.90 (m, 3H), 8.11 (s, 1H), 10.10 (s, 1H). $^{13}$C NMR (D6-DMSO) δ 9.5, 18.3, 21.6, 27.5, 36.8, 52.5, 108.0, 126.5, 126.8, 127.2, 127.6, 128.3, 130.4, 131.8, 133.9, 134.0, 134.5, 137.9, 141.2, 158.7, 164.3, 166.4, 195.2. LCMS t=5.1 min, m/z Calcd for $C_{23}H_{24}ClN_2O_4$; $C_{23}H_{23}ClN_2NaO_4$; $C_{46}H_{47}Cl_2N_4O_8$; $C_{46}H_{46}Cl_2N_4NaO_8$ 427.14; 449.12; 853.28; 875.26 [M+H]⁺; [M+Na]⁺; [2M+H]⁺; [2M+Na]⁺, Found 427.16; 449.14; 853.31; 875.29.

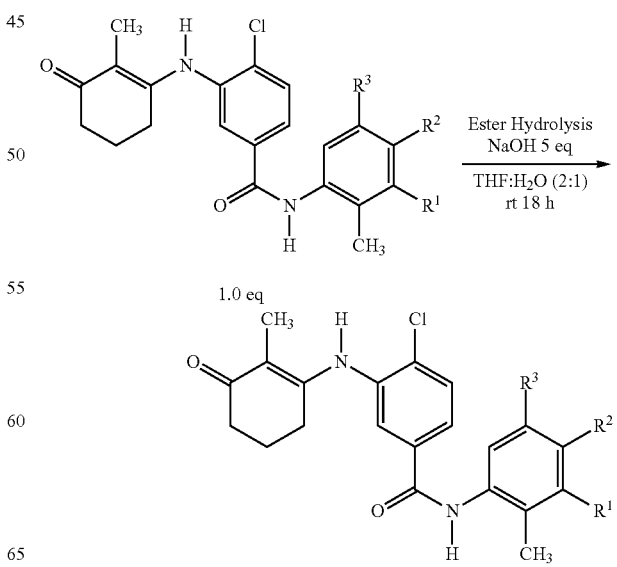

| EXAMPLE 04-# | TITLE COMPOUND NAME | R¹ | R² | R³ |
|---|---|---|---|---|
| 95 | 3-(4-Chloro-3-((2-methyl-3-oxocyclohex-1-en-1-yl)amino)benzamido)-2-methylbenzoic acid | CO$_2$H | H | H |
| 96 | 3-(4-Chloro-3-((2-methyl-3-oxocyclohex-1-en-1-yl)amino)benzamido)-4-methylbenzoic acid | H | H | CO$_2$H |
| 97 | 4-(4-Chloro-3-((2-methyl-3-oxocyclohex-1-en-1-yl)amino)benzamido)-3-methylbenzoic acid | H | CO$_2$H | H |

Preparation of 3-(4-chloro-3-((2-methyl-3-oxocyclohex-1-en-1-yl)amino)benzamido)-2-methylbenzoic acid (04-95)

The title compound was prepared from Example 04-92 according to the procedure of Example 02-01; 0.75 mmol scale yielded 0.29 g (93% yield). $^1$H NMR (D6-DMSO) δ 1.66 (s, 3H), 1.78-1.81 (m, 2H), 2.21 (t, J=6.3 Hz, 2H), 2.27-2.29 (m, 2H), 2.37 (s, 3H), 7.32 (t, J=7.8 Hz, 1H), 7.47 (d, J=8.3 Hz, 1H), 7.68 (d, J=7.8 Hz, 1H), 7.73 (d, J=8.2 Hz, 1H), 7.88-7.90 (m, 2H), 8.12 (s, 1H), 10.16 (s, 1H), 12.98 (s, 1H). $^{13}$C NMR (D6-DMSO) δ 9.5, 15.7, 21.6, 27.4, 36.8, 107.9, 126.1, 126.8, 128.3, 130.4, 130.8, 133.2, 133.9, 134.5, 135.2, 137.6, 137.8, 158.7, 164.4, 169.5, 195.1. LCMS t=4.7 min, m/z Calcd for C$_{22}$H$_{22}$ClN$_2$O$_4$; C$_{22}$H$_{21}$ClN$_2$NaO$_4$; C$_{44}$H$_{43}$Cl$_2$N$_4$O$_8$; C$_{44}$H$_{42}$Cl$_2$N$_4$NaO$_8$ 413.13; 435.11; 825.25; 847.23 [M+H]$^+$; [M+Na]$^+$; [2M+H]$^+$; [2M+Na]$^+$, Found 413.14; 435.12; 825.28; 847.25.

Example 04-96

Preparation of 3-(4-Chloro-3-((2-methyl-3-oxocyclohex-1-en-1-yl)amino)benzamido)-4-methylbenzoic acid (04-96)

The title compound was prepared from Example 04-93 according to the procedure of Example 02-01; 0.7 mmol scale yielded 0.26 g (88% yield). $^1$H NMR (D6-DMSO) δ 1.67 (s, 3H), 1.78-1.81 (m, 2H), 2.21 (t, J=6.4 Hz, 1H), 2.26-2.30 (m, 5H), 7.41 (d, J=8.0 Hz, 1H), 7.72-7.76 (m, 2H), 7.87-7.89 (m, 2H), 7.92 (s, 1H), 8.11 (s, 1H), 10.11 (s, 1H), 12.91 (s, 1H). $^{13}$C NMR (D6-DMSO) δ 9.5, 18.6, 21.6, 27.4, 36.8, 107.9, 126.8, 127.4, 127.9, 128.4, 129.3, 130.3, 131.1, 134.0, 134.5, 136.7, 137.8, 139.6, 158.7, 164.3, 167.4, 195.1. LCMS t=4.7 min, m/z Calcd for C$_{22}$H$_{22}$ClN$_2$O$_4$; C$_{44}$H$_{43}$Cl$_2$N$_4$O$_8$ 413.13; 825.25 [M+H]$^+$; [2M+H]$^+$, Found 413.14; 825.29.

Example 04-97

Preparation of 4-(4-chloro-3-((2-methyl-3-oxocyclohex-1-en-1-yl)amino)benzamido)-3-methylbenzoic acid (04-97)

The title compound was prepared from Example 04-94 according to the procedure of Example 02-01; 0.4 mmol scale yielded 0.1 g (61% yield). $^1$H NMR (D6-DMSO) δ 1.66 (s, 3H), 1.78-1.81 (m, 2H), 2.21 (t, J=6.4 Hz, 1H), 2.26-2.32 (m, 5H), 7.53 (d, J=8.3 Hz, 1H), 7.73 (d, J=8.1 Hz, 1H), 7.80 (d, J=8.2 Hz, 1H), 7.86-7.78 (m, 3H), 8.11 (s, 1H), 10.09 (s, 1H), 12.87 (s, 1H). $^{13}$C NMR (D6-DMSO) δ 9.5, 18.3, 21.6, 27.5, 36.8, 108.0, 126.4, 126.8, 127.7, 128.3, 128.5, 130.4, 131.9, 133.7, 134.0, 134.5, 137.8, 140.8, 158.7, 164.2, 167.5, 195.2. LCMS t=4.8 min, m/z Calcd for C$_{22}$H$_{22}$ClN$_2$O$_4$; C$_{22}$H$_{21}$ClN$_2$NaO$_4$; C$_{44}$H$_{43}$Cl$_2$N$_4$O$_8$; C$_{44}$H$_{42}$Cl$_2$N$_4$NaO$_8$ 413.13; 825.25 [M+H]$^+$; [2M+H]$^+$, Found 413.14; 825.28.

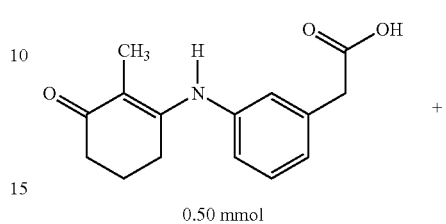

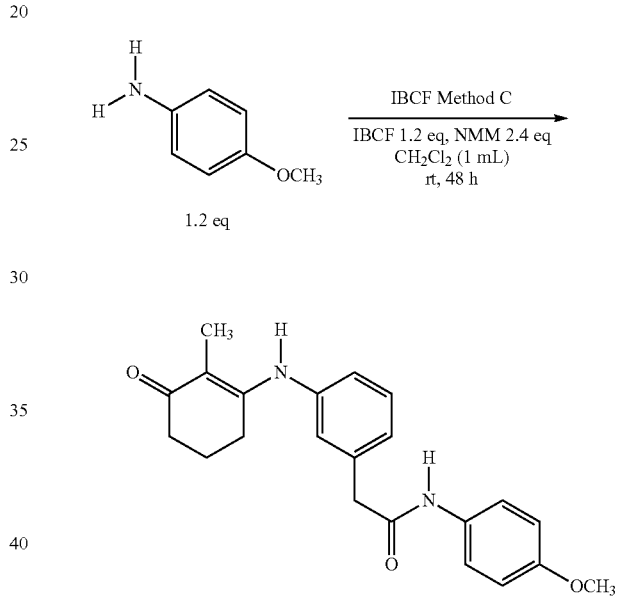

Example 04-98

Preparation of N-(4-methoxyphenyl)-2-(3-((2-methyl-3-oxocyclohex-1-en-1-yl)amino)phenyl)-acetamide (04-98)

The title compound was prepared from Example 01-37 and p-anisidine according to the procedure of Example 04-13; 0.50 mmol scale yielded 10 mg after chromatography (ESS=H:E (1:3)) and EtOAc trituration (6% yield). $^1$H NMR (D6-DMSO) δ 1.66 (s, 3H), 1.75-1.78 (m, 2H), 2.18-2.21 (m, 2H), 2.42-2.45 (m, 2H), 3.59 (s, 2H), 3.71 (s, 3H), 6.87 (d, J=8.7 Hz, 2H), 6.99 (d, J=7.5 Hz, 1H), 7.08 (s, 2H), 7.28 (t, J=7.8 Hz, 1H), 7.49 (d, J=8.7 Hz, 2H), 8.20 (s, 1H), 10.01 (s, 1H). $^{13}$C NMR (D6-DMSO) δ 9.7, 22.1, 27.8, 36.9, 43.5, 55.6, 107.6, 114.3, 121.1, 122.9, 125.4, 129.1, 129.1, 132.8, 137.3, 140.3, 155.6, 158.5, 168.8, 194.8. LCMS t=4.9 min, m/z Calcd for C$_{22}$H$_{25}$N$_2$O$_3$; C$_{22}$H$_{24}$N$_2$NaO$_3$; C$_{44}$H$_{49}$N$_4$O$_6$; C$_{44}$H$_{48}$N$_4$NaO$_6$ 365.19; 387.17; 729.37; 751.35 [M+H]$^+$; [M+Na]$^+$; [2M+H]$^+$; [2M+Na]$^+$, Found 365.17; 387.14; 729.31; 751.29.

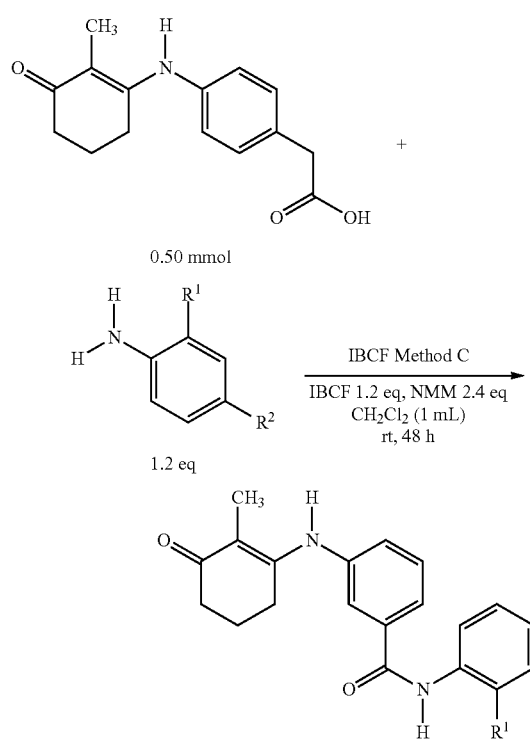

| EXAM-PLE 04-# | TITLE COMPOUND NAME | R¹ | R² |
|---|---|---|---|
| 99 | N-(4-Methoxyphenyl)-2-(4-((2-methyl-3-oxocyclohex-1-en-1-yl)amino)phenyl)acetamide | H | OCH₃ |
| 100 | 2-(4-((2-Methyl-3-oxocyclohex-1-en-1-yl)amino)phenyl)-N-(o-tolyl)acetamide | CH₃ | H |

Example 04-99

Preparation of N-(4-methoxyphenyl)-2-(4-((2-methyl-3-oxocyclohex-1-en-1-yl)amino)phenyl)-acetamide (04-99)

The title compound was prepared from Example 01-38 and p-anisidine according to the procedure of Example 04-13; 0.50 mmol scale yielded 31 mg after chromatography (ESS=H:E (1:3)) and EtOAc trituration (17% yield). ¹H NMR (D6-DMSO) δ 1.68 (s, 3H), 1.75-1.77 (m, 2H), 2.17-2.20 (m, 2H), 2.41-2.43 (m, 2H), 3.57 (s, 2H), 3.71 (s, 3H), 6.87 (d, J=8.6 Hz, 2H), 7.08 (d, J=7.8 Hz, 2H), 7.28 (d, J=7.8 Hz, 2H), 7.50 (d, J=8.6 Hz, 2H), 8.14 (s, 1H), 10.00 (s, 1H). ¹³C NMR (D6-DMSO) δ 9.5, 22.1, 27.7, 36.9, 43.0, 55.6, 107.0, 115.3, 121.1, 125.0, 129.8, 132.5, 132.8, 138.7, 156.0, 158.8, 169.0, 194.6. LCMS t=4.8 min, m/z Calcd for C₂₂H₂₅N₂O₃; C₂₂H₂₄N₂NaO₃; C₄₄H₄₉N₄O₆; C₄₄H₄₈N₄NaO₆ 365.19; 387.17; 729.37; 751.35 [M+H]⁺; [M+Na]⁺; [2M+H]⁺; [2M+Na]⁺, Found 365.16; 387.14; 729.30; 751.28.

Example 04-100

Preparation of 2-(4-((2-methyl-3-oxocyclohex-1-en-1-yl)amino)phenyl)-N-(o-tolyl)acetamide (04-100)

The title compound was prepared from Example 01-37 and o-toluidine according to the procedure of Example 04-13; 0.50 mmol scale yielded 40 mg after chromatography (ESS=H:E (1:3)) and EtOAc trituration (23% yield). ¹H NMR (D6-DMSO) δ 1.68 (s, 3H), 1.75-1.78 (m, 2H), 2.16 (s, 3H), 2.18-2.21 (m, 2H), 2.41-2.44 (m, 2H), 3.65 (s, 3H), 7.05-7.21 (m, 5H), 7.27-7.39 (m, 3H), 8.18 (s, 1H), 9.49 (s, 1H). ¹³C NMR (D6-DMSO) δ 9.5, 18.2, 22.2, 27.7, 36.9, 42.6, 106.9, 112.6, 119.5, 125.0, 125.5, 125.7, 126.4, 129.8, 130.7, 132.2, 132.7, 136.7, 138.7, 158.9, 169.5, 194.6. LCMS t=4.7 min, m/z Calcd for C₂₂H₂₅N₂O₂; C₂₂H₂₄N₂NaO₂; C₄₄H₄₉N₄O₄; C₄₄H₄₈N₄NaO₄ 349.19; 371.17; 697.37; 719.36 [M+H]⁺; [M+Na]⁺; [2M+H]⁺; [2M+Na]⁺, Found 349.18; 371.14; 697.31; 719.29.

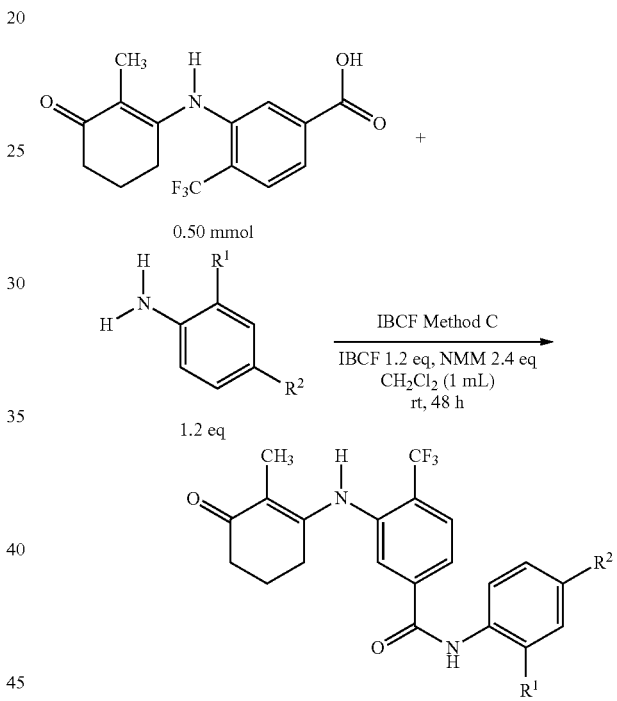

| EXAM-PLE 04-# | TITLE COMPOUND NAME | R¹ | R² |
|---|---|---|---|
| 101 | N-(4-Methoxyphenyl)-3-((2-methyl-3-oxocyclohex-1-en-1-yl)amino)-4-(trifluoromethyl)benzamide | H | OCH₃ |
| 102 | 3-((2-Methyl-3-oxocyclohex-1-en-1-yl)amino)-N-(o-tolyl)-4-(trifluoromethyl)benzamide | CH₃ | H |

Example 04-101

Preparation of N-(4-methoxyphenyl)-3-((2-methyl-3-oxocyclohex-1-en-1-yl)amino)-4-(trifluoromethyl)benzamide (04-101)

The title compound was prepared from Example 01-39 and p-anisidine according to the procedure of Example 04-13; 0.50 mmol scale yielded 10 mg after chromatography (ESS=H:E (1:1)) and EtOAc trituration (5% yield). $^1$H NMR (D6-DMSO) δ 1.66 (s, 3H), 1.75-1.77 (m, 2H), 2.19-2.21 (m, 4H), 3.76 (s, 3H), 6.95 (d, J=8.4 Hz, 2H), 7.67 (d, J=8.3 Hz, 2H), 7.95 (s, 2H), 8.00 (s, 1H), 8.05-8.07 (m, 1H), 10.32 (s, 1H). $^{13}$C NMR (D6-DMSO) δ 9.2, 21.6, 27.6, 36.7, 55.5, 107.2, 114.3, 122.7, 126.6, 127.5, 129.2 ($J_{CF}$=28.8 Hz), 130.1, 132.0, 138.8, 139.7, 156.4, 159.2, 163.4, 195.0. LCMS t=5.1 min, m/z Calcd for $C_{22}H_{22}F_3N_2O_3$; $C_{22}H_{21}F_3N_2NaO_3$; $C_{44}H_{43}F_6N_4O_6$; $C_{44}H_{42}F_6N_4NaO_6$ 419.16; 441.14; 837.31; 859.29 [M+H]$^+$; [M+Na]$^+$; [2M+H]$^+$; [2M+Na]$^+$, Found 419.14; 441.09; 837.22; 859.20.

Example 04-102

Preparation of 3-((2-methyl-3-oxocyclohex-1-en-1-yl)amino)-N-(o-tolyl)-4-(trifluoromethyl)benzamide (04-102)

The title compound was prepared from Example 01-39 and o-toluidine according to the procedure of Example 04-13; 0.50 mmol scale 10 mg after chromatography (ESS=H:E (1:1)) and EtOAc trituration (5% yield). $^1$H NMR (D6-DMSO) δ 1.65 (s, 3H), 1.75-1.78 (m, 2H), 2.18-2.24 (m, 7H), 7.19-7.26 (m, 2H), 7.30 (d, J=7.3 Hz, 1H), 7.34 (d, J=7.4 Hz, 1H), 7.93-7.99 (3H), 8.07 (d, J=7.9 Hz, 1H), 10.15 (s, 1H). $^{13}$C NMR (D6-DMSO) δ 9.3, 18.3, 21.6, 27.6, 36.7, 107.4, 126.6, 127.0, 127.2, 127.6, 129.2 ($J_{CF}$=29.9 Hz), 130.0, 130.9, 134.4, 136.3, 139.0, 139.3, 159.1, 163.8, 195.0. LCMS t=5.1 min, m/z Calcd for $C_{22}H_{22}F_3N_2O_2$; $C_{22}H_{21}F_3N_2NaO_2$; $C_{44}H_{43}F_6N_4O_4$; $C_{44}H_{42}F_6N_4NaO_4$ 403.16; 425.15; 805.32; 827.30 [M+H]$^+$; [M+Na]$^+$; [2M+H]$^+$; [2M+Na]$^+$, Found 403.15; 425.10; 805.24; 827.22.

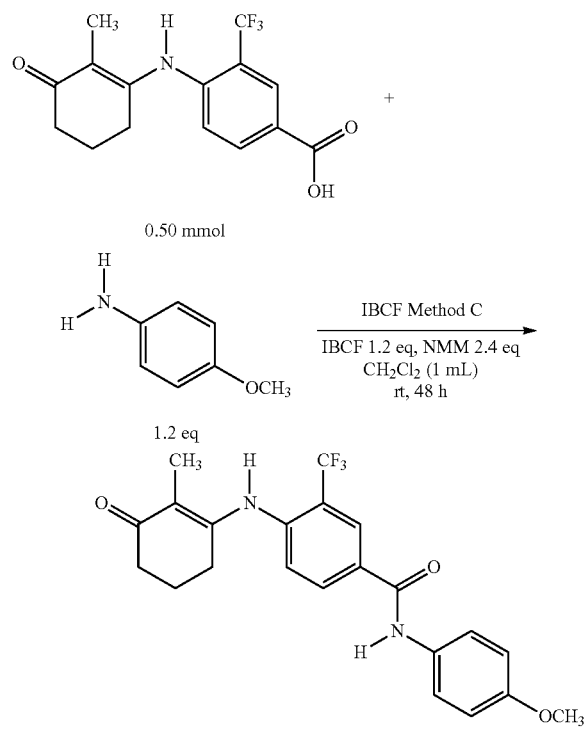

Example 04-103

Preparation of N-(4-methoxyphenyl)-4-((2-methyl-3-oxocyclohex-1-en-1-yl)amino)-3-(trifluoromethyl)benzamide (04-103)

The title compound was prepared from Example 01-40 and p-anisidine according to the procedure of Example 04-13; 0.50 mmol scale yielded 60 mg after chromatography (ESS=H:E (1:1)) and EtOAc trituration (31% yield). $^1$H NMR (D6-DMSO) δ 1.59 (s, 3H), 1.77-1.80 (m, 2H), 2.21-2.24 (m, 2H), 2.29-1.31 (m, 2H), 3.75 (s, 3H), 6.95 (d, J=8.6 Hz, 2H), 7.46 (d, J=8.3 Hz, 1H), 7.66 (d, J=8.6 Hz, 2H), 7.91 (s, 1H), 8.23 (d, J=8.3 Hz, 1H), 8.30 (s, 1H), 10.33 (s, 1H). $^{13}$C NMR (D6-DMSO) δ 9.8, 21.5, 28.1, 36.9, 55.6, 109.6, 114.2, 122.6, 123.9 ($J_{CF}$=273.6 Hz), 124.8 ($J_{CF}$=87.6, 29.2 Hz), 126.5, 129.7, 132.3, 132.4, 132.8, 141.6, 156.2, 158.2, 163.6, 195.7. LCMS t=5.1 min, m/z Calcd for $C_{22}H_{22}F_3N_2O_3$; $C_{22}H_{21}F_3N_2NaO_3$; $C_{44}H_{43}F_6N_4O_6$; $C_{44}H_{42}F_6N_4NaO_6$ 419.16; 441.14; 837.31; 859.29 [M+H]$^+$; [M+Na]$^+$; [2M+H]$^+$; [2M+Na]$^+$, Found 419.14; 441.09; 837.22; 859.20

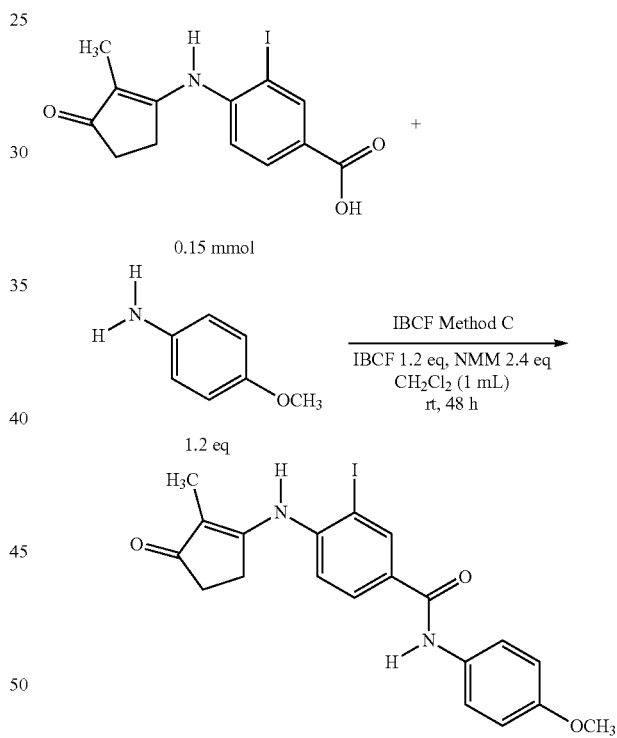

Example 04-104

Preparation of 3-iodo-N-(4-methoxyphenyl)-4-((2-methyl-3-oxocyclopent-1-en-1-yl)amino)benzamide (04-104)

The title compound was prepared from Example 02-08 and p-anisidine according to the procedure of Example 04-13; 0.15 mmol scale yielded 110 mg of pale yellow microcrystals after chromatography (ESS H:E=1:19, mp=222-224° C., 52% yield). $^1$H NMR (D6-DMSO) δ 1.47 (s, 3H), 2.20-2.22 (m, 2H), 2.41-2.46 (m, 1H), 3.75 (s, 3H), 6.94 (d, J=8.9 Hz, 2H), 7.46 (d, J=8.2 Hz, 1H), 7.66 (d, J=8.9

Hz, 2H), 7.98 (dd, J=8.1, 1.2 Hz, 1H), 8.47 (d, J=1.3 Hz, 1H), 8.90 (s, 1H), 10.21 (s, 1H). $^{13}$C NMR (D6-DMSO) δ 7.5, 25.7, 32.7, 55.2, 98.6, 109.6, 113.8, 122.1, 127.2, 128.4, 132.0, 133.9, 138.0, 144.0, 155.7, 162.9, 169.1, 202.3. LCMS t=4.9 min, Calcd for $C_{20}H_{20}IN_2O_3$; $C_{20}H_{19}IN_2NaO_3$; $C_{40}H_{39}I_2N_4O_6$; $C_{40}H_{38}I_2N_4NaO_6$ 463.05; 485.03; 925.10; 947.09 [M+H]+; [M+Na]+; [2M+H]+; [2M+Na]+, Found 463.08; 485.00; 925.11; 947.09.

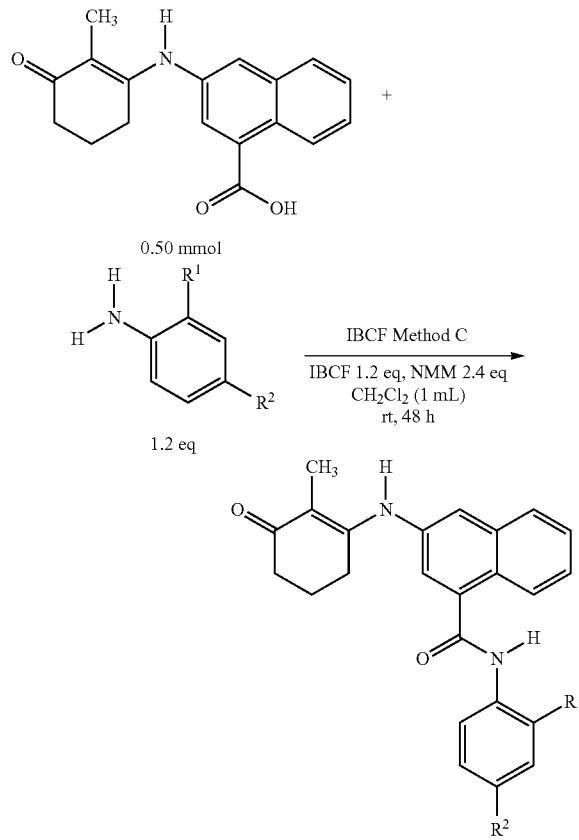

| EXAMPLE 04-# | TITLE COMPOUND NAME | R$^1$ | R$^2$ |
|---|---|---|---|
| 105 | N-(4-Methoxyphenyl)-3-((2-methyl-3-oxocyclohex-1-en-1-yl)amino)-1-naphthamide | H | OCH$_3$ |
| 106 | 3-((2-Methyl-3-oxocyclohex-1-en-1-yl)amino)-N-(o-tolyl)-1-naphthamide | CH$_3$ | H |

Example 04-105

Preparation of N-(4-methoxyphenyl)-3-((2-methyl-3-oxocyclohex-1-en-1-yl)amino)-1-naphthamide (04-105)

The title compound was prepared from Example 01-52 and p-anisidine according to the procedure of Example 04-13; 0.5 mmol scale yielded 1 mg of off-white microcrystals after chromatography (ESS E:H=1:1, 1% yield). $^1$H NMR (D6-DMSO) δ 1.74 (s, 3H), 1.83-1.86 (m, 2H), 2.25-2.28 (m, 2H), 2.63-2.65 (m, 2H), 3.76 (s, 3H), 6.95 (d, J=8.8 Hz, 2H), 7.47-7.50 (m, 1H), 7.53-7.58 (m, 2H), 7.67 (s, 1H), 7.71 (d, J=8.8 Hz, 2H), 7.92 (d, J=8.1 Hz, 1H), 8.08 (d, J=8.3 Hz, 1H), 8.49 (s, 1H), 10.43 (s, 1H). $^{13}$C NMR (D6-DMSO) δ 9.4, 21.8, 27.5, 36.5, 55.2, 108.5, 113.9, 121.0, 121.4, 122.9, 125.1, 125.7, 126.5, 126.9, 127.7, 132.3, 133.8, 135.7, 136.8, 155.6, 157.8, 166.2, 194.7. LCMS t=4.7 min, Calcd for $C_{25}H_{25}N_2O_3$; $C_{25}H_{24}N_2NaO_3$; $C_{50}H_{49}N_4O_6$; $C_{50}H_{48}N_4NaO_6$ 401.187; 423.169; 801.365; 823.347 [M+H]+; [M+Na]+; [2M+H]+; [2M+Na]+, Found 401.184; 423.138; 801.345; 823.331.

Example 04-106

Preparation of 3-((2-methyl-3-oxocyclohex-1-en-1-yl)amino)-N-(o-tolyl)-1-naphthamide (04-106)

The title compound was prepared from Example 01-52 and o-toluidine according to the procedure of Example 04-13; 0.5 mmol scale yielded 12 mg of pale yellow microcrystals after chromatography (ESS=1:1, mp=249-250° C. decomp, 7% yield). $^1$H NMR (D6-DMSO) δ 1.75 (s, 3H), 1.83-1.86 (m, 2H), 2.26-2.29 (m, 2H), 2.34 (s, 3H), 2.64-2.66 (m, 2H), 7.18-7.21 (m, 1H), 7.24-7.31 (m, 3H), 7.48-7.57 (m, 3H), 7.66 (d, J=15.7 Hz, 2H), 7.93 (d, J=8.0 Hz, 1H), 8.18 (d, J=8.2 Hz, 1H), 8.48 (s, 1H), 10.07 (s, 1H). $^{13}$C NMR (D6-DMSO) δ 9.4, 18.1, 21.9, 36.6, 108.6, 121.2, 123.0, 125.1, 125.7, 126.1, 126.3, 126.7, 126.9, 127.7, 130.4, 133.3, 133.8, 135.5, 136.2, 136.8, 157.7, 166.9, 194.8. LCMS t=5.0 min, Calcd for $C_{25}H_{25}N_2O_2$; $C_{25}H_{24}N_2NaO_2$; $C_{50}H_{49}N_4O_4$; $C_{50}H_{48}N_4NaO_4$ 385.19; 407.17; 769.37; 791.36 [M+H]+; [M+Na]+; [2M+H]+; [2M+Na]+, Found 385.18; 407.16; 769.35; 791.34.

Examples 05-01 to 05-86

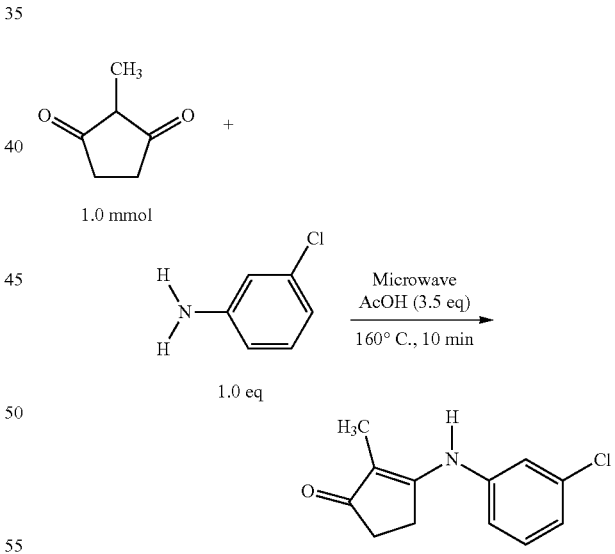

Example 05-01

Preparation of 3-((3-chlorophenyl)amino)-2-methyl-cyclopent-2-enone (05-01)

2-Methyl-1,3-cyclopentandione (112 mg, 1.0 mmol, 1.0 eq) and 3-chloroaniline (106 □L, 1.0 eq) were mixed and treated with AcOH (200 □L, 3.5 eq). Microwave irradiation was applied to a sealed microwave vial for 10 min in a single mode Biotage®-Initiator cavity, producing continuous irradiation to hold temp at 2.45 GHz. The crude products were recrystallized, or were added directly to a KP-Sil™ column (10 g) in a small amount of $CH_2Cl_2$ with products separating from impurities using stepwise gradients on the Biotage®-Isolera Four instrument, monitoring UV Trace at 254/365 nm. The reaction on a 1.0 mmol scale yielded 90 mg of the title compound after recrystallization from EtOAc (41% yield). $^1$H NMR (D6-DMSO) δ 1.58 (s, 3H), 2.21-2.23 (m, 2H), 2.70-2.72 (m, 2H), 7.15 (d, J=7.8 Hz, 1H), 7.21 (d, J=7.9 Hz, 1H), 7.35 (s, 1H), 7.36 (t, J=8.0 Hz, 1H), 9.02 (s, 1H). LCMS t=5.7 min, m/z Calcd for $C_{12}H_{13}ClNO$; $C_{12}H_{12}ClNNaO$; $C_{24}H_{25}Cl_2N_2O_2$; $C_{24}H_{24}Cl_2N_2NaO_2$ 222.07; 244.05; 443.13; 465.11 $[M+H]^+$; $[M+Na]^+$; $[2M+H]^+$; $[2M+Na]^+$, Found 222.07; 244.05; 443.13; 465.11.

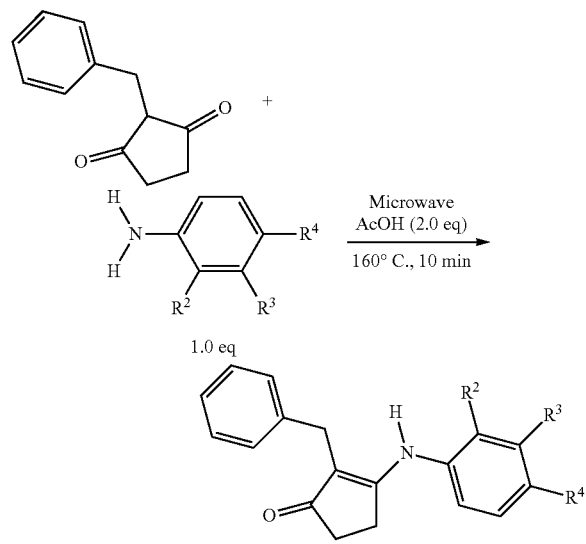

| EXAMPLE 05-# | TITLE COMPOUND NAME | $R^1$ | $R^2$ | $R^3$ | $R^4$ |
|---|---|---|---|---|---|
| 02 | 2-Benzyl-3-((4-methoxyphenyl)amino)cyclopent-2-enone | H | H | H | $OCH_3$ |
| 03 | 2-(4-((2-Benzyl-3-oxocyclopent-1-en-1-yl)amino)phenyl)acetonitrile | H | H | H | $CH_2CN$ |
| 04 | Methyl 4-((2-benzyl-3-oxocyclopent-1-en-1-yl)amino)-3-chlorobenzoate | H | Cl | H | $CO_2CH_3$ |

Example 05-02

Preparation of 2-benzyl-3-((4-methoxyphenyl)amino)cyclopent-2-enone (05-02)

The title compound was prepared from Intermediate 01 and p-anisidine according to the procedure of Example 05-01; 0.53 mmol scale yielded 30 mg after chromatography (ESS=H:E (1:3)) and recrystallization from EtOAc (19% yield). $^1$H NMR (D6-DMSO) δ 2.18-2.20 (m, 2H), 2.54-2.56 (m, 2H), 3.48 (s, 2H), 3.75 (s, 3H), 6.91 (d, J=8.8 Hz, 2H), 7.10-7.13 (m, 1H), 7.15 (d, J=8.7 Hz, 2H), 7.21-7.23 (m, 4H), 9.03 (s, 1H). $^{13}$C NMR (D6-DMSO) δ 25.4, 26.8, 32.5, 55.3, 112.0, 114.1, 125.4, 125.9, 128.0, 128.1, 132.1, 140.9, 156.7, 170.9, 201.1. LCMS t=5.1 min, m/z Calcd for $C_{19}H_{20}NO_2$; $C_{19}H_{19}NNaO_2$; $C_{38}H_{39}N_2O_4$; $C_{38}H_{38}N_2NaO_4$ 294.15; 316.13; 587.29; 609.28 $[M+H]^+$; $[M+Na]^+$; $[2M+H]^+$; $[2M+Na]^+$, Found 294.18; 316.14; 587.24; 609.34.

Example 05-03

Preparation of 2-(4-((2-benzyl-3-oxocyclopent-1-en-1-yl)amino)phenyl)acetonitrile (05-03)

The title compound was prepared from Intermediate 01 and 4-aminobenzyl cyanide according to the procedure of Example 05-01; 0.53 mmol scale yielded 10 mg after chromatography (ESS=H:E (1:3)) and recrystallization from EtOAc (6% yield). $^1$H NMR (D6-DMSO) δ 2.23-2.25 (m, 2H), 2.70-2.72 (m, 2H), 3.53 (s, 2H), 4.01 (s, 2H), 7.10-7.3 (m, 1H), 7.19-7.24 (4H), 7.26 (d, J=8.4 Hz, 2H), 7.31 (d, J=8.3 Hz, 2H), 9.19 (s, 1H). $^{13}$C NMR (D6-DMSO) δ 21.8, 25.6, 26.8, 32.8, 113.5, 119.3, 123.6, 125.4, 127.1, 128.0, 128.1, 128.8, 139.0, 140.6, 169.8, 201.5. LCMS t=4.9 min, m/z Calcd for $C_{20}H_{19}N_2O$; $C_{20}H_{18}N_2NaO$; $C_{40}H_{37}N_4O_2$; $C_{40}H_{36}N_4NaO_2$ 303.15; 325.13; 605.29; 627.27 $[M+H]^+$; $[M+Na]^+$; $[2M+H]^+$; $[2M+Na]^+$, Found 303.17; 332.15; 605.24 627.25.

Example 05-04

Preparation of methyl 4-((2-benzyl-3-oxocyclopent-1-en-1-yl)amino)-3-chlorobenzoate (05-04)

The title compound was prepared from Intermediate 01 and methyl 4-amino-3-chlorobenzoate according to the procedure of Example 05-01; 1.07 mmol scale and 30 min irradiation, yielded 20 mg after chromatography (ESS=H:E (1:3)) and recrystallization from EtOAc (5% yield). $^1$H NMR (D6-DMSO) δ 2.28-2.30 (m, 2H), 2.59-2.61 (m, 2H), 3.46 (s, 2H), 3.86 (s, 3H), 7.05-7.12 (m, 3H), 7.14-7.20 (m, 2H), 7.50 (d, J=8.1 Hz, 1H), 7.88 (d, J=8.3 Hz, 1H), 7.96 (s, 1H), 9.01 (s, 1H). $^{13}$C NMR (D6-DMSO) δ 25.8, 27.3, 32.7, 52.5, 114.9, 125.6, 126.9, 127.9, 128.0, 128.5, 130.3, 139.9, 140.6, 164.7, 168.7, 202.5. LCMS t=5.3 min, m/z Calcd for $C_{20}H_{19}ClNO_3$; $C_{20}H_{18}ClNNaO_3$; $C_{40}H_{36}Cl_2N_2NaO_6$ 356.11; 378.09; 733.18 $[M+H]^+$; $[M+Na]^+$; $[2M+Na]^+$, Found 356.11; 378.07; 733.15.

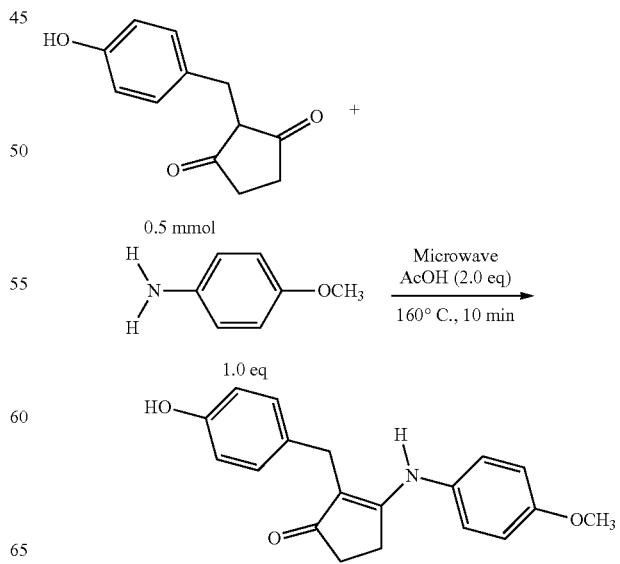

Example 05-05

Preparation of 2-(4-hydroxybenzyl)-3-((4-methoxyphenyl)amino)cyclopent-2-enone (05-05)

The title compound was prepared from Intermediate 02 and p-anisidine according to the procedure of Example 05-01; 0.5 mmol scale yielded 20 mg after chromatography (ESS=EtOAc) and recrystallization from EtOAc (13% yield). $^1$H NMR (D6-DMSO) δ 2.17-2.19 (m, 2H), 2.50-2.53 (m, 2H), 3.37 (s, 2H), 3.75 (3H), 6.61 (d, J=7.8 Hz, 2H), 6.91 (d, J=8.3 Hz, 2H), 7.00 (d, J=7.8 Hz, 2H), 7.15 (d, J=8.3 Hz, 2H), 8.96 (s, 1H), 9.05 (s, 1H). $^{13}$C NMR (D6-DMSO) δ 25.3, 25.9, 32.5, 55.3, 112.8, 114.1, 114.7, 125.8, 129.0, 130.9 132.2, 155.1, 156.7, 170.6, 201.1. LCMS t=4.7 min, m/z Calcd for $C_{19}H_{20}NO_3$; $C_{19}H_{19}NNaO_3$; $C_{38}H_{39}N_2O_6$; $C_{38}H_{38}N_2NaO_6$ 310.14; 332.13; 619.28; 641.26 $[M+H]^+$; $[M+Na]^+$; $[2M+H]^+$; $[2M+Na]^+$, Found 310.17; 332.13; 619.23; 641.25.

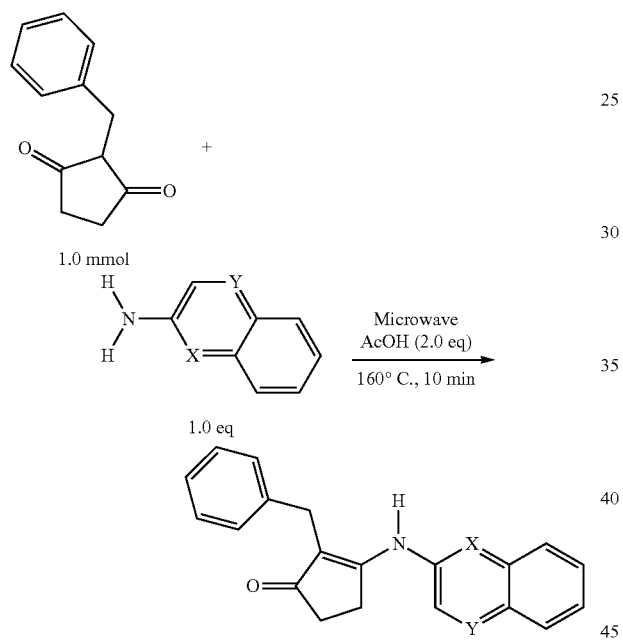

Example 05-06

Preparation of 2-benzyl-3-(quinolin-3-ylamino)cyclopent-2-enone (05-06)

The title compound was prepared from Intermediate 01 and 3-aminoquinoline according to the procedure of Example 05-01; 0.53 mmol scale yielded 15 mg after chromatography (ESS=H:E (1:3)) and recrystallization from EtOAc (9% yield). $^1$H NMR (D6-DMSO) δ 2.30-2.32 (m, 2H), 2.86-2.88 (m, 2H), 3.59 (s, 2H), 7.12-7.15 (m, 1H), 7.22-7.24 (m, 4H), 7.60 (t, J=7.5 Hz, 1H), 7.68 (t, J=7.5 Hz, 1H), 7.93 (d, J=8.1 Hz, 1H), 7.98 (d, J=8.4 Hz, 1H), 8.19 (d, J=1.6 Hz, 1H), 8.84 (d, J=2.1 Hz, 1H), 9.48 (s, 1H). $^{13}$C NMR (D6-DMSO) δ 25.6, 26.9, 32.9, 114.7, 125.6, 125.7, 127.2, 127.6, 127.8, 128.1, 128.3, 128.6, 133.4, 140.3, 144.5, 147.5, 169.6, 201.9. LCMS t=4.9 min, m/z Calcd for $C_{21}H_{19}N_2O$; $C_{21}H_{18}N_2NaO$; $C_{42}H_{37}N_4O_2$; $C_{42}H_{36}N_4NaO_2$ 315.15; 337.13; 629.29; 651.27 $[M+H]^+$; $[M+Na]^+$; $[2M+H]^+$; $[2M+Na]^+$, Found 315.17; 337.14; 629.24; 651.29.

Example 05-07

Preparation of 2-benzyl-3-(quinolin-2-ylamino)cyclopent-2-enone (05-07)

The title compound was prepared from Intermediate 01 and 2-aminoquinoline according to the procedure of Example 05-01; 0.53 mmol scale yielded 5 mg after chromatography (ESS=H:E (1:3)) and recrystallization from EtOAc (3% yield). $^1$H NMR (D6-DMSO) δ 2.35-2.37 (m, 2H), 3.52-3.54 (m, 2H), 3.68 (s, 2H), 7.11-7.14 (m, 1H), 7.22-7.25 (m, 4H), 7.39 (d, J=8.8 Hz, 1H), 7.42 (t, J=7.4 Hz, 1H), 7.66 (t, J=7.4 Hz, 1H), 7.74 (d, J=8.3 Hz, 1H), 7.83 (d, J=7.9 Hz, 1H), 8.23 (d, J=8.8 Hz, 1H), 9.74 (s, 1H). $^{13}$C NMR (D6-DMSO) δ 26.7, 28.5, 33.2, 114.7, 117.8, 124.4, 125.6, 127.1, 127.7, 128.0, 128.1, 129.9, 138.0, 140.2, 146.3, 152.5, 168.0, 203.4. LCMS t=5.4 min, m/z Calcd for $C_{21}H_{19}N_2O$; $C_{21}H_{18}N_2NaO$; $C_{42}H_{37}N_4O_2$; $C_{42}H_{36}N_4NaO_2$ 315.15; 337.13; 629.29; 651.27 $[M+H]^+$; $[M+Na]^+$; $[2M+H]^+$; $[2M+Na]^+$, Found 315.17; 337.13; 629.25; 651.32.

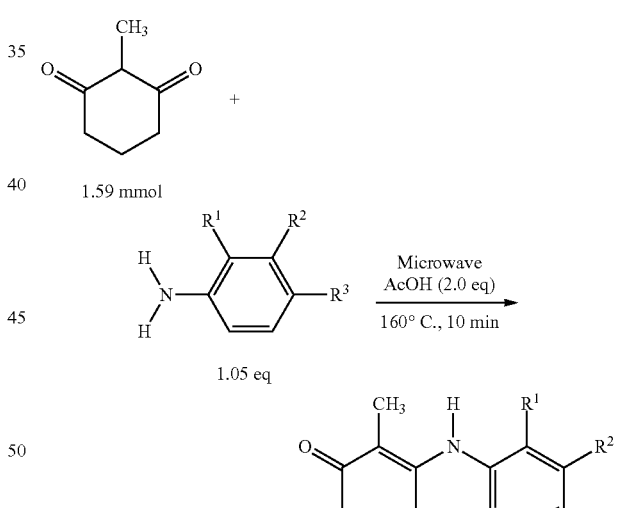

| EXAMPLE 05-# | TITLE COMPOUND NAME | X | Y |
|---|---|---|---|
| 06 | 2-Benzyl-3-(quinolin-3-ylamino)cyclopent-2-enone | CH | N |
| 07 | 2-Benzyl-3-(quinolin-2-ylamino)cyclopent-2-enone | N | CH |

| EXAMPLE 05-# | TITLE COMPOUND NAME | $R^1$ | $R^2$ | $R^3$ |
|---|---|---|---|---|
| 08 | 3-((3-Chlorophenyl)amino)-2-methylcyclohex-2-enone | H | Cl | H |
| 09 | 2-Methyl-3-(o-tolylamino)cyclohex-2-enone | $CH_3$ | H | H |
| 10 | 2-Methyl-3-(m-tolylamino)cyclohex-2-enone | H | $CH_3$ | H |
| 11 | 2-Methyl-3-(p-tolylamino)cyclohex-2-enone | H | H | $CH_3$ |

-continued

| EXAMPLE 05-# | TITLE COMPOUND NAME | $R^1$ | $R^2$ | $R^3$ |
|---|---|---|---|---|
| 12 | Methyl 3-chloro-4-((2-methyl-3-oxocyclohex-1-en-1-yl)amino)benzoate | Cl | H | $CO_2CH_3$ |

Example 05-08

Preparation of 3-((3-chlorophenyl)amino)-2-methyl-cyclohex-2-enone (05-08)

The title compound was prepared from 2-methyl-1,3-cyclohexandione and 3-chloroaniline according to the procedure of Example 05-01; 1.59 mmol scale yielded 300 mg after chromatography (ESS=$CH_2Cl_2$:EtOAc (9:1), 80% yield). $^1$H NMR (D6-DMSO) δ 1.64 (s, 3H), 1.78-1.81 (m, 2H), 2.21-2.24 (m, 2H), 2.47-2.50 (m, 2H), 7.05 (d, J=7.9 Hz, 1H), 7.12-7.15 (m, 2H), 7.33 (t, J=7.9 Hz, 1H), 8.26 (s, 1H). $^{13}$C NMR (D6-DMSO) δ 9.5, 21.7, 27.5, 36.5, 108.8, 121.9, 122.9, 123.2, 130.3, 133.0, 141.7, 157.2, 195.0. LCMS t=5.1 min, m/z Calcd for $C_{13}H_{15}ClNO$; $C_{13}H_{14}ClNNaO$; $C_{26}H_{29}Cl_2N_2O_2$; $C_{26}H_{28}Cl_2N_2NaO_2$ 236.08; 258.07; 471.16; 493.14 [M+H]$^+$; [M+Na]$^+$; [2M+H]$^+$; [2M+Na]$^+$, Found 236.10; 258.07; 471.14; 493.16.

Example 05-09

Preparation of 2-methyl-3-(o-tolylamino)cyclohex-2-enone (05-09)

The title compound was prepared from 2-methyl-1,3-cyclohexandione and o-toluidine according to the procedure of Example 05-01; 1.59 mmol scale yielded 130 mg after chromatography (ESS=$CH_2Cl_2$:EtOAc (9:1), 38% yield). $^1$H NMR (D6-DMSO) δ 1.67-1.73 (m, 5H), 2.13-2.21 (m, 7H), 7.11 (d, J=6.8 Hz, 1H), 7.18-7.22 (m, 2H), 7.28 (d, J=6.4 Hz, 1H), 7.84 (s, 1H). $^{13}$C NMR (D6-DMSO) δ 8.7, 17.7, 21.3, 26.8, 36.3, 105.0, 126.3, 126.4, 128.1, 130.5, 135.2, 138.4, 159.7, 193.8. LCMS t=4.9 min, m/z Calcd for $C_{14}H_{18}NO$; $C_{14}H_{17}NNaO$; $C_{28}H_{35}N_2O_2$; $C_{28}H_{34}N_2NaO_2$ 216.14; 238.12; 431.27; 453.25 [M+H]$^+$; [M+Na]$^+$; [2M+H]$^+$; [2M+Na]$^+$, Found 216.17; 238.12; 431.27; 453.46.

Example 05-10

Preparation of 2-methyl-3-(m-tolylamino)cyclohex-2-enone (05-10)

The title compound was prepared from 2-methyl-1,3-cyclohexandione and m-toluiline according to the procedure of Example 05-01; 1.59 mmol scale yielded 190 mg after chromatography (ESS=$CH_2Cl_2$:EtOAc (9:1), 56% yield). $^1$H NMR (D6-DMSO) δ 1.67 (s, 3H), 1.74-1.79 (m, 2H), 2.17-2.20 (m, 2H), 2.29 (s, 3H), 2.41-2.44 (m, 2H), 6.91 (d, J=8.3 Hz, 1H), 6.94-6.96 (m, 2H), 7.21 (t, J=7.7 Hz, 1H), 8.12 (s, 1H). $^{13}$C NMR (D6-DMSO) δ 9.1, 20.9, 21.7, 27.3, 36.5, 106.7, 121.6, 124.9, 125.1, 128.6, 138.1, 139.7, 158.3, 194.3. LCMS t=5.0 min, m/z Calcd for $C_{14}H_{18}NO$; $C_{14}H_{17}NNaO$; $C_{28}H_{35}N_2O_2$; $C_{28}H_{34}N_2NaO_2$ 216.14; 238.12; 431.27; 453.25 [M+H]$^+$; [M+Na]$^+$; [2M+H]$^+$; [2M+Na]$^+$, Found 216.22; 238.12; 431.27; 453.25.

Example 05-11

Preparation of 2-methyl-3-(p-tolylamino)cyclohex-2-enone (05-11)

The title compound was prepared from 2-methyl-1,3-cyclohexandione and p-toluiline according to the procedure of Example 05-01; 1.59 mmol scale yielded 160 mg after chromatography (ESS=$CH_2Cl_2$:EtOAc (9:1), 47% yield). $^1$H NMR (D6-DMSO) δ 1.67 (s, 3H), 1.74-1.77 (m, 2H), 2.16-2.19 (m, 2H), 2.28 (s, 3H), 2.36-2.29 (m, 2H), 7.02 (d, J=8.0 Hz, 2H), 7.15 (d, J=7.8 Hz, 2H), 8.09 (s, 1H). $^{13}$C NMR (D6-DMSO) δ 9.0, 20.5, 21.7, 27.1, 36.4, 106.0, 124.9, 129.2, 133.6, 137.2, 158.7, 194.0. LCMS t=5.0 min, m/z Calcd for $C_{14}H_{18}NO$; $C_{14}H_{17}NNaO$; $C_{28}H_{35}N_2O_2$; $C_{28}H_{34}N_2NaO_2$ 216.14; 238.12; 431.27; 453.25 [M+H]$^+$; [M+Na]$^+$; [2M+H]$^+$; [2M+Na]$^+$, Found 216.17; 238.12; 431.27; 453.26.

Example 05-12

Preparation of methyl 3-chloro-4-((2-methyl-3-oxo-cyclohex-1-en-1-yl)amino)benzoate (05-10)

The title compound was prepared from 2-methyl-1,3-cyclohexandione and methyl 4-amino-3-chlorobenzoate according to the procedure of Example 05-01; 1.59 mmol scale, irradiation for 30 min, yielded 260 mg after chromatography (ESS=$CH_2Cl_2$:EtOAc (9:1), 56% yield). $^1$H NMR (D6-DMSO) δ 1.52 (s, 3H), 1.81-1.83 (m, 2H), 2.24-2.27 (m, 2H), 2.42-2.43 (m, 2H), 3.85 (s, 3H), 7.18 (d, J=8.3 Hz, 1H), 7.86 (d, J=8.4 Hz, 1H), 7.98 (s, 1H), 8.06 (s, 1H). LCMS t=5.1 min, m/z Calcd for $C_{15}H_{17}ClNO_3$; $C_{15}H_{16}ClNNaO_3$; $C_{30}H_{33}Cl_2N_2O_6$; $C_{30}H_{32}Cl_2N_2NaO_6$ 294.09; 316.07; 587.17; 609.15 [M+H]$^+$; [M+Na]$^+$; [2M+H]$^+$; [2M+Na]$^+$, Found 294.12; 316.09; 587.13; 609.15.

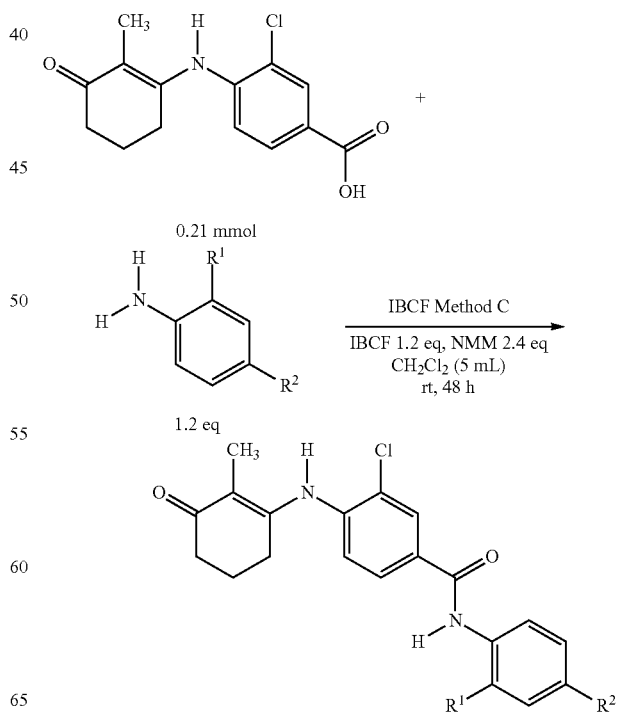

| EXAMPLE 05-# | TITLE COMPOUND NAME | R¹ | R² |
|---|---|---|---|
| 13 | 3-Chloro-N-(4-methoxyphenyl)-4-((2-methyl-3-oxocyclohex-1-en-1-yl)amino)benzamide | H | OCH₃ |
| 14 | 3-Chloro-N-(2-methoxyphenyl)-4-((2-methyl-3-oxocyclohex-1-en-1-yl)amino)benzamide | OCH₃ | H |
| 15 | 3-Chloro-4-((2-methyl-3-oxocyclohex-1-en-1-yl)amino)-N-(o-tolyl)benzamide | CH₃ | H |

Example 05-13

Preparation of 3-chloro-N-(4-methoxyphenyl)-4-((2-methyl-3-oxocyclohex-1-en-1-yl)amino)benzamide (05-13)

Example 05-12 (239 mg, 0.82 mmol) was hydrolyzed to 3-chloro-4-((2-methyl-3-oxocyclohex-1-en-1-yl)amino) benzoic acid to the procedure of Example 02-01. The title compound was prepared from 3-chloro-4-((2-methyl-3-oxocyclohex-1-en-1-yl)amino)benzoic acid and p-anisidine according to the procedure of Example 04-13; 0.21 mmol scale yielded 10 mg after chromatography (ESS=H:E (1:3)) and EtOAc trituration (12% yield). ¹H NMR (D6-DMSO) δ 1.61 (s, 3H), 1.80-1.82 (m, 2H), 2.22-2.25 (m, 2H), 2.36-2.38 (m, 2H), 3.75 (s, 3H), 6.94 (d, J=8.8 Hz, 2H), 7.31 (d, J=8.3 Hz, 1H), 7.66 (d, J=8.7 Hz, 2H), 7.91 (d, J=8.2 Hz, 1H), 8.06 (s, 1H), 8.11 (s, 1H), 10.18 (s, 1H). ¹³C NMR (D6-DMSO) δ 9.6, 12.1, 27.6, 36.5, 55.2, 109.7, 113.8, 122.0, 126.6, 127.1, 128.4, 128.8, 132.0, 132.1, 140.1, 155.7, 157.3, 163.1, 195.3. LCMS t=5.0 min, m/z Calcd for $C_{21}H_{22}ClN_2O_3$; $C_{21}H_{21}ClN_2NaO_3$; $C_{42}H_{43}Cl_2N_4O_6$; $C_{42}H_{42}Cl_2N_4NaO_6$ 385.13; 407.11; 769.26; 791.24 [M+H]⁺; [M+Na]⁺; [2M+H]⁺; [2M+Na]⁺, Found 385.12; 407.09; 769.22; 791.22.

Example 05-14

Preparation of 3-chloro-N-(2-methoxyphenyl)-4-((2-methyl-3-oxocyclohex-1-en-1-yl)amino)benzamide (05-14)

The title compound was prepared from 3-chloro-4-((2-methyl-3-oxocyclohex-1-en-1-yl)amino)benzoic acid and o-anisidine according to the procedure of Example 05-13; 0.21 mmol scale yielded 5 mg after chromatography (ESS=H:E (1:3)) and EtOAc trituration (6% yield). ¹H NMR (D6-DMSO) δ 1.61 (s, 3H), 1.80-1.87 (m, 2H), 2.23-2.25 (m, 2H), 2.37-2.39 (m, 2H), 3.83 (s, 3H), 6.96-7.01 (m, 1H), 7.10-7.15 (m, 1H), 7.21-7.26 (m, 1H), 7.30-7.35 (m, 1H), 7.67 (d, J=6.3 Hz, 1H), 7.92 (d, J=6.9 Hz, 1H), 8.07 (s, 1H), 8.11 (s, 1H), 9.60 (s, 1H). ¹³C NMR (D6-DMSO) δ 9.7, 21.1, 27.6, 36.5, 55.7, 109.9, 111.5, 120.2, 125.2, 126.2, 126.5, 126.6, 127.0, 128.4, 129.0, 131.6, 140.3, 152.0, 157.3, 163.3, 195.4. LCMS t=5.3 min, m/z Calcd for $C_{21}H_{22}ClN_2O_3$; $C_{21}H_{21}ClN_2NaO_3$; $C_{42}H_{43}Cl_2N_4O_6$; $C_{42}H_{42}Cl_2N_4NaO_6$ 385.13; 407.11; 769.26; 791.24 [M+H]⁺; [M+Na]⁺; [2M+H]⁺; [2M+Na]⁺, Found 385.13; 407.09; 769.20; 791.39.

Example 05-15

Preparation of 3-chloro-4-((2-methyl-3-oxocyclohex-1-en-1-yl)amino)-N-(o-tolyl)benzamide (05-15)

The title compound was prepared from 3-chloro-4-((2-methyl-3-oxocyclohex-1-en-1-yl)amino)benzoic acid and o-toluidine according to the procedure of Example 05-13; 0.21 mmol scale yielded 2 mg after chromatography (ESS=H:E (1:3)) and EtOAc trituration (3% yield). ¹H NMR (D6-DMSO) δ 1.61 (s, 3H), 1.79-1.88 (m, 2H), 2.20-2.32 (m, 5H), 2.34-2.45 (m, 2H), 7.15-7.39 (m, 5H), 7.93 (s, 1H), 8.07 (s, 1H), 8.12 (s, 1H), 9.96 (s, 1H). ¹³C NMR (D6-DMSO) δ 9.7, 17.9, 21.1, 27.6, 36.5, 109.8, 126.0, 126.2, 126.7, 127.1, 128.5, 129.0, 130.4, 131.7, 133.8, 136.2, 140.3, 157.3, 163.5, 195.4. LCMS t=5.2 min, m/z Calcd for $C_{21}H_{22}ClN_2O_2$; $C_{21}H_{21}ClN_2NaO_2$; $C_{42}H_{42}Cl_2N_4NaO_4$ 369.14; 391.12; 759.25 [M+H]⁺; [M+Na]⁺; [2M+Na]⁺, Found 369.14; 391.10; 759.24.

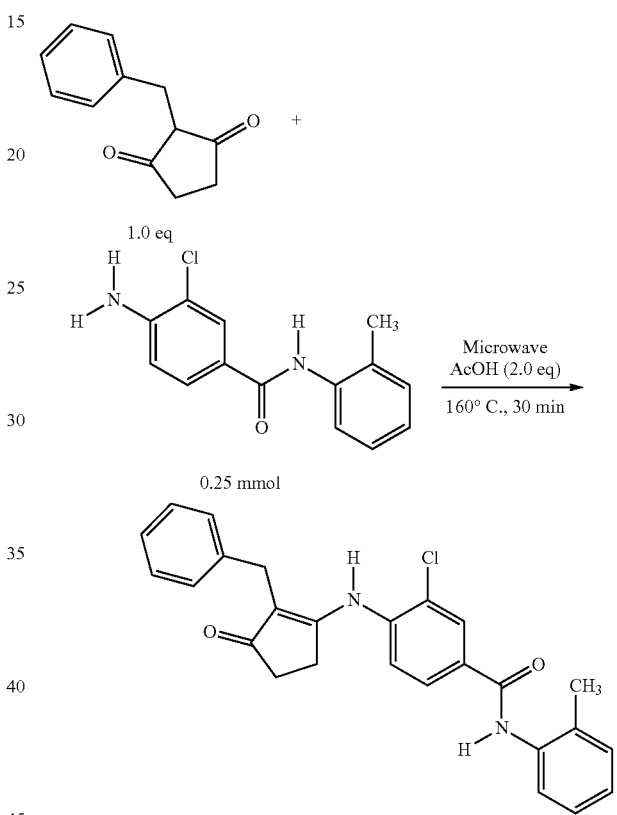

Example 05-16

Preparation of 4-((2-benzyl-3-oxocyclopent-1-en-1-yl)amino)-3-chloro-N-(o-tolyl)benzamide (05-16)

The title compound was prepared from Intermediate 01 and free base Intermediate 03 according to the procedure of Example 05-13; 0.25 mmol scale yielded 5 mg after chromatography (ESS=H:E (1:3)) and recrystallization from MeOH (5% yield). ¹H NMR (D6-DMSO) δ 2.24 (s, 3H), 2.27-2.28 (m, 2H), 2.56-2.58 (m, 2H), 3.50 (s, 2H), 7.12-7.24 (m, 7H), 7.28 (d, J=7.0 Hz, 1H), 7.32 (d, J=7.5 Hz, 1H), 7.56 (d, J=8.2 Hz, 1H), 7.94 (d, J=7.9 Hz, 1H), 8.10 (s, 1H), 9.06 (s, 1H), 10.00 (s, 1H). LCMS t=5.6 min, m/z Calcd for $C_{26}H_{24}ClN_2O_2$; $C_{26}H_{23}ClN_2NaO_2$; $C_{52}H_{47}Cl_2N_4O_4$; $C_{52}H_{46}Cl_2N_4NaO_4$ 431.15; 453.13; 861.30; 883.28 [M+H]⁺; [M+Na]⁺; [2M+H]⁺; [2M+Na]⁺, Found 431.15; 453.13; 861.30; 883.28.

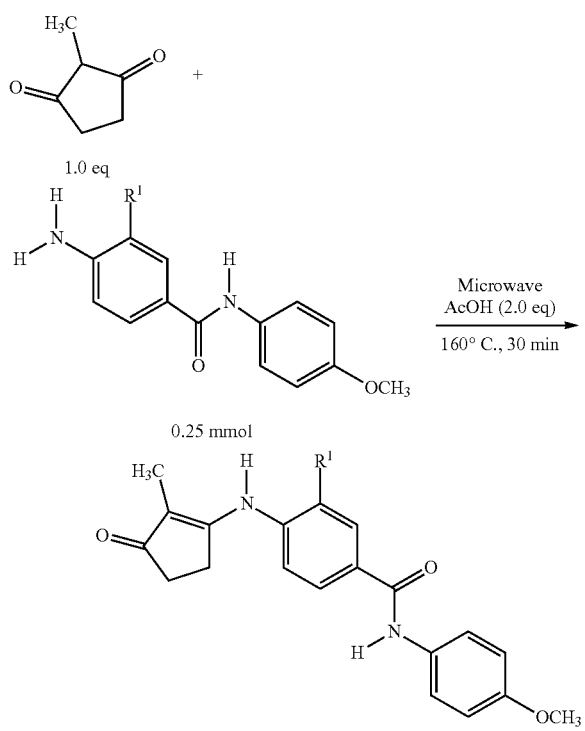

| EXAMPLE 05-# | TITLE COMPOUND NAME | $R^1$ |
|---|---|---|
| 17 | 3-Fluoro-N-(4-methoxyphenyl)-4-((2-methyl-3-oxocyclopent-1-en-1-yl)amino)benzamide | F |
| 18 | 3-Bromo-N-(4-methoxyphenyl)-4-((2-methyl-3-oxocyclopent-1-en-1-yl)amino)benzamide | Br |

Example 05-17

Preparation of 3-fluoro-N-(4-methoxyphenyl)-4-((2-methyl-3-oxocyclopent-1-en-1-yl)amino)benzamide (05-17)

The title compound was prepared from 2-methyl-1,3-cyclopentandione and free base Intermediate 04 according to the procedure of Example 05-13; 0.25 mmol scale yielded 50 mg after recrystallization from MeOH (56% yield). $^1$H NMR (D6-DMSO) δ 1.54 (s, 3H), 2.22-2.25 (m, 2H), 2.50-2.52 (m, 2H), 3.75 (s, 3H), 6.92-6.95 (m, 2H), 7.44-7.48 (m, 1H), 7.65-7.67 (m, 2H), 7.80-7.82 (m, 1H), 7.88 (dd, J=11.3, 1.7 Hz, 1H), 9.03 (s, 1H), 10.15 (s, 1H). LCMS t=4.8 min, m/z Calcd for $C_{20}H_{20}FN_2O_3$; $C_{20}H_{19}FN_2NaO_3$; $C_{40}H_{39}F_2N_4O_6$; $C_{40}H_{38}F_2N_4NaO_6$ 355.15; 377.13; 709.28; 731.27 [M+H]$^+$; [M+Na]$^+$; [2M+H]$^+$; [2M+Na]$^+$, Found 355.17; 377.10; 709.24; 731.22.

Example 05-18

Preparation of 3-bromo-N-(4-methoxyphenyl)-4-((2-methyl-3-oxocyclopent-1-en-1-yl)amino)benzamide (05-18)

The title compound was prepared from 2-methyl-1,3-cyclopentandione and free base Intermediate 05 according to the procedure of Example 05-13; 0.25 mmol scale yielded 10 mg after recrystallization from MeOH (10% yield). $^1$H NMR (D6-DMSO) δ 1.47 (s, 3H), 2.21-2.24 (m, 2H), 2.47-2.49 (m, 2H), 3.75 (s, 3H), 6.93-6.95 (m, 2H), 7.49 (d, J=8.3 Hz, 1H), 7.66 (d, J=8.9 Hz, 2H), 7.97 (dd, J=8.2, 1.6 Hz, 1H), 8.27 (d, J=1.7 Hz, 1H), 8.93 (s, 1H), 10.22 (s, 1H). LCMS t=4.9 min, m/z Calcd for $C_{20}H_{20}BrN_2O_3$; $C_{20}H_{19}BrN_2NaO_3$; $C_{40}H_{39}Br_2N_4O_6$; $C_{40}H_{38}Br_2N_4NaO_6$ 415.07, 417.06; 437.05, 439.05; 831.12; 853.10 [M+H]$^+$; [M+Na]$^+$; [2M+H]$^+$; [2M+Na]$^+$, Found 415.05, 417.05; 437.01, 439.01; 831.05; 853.03.

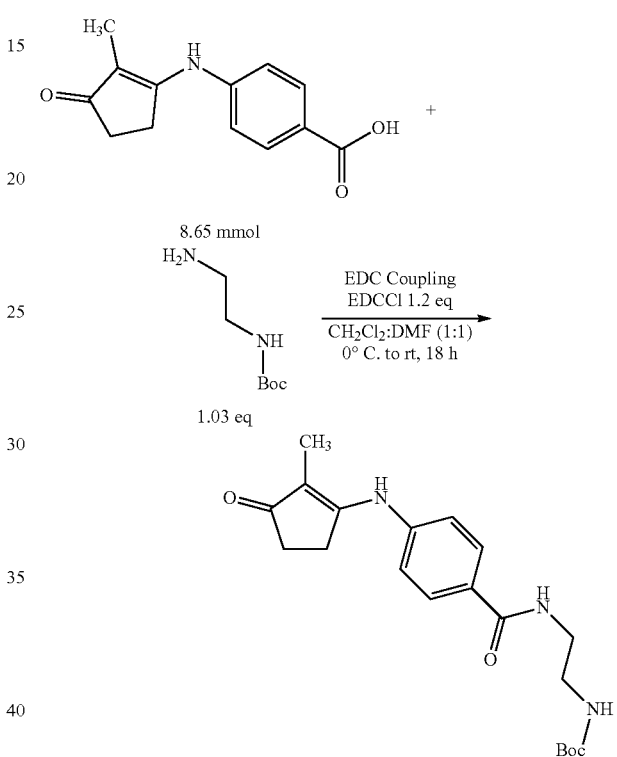

Example 05-19

Preparation of tert-butyl (2-(4-((2-methyl-3-oxocyclopent-1-en-1-yl)amino)benzamido)ethyl)-carbamate (05-19)

tert-Butyl-N-(2-aminoethyl)carbamate (1.4 mL, 1.03 eq) was added to Example 02-01 (2.0 g, 8.65 mmol) stirring in $CH_2Cl_2$:DMF (90 mL, 1:1) at 0° C. 3-(Ethyliminomethylene-amino)-N,N-dimethyl-propan-1-amine hydrochloride (EDCCl, 2.0 g, 1.2 eq) was added and stirred for 2 h at 0° C. After warming to rt overnight, the solvent was removed on the rotovap. Work-up was performed with DI $H_2O$ (500 mL) and EtOAc (8×125 mL). The organic layer was dried over anhyd sodium sulfate and concentrated on the rotovap. Crude material was added directly to a KP-Sil™ column (100 g) with products separating from impurities using stepwise gradients on the Biotage®-Isolera Four instrument, monitoring UV Trace at 254/365 nm. The reaction on a 8.65 mmol scale yielded 1.5 g of the title compound after chromatography (ESS=EtOAc, 46% yield). $^1$H NMR (D6-DMSO) δ 1.37 (s, 9H), 1.59 (s, 3H), 2.23-2.25 (m, 2H), 2.75-2.77 (m, 2H), 3.08-3.10 (m, 2H), 3.26-3.28 (m, 2H), 6.92 (s, 1H), 7.29 (d, J=8.0 Hz, 2H), 7.81 (d, J=7.8 Hz, 2H), 8.38 (s, 1H), 9.11 (s, 1H). LCMS t=Direct Injection, m/z Calcd for $C_{20}H_{28}N_3O_4$; $C_{20}H_{27}N_3NaO_4$; $C_{40}H_{54}N_6NaO_8$ 374.21; 396.19; 769.39 [M+H]$^+$; [M+Na]$^+$; [2M+Na]$^+$, Found 374.21; 396.19; 769.39.

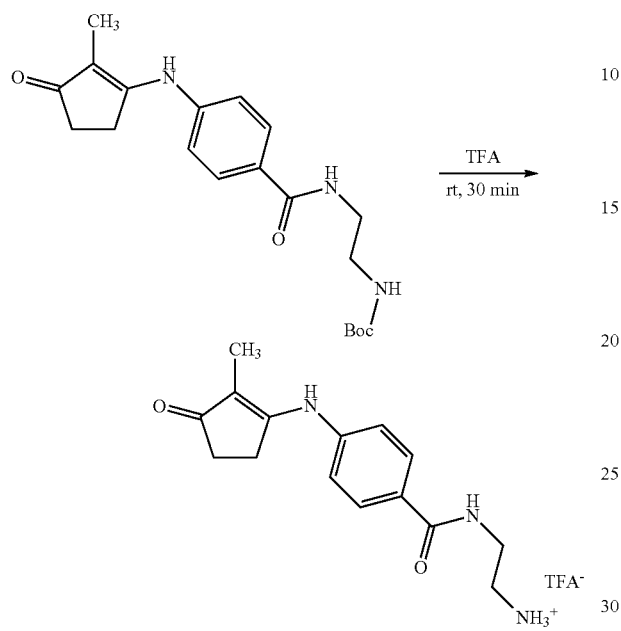

Example 05-20

Preparation of 2-(4-((2-methyl-3-oxocyclopent-1-en-1-yl)amino)benzamido)ethanaminium 2,2,2-trifluoroacetate (05-20)

Example 05-19 (750 mg, 2.0 mmol) was stirred in a minimum amount of CH$_2$Cl$_2$:TFA (1:1) for 30 min at rt. Solvents were removed on the rotovap and the title compound was recrystallized from EtOAc. $^1$H NMR (MeOD) δ 1.68 (s, 3H), 2.41-2.43 (m, 2H), 2.84-2.86 (m, 2H), 3.15-3.18 (m, 2H), 3.65-3.67 (m, 2H), 7.35 (d, J=8.4 Hz, 2H), 7.89 (d, J=8.3 Hz, 2H). LCMS t=3.0 min, m/z Calcd for $C_{15}H_{20}N_3O_2$; $C_{15}H_{19}N_3NaO_2$; $C_{30}H_{39}N_6O_4$; $C_{30}H_{38}N_6NaO_4$ 274.16; 296.14; 547.30; 569.29 [M+H]$^+$; [M+Na]$^+$; [2M+H]$^+$; [2M+Na]$^+$, Found 274.20; 296.17; 547.27; 569.26.

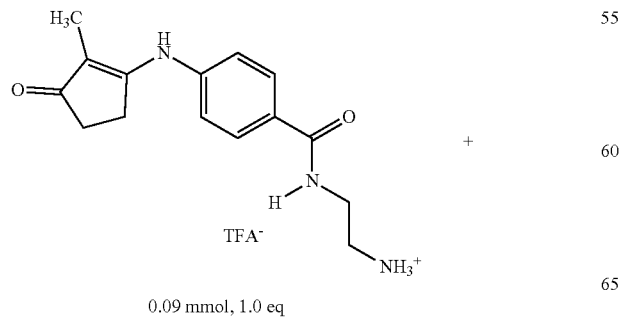

0.09 mmol, 1.0 eq

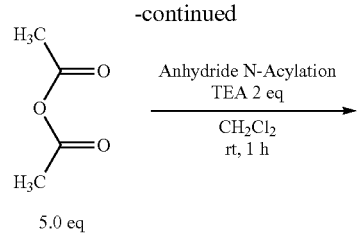

5.0 eq

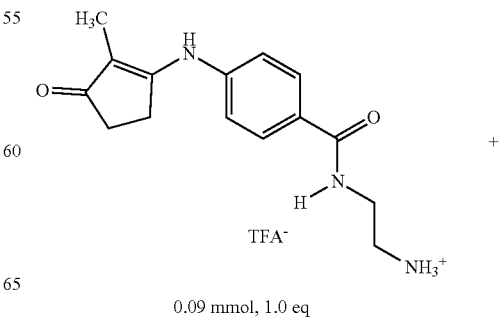

Example 05-21

Preparation of N-(2-acetamidoethyl)-4-((2-methyl-3-oxocyclopent-1-en-1-yl)amino)benzamide (05-21)

Anhydride N-Acylation; Anhydride (5 eq), TEA (2 eq) and Example 05-20 (25 mg, 0.09 mmol, 1.0 eq) were mixed in CH$_2$Cl$_2$ and stirred at rt for 1 h. Solvents were removed on the rotovap. The crude was added to a KP-Sil™ column (10 g). Alternatively a precipitate was filtered from the reaction mixture. The reaction on a 0.09 mmol scale yielded 15 mg of the title compound after chromatography (ESS=EtOAc, 53% yield). $^1$H NMR (D6-DMSO) δ 1.72 (s, 3H), 1.95 (s, 3H), 2.48-2.50 (m, 2H), 2.85-2.87 (m, 2H), 3.38-3.41 (m, 2H), 3.47-3.50 (m, 2H), 7.37 (d, J=8.4 Hz, 2H), 7.86 (d, J=8.4 Hz, 2H). LCMS Direct Injection, m/z Calcd for $C_{17}H_{22}N_3O_3$; $C_{17}H_{21}N_3NaO_3$; $C_{34}H_{42}N_6NaO_6$ 316.17; 338.15; 653.31 [M+H]$^+$; [M+Na]$^+$; [2M+Na]$^+$, Found 316.17; 338.15; 653.31.

0.09 mmol, 1.0 eq

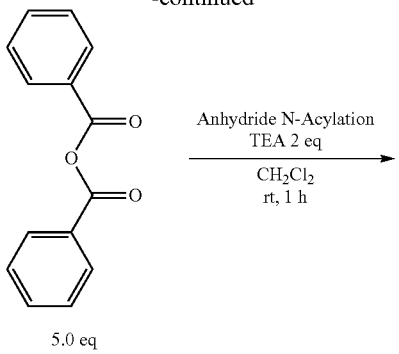

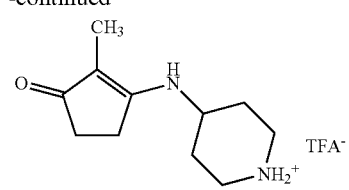

Example 05-23

Preparation of 4-((2-methyl-3-oxocyclopent-1-en-1-yl)amino)piperidin-1-ium 2,2,2-trifluoroacetate (05-23)

The title compound was prepared from Example 01-32 according to the procedure of Example 05-20. $^1$H NMR (D6-DMSO) δ 1.66 (s, 3H), 1.71 (dd, J=23.4, 10.5 Hz, 2H), 2.03 (d, J=12.9 Hz, 2H), 2.12-2.14 (m, 2H), 2.50-2.52 (m, 2H), 2.96 (t, J=12.1 Hz, 2H), 3.30-3.38 (m, 2H), 3.60-3.72 (m, 1H), 7.08 (d, J=8.9 Hz, 1H), 8.54 (br s, 1H), 8.77 (br s, 1H). LCMS t=1.1 min, m/z Calcd for $C_{11}H_{19}N_2O$; $C_{11}H_{18}N_2NaO$; $C_{22}H_{37}N_4O_2$, $C_{22}H_{36}N_4NaO_2$ 195.15; 217.13; 389.29; 411.27 [M+H]$^+$; [M+Na]$^+$; [2M+H]$^+$; [2M+Na]$^+$, Found 195.27; 217.25; 389.36; 411.34.

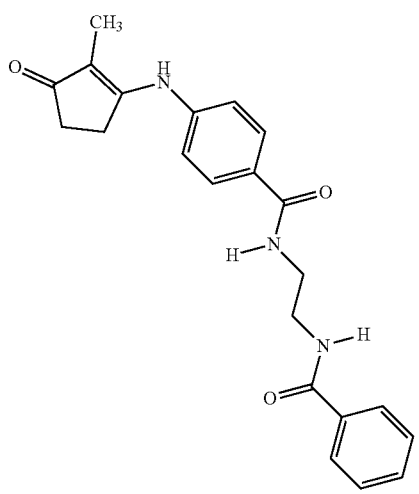

Example 05-22

Preparation of N-(2-benzamidoethyl)-4-((2-methyl-3-oxocyclopent-1-en-1-yl)amino)benzamide (05-22)

The title compound was prepared from Example 05-20 and phenylacetic anhydride according to the procedure of Example 05-21; 0.09 mmol scale yielded 10 mg after chromatography (ESS=EtOAc, 29% yield). $^1$H NMR (CD$_3$OD) δ 1.68 (s, 3H), 2.40-2.43 (m, 2H), 2.82-2.84 (m, 2H), 3.61-3.63 (m, 4H), 7.33 (d, J=8.4 Hz, 2H), 7.45 (t, J=7.6 Hz, 2H), 7.51 (t, J=7.3 Hz, 1H), 7.81 (d, J=7.6 Hz, 2H), 7.84 (d, J=8.4 Hz, 2H). LCMS Direct Injection, m/z Calcd for $C_{22}H_{24}N_3O_3$; $C_{22}H_{23}N_3NaO_3$; $C_{44}H_{46}N_6NaO_6$ 378.18; 400.16; 777.34 [M+H]$^+$; [M+Na]$^+$; [2M+Na]$^+$, Found 378.18; 400.16; 777.34.

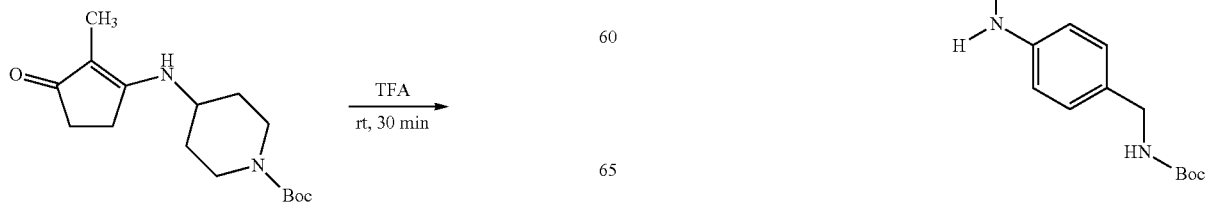

Example 05-24

Preparation of tert-butyl 4-(3-chloro-4-((2-methyl-3-oxocyclopent-1-en-1-yl)amino)benzamido)benzyl-carbamate (05-24)

The title compound was prepared from Example 02-02 and 4-(N-Boc)aminomethyl-aniline according to the procedure of Example 04-13; 1.0 mmol scale yielded 400 mg after chromatography (ESS=H:E (1:19), 85% yield). $^1$H NMR (D6-DMSO) δ 1.40 (s, 9H), 1.48 (s, 3H), 2.23-2.25 (m, 2H), 2.49-2.50 (m, 2H), 4.10 (d, J=4.6 Hz, 2H), 7.22 (d, J=7.8 Hz, 2H), 7.36-7.38 (m, 1H), 7.49 (d, J=8.2 Hz, 1H), 7.69 (d, J=7.8 Hz, 2H), 7.94 (d, J=8.3 Hz, 1H), 8.13 (s, 1H), 8.97 (s, 1H), 10.30 (s, 1H). LCMS t=5.9 min, m/z Calcd for $C_{25}H_{29}ClN_3O_4$; $C_{25}H_{28}ClN_3NaO_4$; $C_{50}H_{57}Cl_2N_6O_8$; $C_{50}H_{56}Cl_2N_6NaO_8$ 470.18; 492.17; 939.36; 961.34 [M+H]$^+$; [M+Na]$^+$; [2M+H]$^+$; [2M+Na]$^+$, Found 470.19; 492.13; 939.39; 961.37.

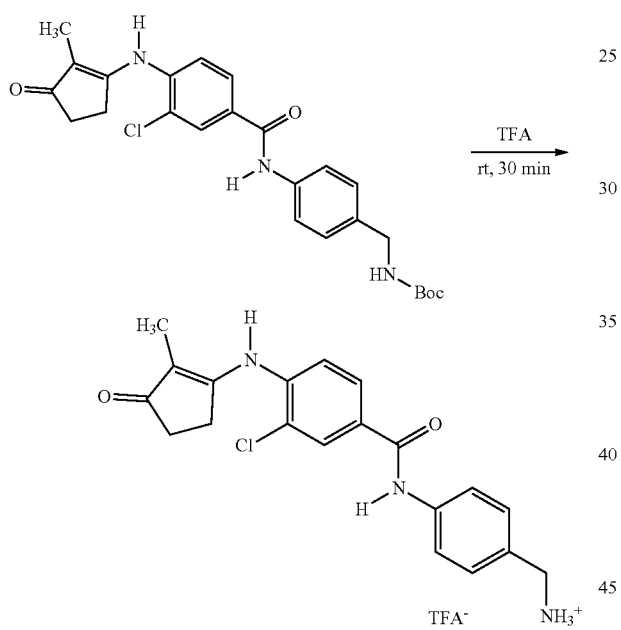

Example 05-25

Preparation of (4-(3-chloro-4-((2-methyl-3-oxocyclopent-1-en-1-yl)amino)benzamido)phenyl)methan-aminium 2,2,2-trifluoroacetate (05-25)

The title compound was prepared from Example 05-24 according to the procedure of Example 05-20. $^1$H NMR (D6-DMSO) δ 1.47 (s, 3H), 2.24-2.26 (m, 2H), 2.49-2.51 (m, 2H), 4.01 (d, J=5.5 Hz, 2H), 7.44 (d, J=8.4 Hz, 2H), 7.49 (d, J=8.3 Hz, 1H), 7.80 (d, J=8.4 Hz, 2H), 7.94 (d, J=8.3 Hz, 1H), 8.09 (br s, 3H), 8.14 (s, 1H), 8.98 (s, 1H), 10.42 (s, 1H). LCMS t=5.1 min, m/z Calcd for $C_{20}H_{21}ClN_3O_2$; $C_{20}H_{20}ClN_3NaO_2$; $C_{40}H_{41}Cl_2N_6O_4$; $C_{40}H_{40}Cl_2N_6NaO_4$ 370.13; 392.11; 739.26; 761.24 [M+H]$^+$; [M+Na]$^+$; [2M+H]$^+$; [2M+Na]$^+$, Found 370.13; 392.11; 739.26; 761.24.

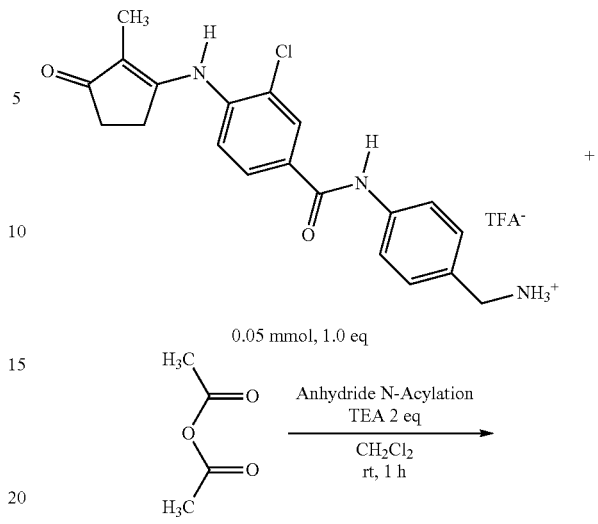

Example 05-26

Preparation of N-(4-(acetamidomethyl)phenyl)-3-chloro-4-((2-methyl-3-oxocyclopent-1-en-1-yl)amino)benzamide (05-26)

The title compound was prepared from Example 05-25 and acetic anhydride according to the procedure of Example 05-21; 0.05 mmol scale yielded 10 mg from precipitate (49% yield). $^1$H NMR (D6-DMSO) δ 1.48 (s, 3H), 1.87 (s, 3H), 2.23-2.25 (m, 2H), 2.49-2.51 (m, 2H), 4.22 (d, J=5.7 Hz, 2H), 7.23 (d, J=8.2 Hz, 2H), 7.49 (d, J=8.3 Hz, 1H), 7.70 (d, J=8.3 Hz, 2H), 7.94 (d, J=8.2 Hz, 1H), 8.14 (s, 1H), 8.13-8.15 (m, 1H), 8.97 (s, 1H), 10.31 (s, 1H). LCMS t=4.6 min, m/z Calcd for $C_{22}H_{23}ClN_3O_3$; $C_{22}H_{22}ClN_3NaO_3$; $C_{44}H_{44}Cl_2N_6NaO_6$ 412.14; 434.12; 845.26 [M+H]$^+$; [M+Na]$^+$; [2M+Na]$^+$, Found 412.15; 434.09; 845.24.

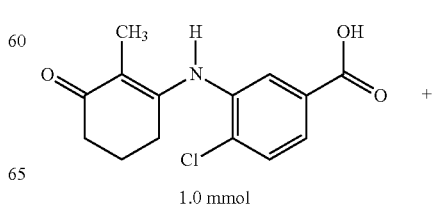

139

-continued

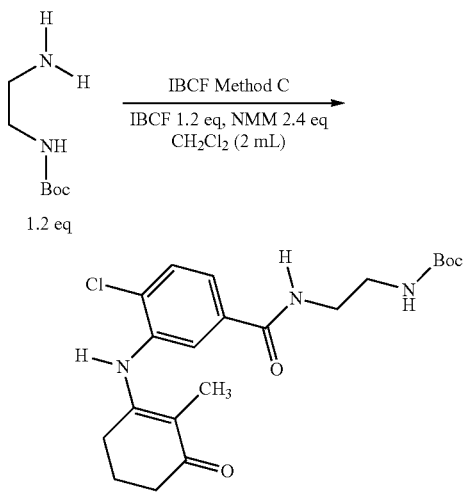

Example 05-27

Preparation of tert-butyl (2-(4-chloro-3-((2-methyl-3-oxocyclohex-1-en-1-yl)amino)benzamido)ethyl)carbamate (05-27)

The title compound was prepared from Example 01-36 and tert-butyl (2-aminoethyl)carbamate according to the procedure of Example 04-13; 0.5 mmol scale yielded 300 mg from precipitate (71% yield). $^1$H NMR (D6-DMSO) δ 1.36 (s, 9H), 1.65 (s, 3H), 1.76-1.78 (m, 2H), 2.18-2.21 (m, 4H), 3.09-3.11 (s, 2H), 3.26-3.29 (m, 2H), 6.93-6.95 (m, 1H), 7.64-7.66 (m, 1H), 7.72-7.75 (m, 2H), 8.08-8.10 (m, 1H), 8.58 (s, 1H). $^{13}$C NMR (D6-DMSO) δ 9.4, 21.6, 27.3, 28.6, 36.8, 78.1, 107.5, 126.6, 128.2, 130.1, 134.2, 134.3, 137.5, 156.2, 128.9, 165.2, 195.0. LCMS t=4.9 min, m/z Calcd for $C_{21}H_{29}ClN_3O_4$; $C_{21}H_{28}ClN_3NaO_4$; $C_{42}H_{57}Cl_2N_6O_8$; $C_{42}H_{56}Cl_2N_6NaO_8$ 422.18; 444.17; 843.36; 865.34 [M+H]$^+$; [M+Na]$^+$; [2M+H]$^+$; [2M+Na]$^+$, Found 422.20; 444.18; 843.39; 865.37.

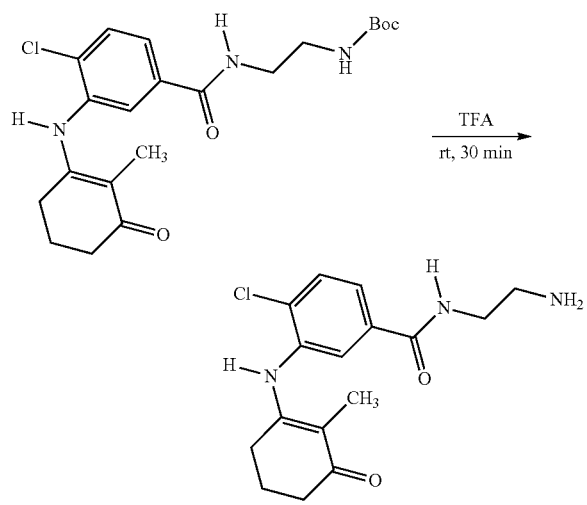

140

Example 05-28

Preparation of N-(2-aminoethyl)-4-chloro-3-((2-methyl-3-oxocyclohex-1-en-1-yl)amino)benzamide (05-28)

The title compound was prepared from Example 05-24 according to the procedure of Example 05-20. TFA salt was hygroscopic. Freebase was isolated. $^1$H NMR (D6-DMSO) δ 1.65 (s, 3H), 1.77-1.79 (m, 2H), 2.19-2.23 (m, 4H), 2.99-3.01 (m, 2H), 3.45-3.51 (m, 2H), 7.68 (d, J=8.2 Hz, 1H), 7.74-7.89 (m, 4H), 8.09-8.11 (m, 1H), 8.75 (s, 1H). $^{13}$C NMR (D6-DMSO) δ 9.5, 21.6, 27.4, 36.8, 37.6, 39.0, 107.7, 126.6, 128.2, 130.2, 133.9, 134.3, 137.6, 158.7, 165.8, 195.1. LCMS t=3.8 min, m/z Calcd for $C_{16}H_{21}ClN_3O_2$; $C_{16}H_{20}ClN_3NaO_2$; $C_{32}H_{41}Cl_2N_6O_4$; $C_{32}H_{40}Cl_2N_6NaO_4$ 322.13; 344.11; 643.26; 665.24 [M+H]$^+$; [M+Na]$^+$; [2M+H]$^+$; [2M+Na]$^+$, Found 322.14; 344.13; 643.28; 665.26.

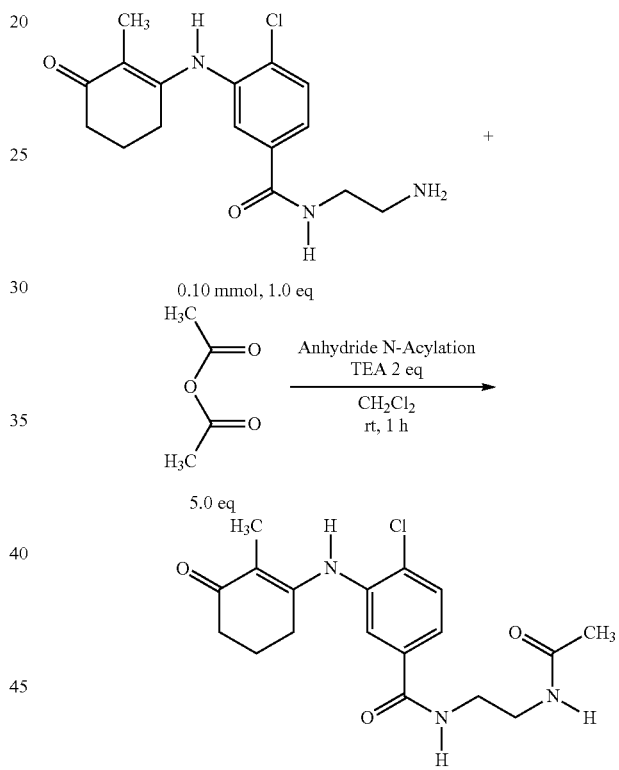

Example 05-29

Preparation of N-(2-acetamidoethyl)-4-chloro-3-((2-methyl-3-oxocyclohex-1-en-1-yl)amino)benzamide (05-29)

The title compound was prepared from Example 05-28 and acetic anhydride according to the procedure of Example 05-21; 0.10 mmol scale yielded 5 mg from precipitate (14% yield). $^1$H NMR (D6-DMSO) δ 1.65 (s, 3H), 1.77-1.81 (m, 5H), 2.19-2.23 (m, 4H), 3.19-3.21 (m, 2H), 3.28-3.30 (m, 2H), 7.65 (d, J=8.7 Hz, 1H), 7.73 (s, 2H), 7.97 (s, 1H), 8.06 (s, 1H), 8.62 (s, 1H). LCMS t=4.2 min, m/z Calcd for $C_{18}H_{23}ClN_3O_3$; $C_{18}H_{22}ClN_3NaO_3$; $C_{36}H_{45}Cl_2N_6O_6$; $C_{36}H_{45}Cl_2N_6NaO_6$ 364.14; 386.12; 727.28; 749.26 [M+H]$^+$; [M+Na]$^+$; [2M+H]$^+$; [2M+Na]$^+$, Found 364.15; 386.14; 727.30; 749.28.

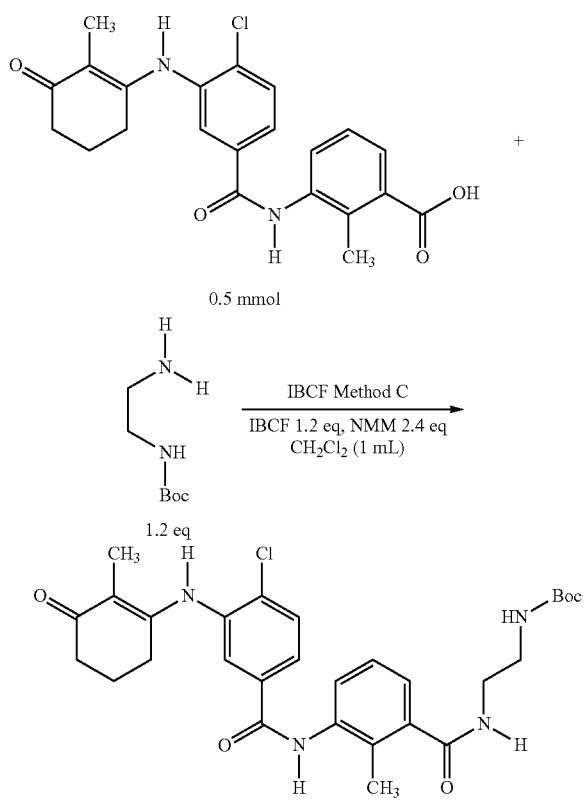

Example 05-30

Preparation of tert-butyl (2-(3-(4-chloro-3-((2-methyl-3-oxocyclohex-1-en-1-yl)amino)benzamido)-2-methylbenzamido)ethyl)carbamate (05-30)

The title compound was prepared from Example 04-95 and tert-butyl (2-aminoethyl)carbamate according to the procedure of Example 04-13; 0.5 mmol scale yielded 50 mg after chromatography (ESS=EtOAc, 18% yield). $^1$H NMR (D6-DMSO) δ 1.40 (s, 9H), 1.66 (s, 3H), 1.78-1.81 (m, 2H), 2.18-2.22 (m, 4H), 2.26-2.28 (m, 2H), 3.09-2.12 (m, 2H), 3.24-3.28 (m, 2H), 6.87 (t, J=5.4 Hz, 1H), 7.25-7.26 (m, 2H), 7.36 (t, J=4.5 Hz, 1H), 7.72 (d, J=8.1 Hz, 1H), 7.86-7.89 (m, 2H), 8.12 (s, 1H), 8.31 (t, J=5.4 Hz, 1H), 10.07 (s, 1H). LCMS t=4.9 min, m/z Calcd for $C_{29}H_{36}ClN_4O_5$; $C_{29}H_{35}ClN_4NaO_5$; $C_{58}H_{71}Cl_2N_8O_{10}$; $C_{58}H_{70}Cl_2N_8NaO_{10}$ 555.24; 577.22; 1109.47; 1131.45 $[M+H]^+$; $[M+Na]^+$; $[2M+H]^+$; $[2M+Na]^+$, Found 555.26; 577.24; 1109.51; 1131.49.

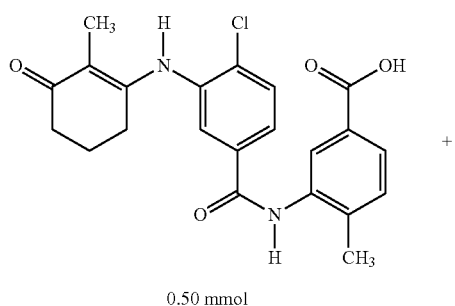

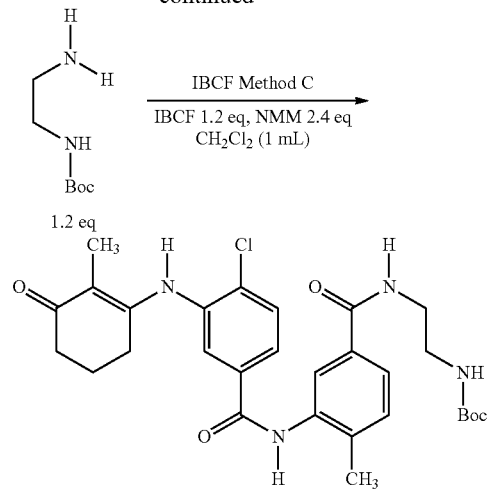

Example 05-31

Preparation of tert-butyl (2-(3-(4-chloro-3-((2-methyl-3-oxocyclohex-1-en-1-yl)amino)benzamido)-4-methylbenzamido)ethyl)carbamate (05-31)

The title compound was prepared from Example 04-96 and tert-butyl (2-aminoethyl)carbamate according to the procedure of Example 04-13; 0.5 mmol scale yielded after chromatography (ESS=EtOAc, 36% yield). $^1$H NMR (D6-DMSO) δ 1.39 (s, 9H), 1.66 (s, 3H), 1.78-1.80 (m, 2H), 2.19-2.22 (m, 2H), 2.26-2.28 (m, 4H), 3.09-3.11 (m, 2H), 3.27-3.30 (m, 2H), 6.91 (t, J=5.6 Hz, 1H), 7.37 (d, J=8.0 Hz, 1H), 7.68 (d, J=7.8 Hz, 1H), 7.73 (d, J=8.1 Hz, 1H), 7.81 (s, 1H), 7.87-7.90 (m, 2H), 8.11 (s, 1H), 8.43 (t, J=5.3 Hz, 1H), 10.12 (s, 1H). LCMS t=5.0 min, m/z Calcd for $C_{29}H_{36}ClN_4O_5$; $C_{29}H_{35}ClN_4NaO_5$; $C_{58}H_{71}Cl_2N_8O_{10}$; $C_{58}H_{70}Cl_2N_8NaO_{10}$ 555.24; 577.22; 1109.47; 1131.45 $[M+H]^+$; $[M+Na]^+$; $[2M+H]^+$; $[2M+Na]^+$, Found 555.26; 577.24; 1109.50; 1131.49.

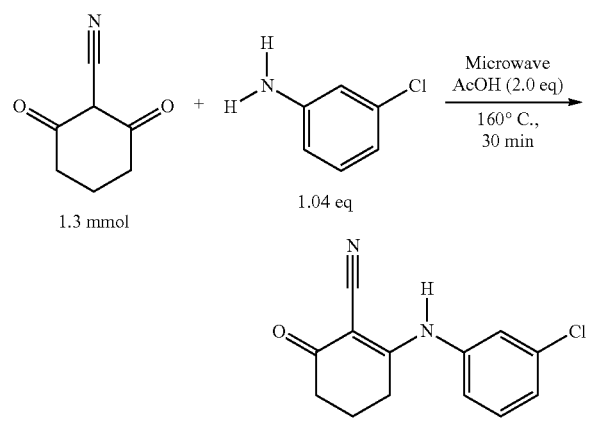

Example 05-32

Preparation of 2-((3-chlorophenyl)amino)-6-oxocyclohex-1-enecarbonitrile (05-32)

The title compound was prepared from Intermediate 06 and 3-chloroaniline according to the procedure of Example 05-13; 1.3 mmol scale yielded 24 mg after chromatography (ESS=H:E (1:1), 8% yield). $^1$H NMR (D6-DMSO) δ 1.82-1.85 (m, 2H), 2.26-2.29 (m, 2H), 2.58-2.60 (m, 2H), 7.26 (d, J=7.7 Hz, 1H), 7.37-7.46 (m, 3H), 10.15 (s, 1H). $^{13}$C NMR (D6-DMSO) δ 20.6, 26.7, 36.4, 86.0, 116.2, 125.4, 126.6, 127.4, 130.9, 133.5, 139.1, 170.9, 193.2. LCMS t=4.6 min, m/z Calcd for $C_{13}H_{12}ClN_2O$; $C_{13}H_{11}ClN_2NaO$; $C_{26}H_{23}Cl_2N_4O_2$; $C_{26}H_{22}Cl_2N_4NaO_2$ 247.06; 269.05; 493.12; 515.10 [M+H]$^+$; [M+Na]$^+$; [2M+H]$^+$; [2M+Na]$^+$, Found 247.07; 269.06; 493.14; 515.12.

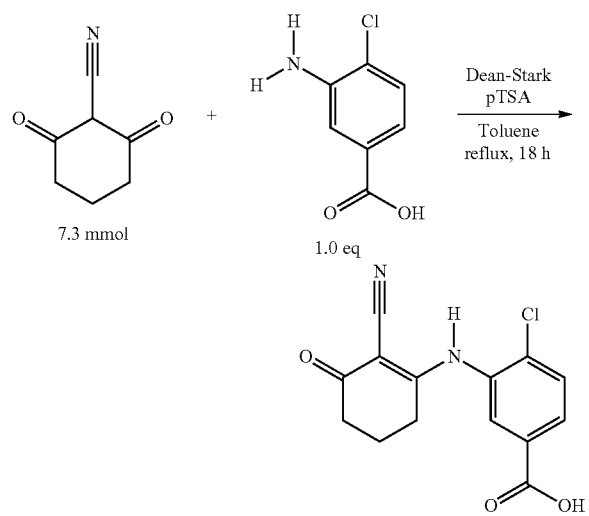

Example 05-33

Preparation of 4-chloro-3-((2-cyano-3-oxocyclohex-1-en-1-yl)amino)benzoic acid (05-33)

The title compound was prepared Intermediate 06 and 3-amino-4-chlorobenzoic acid according to the procedure of Example 01-01; 7.3 mmol scale yielded 0.7 g after chromatography (ESS=CH$_2$Cl$_2$:MeOH (19:1), 33% yield). $^1$H NMR (D6-DMSO) δ 1.85-1.88 (m, 2H), 2.28-2.30 (m, 2H), 2.50-2.58 (m, 2H), 7.72 (d, J=8.1 Hz, 1H), 7.91-7.96 (m, 2H), 10.17 (s, 1H), 13.40 (br s, 1H). $^{13}$C NMR (D6-DMSO) δ 20.3, 29.1, 36.9, 85.5, 115.6, 130.6, 130.7, 130.9, 135.3, 136.7, 166.4, 193.4. LCMS t=4.1 min, m/z Calcd for $C_{14}H_{12}ClN_2O_3$; $C_{14}H_{11}ClN_2NaO_3$; $C_{28}H_{23}Cl_2N_4O_6$; $C_{28}H_{23}Cl_2N_4NaO_6$ 291.05; 313.04; 581.10; 603.08 [M+H]$^+$; [M+Na]$^+$; [2M+H]$^+$; [2M+Na]$^+$, Found 291.06; 313.05; 581.12; 603.10.

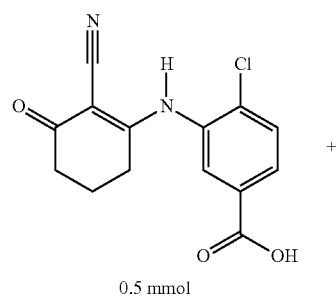

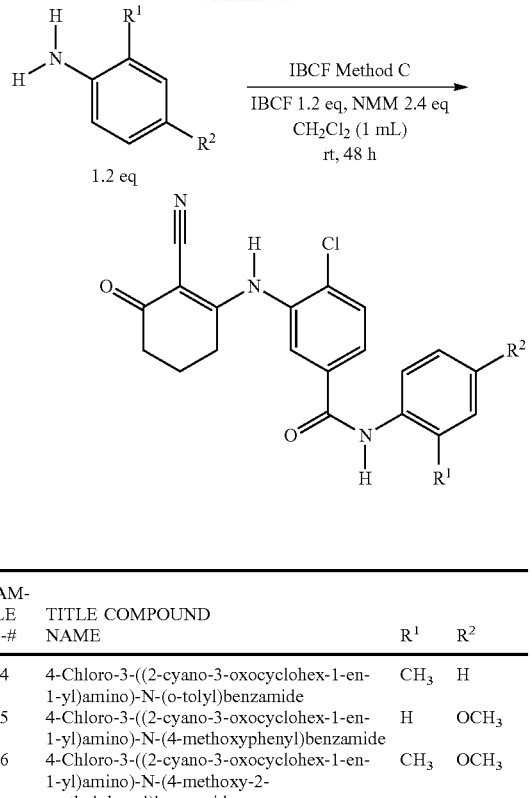

| EXAMPLE 05-# | TITLE COMPOUND NAME | R$^1$ | R$^2$ |
|---|---|---|---|
| 34 | 4-Chloro-3-((2-cyano-3-oxocyclohex-1-en-1-yl)amino)-N-(o-tolyl)benzamide | CH$_3$ | H |
| 35 | 4-Chloro-3-((2-cyano-3-oxocyclohex-1-en-1-yl)amino)-N-(4-methoxyphenyl)benzamide | H | OCH$_3$ |
| 36 | 4-Chloro-3-((2-cyano-3-oxocyclohex-1-en-1-yl)amino)-N-(4-methoxy-2-methylphenyl)benzamide | CH$_3$ | OCH$_3$ |

Example 05-34

Preparation of 4-chloro-3-((2-cyano-3-oxocyclohex-1-en-1-yl)amino)-N-(o-tolyl)benzamide (05-34)

The title compound was prepared from Example 05-33 and o-toluidine according to the procedure of Example 04-13; 0.5 mmol scale yielded 130 mg from precipitate (67% yield). $^1$H NMR (D6-DMSO) δ 1.86-1.91 (m, 2H), 2.23 (s, 3H), 2.29-2.34 (m, 2H), 2.50-2.60 (m, 2H), 7.19-7.24 (m, 2H), 7.28-7.32 (m, 2H), 7.77 (d, J=6.8 Hz, 1H), 8.03 (s, 2H), 10.04 (s, 1H), 10.21 (s, 1H). LCMS t=4.7 min, m/z Calcd for $C_{21}H_{19}ClN_3O_2$; $C_{21}H_{18}ClN_3NaO_2$; $C_{42}H_{37}Cl_2N_6O_4$; $C_{42}H_{36}Cl_2N_6NaO_4$ 380.12; 402.10; 759.23; 781.21 [M+H]$^+$; [M+Na]$^+$; [2M+H]$^+$; [2M+Na]$^+$, Found 380.13; 402.11; 759.25; 781.24.

Example 05-35

Preparation of 4-chloro-3-((2-cyano-3-oxocyclohex-1-en-1-yl)amino)-N-(4-methoxyphenyl)benzamide (05-35)

The title compound was prepared from Example 05-33 and p-anisidine according to the procedure of Example 04-13; 0.5 mmol scale yielded 113 mg from precipitate (57% yield). $^1$H NMR (D6-DMSO) δ 1.85-1.91 (m, 2H), 2.28-2.35 (m, 2H), 2.50-2.62 (m, 2H), 3.75 (s, 3H), 6.94 (d, J=8.9 Hz, 2H), 7.66 (d, J=8.8 Hz, 2H), 7.76 (d, J=8.3 Hz, 1H), 8.00-8.04 (m, 2H), 10.23 (s, 1H). LCMS t=4.7 min, m/z Calcd for $C_{21}H_{19}ClN_3O_3$; $C_{21}H_{18}ClN_3NaO_3$; $C_{42}H_{37}Cl_2N_6O_6$; $C_{42}H_{36}Cl_2N_6NaO_6$ 396.11; 418.09;

791.22; 813.20 [M+H]+; [M+Na]+; [2M+H]+; [2M+Na]+, Found 396.13; 418.11; 791.24; 813.23.

Example 05-36

Preparation of 4-chloro-3-((2-cyano-3-oxocyclohex-1-en-1-yl)amino)-N-(4-methoxy-2-methylphenyl)benzamide (05-36)

The title compound was prepared from Example 05-33 and 4-methoxy-2-methylaniline according to the procedure of Example 04-13; 0.5 mmol scale yielded 82 mg after chromatography (ESS=H:E (1:3), 41% yield). $^1$H NMR (D6-DMSO) δ 1.85-1.92 (m, 2H), 2.19 (s, 3H), 2.28-2.36 (m, 2H), 2.50-2.63 (m, 2H), 3.75 (s, 3H), 6.79 (d, J=7.1 Hz, 1H), 6.86 (s, 1H), 7.19 (d, J=8.3 Hz, 1H), 7.76 (d, J=7.7 Hz, 1H), 8.03 (s, 2H), 9.92 (s, 1H), 10.21 (s, 1H). $^{13}$C NMR (D6-DMSO) δ 18.5, 20.4, 28.9, 36.4, 55.6, 85.6, 111.8, 115.8, 128.5, 129.1, 129.2, 129.5, 130.3, 134.3, 135.1, 135.2, 136.0, 157.9, 163.9, 193.3. LCMS t=4.7 min, m/z Calcd for $C_{22}H_{21}ClN_3O_3$; $C_{22}H_{20}ClN_3NaO_3$; $C_{44}H_{41}Cl_2N_6O_6$; $C_{44}H_{40}Cl_2N_6NaO_6$ 410.13; 432.11; 819.25; 841.23 [M+H]+; [M+Na]+; [2M+H]+; [2M+Na]+, Found 410.14; 432.12; 819.27; 841.26.

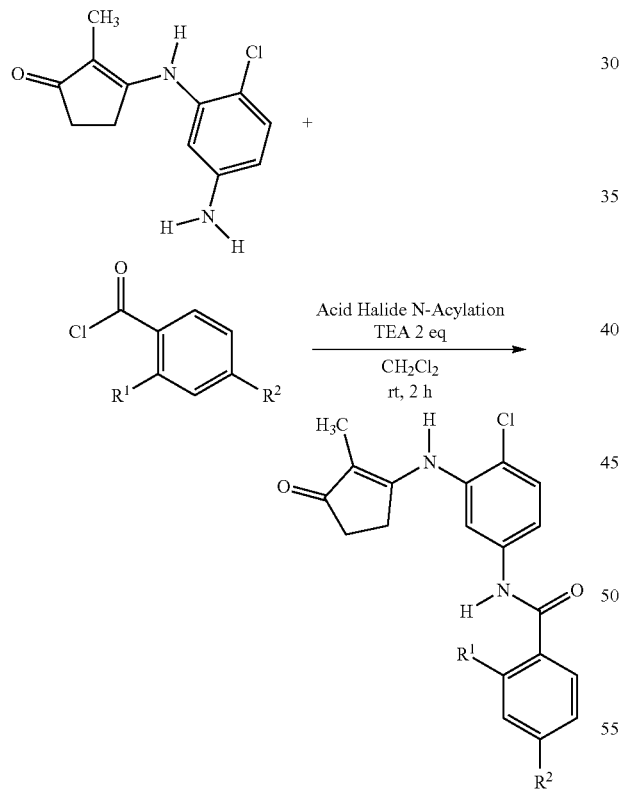

| EXAMPLE 05-# | TITLE COMPOUND NAME | R$^1$ | R$^2$ |
|---|---|---|---|
| 37 | N-(4-Chloro-3-((2-methyl-3-oxocyclopent-1-en-1-yl)amino)phenyl)-4-methoxybenzamide | H | OCH$_3$ |
| 38 | N-(4-Chloro-3-((2-methyl-3-oxocyclopent-1-en-1-yl)amino)phenyl)-2-methylbenzamide | CH$_3$ | H |

Example 05-37

Preparation of N-(4-chloro-3-((2-methyl-3-oxocyclopent-1-en-1-yl)amino)phenyl)-4-methoxybenzamide (05-37)

Triethylamine (0.279 mL, 2.0 mmol) was added to Example 02-14 (0.27 g, 1.0 mmol) in dichloromethane (5 mL). p-Anisoyl chloride (0.142 mL, 1.05 mmol) was added to the solution stirring at 0° C. After 2 h, the solvent was removed on the rotovap and the subsequent crude material was added directly to a KP-Sil™ column (10 g) with products separating from impurities using stepwise gradients, on the Biotage®-Isolera Four instrument, monitoring UV Trace at 254/365 nm. The stepwise gradient utilized two solvents (hexanes and EtOAc) running from non-polar to polar steps (3:1-1:1-1:3). The 1.0 mmol scale yielded 75 mg of pale yellow microcrystals after chromatography (ESS=H:E (1:3), mp=254-257° C., 20% yield). $^1$H NMR (D6-DMSO) δ 1.48 (s, 3H), 2.20-2.23 (m, 2H), 2.44-2.48 (m, 2H), 3.84 (s, 3H), 7.07 (d, J=8.8 Hz, 2H), 7.52 (d, J=8.8 Hz, 1H), 7.69 (dd, J=8.8, 2.3 Hz, 1H), 7.85 (d, J=2.2 Hz, 1H), 7.96 (d, J=8.7 Hz, 1H), 8.89 (s, 1H), 10.25 (s, 1H). $^{13}$C NMR (D6-DMSO) δ 7.4, 25.6, 32.6, 55.5, 109.4, 113.7, 118.9, 119.6, 123.7, 126.5, 129.6, 129.7, 136.5, 138.8, 162.1, 165.1, 169.5, 202.3. LCMS t=5.0 min, m/z Calcd for $C_{20}H_{20}ClN_2O_3$; $C_{20}H_{19}ClN_2NaO_3$; $C_{40}H_{39}Cl_2N_4O_6$; $C_{40}H_{38}Cl_2N_2NaO_6$ 371.116; 393.098; 741.225; 763.207 [M+H]+; [M+Na]+; [2M+H]+; [2M+Na]+, Found 371.116; 393.090; 741.217; 763.203.

Example 05-38

Preparation of N-(4-chloro-3-((2-methyl-3-oxocyclopent-1-en-1-yl)amino)phenyl)-2-methylbenzamide (05-38)

The title compound was prepared from Example 02-14 and o-toluoyl chloride according to the procedure of Example 05-37; 1.0 mmol scale yielded 65 mg of pale yellow microcrystals after chromatography (ESS=H:E (1:3), mp=230-232° C., 18% yield). $^1$H NMR (D6-DMSO) δ 1.48 (s, 3H), 2.20-2.22 (m, 2H), 2.38 (s, 3H), 2.44-2.48 (m, 2H), 7.29-7.33 (m, 2H), 7.40 (t, J=7.5 Hz, 1H), 7.48 (d, J=7.5 Hz, 1H), 7.51 (d, J=8.8 Hz, 1H), 7.62 (dd, J=8.7, 2.0 Hz, 1H), 7.82 (d, J=1.6 Hz, 1H), 8.89 (s, 1H), 10.49 (s, 1H). $^{13}$C NMR (D6-DMSO) δ 7.4, 19.3, 25.6, 32.6, 109.4, 118.4, 118.9, 123.8, 125.7, 127.3, 129.8, 129.9, 130.6, 135.3, 136.6, 136.8, 138.7, 168.1, 169.5, 202.4. LCMS t=5.1 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_2NaO_4$ 355.121; 377.103; 709.235; 731.217 [M+H]+; [M+Na]+; [2M+H]+; [2M+Na]+, Found 355.126; 377.099, 709.220; 731.208.

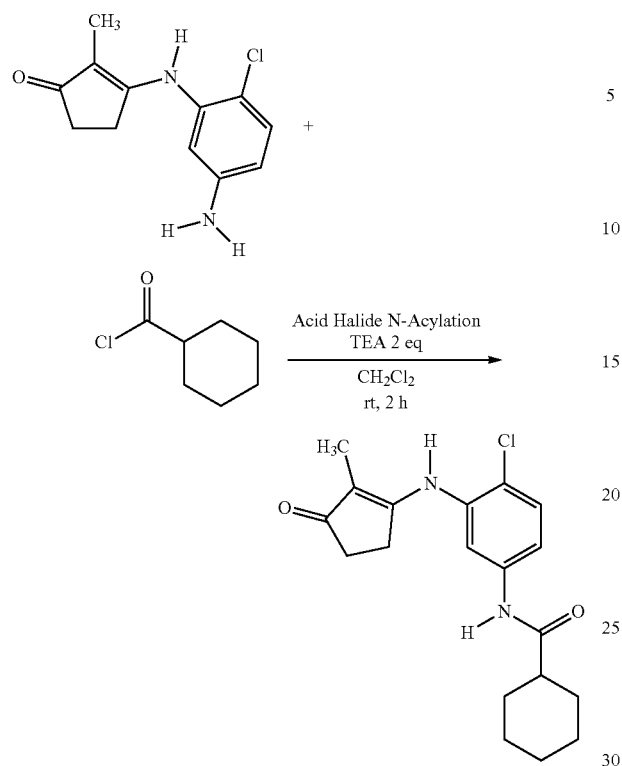

Example 05-39

Preparation of N-(4-chloro-3-[(2-methyl-3-oxocyclopent-1-en-1-yl)amino]phenyl)-cyclohexanecarboxamide (05-39)

The title compound was prepared from Example 02-14 and cyclohexanecarbonyl chloride according to the procedure of Example 05-37 (mp=240-242° C.). $^1$H NMR (D6-DMSO) δ 1.12-1.30 (m, 3H), 1.34-1.43 (m, 2H), 1.44 (s, 3H), 1.62-1.67 (m, 1H), 1.71-1.84 (m, 5H), 2.17-2.22 (m, 2H), 2.26-2.34 (m, 1H), 2.41 (d, J=4.9 Hz, 2H), 7.39-7.50 (m, 2H), 7.69 (s, 1H), 8.86 (s, 1H), 10.02 (s, 1H). $^{13}$C NMR (D6-DMSO) δ 7.5, 25.2 (2C), 25.4, 25.6, 29.0 (2C), 32.6, 44.9, 109.3, 117.8, 118.4, 123.1, 129.7, 136.5, 138.9, 169.5, 174.6, 202.4. LCMS t=4.8 min, m/z Calcd for $C_{19}H_{24}ClN_2O_2$; $C_{19}H_{23}ClN_2NaO_2$; $C_{38}H_{47}Cl_2N_4O_4$; $C_{38}H_{46}Cl_2N_4NaO_4$ 347.152; 369.135; 693.297; 715.279 [M+H]$^+$; [M+Na]$^+$; [2M+H]$^+$; [2M+Na]$^+$, Found 347.152; 369.135; 693.297; 715.279.

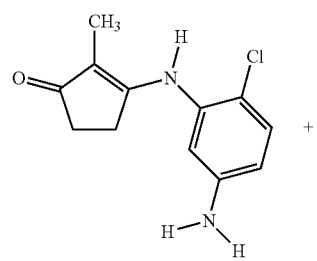

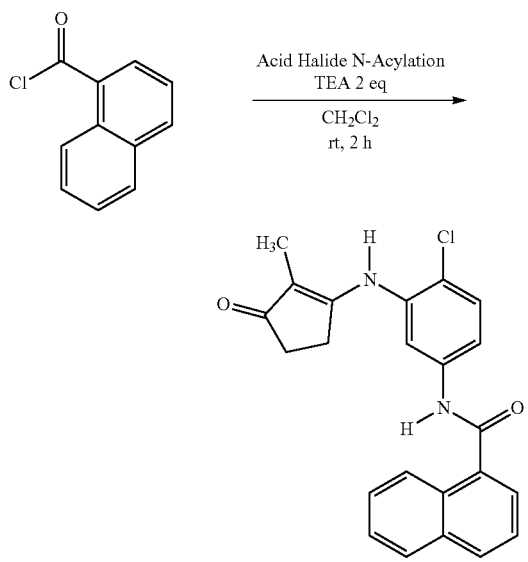

Example 05-40

Preparation of N-(4-chloro-3-[(2-methyl-3-oxocyclopent-1-en-1-yl)amino]phenyl)-naphthalene-1-carboxamide (05-40)

The title compound was prepared from Example 02-14 and 1-naphthoyl chloride according to the procedure of Example 05-37 (mp=243-245° C.). $^1$H NMR (D6-DMSO) δ 1.49 (s, 3H), 2.19-2.25 (m, 2H), 2.47 (br s, 2H), 7.56 (d, J=8.5 Hz, 1H), 7.58-7.65 (m, 3H), 7.69 (dd, J=8.5, 2.4 Hz, 1H), 7.79 (d, J=7.3 Hz, 1H), 7.90 (d, J=2.4 Hz, 1H), 8.02-8.05 (m, 1H), 8.10 (d, J=7.3 Hz, 1H), 8.16-8.21 (m, 1H), 8.95 (s, 1H), 10.79 (s, 1H). $^{13}$C NMR (D6-DMSO) δ 7.5, 25.6, 32.6, 109.5, 118.6, 119.2, 124.0, 125.0, (2C), 125.7, 126.5, 127.2, 128.4, 129.6, 129.8, 130.5, 133.2, 134.2, 136.7, 138.7, 167.5, 169.5, 202.4. LCMS t=4.8 min, m/z Calcd for $C_{23}H_{20}ClN_2O_2$; $C_{23}H_{19}ClN_2NaO_2$; $C_{46}H_{39}Cl_2N_4O_4$; $C_{46}H_{38}Cl_2N_4NaO_4$ 391.125; 413.103; 781.235; 803.217 [M+H]$^+$; [M+Na]$^+$; [2M+H]$^+$; [2M+Na]$^+$, Found 391.122; 413.103; 781.235; 803.217.

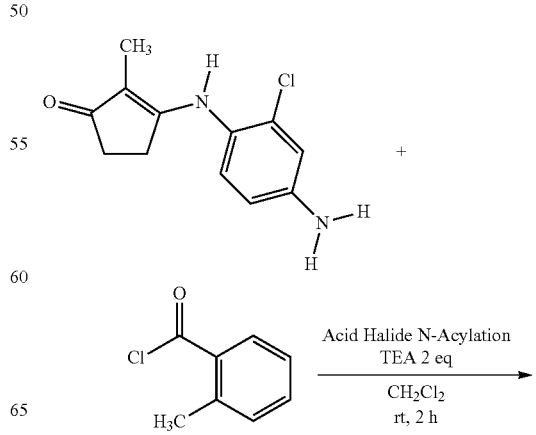

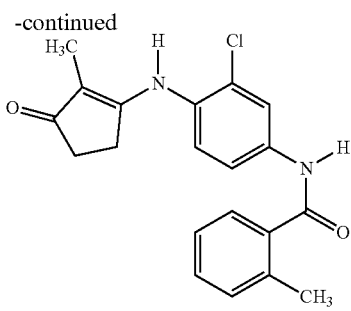

Example 05-41

Preparation of N-(3-chloro-4-((2-methyl-3-oxocyclopent-1-en-1-yl)amino)phenyl)-2-methylbenzamide (05-41)

The title compound was prepared from Example 02-15 and o-toluoyl chloride according to the procedure of Example 05-37 (mp=280-283° C.). $^1$H NMR (D6-DMSO) δ 1.48 (s, 3H), 2.15-2.20 (m, 2H), 2.32-2.36 (m, 2H), 2.39 (s, 3H), 7.29-7.35 (m, 2H), 7.37-7.45 (m, 2H), 7.49 (d, J=7.3 Hz, 1H), 7.66 (dd, J=8.5, 2.4 Hz, 1H), 8.07 (s, 1H), 8.87 (s, 1H), 10.55 (s, 1H). $^{13}$C NMR (D6-DMSO) δ 7.1, 19.3, 25.2, 32.6, 108.4, 118.6, 119.9, 125.7, 127.3, 129.5, 129.9, 130.6, 130.8, 131.6, 135.4, 136.7, 138.6, 168.0, 170.4, 201.9. LCMS t=4.4 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.121; 377.103; 709.235; 731.217 [M+H]$^+$; [M+Na]$^+$; [2M+H]$^+$; [2M+Na]$^+$, Found 355.121; 377.103; 709.235; 731.217.

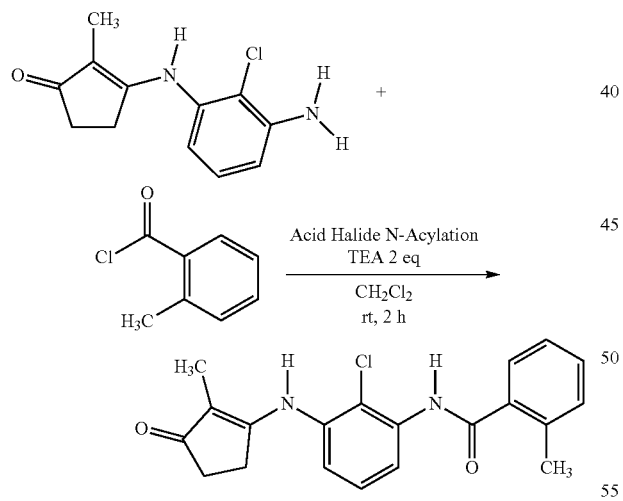

Example 05-42

Preparation of N-(2-chloro-3-((2-methyl-3-oxocyclopent-1-en-1-yl)amino)phenyl)-2-methylbenzamide (05-42)

The title compound was prepared from Example 02-13 and o-toluoyl chloride according to the procedure of Example 05-37 (mp=118-120° C.). $^1$H NMR (D6-DMSO) δ 1.48 (s, 3H), 2.15-2.22 (m, 2H), 2.40 (br s, 2H), 2.45 (s, 3H), 7.25-7.35 (m, 3H), 7.40 (q, J=7.3 Hz, 2H), 7.48-7.60 (m, 2H), 8.96 (s, 1H), 10.07 (s, 1H). $^{13}$C NMR (D6-DMSO) δ 7.3, 19.5, 25.4, 32.6, 109.1, 125.6, 125.6, 125.9, 126.8, 126.9, 127.4, 129.9, 130.6, 135.6, 135.9, 136.3, 137.4, 167.9, 169.8, 202.2. LCMS t=4.4 min, m/z Calcd for $C_{20}H_{20}ClN_2O_2$; $C_{20}H_{19}ClN_2NaO_2$; $C_{40}H_{39}Cl_2N_4O_4$; $C_{40}H_{38}Cl_2N_4NaO_4$ 355.121; 377.103; 709.235; 731.217 [M+H]$^+$; [M+Na]$^+$; [2M+H]$^+$; [2M+Na]$^+$, Found 355.121; 377.103; 709.235; 731.217.

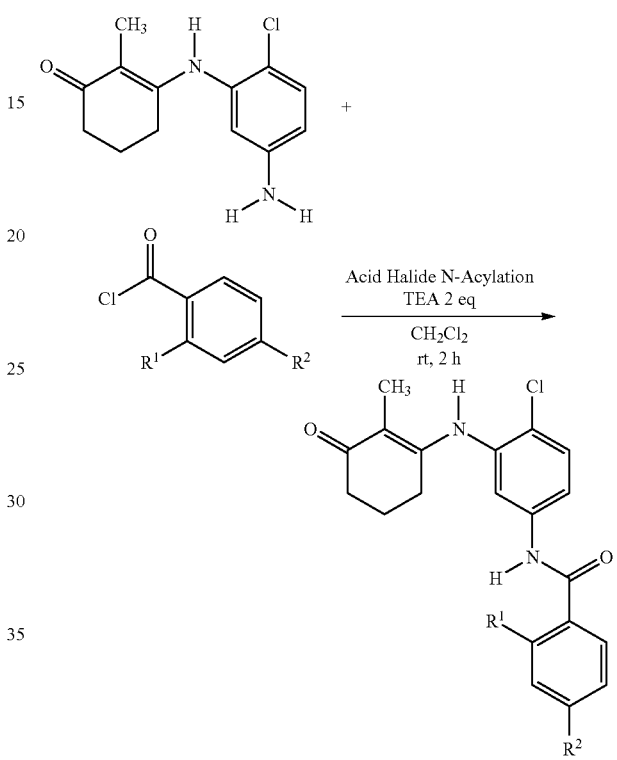

| EXAMPLE 05-# | TITLE COMPOUND NAME | R$^1$ | R$^2$ |
|---|---|---|---|
| 43 | N-(4-Chloro-3-((2-methyl-3-oxocyclohex-1-en-1-yl)amino)phenyl)-4-methoxybenzamide | H | OCH$_3$ |
| 44 | N-(4-Chloro-3-((2-methyl-3-oxocyclohex-1-en-1-yl)amino)phenyl)-2-methylbenzamide | CH$_3$ | H |

Example 05-43

Preparation of N-(4-chloro-3-((2-methyl-3-oxocyclohex-1-en-1-yl)amino)phenyl)-4-methoxybenzamide (05-43)

The title compound was prepared from Example 02-10 and p-anisoyl chloride according to the procedure of Example 05-37; 1.0 mmol scale yielded 60 mg after chromatography (ESS=H:E (1:3), mp=190-195° C., 16% yield). $^1$H NMR (D6-DMSO) δ 1.67 (s, 3H), 1.77-1.80 (m, 2H), 2.18-2.21 (m, 2H), 2.25-2.27 (m, 2H), 3.84 (s, 3H), 7.07 (d, J=8.6 Hz, 2H), 7.49 (d, J=8.7 Hz, 1H), 7.68 (dd, J=8.7, 2.1 Hz, 1H), 7.77 (d, J=2.1 Hz, 1H), 7.96 (d, J=8.6 Hz, 2H), 8.00

(s, 1H), 10.25 (s, 1H). $^{13}$C NMR (D6-DMSO) δ 9.0, 21.2, 27.0, 36.4, 55.5, 107.1, 113.7, 118.9, 120.2, 124.5, 126.5, 129.5, 129.7, 137.0, 138.9, 158.4, 162.1, 165.1, 194.5. LCMS t=5.1 min, Calcd for $C_{21}H_{22}ClN_2O_3$; $C_{21}H_{21}ClN_2NaO_3$; $C_{42}H_{42}Cl_2N_2NaO_6$ 385.13; 407.11; 791.24 [M+H]+; [M+Na]+; [2M+Na]+, Found 385.20; 407.10; 791.22.

Example 05-44

Preparation of N-(4-chloro-3-((2-methyl-3-oxocyclohex-1-en-1-yl)amino)phenyl)-2-methylbenzamide (05-44)

The title compound was prepared from Example 02-10 and o-toluoyl chloride according to the procedure of Example 05-37 (mp=199-201° C.). $^1$H NMR (D6-DMSO) δ 1.66 (s, 3H), 1.76-1.80 (m, 2H), 2.19 (t, J=6.1 Hz, 2H), 2.25 (t, J=5.5 Hz, 2H), 2.38 (s, 3H), 7.28-7.36 (m, 2H), 7.38-7.43 (m, 1H), 7.44-7.56 (m, 2H), 7.62 (d, J=7.3 Hz, 1H), 7.74 (s, 1H), 8.03 (s, 1H), 10.50 (s, 1H). $^{13}$C NMR (D6-DMSO) δ 9.1, 19.3, 21.2, 27.0, 36.4, 107.2, 118.2, 119.4, 124.5, 125.7, 127.2, 129.7, 129.9, 130.6, 135.3, 136.8, 137.2, 138.7, 158.4, 168.0, 194.6. LCMS t=4.7 min, m/z Calcd for $C_{21}H_{22}ClN_2O_2$; $C_{21}H_{21}ClN_2NaO_2$; $C_{42}H_{42}Cl_2N_4NaO_4$ 369.137; 391.119; 759.248 [M+H]+; [M+Na]+; [2M+Na]+, Found 369.137; 391.119; 759.248.

DMSO) δ 1.14-1.22 (m, 1H), 1.22-1.30 (m, 2H), 1.35-1.43 (m, 2H), 1.63 (s, 4H), 1.72-1.82 (m, 6H), 2.18 (t, J=6.1 Hz, 2H), 2.22 (t, J=5.5 Hz, 2H), 2.27-2.33 (m, 1H), 7.41-7.47 (m, 2H), 7.61 (s, 1H), 7.97 (s, 1H), 10.00 (s, 1H). $^{13}$C NMR (D6-DMSO) δ 9.1, 21.2, 25.2 (2C), 25.4, 27.0, 29.1 (2C), 36.4, 44.9, 107.1, 117.7, 118.9, 123.8, 129.6, 137.1, 138.9, 158.4, 174.6, 194.6. LCMS t=4.9 min, m/z Calcd for $C_{20}H_{26}ClN_2O_2$; $C_{20}H_{25}ClN_2NaO_2$; $C_{40}H_{50}Cl_2N_4NaO_4$ 361.168; 383.150; 743.311 [M+H]+; [M+Na]+; [2M+Na]+, Found 361.168; 383.150; 743.311.

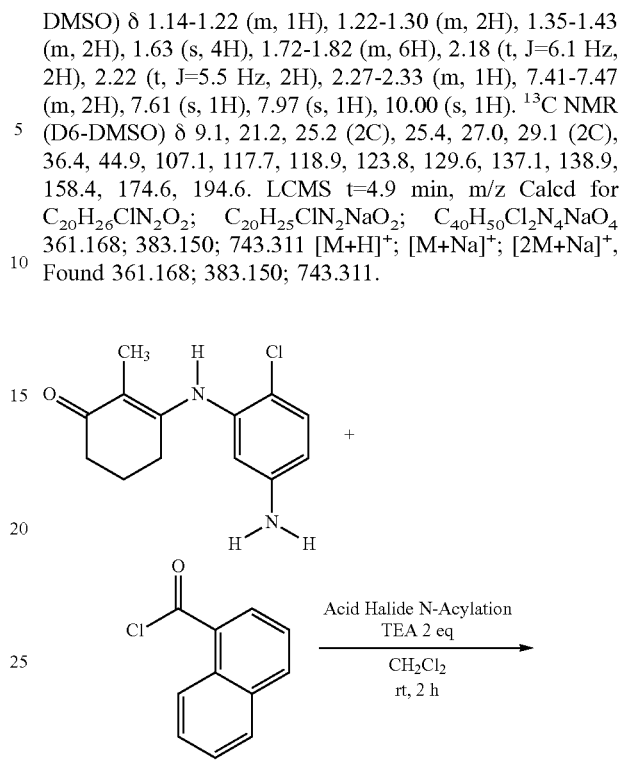

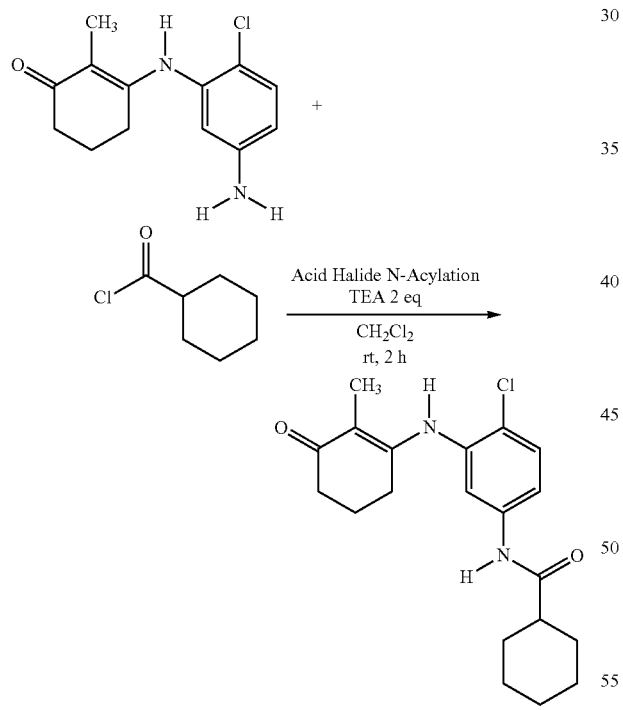

Example 05-45

Preparation of N-(4-chloro-3-((2-methyl-3-oxocyclohex-1-en-1-yl)amino)phenyl)-cyclohexanecarboxamide (05-45)

The title compound was prepared from Example 02-10 and cyclohexanecarbonyl chloride according to the procedure of Example 05-37 (mp=192-195° C.). $^1$H NMR (D6-

Example 05-46

Preparation of N-(4-chloro-3-((2-methyl-3-oxocyclohex-1-en-1-yl)amino)phenyl)-1-naphthamide (05-46)

The title compound was prepared from Example 02-10 and 1-naphthoyl chloride according to the procedure of Example 05-37 (mp=245-247° C.). $^1$H NMR (D6-DMSO) δ 1.67 (s, 3H), 1.77-1.83 (m, 2H), 2.20 (t, J=6.1 Hz, 2H), 2.26-2.31 (m, 2H), 7.54 (d, J=8.5 Hz, 1H), 7.58-7.65 (m, 3H), 7.69 (d, J=7.3 Hz, 1H), 7.78 (d, J=7.3 Hz, 1H), 7.81 (d, J=2.4 Hz, 1H), 8.02-8.07 (m, 2H), 8.10 (d, J=8.5 Hz, 1H), 8.16-8.20 (m, 1H), 10.77 (s, 1H). $^{13}$C NMR (D6-DMSO) δ 9.1, 21.2, 27.1, 36.4, 107.3, 118.4, 119.6, 124.7, 125.1 (2C), 125.7, 126.5, 127.2, 128.4, 129.6, 129.8, 130.4, 133.2, 134.3, 137.2, 138.7, 158.4, 167.5, 194.6. LCMS t=5.0 min, m/z Calcd for $C_{24}H_{22}ClN_2O_2$; $C_{24}H_{21}ClN_2NaO_2$; $C_{48}H_{43}Cl_2N_4O_4$; $C_{48}H_{42}Cl_2N_4NaO_4$ 405.136; 427.118; 809.266; 831.248 [M+H]+; [M+Na]+; [2M+H]+; [2M+Na]+, Found 405.136; 427.118; 809.266; 831.248.

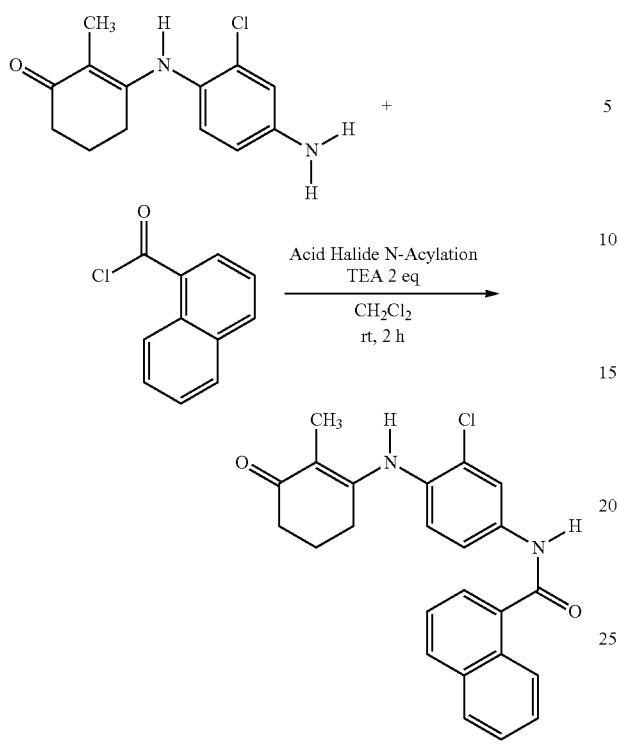

Example 05-47

Preparation of N-(3-chloro-4-((2-methyl-3-oxocyclohex-1-en-1-yl)amino)phenyl)-1-naphthamide (05-47)

The title compound was prepared from Example 02-12 and 1-naphthoyl chloride according to the procedure of Example 05-37 (mp=245-247° C.). $^1$H NMR (D6-DMSO) δ 1.69 (s, 3H), 1.77 (quin, J=6.4 Hz, 2H), 2.16-2.21 (m, 4H), 7.35 (d, J=8.5 Hz, 1H), 7.51-7.68 (m, 3H), 7.72 (dd, J=8.5, 2.4 Hz, 1H), 7.79 (d, J=7.3 Hz, 1H), 8.00-8.07 (m, 2H), 8.11 (d, J=8.5 Hz, 1H), 8.14 (d, J=2.4 Hz, 1H), 8.17-8.23 (m, 1H), 10.82 (s, 1H). $^{13}$C NMR (D6-DMSO) δ 8.8, 21.2, 26.7, 36.3, 105.9, 118.8, 120.1, 125.1 (2C), 125.7, 126.5, 127.2, 128.4, 129.6, 130.0, 130.5, 131.4, 132.3, 133.2, 134.2, 138.5, 159.4, 167.5, 194.1. LCMS t=4.9 min, m/z Calcd for $C_{24}H_{22}ClN_2O_2$; $C_{24}H_{21}ClN_2NaO_2$; $C_{48}H_{43}Cl_2N_4O_4$; $C_{48}H_{42}Cl_2N_4NaO_4$ 405.136; 427.118; 809.266; 831.248 [M+H]$^+$; [M+Na]$^+$; [2M+H]$^+$; [2M+Na]$^+$, Found 405.136; 427.118; 809.266; 831.248.

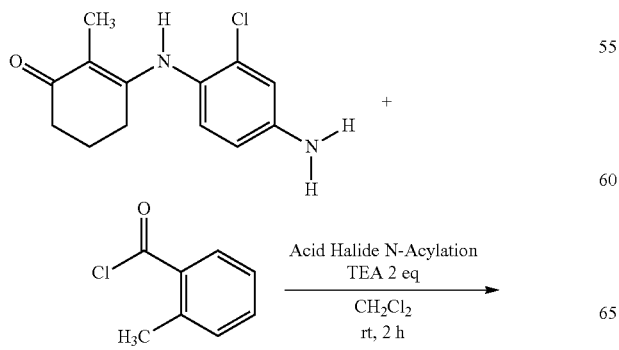

Example 05-48

Preparation of N-(3-chloro-4-((2-methyl-3-oxocyclohex-1-en-1-yl)amino)phenyl)-2-methylbenzamide (05-48)

The title compound was prepared from Example 02-12 and o-toluoyl chloride according to the procedure of Example 05-37 (mp=234-236° C.). $^1$H NMR (D6-DMSO) δ 1.68 (s, 3H), 1.76 (quin, J=6.1 Hz, 2H), 2.15-2.18 (m, 4H), 2.39 (s, 3H), 7.29-7.35 (m, 3H), 7.39-7.44 (m, 1H), 7.48 (d, J=7.3 Hz, 1H), 7.65 (dd, J=8.5, 2.4 Hz, 1H), 8.00 (s, 1H), 8.06 (d, J=2.4 Hz, 1H), 10.55 (s, 1H). $^{13}$C NMR (D6-DMSO) δ 8.8, 19.3, 21.2, 26.7, 36.3, 105.9, 118.6, 119.9, 125.7, 127.3, 129.9, 130.0, 130.6, 131.4, 132.1, 135.4, 136.7, 138.5, 159.3, 168.0, 194.2. LCMS t=4.7 min, m/z Calcd for $C_{21}H_{22}ClN_2O_2$; $C_{21}H_{21}ClN_2NaO_2$; $C_{42}H_{42}Cl_2N_4NaO_4$ 369.137; 391.119; 759.248 [M+H]$^+$; [M+Na]$^+$; [2M+Na]$^+$, Found 369.137; 391.119; 759.248.

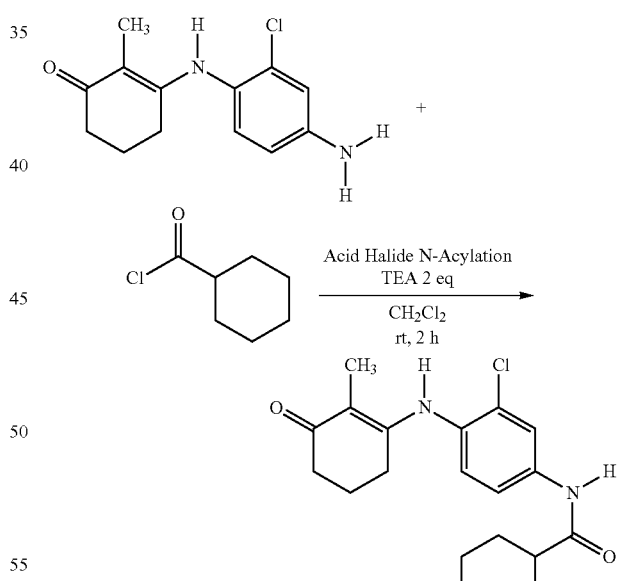

Example 05-49

Preparation of N-(3-chloro-4-((2-methyl-3-oxocyclohex-1-en-1-yl)amino)phenyl)-cyclohexanecarboxamide (05-49)

The title compound was prepared from Example 02-12 and cyclohexanecarbonyl chloride according to the procedure of Example 05-37 (mp=248-250° C.). $^1$H NMR (D6-DMSO) δ 1.14-1.32 (m, 3H), 1.35-1.45 (m, 2H), 1.66 (s, 4H), 1.71-1.82 (m, 6H), 2.11-2.17 (m, 4H), 2.28-2.35 (m, 1H), 7.25 (d, J=9.8 Hz, 1H), 7.47 (dd, J=8.5, 2.4 Hz, 1H), 7.91-8.00 (m, 2H), 10.06 (s, 1H). $^{13}$C NMR (D6-DMSO) δ 8.7, 21.2, 25.2 (2C), 25.4, 26.6, 29.0 (2C), 36.3, 44.9, 105.7, 118.0, 119.3, 130.1, 131.5 (2C), 138.8, 159.4, 174.6, 194.1. LCMS t=4.8 min, m/z Calcd for $C_{20}H_{26}ClN_2O_2$; $C_{20}H_{25}ClN_2NaO_2$; $C_{40}H_{50}Cl_2N_4NaO_4$ 361.168; 383.150; 743.311 [M+H]$^+$; [M+Na]$^+$; [2M+Na]$^+$, Found 361.168; 383.150; 743.311.

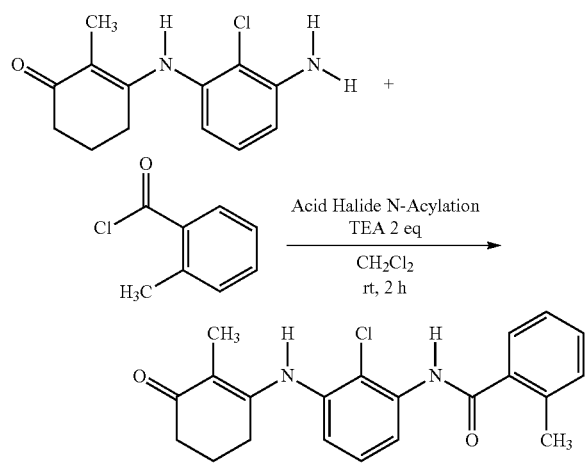

Example 05-50

Preparation of N-(2-chloro-3-((2-methyl-3-oxocyclohex-1-en-1-yl)amino)phenyl)-2-methylbenzamide (05-50)

The title compound was prepared from Example 02-11 and o-toluoyl chloride according to the procedure of Example 05-37. $^1$H NMR (D6-DMSO) δ 1.66 (s, 3H), 1.74-1.81 (m, 2H), 2.18 (t, J=6.7 Hz, 2H), 2.23 (br s, 2H), 2.44 (s, 3H), 7.21 (d, J=7.3 Hz, 1H), 7.31 (d, J=7.3 Hz, 2H), 7.35-7.44 (m, 2H), 7.49-7.57 (m, 2H), 8.08 (s, 1H), 10.06 (s, 1H). $^{13}$C NMR (D6-DMSO) δ 9.0, 19.5, 21.2, 26.9, 36.4, 106.9, 107.9, 111.2, 115.9, 125.4, 125.7, 126.3, 126.9, 127.4, 129.9, 130.6, 135.6, 138.0, 158.7, 167.0, 194.5. LCMS t=4.5 min, m/z Calcd for $C_{21}H_{22}ClN_2O_2$; $C_{21}H_{21}ClN_2NaO_2$; $C_{42}H_{42}Cl_2N_4NaO_4$ 369.137; 391.119; 759.248 [M+H]$^+$; [M+Na]$^+$; [2M+Na]$^+$, Found 369.137; 391.119; 759.248.

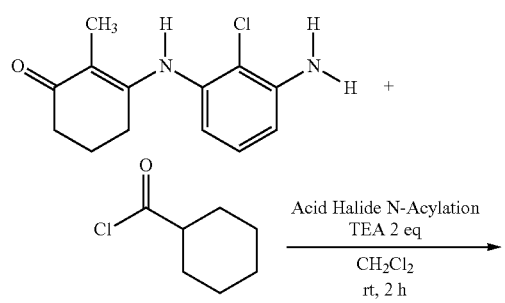

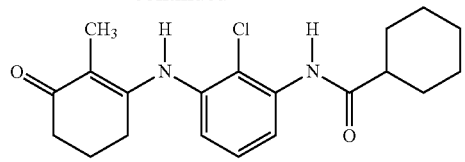

Example 05-51

Preparation of N-(2-chloro-3-((2-methyl-3-oxocyclohex-1-en-1-yl)amino)phenyl)-cyclohexanecarboxamide (05-51)

The title compound was prepared from Example 02-11 and cyclohexanecarbonyl chloride according to the procedure of Example 05-37 (mp=205-208° C.). $^1$H NMR (D6-DMSO) δ 1.14-1.22 (m, 1H), 1.23-1.32 (m, 2H), 1.40 (qd, J=12.4, 3.1 Hz, 2H), 1.65 (br s, 4H), 1.71-1.78 (m, 4H), 1.80-1.87 (m, 2H), 2.13-2.24 (m, 4H), 2.44-2.49 (m, 1H), 7.10 (d, J=7.3 Hz, 1H), 7.30 (t, J=7.9 Hz, 1H), 7.56 (d, J=7.3 Hz, 1H), 8.03 (s, 1H), 9.42 (s, 1H). $^{13}$C NMR (D6-DMSO) δ 9.4, 21.6, 25.7 (2C), 25.9, 27.3, 29.6 (2C), 36.8, 44.5, 107.1, 124.3, 125.7 (2C), 127.2, 136.5, 138.2, 159.2, 174.9, 194.9. LCMS t=5.3 min, m/z Calcd for $C_{20}H_{26}ClN_2O_2$; $C_{20}H_{25}ClN_2NaO_2$ 361.168; 383.150 [M+H]$^+$; [M+Na]$^+$, Found 361.157; 383.138.

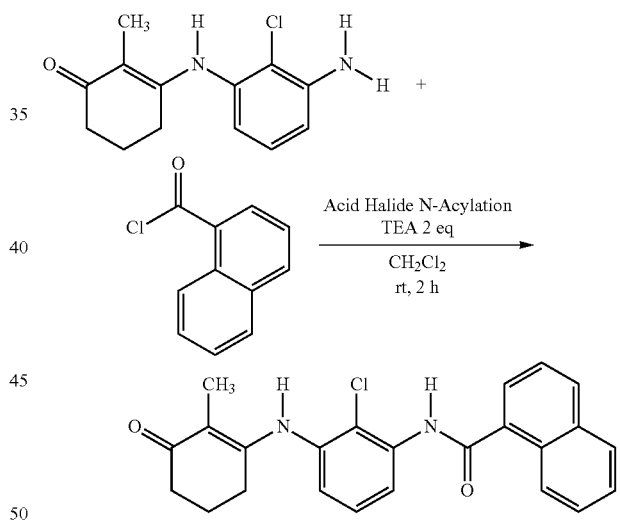

Example 05-52

Preparation of N-(2-chloro-3-((2-methyl-3-oxocyclohex-1-en-1-yl)amino)phenyl)-1-naphthamide (05-52)

The title compound was prepared from Example 02-11 and 1-naphthoyl chloride according to the procedure of Example 05-37 (mp=178-180° C.). $^1$H NMR (D6-DMSO) δ 1.68 (s, 3H), 1.73-1.84 (m, 2H), 2.19 (t, J=6.7 Hz, 2H), 2.26 (br s, 2H), 7.25 (d, J=7.3 Hz, 1H), 7.38-7.47 (m, 1H), 7.56-7.67 (m, 4H), 7.79-7.91 (m, 1H), 8.03 (d, J=7.3 Hz, 1H), 8.08-8.15 (m, 2H), 8.34 (d, J=7.3 Hz, 1H), 10.36 (s, 1H). $^{13}$C NMR (D6-DMSO) δ 9.5, 21.6, 27.4, 36.8, 107.3, 125.5, 125.7, 126.0, 126.3, 126.9, 126.9, 127.4, 127.5, 128.0, 128.8, 130.2, 130.9, 133.6, 134.3, 136.4, 138.5, 159.2, 167.9, 195.0. LCMS t=4.7 min, m/z Calcd for $C_{24}H_{22}ClN_2O_2$; $C_{24}H_{21}ClN_2NaO_2$; $C_{48}H_{42}Cl_2N_4NaO_4$ 405.136; 427.118; 831.248 [M+H]$^+$; [M+Na]$^+$; [2M+Na]$^+$, Found 405.136; 427.118; 831.248.

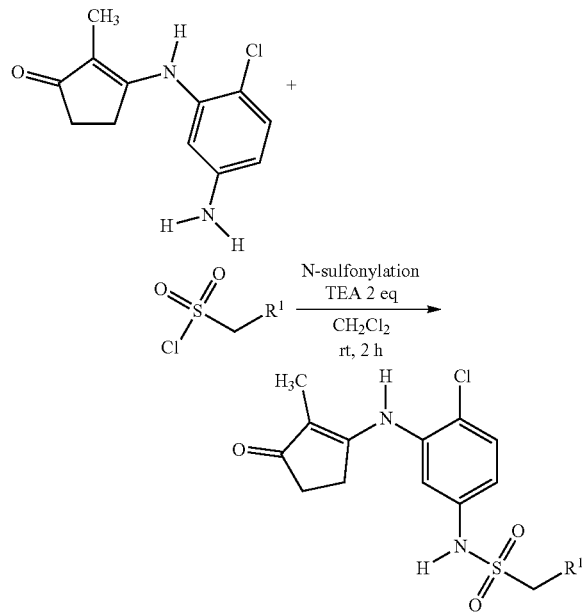

| EXAMPLE 05-# | TITLE COMPOUND NAME | R$^1$ |
|---|---|---|
| 53 | N-(4-Chloro-3-((2-methyl-3-oxocyclopent-1-en-1-yl)amino)-phenyl)methanesulfonamide | H |
| 54 | N-(4-Chloro-3-((2-methyl-3-oxocyclopent-1-en-1-yl)amino)phenyl)-1-phenylmethanesulfonamide | Ph |

Preparation of N-(4-chloro-3-((2-methyl-3-oxocyclopent-1-en-1-yl)amino)-phenyl)-methanesulfonamide (05-53)

The title compound was prepared from Example 02-14 and methanesulfonyl chloride according to the procedure of Example 05-37 (mp=213-215° C.). $^1$H NMR (D6-DMSO) δ 1.45 (s, 3H), 2.16-2.23 (m, 2H), 2.39-2.43 (m, 2H), 3.04 (s, 3H), 7.10 (dd, J=8.5, 2.4 Hz, 1H), 7.15 (d, J=2.4 Hz, 1H), 7.51 (d, J=8.5 Hz, 1H), 8.88 (s, 1H), 10.00 (s, 1H). $^{13}$C NMR (D6-DMSO) δ 7.4, 25.6, 32.6, 40.0, 109.6, 118.2, 118.8, 124.5, 130.4, 137.2, 137.8, 169.3, 202.4. LCMS t=3.8 min, m/z Calcd for $C_{13}H_{16}ClN_2O_3S$; $C_{13}H_{15}ClN_2NaO_3S$; $C_{26}H_{31}Cl_2N_4O_6S_2$; $C_{26}H_{30}Cl_2N_4NaO_6S_2$ 315.057; 337.039; 629.106; 651.088 [M+H]$^+$; [M+Na]$^+$; [2M+H]$^+$; [2M+Na]$^+$, Found 315.057; 337.039; 629.106; 651.088.

Example 05-54

Preparation of N-(4-chloro-3-((2-methyl-3-oxocyclopent-1-en-1-yl)amino)phenyl)-1-phenylmethanesulfonamide (05-55)

The title compound was prepared from Example 02-14 and phenylmethanesulfonyl chloride according to the procedure of Example 05-37 (mp=196-198° C.). $^1$H NMR (D6-DMSO) δ 1.47 (s, 3H), 2.17-2.25 (m, 2H), 2.37-2.42 (m, 2H), 4.54 (s, 2H), 7.05 (d, J=2.4 Hz, 1H), 7.07 (dd, J=8.5, 2.4 Hz, 1H), 7.21-7.28 (m, 2H), 7.31-7.38 (m, 3H), 7.48 (d, J=8.5 Hz, 1H), 8.87 (s, 1H), 10.09 (s, 1H). $^{13}$C NMR (D6-DMSO) δ 7.4, 25.5, 32.6, 57.1, 109.5, 117.3, 117.9, 123.9, 128.3, 128.4 (2C), 129.3, 130.3, 130.9 (2C), 137.1, 138.0, 169.4, 202.4. LCMS t=4.3 min, m/z Calcd for $C_{19}H_{20}ClN_2O_3S$; $C_{19}H_{19}ClN_2NaO_3S$; $C_{38}H_{39}Cl_2N_4O_6S_2$; $C_{38}H_{38}Cl_2N_4NaO_6S_2$ 391.088; 413.070; 781.169; 803.151 [M+H]$^+$; [M+Na]$^+$; [2M+H]$^+$; [2M+Na]$^+$, Found 391.088; 413.070; 781.169; 803.151.

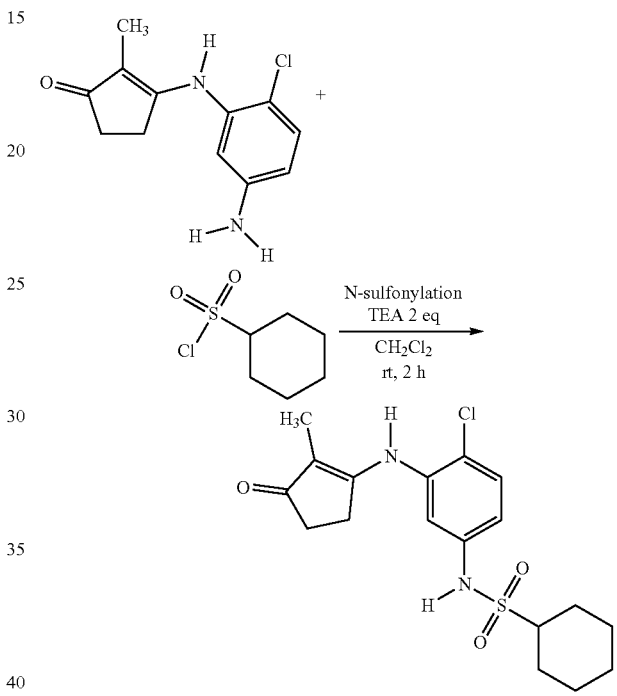

Example 05-55

Preparation of N-(4-chloro-3-((2-methyl-3-oxocyclopent-1-en-1-yl)amino)phenyl)-cyclohexanesulfonamide (05-54)

The title compound was prepared from Example 02-14 and cyclohexanesulfonyl chloride according to the procedure of Example 05-37 (mp=158-160° C.). $^1$H NMR (D6-DMSO) δ 1.08-1.23 (m, 3H), 1.35-1.46 (m, 5H), 1.54-1.61 (m, 1H), 1.72-1.78 (m, 2H), 2.00 (d, J=11.0 Hz, 2H), 2.18-2.23 (m, 2H), 2.39-2.43 (m, 2H), 2.99-3.07 (m, 1H), 7.09-7.19 (m, 2H), 7.48 (d, J=8.5 Hz, 1H), 8.88 (s, 1H), 10.02 (s, 1H). $^{13}$C NMR (D6-DMSO) δ 7.4, 24.3 (2C), 24.7, 25.6, 26.0 (2C), 32.6, 59.4, 109.5, 117.7, 118.3, 124.1, 130.4, 137.1, 138.2, 169.2, 202.5. LCMS t=4.1 min, m/z Calcd for $C_{18}H_{24}ClN_2O_3S$; $C_{18}H_{23}ClN_2NaO_3S$; $C_{36}H_{47}Cl_2N_4O_6S_2$; $C_{36}H_{46}Cl_2N_4NaO_6S_2$ 383.120; 405.101; 765.231; 787.213 [M+H]$^+$; [M+Na]$^+$; [2M+H]$^+$; [2M+Na]$^+$, Found 383.120; 405.103; 765.229; 787.213.

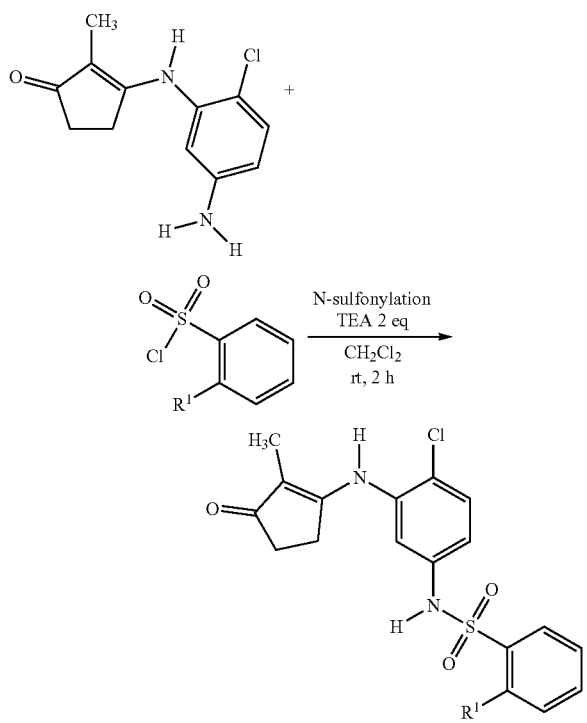

| EXAMPLE 05-# | TITLE COMPOUND NAME | R¹ |
|---|---|---|
| 56 | N-(4-Chloro-3-((2-methyl-3-oxocyclopent-1-en-1-yl)amino)phenyl)-2-chlorobenzenesulfonamide | Cl |
| 57 | N-(4-Chloro-3-((2-methyl-3-oxocyclopent-1-en-1-yl)amino)phenyl)-2-methylbenzenesulfonamide | CH₃ |
| 58 | N-(4-Chloro-3-((2-methyl-3-oxocyclopent-1-en-1-yl)amino)phenyl)-2-fluorobenzenesulfonamide | F |
| 59 | N-(4-Chloro-3-((2-methyl-3-oxocyclopent-1-en-1-yl)amino)phenyl)-2-cyanobenzenesulfonamide | CN |
| 60 | N-(4-Chloro-3-((2-methyl-3-oxocyclopent-1-en-1-yl)amino)phenyl)-2-methoxybenzenesulfonamide | OCH₃ |

Example 05-56

Preparation of N-(4-chloro-3-((2-methyl-3-oxocyclopent-1-en-1-yl)amino)-phenyl)-2-chlorobenzenesulfonamide (05-56)

The title compound was prepared from Example 02-14 and 2-chlorobenzene-1-sulfonyl chloride according to the procedure of Example 05-37. $^1$H NMR (D6-DMSO) δ 1.32 (s, 3H), 2.15-2.20 (m, 4H), 6.98 (d, J=2.4 Hz, 1H), 7.01 (dd, J=8.5, 2.4 Hz, 1H), 7.41 (d, J=8.5 Hz, 1H), 7.51-7.55 (m, 1H), 7.63-7.67 (m, 2H), 8.05 (d, J=7.3 Hz, 1H), 8.80 (s, H), 10.90 (s, 1H). $^{13}$C NMR (D6-DMSO) δ 7.2, 25.4, 32.5, 109.6, 117.9, 118.5, 124.9, 127.9, 130.4, 130.7, 131.8, 132.0, 135.0, 135.9, 136.4, 137.1, 169.0, 202.4. LCMS t=4.4 min, m/z Calcd for $C_{18}H_{17}Cl_2N_2O_3S$; $C_{18}H_{16}Cl_2N_2NaO_3S$; $C_{36}H_{33}C_{14}N_4O_6S_2$; $C_{36}H_{32}C_{14}N_4NaO_6S_2$ 411.033; 433.016; 823.057; 843.041 [M+H]⁺; [M+Na]⁺; [2M+H]⁺; [2M+Na]⁺, Found 411.033; 433.016; 823.057; 843.041.

Example 05-57

Preparation of N-(4-chloro-3-((2-methyl-3-oxocyclopent-1-en-1-yl)amino)phenyl)-2-methylbenzenesulfonamide (05-57)

The title compound was prepared from Example 02-14 and 2-methylbenzene-1-sulfonyl chloride according to the procedure of Example 05-37 (mp=236-238° C.). $^1$H NMR (D6-DMSO) δ 1.33 (s, 3H), 2.17 (m, J=4.9 Hz, 4H), 2.59 (s, 3H), 6.94 (d, J=2.4 Hz, 1H), 6.99 (dd, J=8.5, 2.4 Hz, 1H), 7.33-7.45 (m, 3H), 7.52 (t, J=7.3 Hz, 1H), 7.87 (d, J=7.3 Hz, 1H), 8.80 (s, 1H), 10.68 (s, 1H). $^{13}$C NMR (D6-DMSO) δ 7.2, 19.7, 25.4, 32.5, 109.6, 117.6, 118.1, 124.4, 126.4, 129.4, 130.3, 132.8, 133.3, 136.8, 137.0, 137.0, 137.0, 169.0, 202.4. LCMS t=5.3 min, m/z Calcd for $C_{19}H_{20}ClN_2O_3S$; $C_{19}H_{19}ClN_2NaO_3S$; $C_{38}H_{38}Cl_2N_4NaO_6S_2$ 391.088; 413.070; 803.151 [M+H]⁺; [M+Na]⁺; [2M+Na]⁺, Found 391.088; 413.071; 803.150.

Example 05-58

Preparation of N-(4-chloro-3-((2-methyl-3-oxocyclopent-1-en-1-yl)amino)phenyl)-2-fluorobenzenesulfonamide (05-58)

The title compound was prepared from Example 02-14 and 2-fluorobenzene-1-sulfonyl chloride according to the procedure of Example 05-37 (mp=215-217° C.). $^1$H NMR (D6-DMSO) δ 1.32 (s, 3H), 2.16-2.22 (m, 4H), 7.00 (d, J=3.7 Hz, 1H), 7.03 (dd, J=8.5, 2.4 Hz, 1H), 7.37 (t, J=7.9 Hz, 1H), 7.41-7.46 (m, 2H), 7.69-7.73 (m, 1H), 7.82-7.87 (m, 1H), 8.82 (s, 1H), 10.88 (s, 1H). $^{13}$C NMR (D6-DMSO) δ 7.7, 25.9, 33.0, 110.0, 117.9 ($J_{CF}$=21.8 Hz), 118.9, 119.5, 125.6, 126.9 ($J_{CF}$=13.8 Hz), 130.8, 131.0, 136.8 ($J_{CF}$=9.2 Hz), 137.0, 137.5, 158.5 ($J_{CF}$=254.7 Hz), 169.5, 202.9. LCMS t=4.3 min, m/z Calcd for $C_{18}H_{17}ClFN_2O_3S$; $C_{18}H_{16}ClFN_2NaO_3S$; $C_{36}H_{33}Cl_2F_2N_4O_6S_2$; $C_{36}H_{32}C_{12}F_2N_4NaO_6S_2$ 395.063; 417.045; 789.119; 811.101 [M+H]⁺; [M+Na]⁺; [2M+H]⁺; [2M+Na]⁺, Found 395.063; 417.045; 789.119; 811.101.

Example 05-59

Preparation of N-(4-chloro-3-((2-methyl-3-oxocyclopent-1-en-1-yl)amino)phenyl)-2-cyanobenzenesulfonamide (05-59)

The title compound was prepared from Example 02-14 and 2-cyanobenzene-1-sulfonyl chloride according to the procedure of Example 05-37 (mp=235-238° C.). $^1$H NMR (D6-DMSO) δ 1.31 (s, 3H), 2.14-2.19 (m, 2H), 2.21-2.26 (m, 2H), 6.96 (d, J=2.4 Hz, 1H), 7.03 (dd, J=8.5, 2.4 Hz, 1H), 7.46 (d, J=8.5 Hz, 1H), 7.85 (t, J=7.3 Hz, 1H), 7.91 (t, J=7.3 Hz, 1H), 8.04 (d, J=7.3 Hz, 1H), 8.10 (d, J=7.3 Hz, 1H), 8.82 (s, 1H), 11.06 (s, 1H). $^{13}$C NMR (D6-DMSO) δ 7.3, 25.5, 32.5, 109.2, 109.7, 115.6, 119.0, 119.5, 125.5, 129.6, 130.5, 133.8, 134.1, 136.1, 136.2, 137.2, 140.5, 169.0, 202.5. LCMS t=4.3 min, m/z Calcd for $C_{19}H_{17}ClN_3O_3S$; $C_{19}H_{16}ClN_3NaO_3S$; $C_{38}H_{32}Cl_2N_6NaO_6S_2$ 402.068; 424.050; 825.110 [M+H]⁺; [M+Na]⁺; [2M+Na]⁺, Found 402.068; 424.050; 825.110.

Example 05-60

Preparation of N-(4-chloro-3-((2-methyl-3-oxocyclopent-1-en-1-yl)amino)phenyl)-2-methoxybenzenesulfonamide (05-60)

The title compound was prepared from Example 02-14 and 2-methoxybenzene-1-sulfonyl chloride according to the procedure of Example 05-37 (mp=198-200° C.). $^1$H NMR (D6-DMSO) δ 1.33 (s, 3H), 2.12-2.17 (m, 4H), 3.86 (s, 3H), 6.97-7.01 (m, 2H), 7.05 (t, J=7.9 Hz, 1H), 7.18 (d, J=8.5 Hz, 1H), 7.34-7.41 (m, 1H), 7.58 (t, J=7.9 Hz, 1H), 7.77 (d, J=7.3 Hz, 1H), 8.79 (s, 1H), 10.30 (s, 1H). $^{13}$C NMR (D6-DMSO) δ 7.1, 25.3, 32.5, 56.2, 109.4, 112.9, 118.2, 118.7, 120.2, 124.6, 125.7, 130.1, 130.4, 135.4, 136.8, 137.4, 156.3, 169.2, 202.3. LCMS t=4.2 min, m/z Calcd for $C_{19}H_{20}ClN_2O_4S$; $C_{19}H_{19}ClN_2NaO_4S$; $C_{38}H_{39}Cl_2N_4O_8S_2$; $C_{38}H_{38}Cl_2N_4NaO_8S_2$ 407.083; 429.065; 813.159; 835.141 $[M+H]^+$; $[M+Na]^+$; $[2M+H]^+$; $[2M+Na]^+$, Found 407.083; 429.065; 813.159; 835.141.

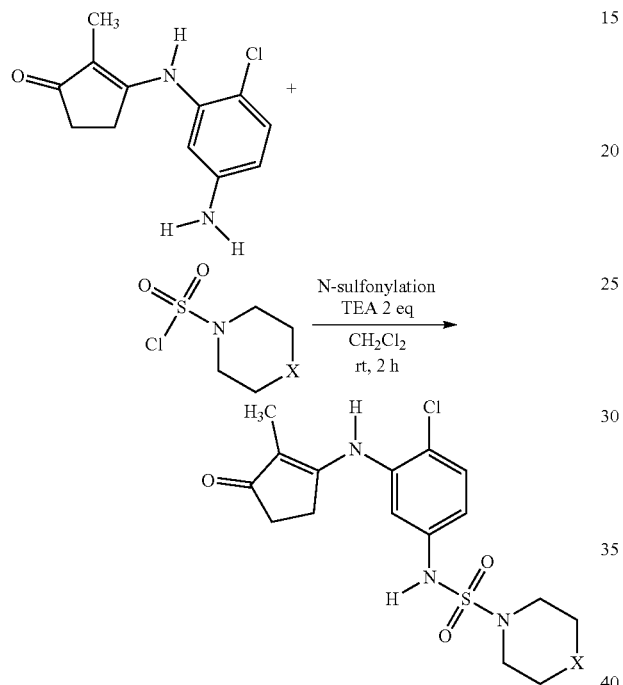

| EXAMPLE 05-# | TITLE COMPOUND NAME | X |
|---|---|---|
| 61 | N-(4-Chloro-3-((2-methyl-3-oxocyclopent-1-en-1-yl)amino)phenyl)-piperidine-1-sulfonamide | CH$_2$ |
| 62 | N-(4-Chloro-3-((2-methyl-3-oxocyclopent-1-en-1-yl)amino)phenyl)-morpholine-4-sulfonamide | O |

Example 05-61

Preparation of N-(4-chloro-3-((2-methyl-3-oxocyclopent-1-en-1-yl)amino)phenyl)-piperidine-1-sulfonamide (05-61)

The title compound was prepared from Example 02-14 and piperidine-1-sulfonyl chloride according to the procedure of Example 05-37 (mp=78-80° C.). $^1$H NMR (D6-DMSO) δ ppm 1.36-1.48 (m, 9H), 2.18-2.22 (m, 2H), 2.38-2.41 (m, 2H), 3.05-3.14 (m, 4H), 7.04-7.14 (m, 2H), 7.47 (d, J=8.5 Hz, 1H), 8.88 (s, 1H), 10.14 (br s, 1H). $^{13}$C NMR (D6-DMSO) δ 7.3, 23.1, 24.7 (2C), 25.6, 32.6, 46.5 (2C), 109.4, 117.7, 118.3, 123.7, 130.1, 136.9, 138.3, 169.2, 202.4. LCMS t=4.5 min, m/z Calcd for $C_{17}H_{23}ClN_3O_3S$; $C_{17}H_{22}ClN_3NaO_3S$; $C_{34}H_{45}Cl_2N_6O_6S_2$; $C_{34}H_{44}Cl_2N_6NaO_6S_2$ 384.114; 406.096; 767.221; 789.203 $[M+H]^+$; $[M+Na]^+$; $[2M+H]^+$; $[2M+Na]^+$, Found 384.114; 406.096; 767.221; 789.203.

Example 05-62

Preparation of N-(4-chloro-3-((2-methyl-3-oxocyclopent-1-en-1-yl)amino)phenyl)-morpholine-4-sulfonamide (05-62)

The title compound was prepared from Example 02-14 and morpholine-4-sulfonyl chloride according to the procedure of Example 05-37 (mp=60-67° C.). $^1$H NMR (D6-DMSO) δ 1.44 (s, 3H), 2.17-2.23 (m, 2H), 2.38-2.43 (m, 2H), 3.05-3.09 (m, 4H), 3.51-3.55 (m, 4H), 7.04-7.15 (m, 2H), 7.49 (d, J=8.5 Hz, 1H), 8.88 (s, 1H), 10.28 (br s, 1H). $^{13}$C NMR (D6-DMSO) δ ppm 7.4, 25.6, 32.6, 46.0 (2C), 65.4 (2C), 109.5, 118.1, 118.6, 124.1, 130.2, 137.0, 138.0, 169.3, 202.4. LCMS t=3.9 min, m/z Calcd for $C_{16}H_{21}ClN_3O_4S$; $C_{16}H_{20}ClN_3NaO_4S$; $C_{32}H_{41}Cl_2N_6O_8S_2$; $C_{32}H_{40}Cl_2N_6NaO_8S_2$ 386.094; 408.076; 771.180; 793.162 $[M+H]^+$; $[M+Na]^+$; $[2M+H]^+$; $[2M+Na]^+$, Found 386.094; 408.076; 771.180; 793.162.

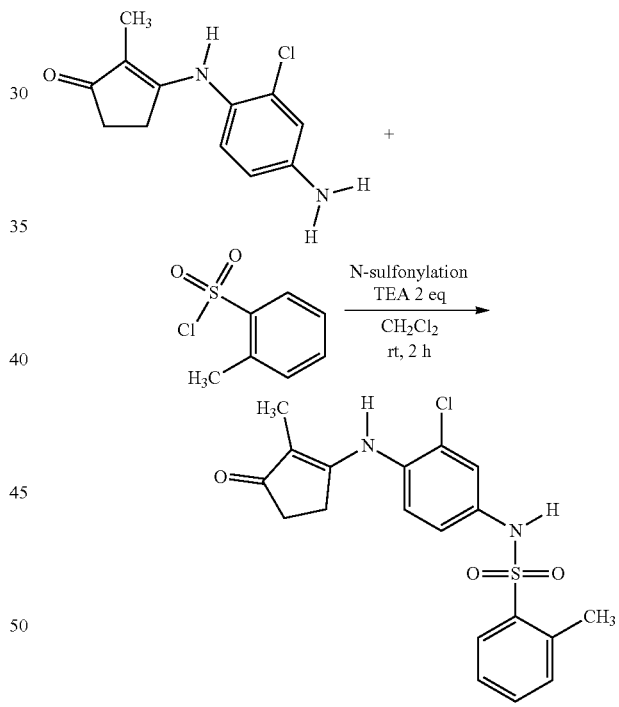

Example 05-63

Preparation of N-(3-chloro-4-((2-methyl-3-oxocyclopent-1-en-1-yl)amino)phenyl)-2-methylbenzenesulfonamide (05-63)

The title compound was prepared from Example 02-15 and 2-methylbenzene-1-sulfonyl chloride according to the procedure of Example 05-37 (mp=215-218° C.). $^1$H NMR (D6-DMSO) δ 1.35 (s, 3H), 2.09-2.15 (m, 2H), 2.22-2.27 (m, 2H), 2.59 (s, 3H), 7.03 (dd, J=8.5, 2.4 Hz, 1H), 7.18 (d, J=2.4 Hz, 1H), 7.26 (d, J=9.8 Hz, 1H), 7.36-7.42 (m, 2H), 7.53 (t, J=6.7 Hz, 1H), 7.89 (d, J=8.5 Hz, 1H), 8.72 (s, 1H), 10.74 (s, 1H). $^{13}$C NMR (D6-DMSO) δ 7.0, 19.7, 25.2, 32.5, 108.5, 117.8, 119.1, 126.4, 129.4, 130.0, 131.2, 131.9, 132.8, 133.4, 136.8, 136.9, 137.0, 170.1, 202.0. LCMS t=4.3 min, m/z Calcd for $C_{19}H_{20}ClN_2O_3S$; $C_{19}H_{19}ClN_2NaO_3S$; $C_{38}H_{39}Cl_2N_4O_6S_2$; $C_{38}H_{38}Cl_2N_4NaO_6S_2$ 391.088; 413.070; 781.169; 803.151 [M+H]; [M+Na]$^+$; [2M+H]$^+$; [2M+Na]$^+$, Found 391.088; 413.070; 781.169; 803.151.

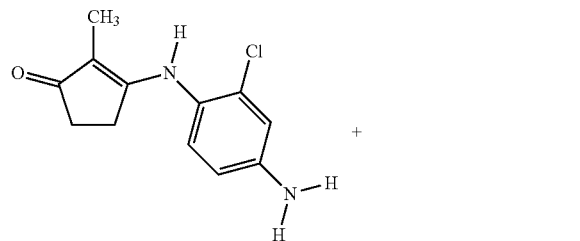

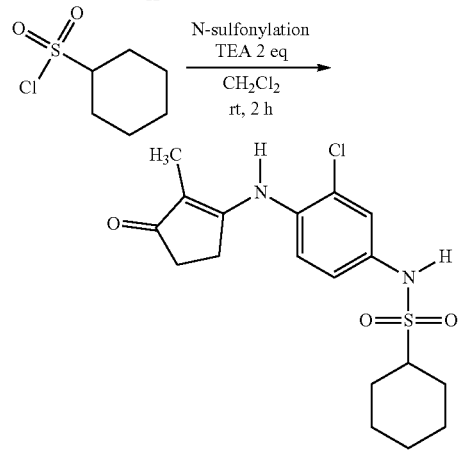

Example 05-64

Preparation of N-(3-chloro-4-((2-methyl-3-oxocyclopent-1-en-1-yl)amino)phenyl)-cyclohexanesulfonamide (05-64)

The title compound was prepared from Example 02-15 and cyclohexanesulfonyl chloride according to the procedure of Example 05-37 (mp=210-213° C.). $^1$H NMR (D6-DMSO) δ 1.05-1.17 (m, 1H), 1.18-1.27 (m, 2H), 1.33-1.50 (m, 5H), 1.54-1.63 (m, 1H), 1.72-1.80 (m, 2H), 1.98-2.05 (m, 2H), 2.14-2.18 (m, 2H), 2.30-2.35 (m, 2H), 3.02-3.12 (m, 1H), 7.20 (dd, J=8.5, 2.4 Hz, 1H), 7.34-7.38 (m, 1H), 8.81 (s, 1H), 10.09 (s, 1H). $^{13}$C NMR (D6-DMSO) δ 7.0, 24.3 (2C), 24.7, 25.3, 26.0 (2C), 32.6, 59.6, 108.4, 117.9, 119.1, 130.1, 131.4, 131.7, 138.1, 170.4, 202.0. LCMS t=4.5 min, m/z Calcd for $C_{18}H_{24}ClN_2O_3S$; $C_{18}H_{23}ClN_2NaO_3S$; $C_{36}H_{47}Cl_2N_4O_6S_2$; $C_{36}H_{46}Cl_2N_4NaO_6S_2$ 383.120; 405.101; 765.231; 787.213 [M+H]$^+$; [M+Na]$^+$; [2M+H]$^+$; [2M+Na]$^+$, Found 383.120; 405.101; 765.231; 787.213.

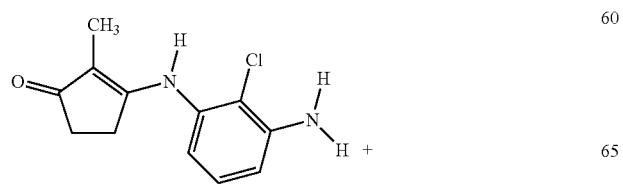

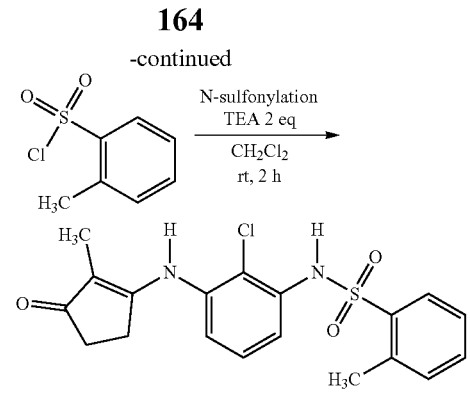

Example 05-65

Preparation of N-(2-chloro-3-((2-methyl-3-oxocyclopent-1-en-1-yl)amino)phenyl)-2-methylbenzenesulfonamide (05-65)

The title compound was prepared from Example 02-13 and 2-methylbenzene-1-sulfonyl chloride according to the procedure of Example 05-37 (mp=75-77° C.). $^1$H NMR (D6-DMSO) δ 1.32 (s, 3H), 2.10-2.13 (m, 2H), 2.15-2.19 (m, 2H), 2.61 (s, 3H), 7.21 (t, J=7.3 Hz, 1H), 7.19-7.24 (m, 1H), 7.26-7.31 (m, 2H), 7.39 (d, J=8.5 Hz, 1H), 7.51 (t, J=7.5 Hz, 1H), 7.64 (d, J=7.3 Hz, 1H), 8.85 (s, 1H), 10.16 (s, 1H). $^{13}$C NMR (D6-DMSO) δ 7.1, 20.2, 25.3, 32.5, 109.0, 125.4, 126.2, 126.5, 127.1, 127.3, 128.9, 132.7, 133.0, 134.4, 137.1, 137.6, 138.2, 169.6, 202.2. LCMS t=4.3 min, m/z Calcd for $C_{19}H_{20}ClN_2O_3S$; $C_{19}H_{19}ClN_2NaO_3S$; $C_{38}H_{39}Cl_2N_4O_6S_2$; $C_{38}H_{38}Cl_2N_4NaO_6S_2$ 391.088; 413.070; 781.169; 803.151 [M+H]$^+$; [M+Na]$^+$; [2M+H]$^+$; [2M+Na]$^+$, Found 391.088; 413.070; 781.169; 803.151.

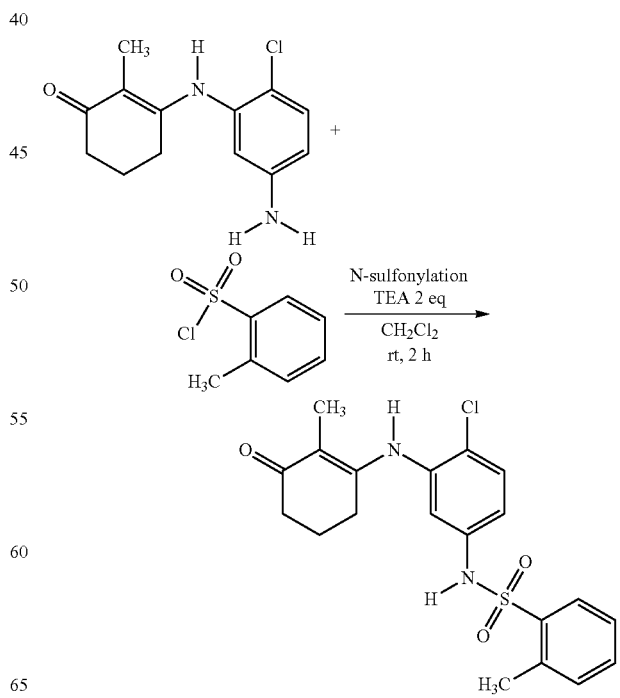

Example 05-66

Preparation of N-(4-chloro-3-((2-methyl-3-oxocyclohex-1-en-1-yl)amino)phenyl)-2-methylbenzenesulfonamide (05-66)

The title compound was prepared from Example 02-10 and 2-methylbenzene-1-sulfonyl chloride according to the procedure of Example 05-37 (mp=246-248° C.). $^1$H NMR (D6-DMSO) δ 1.55 (s, 3H), 1.67-1.73 (m, 3H), 1.96 (t, J=5.5 Hz, 3H), 2.17 (t, J=6.7 Hz, 3H), 2.58 (s, 3H), 6.85 (d, J=2.4 Hz, 1H), 6.94 (dd, J=8.5, 2.4 Hz, 1H), 7.33-7.43 (m, 3H), 7.50-7.55 (m, 1H), 7.85-7.90 (m, 2H), 10.66 (s, 1H). $^{13}$C NMR (D6-DMSO) δ 9.0, 19.7, 21.1, 26.9, 36.4, 107.8, 117.3, 118.2, 124.7, 126.4, 129.5, 130.3, 132.7, 133.3, 136.8, 137.0 (2C), 137.6, 157.8, 194.7. LCMS t=4.7 min, m/z Calcd for $C_{20}H_{22}ClN_2O_3S$; $C_{20}H_{21}ClN_2NaO_3S$; $C_{40}H_{42}Cl_2N_4NaO_6S_2$ 405.104; 427.086; 831.182 [M+H]$^+$; [M+Na]$^+$; [2M+Na]$^+$, Found 405.104; 427.086; 831.182.

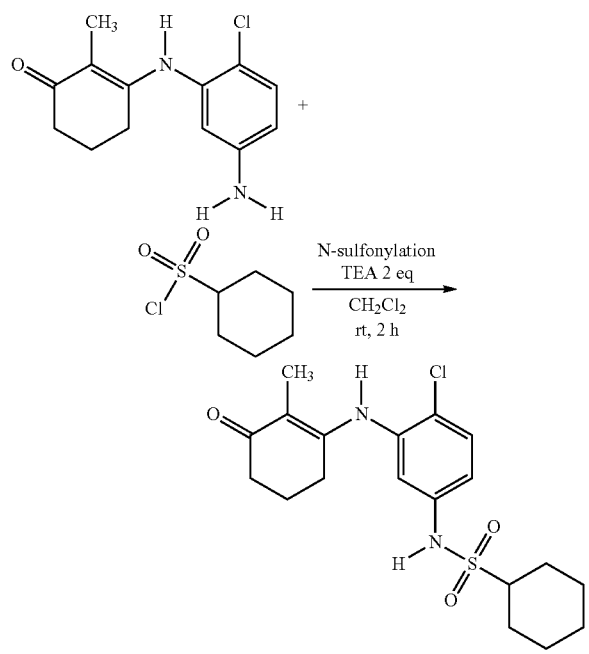

Example 05-67

Preparation of N-(4-chloro-3-((2-methyl-3-oxocyclohex-1-en-1-yl)amino)phenyl)-cyclohexanesulfonamide (05-67)

The title compound was prepared from Example 02-10 and cyclohexanesulfonyl chloride according to the procedure of Example 05-37 (mp=215-217° C.). $^1$H NMR (D6-DMSO) δ 1.08-1.15 (m, 1H), 1.16-1.24 (m, 2H), 1.39 (qd, J=12.4, 3.1 Hz, 2H), 1.58 (d, J=13.4 Hz, 1H), 1.62 (s, 3H), 1.72-1.79 (m, 4H), 1.96-2.03 (m, 2H), 2.17-2.24 (m, 4H), 2.97-3.06 (m, 1H), 7.07 (d, J=2.4 Hz, 1H), 7.10 (dd, J=8.5, 2.4 Hz, 1H), 7.46 (d, J=8.5 Hz, 1H), 7.98 (s, 1H), 9.98-10.02 (m, 1H). $^{13}$C NMR (D6-DMSO) δ 9.1, 21.1, 24.4 (2C), 24.7, 26.0 (2C), 27.1, 36.4, 59.4, 107.7, 117.3, 118.5, 124.5, 130.3, 137.7, 138.2, 158.1, 194.7. LCMS t=4.7 min, m/z Calcd for $C_{19}H_{26}ClN_2O_3S$; $C_{19}H_{25}ClN_2NaO_3S$; $C_{38}H_{50}Cl_2N_4NaO_6S_2$ 397.135; 419.117; 815.245 [M+H]$^+$; [M+Na]$^+$; [2M+Na]$^+$, Found 397.135; 419.117; 815.244.

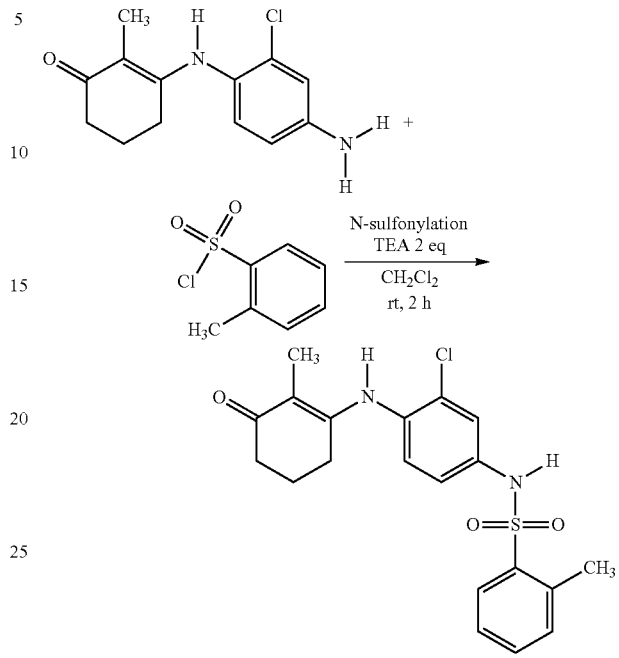

Example 05-68

Preparation of N-(3-chloro-4-((2-methyl-3-oxocyclohex-1-en-1-yl)amino)phenyl)-2-methylbenzenesulfonamide (05-68)

The title compound was prepared from Example 02-12 and 2-methylbenzene-1-sulfonyl chloride according to the procedure of Example 05-37 (mp=248-250° C.). $^1$H NMR (D6-DMSO) δ 1.59 (s, 3H), 1.70 (quin, J=6.1 Hz, 2H), 2.05 (t, J=5.5 Hz, 2H), 2.12 (t, J=6.1 Hz, 2H), 2.59 (s, 3H), 7.03 (dd, J=8.5, 2.4 Hz, 1H), 7.15-7.21 (m, 2H), 7.36-7.44 (m, 2H), 7.53 (t, J=6.7 Hz, 1H), 7.84 (s, 1H), 7.90 (d, J=7.3 Hz, 1H), 10.74 (s, 1H). $^{13}$C NMR (D6-DMSO) δ 8.7, 19.7, 21.1, 26.6, 36.3, 106.0, 117.7, 119.1, 126.4, 129.4, 130.5, 131.8, 132.3, 132.3, 132.8, 133.4, 136.8, 137.1, 159.0, 194.2. LCMS t=4.6 min, m/z Calcd for $C_{20}H_{22}ClN_2O_3S$; $C_{20}H_{21}ClN_2NaO_3S$; $C_{40}H_{42}Cl_2N_4NaO_6S_2$ 405.104; 427.086; 831.182 [M+H]$^+$; [M+Na]$^+$; [2M+Na]$^+$, Found 405.104; 427.086; 831.182.

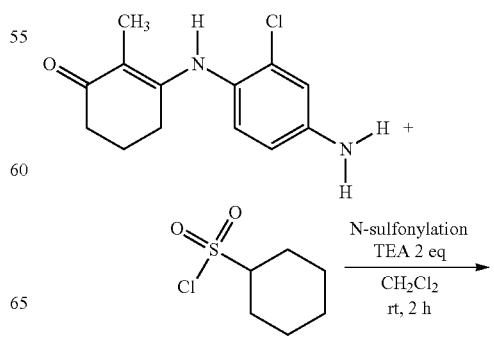

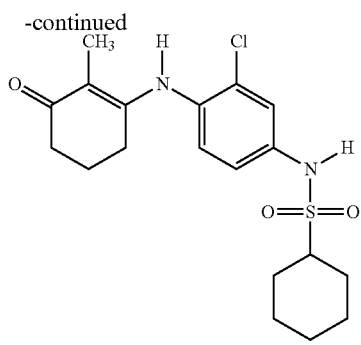

Example 05-69

Preparation of N-(3-chloro-4-((2-methyl-3-oxocyclohex-1-en-1-yl)amino)phenyl)-cyclohexanesulfonamide (05-69)

The title compound was prepared from Example 02-12 and cyclohexanesulfonyl chloride according to the procedure of Example 05-37 (mp=230-232° C.). $^1$H NMR (D6-DMSO) δ 1.07-1.17 (m, 1H), 1.18-1.27 (m, 2H), 1.36-1.46 (m, 2H), 1.56-1.62 (m, 1H), 1.65 (s, 3H), 1.73-1.79 (m, 4H), 2.02 (d, J=12.2 Hz, 2H), 2.13-2.17 (m, 4H), 3.03-3.11 (m, 1H), 7.19 (dd, J=8.5, 2.4 Hz, 1H), 7.28 (d, J=8.5 Hz, 1H), 7.34 (d, J=2.4 Hz, 1H), 7.93 (s, 1H), 10.08 (s, 1H). $^{13}$C NMR (D6-DMSO) δ 8.7, 21.2, 24.3 (2C), 24.7, 26.0 (2C), 26.6, 36.3, 59.5, 105.9, 117.9, 119.2, 130.6, 132.0, 132.1, 138.0, 159.2, 194.1. LCMS t=4.3 min, m/z Calcd for $C_{19}H_{26}ClN_2O_3S$; $C_{38}H_{50}Cl_2N_4NaO_6S_2$ 397.135; 815.245 [M+H]$^+$; [2M+Na]$^+$, Found 397.134; 815.245.

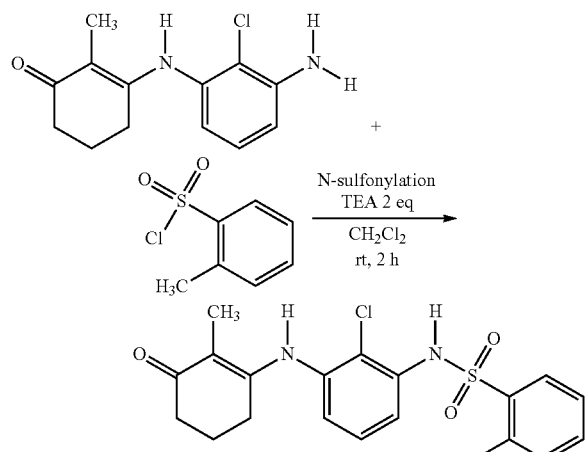

Example 05-70

Preparation of N-(2-chloro-3-((2-methyl-3-oxocyclohex-1-en-1-yl)amino)phenyl)-2-methylbenzenesulfonamide (05-70)

The title compound was prepared from Example 02-11 and 2-methylbenzene-1-sulfonyl chloride according to the procedure of Example 05-37 (mp=185-187° C.). $^1$H NMR (D6-DMSO) δ 1.56 (s, 3H), 1.62-1.71 (m, 2H), 1.92 (t, J=5.5 Hz, 2H), 2.13 (t, J=6.1 Hz, 2H), 2.61 (s, 3H), 7.10 (d, J=7.3 Hz, 1H), 7.20 (d, J=8.5 Hz, 1H), 7.24-7.31 (m, 2H), 7.38 (d, J=7.3 Hz, 1H), 7.50 (t, J=7.2 Hz, 2H), 7.62 (d, J=8.5 Hz, 1H), 7.96 (s, 1H), 10.13 (br s, 1H). $^{13}$C NMR (D6-DMSO) δ 9.4, 20.7, 21.5, 27.1, 36.8, 107.3, 120.0, 125.6, 126.5, 127.2, 127.5, 128.2, 129.3, 133.1, 133.4, 135.0, 137.6, 138.6, 159.0, 194.9. LCMS t=4.5 min, m/z Calcd for $C_{20}H_{22}ClN_2O_3S$; $C_{20}H_{21}ClN_2NaO_3S$; 405.104; 427.086; 831.182 [M+H]$^+$; [M+Na]$^+$; Found 405.104; 427.086.

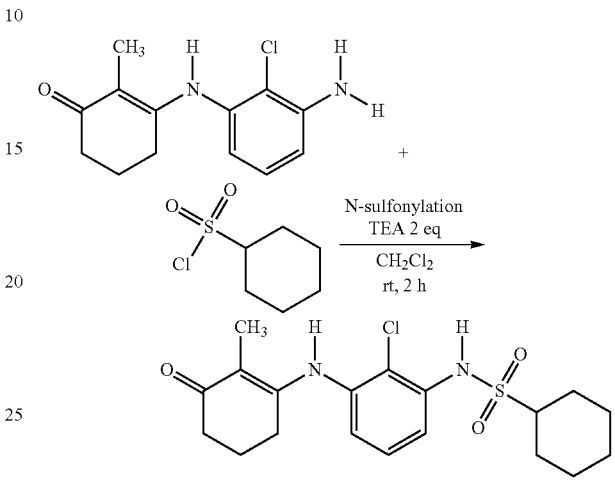

Example 05-71

Preparation of N-(2-chloro-3-((2-methyl-3-oxocyclohex-1-en-1-yl)amino)phenyl)-cyclohexanesulfonamide (05-71)

The title compound was prepared from Example 02-11 and cyclohexanesulfonyl chloride according to the procedure of Example 05-37. $^1$H NMR (D6-DMSO) δ 1.08-1.17 (m, 1H), 1.19-1.29 (m, 2H), 1.41 (qd, J=12.4, 3.1 Hz, 2H), 1.57-1.67 (m, 4H), 1.73-1.80 (m, 4H), 2.06-2.12 (m, 2H), 2.13-2.22 (m, 4H), 2.96-3.06 (m, 1H), 7.15 (d, J=7.3 Hz, 1H), 7.32 (t, J=8.0 Hz, 1H), 7.39 (d, J=9.8 Hz, 1H), 8.04 (s, 1H), 9.48 (br s, 1H). $^{13}$C NMR (D6-DMSO) δ 9.0, 21.2, 24.5 (2C), 24.8, 26.2 (2C), 26.9, 36.4, 61.3, 104.7, 114.9, 115.4, 119.7, 127.1, 138.1, 143.9, 158.5, 194.5. LCMS t=4.5 min, m/z Calcd for $C_{19}H_{26}ClN_2O_3S$; $C_{19}H_{25}ClN_2NaO_3S$; $C_{38}H_{50}Cl_2N_4NaO_6S_2$ 397.135; 419.117; 815.245 [M+H]; [M+Na]$^+$; [2M+Na]$^+$, Found 397.135; 419.117; 815.245.

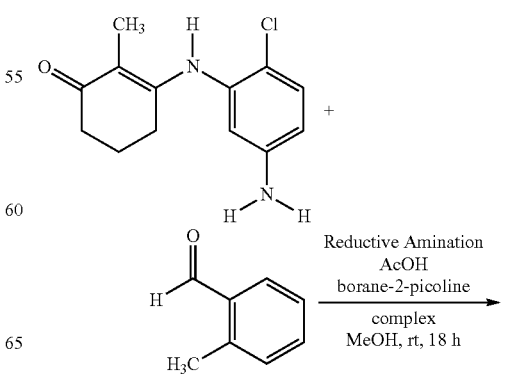

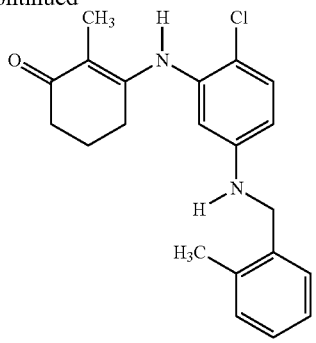

Example 05-72

Preparation of 3-((2-chloro-5-((2-methylbenzyl)amino)phenyl)amino)-2-methylcyclohex-2-enone (05-72)

Acetic acid (0.4 mL) was added to Example 02-10 (0.3 g, 1.20 mmol) and 2-methylbenzaldehyde (0.25 g, 2.04 mmol) stirring in MeOH (8 mL). After stirring for 1 h, borane-2-methylpyridine (0.17 g, 1.59 mmol) was added to the mixture. The mixture was stirred for 18 h. The crude was concentrated under vacuum and purified by HPLC to afford the title compound (0.13 g, 23% yield, mp=158-160° C.). $^1$H NMR (D6-DMSO) δ 1.63 (s, 3H), 1.70 (quin, J=6.4 Hz, 2H), 2.11-2.14 (m, 4H), 2.31 (s, 3H), 4.21 (d, J=4.9 Hz, 2H), 6.40 (t, J=5.5 Hz, 1H), 6.44 (d, J=2.4 Hz, 1H), 6.53 (dd, J=9.2, 3.1 Hz, 1H), 7.08-7.22 (m, 4H), 7.23 (d, J=6.1 Hz, 1H), 7.84 (s, 1H). $^{13}$C NMR (D6-DMSO) δ 8.7, 18.6, 21.2, 26.6, 36.3, 44.6, 105.9, 111.6, 112.2, 116.7, 125.7, 126.8, 127.2, 129.5, 130.1, 135.9, 137.0, 137.0, 148.4, 159.2, 194.0. LCMS t=5.3 min, m/z Calcd for $C_{21}H_{24}ClN_2O$; $C_{21}H_{23}ClN_2NaO$; $C_{42}H_{46}Cl_2N_4NaO_2$ 355.158; 377.139; 731.290 [M+H]$^+$; [M+Na]$^+$; [2M+Na]$^+$, Found 355.158; 377.139; 731.290.

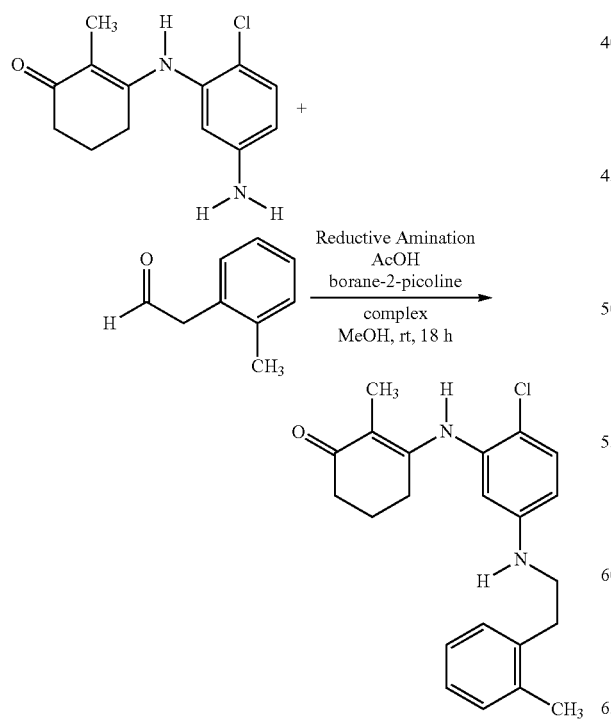

Example 05-73

Preparation of 3-((2-chloro-5-((2-methylphenethyl)amino)phenyl)amino)-2-methylcyclohex-2-enone (05-73)

The title compound was prepared from Example 02-10 and 2-(o-tolyl)acetaldehyde according to the procedure of Example 05-72 (mp=85-87° C.). $^1$H NMR (D6-DMSO) δ 1.65 (s, 3H), 1.75 (quin, J=6.1 Hz, 2H), 2.15 (t, J=6.1 Hz, 2H), 2.21 (t, J=5.5 Hz, 2H), 2.28 (s, 3H), 2.81 (t, J=7.9 Hz, 2H), 3.15-3.26 (m, 2H), 6.05 (t, J=5.5 Hz, 1H), 6.48 (d, J=2.4 Hz, 1H), 6.53 (dd, J=8.5, 2.4 Hz, 1H), 6.89-7.37 (m, 5H), 7.87 (s, 1H). $^{13}$C NMR (D6-DMSO) δ 8.8, 19.0, 21.3, 26.7, 32.1, 36.4, 43.3, 105.8, 111.5, 112.2, 116.7, 125.9, 126.2, 129.1, 129.6, 130.0, 135.8, 137.2, 137.8, 148.3, 159.3, 194.1. LCMS t=5.5 min, m/z Calcd for $C_{22}H_{26}ClN_2O$; $C_{22}H_{25}ClN_2NaO$; $C_{44}H_{50}Cl_2N_4NaO_2$ 369.173; 391.155; 759.321 [M+H]$^+$; [M+Na]$^+$; [2M+Na]$^+$, Found 369.173; 391.155; 759.321.

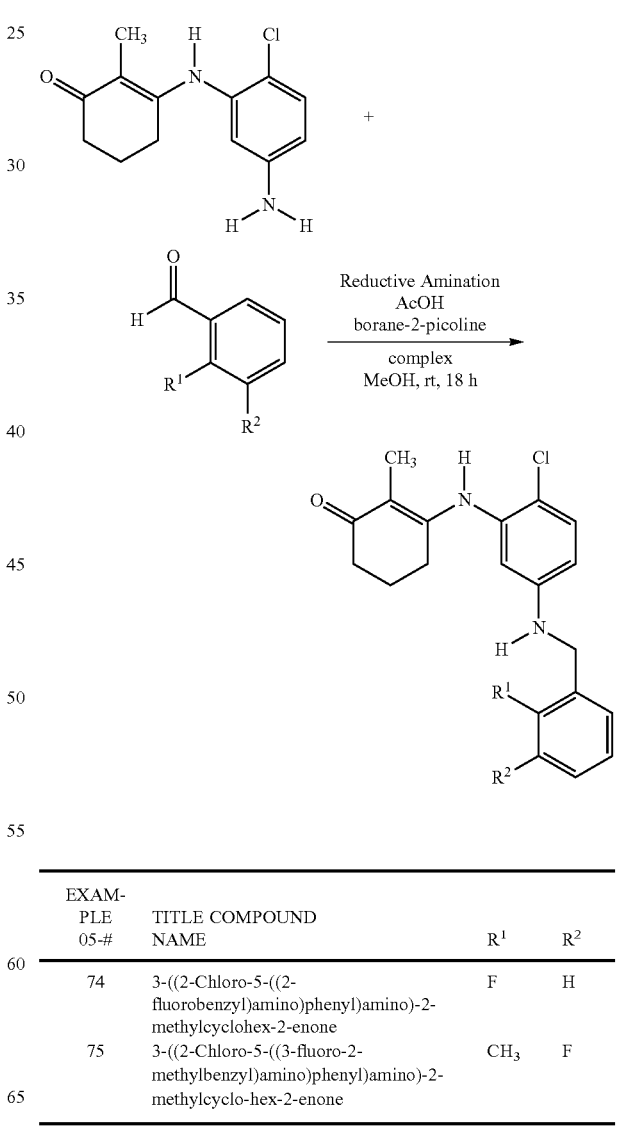

| EXAMPLE 05-# | TITLE COMPOUND NAME | R$^1$ | R$^2$ |
|---|---|---|---|
| 74 | 3-((2-Chloro-5-((2-fluorobenzyl)amino)phenyl)amino)-2-methylcyclohex-2-enone | F | H |
| 75 | 3-((2-Chloro-5-((3-fluoro-2-methylbenzyl)amino)phenyl)amino)-2-methylcyclo-hex-2-enone | CH$_3$ | F |

Example 05-74

Preparation of 3-((2-chloro-5-((2-fluorobenzyl)amino)phenyl)amino)-2-methylcyclohex-2-enone (05-74)

The title compound was prepared from Example 02-10 and 2-fluorobenzaldehyde according to the procedure of Example 05-72 (mp=103-105° C.). $^1$H NMR (D6-DMSO) δ 1.63 (s, 3H), 1.70 (quin, J=6.4 Hz, 2H), 2.09-2.15 (m, 4H), 4.31 (d, J=6.1 Hz, 2H), 6.45 (d, J=2.4 Hz, 1H), 6.50-6.56 (m, 2H), 7.09-7.25 (m, 3H), 7.26-7.33 (m, 1H), 7.37 (t, J=7.9 Hz, 1H), 7.83 (s, 1H). $^{13}$C NMR (D6-DMSO) δ 8.7, 21.2, 26.6, 36.3, 40.0, 106.0, 111.7, 112.3, 115.2 ($J_{CF}$=20.7 Hz), 117.1, 124.3, 126.1 ($J_{CF}$=14.9 Hz), 128.9 ($J_{CF}$=6.9 Hz), 129.4 ($J_{CF}$=4.6 Hz), 129.6, 137.1, 147.9, 159.1, 160.4 ($J_{CF}$=244.4 Hz), 194.1. LCMS t=5.1 min, m/z Calcd for $C_{20}H_{21}ClFN_2O$; $C_{20}H_{20}ClFN_2NaO$; 359.13; 381.12; [M+H]$^+$; [M+Na]$^+$, Found 359.13; 381.10.

Example 05-75

Preparation of 3-((2-chloro-5-((3-fluoro-2-methylbenzyl)amino)phenyl)amino)-2-methylcyclohex-2-enone (05-75)

The title compound was prepared from Example 02-10 and 2-fluoro-3-methylbenzaldehyde according to the procedure of Example 05-72 (mp=160-162° C.). $^1$H NMR (D6-DMSO) δ 1.63 (s, 3H), 1.71 (quin, J=6.4 Hz, 2H), 2.10-2.16 (m, 4H), 2.21 (s, 3H), 4.25 (d, J=6.1 Hz, 2H), 6.42-6.47 (m, 2H), 6.52 (dd, J=8.5, 2.4 Hz, 1H), 7.03-7.07 (m, 1H), 7.09 (d, J=8.5 Hz, 1H), 7.14-7.20 (m, 2H), 7.83 (s, 1H). $^{13}$C NMR (D6-DMSO) δ 9.2, 10.2 ($J_{CF}$=5.7 Hz), 21.7, 27.1, 36.8, 44.8, 106.4, 112.1, 112.7, 113.9 ($J_{CF}$=24.1 Hz), 117.4, 123.1 ($J_{CF}$=16.1 Hz), 123.5, 127.2 ($J_{CF}$=9.2 Hz), 130.1, 137.5, 140.5, 148.6, 159.6, 161.1 ($J_{CF}$=242.1 Hz), 194.6. LCMS t=5.2 min, m/z Calcd for $C_{21}H_{23}ClFN_2O$; $C_{21}H_{22}ClFN_2NaO$; $C_{42}H_{44}Cl_2F_2N_4NaO_2$ 373.148; 395.130; 767.271 [M+H]$^+$; [M+Na]$^+$; [2M+Na]$^+$, Found 373.148; 395.130; 767.271.

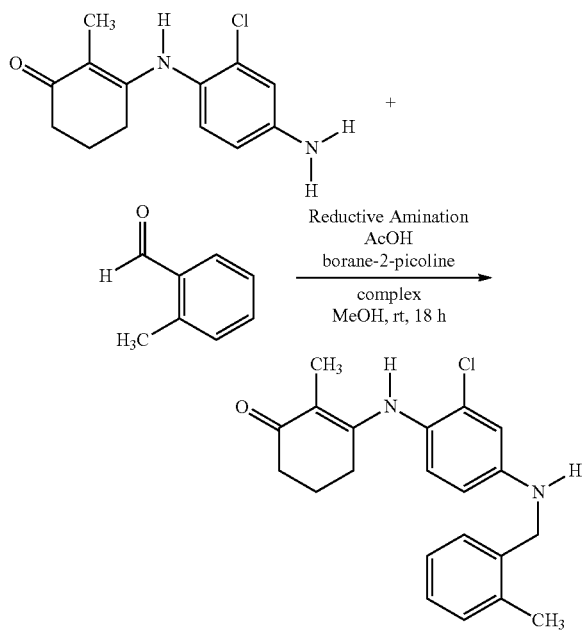

Example 05-76

Preparation of 3-((2-chloro-4-((2-methylbenzyl)amino)phenyl)amino)-2-methylcyclohex-2-enone (05-76)

The title compound was prepared from Example 02-12 and 2-methylbenzaldehyde according to the procedure of Example 05-72 (mp=220-221° C.). $^1$H NMR (D6-DMSO) δ 1.66 (s, 3H), 1.71 (quin, J=6.4 Hz, 2H), 2.07 (t, J=6.1 Hz, 2H), 2.11 (t, J=6.7 Hz, 2H), 2.32 (s, 3H), 4.22 (d, J=4.9 Hz, 2H), 6.46 (t, J=5.5 Hz, 1H), 6.56 (dd, J=8.5, 2.4 Hz, 1H), 6.71 (d, J=2.4 Hz, 1H), 7.02 (d, J=8.5 Hz, 1H), 7.11-7.22 (m, 3H), 7.25 (d, J=7.3 Hz, 1H), 7.78 (s, 1H). $^{13}$C NMR (D6-DMSO) δ 8.4, 18.6, 21.2, 26.3, 36.2, 44.7, 104.2, 111.1, 111.6, 124.3, 125.7, 126.9, 127.3, 130.1, 130.9, 132.8, 136.0, 136.8, 148.8, 160.7, 193.5. LCMS t=5.2 min, m/z Calcd for $C_{21}H_{24}ClN_2O$; $C_{21}H_{23}ClN_2NaO$; $C_{42}H_{46}Cl_2N_4NaO_2$ 355.158; 377.139; 731.290 [M+H]$^+$; [M+Na]$^+$; [2M+Na]$^+$, Found 355.156; 377.139; 731.290.

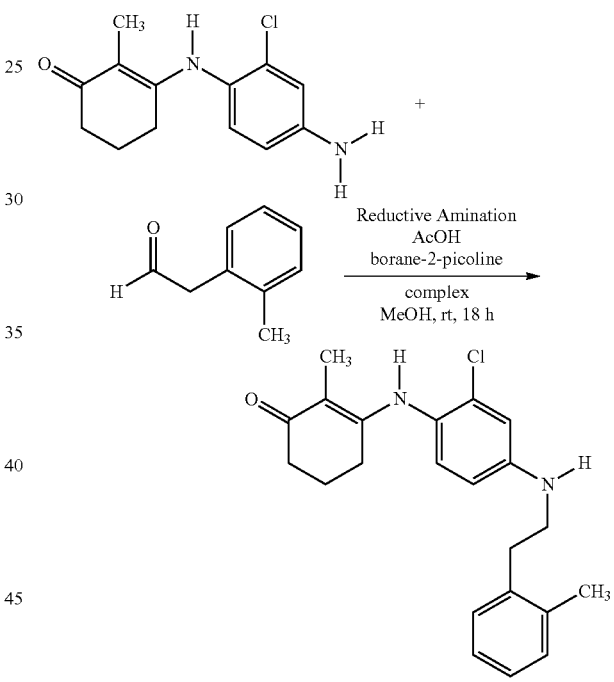

Example 05-77

Preparation of 3-((2-chloro-4-((2-methylphenethyl)amino)phenyl)amino)-2-methyl-cyclohex-2-enone (05-77)

The title compound was prepared from Example 02-12 and 2-(o-tolyl)acetaldehyde according to the procedure of Example 05-72 (mp=160-162° C.). $^1$H NMR (D6-DMSO) δ 1.66 (s, 3H), 1.72 (quin, J=6.1 Hz, 2H), 2.06-2.10 (m, 2H), 2.12 (t, J=6.1 Hz, 2H), 2.30 (s, 3H), 2.83 (t, J=7.3 Hz, 2H), 3.19-3.26 (m, 2H), 6.16 (t, J=5.5 Hz, 1H), 6.57 (dd, J=8.5, 2.4 Hz, 1H), 6.66-6.73 (m, 1H), 7.03 (d, J=8.5 Hz, 1H), 7.08-7.18 (m, 3H), 7.21 (d, J=8.5 Hz, 1H), 7.80 (s, 1H). $^{13}$C NMR (D6-DMSO) δ 8.4, 19.0, 21.2, 26.3, 32.1, 36.2, 43.2, 104.3, 111.0, 111.4, 124.2, 125.9, 126.2, 129.1, 130.0, 130.9, 132.9, 135.8, 137.7, 148.7, 160.7, 193.5. LCMS t=5.4 min, m/z Calcd for $C_{22}H_{26}ClN_2O$; $C_{22}H_{25}ClN_2NaO$; $C_{44}H_{50}Cl_2N_4NaO_2$ 369.173; 391.155; 759.321 [M+H]$^+$; [M+Na]$^+$; [2M+Na]$^+$, Found 369.173; 391.155; 759.321.

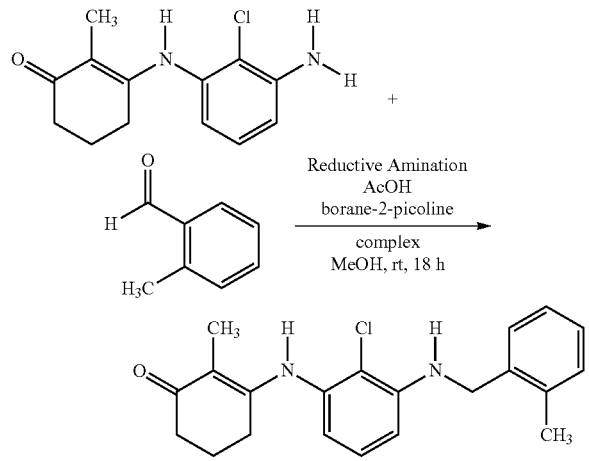

Example 05-78

Preparation of 3-((2-chloro-3-((2-methylbenzyl)amino)phenyl)amino)-2-methylcyclohex-2-enone (05-78)

The title compound was prepared from Example 02-11 and 2-(o-tolyl)acetaldehyde according to the procedure of Example 05-72 (mp=132-135° C.). $^1$H NMR (D6-DMSO) δ 1.67 (s, 3H), 1.75 (quin, J=6.1 Hz, 2H), 2.16 (t, J=6.7 Hz, 2H), 2.21 (t, J=6.1 Hz, 2H), 2.34 (s, 3H), 4.38 (d, J=6.1 Hz, 2H), 6.07 (t, J=6.1 Hz, 1H), 6.39 (d, J=8.5 Hz, 1H), 6.51 (d, J=7.3 Hz, 1H), 7.03 (t, J=7.9 Hz, 1H), 7.07-7.24 (m, 4H), 7.91 (s, 1H). $^{13}$C NMR (D6-DMSO) δ 8.7, 18.6, 21.3, 26.7, 36.4, 44.3, 105.8, 109.2, 115.9, 116.1, 125.7, 126.1, 126.5, 127.2, 130.1, 135.4, 136.8, 137.3, 144.9, 159.2, 194.1. LCMS t=5.1 min, m/z Calcd for $C_{21}H_{24}ClN_2O$; $C_{21}H_{23}ClN_2NaO$ 355.158; 377.139; [M+H]$^+$; [M+Na]$^+$, Found 355.152; 377.133.

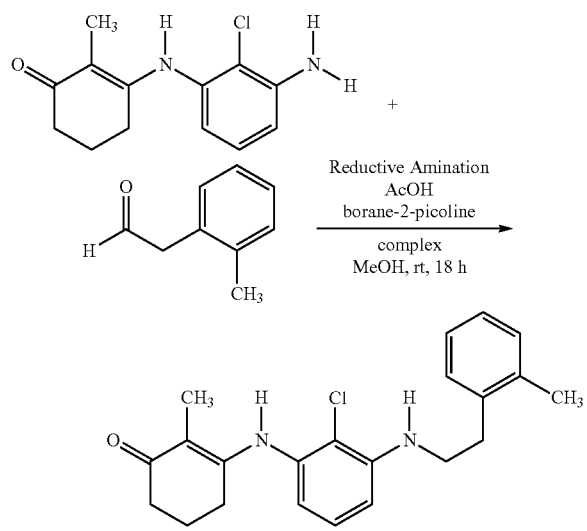

Example 05-79

Preparation of 3-((2-chloro-3-((2-methylphenethyl)amino)phenyl)amino)-2-methylcyclohex-2-enone (05-79)

The title compound was prepared from Example 02-11 and 2-(o-tolyl)acetaldehyde according to the procedure of Example 05-72 (mp=157-160° C.). $^1$H NMR (D6-DMSO) δ 1.66 (s, 3H), 1.74 (quin, J=6.4 Hz, 2H), 2.14-2.20 (m, 4H), 2.32 (s, 3H), 2.86-2.91 (m, 2H), 3.34-3.36 (m, 2H), 5.51 (t, J=5.5 Hz, 1H), 6.53 (d, J=8.5 Hz, 1H), 6.71 (d, J=8.5 Hz, 1H), 7.09-7.17 (m, 4H), 7.20 (d, J=7.3 Hz, 1H), 7.92 (s, 1H). $^{13}$C NMR (D6-DMSO) δ 8.8, 19.0, 21.2, 26.6, 32.1, 36.3, 43.3, 105.8, 108.7, 116.0, 116.1, 125.9, 126.2, 127.4, 129.3, 130.0, 136.0, 137.4, 137.6, 144.9, 159.2, 194.1. LCMS t=5.5 min, m/z Calcd for $C_{22}H_{26}ClN_2O$; $C_{22}H_{25}ClN_2NaO$; $C_{44}H_{50}Cl_2N_4NaO_2$ 369.173; 391.155; 759.321 [M+H]$^+$; [M+Na]$^+$; [2M+Na]$^+$, Found 369.175; 391.155; 759.321.

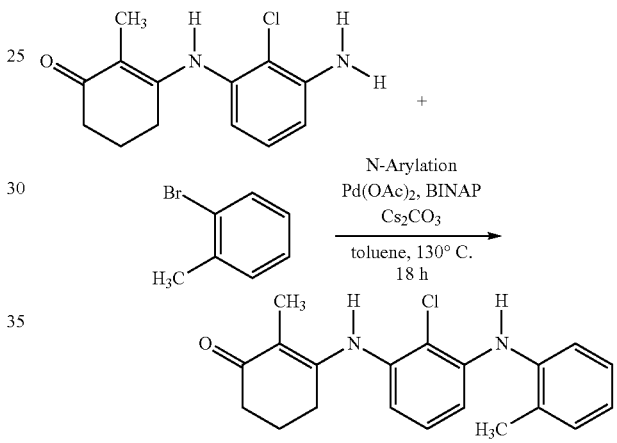

Example 05-80

Preparation of 3-((2-chloro-3-(o-tolylamino)phenyl)amino)-2-methylcyclohex-2-enone (05-80)

Example 02-11 (0.5 g, 2.00 mmol), 1-bromo-2-methylbenzene (0.408 g, 2.39 mmol), palladium acetate (0.045 g, 0.20 mmol), BINAP (0.249 g, 0.40 mmol), cesium carbonate (1.30 g, 3.99 mmol) and toluene (10 mL) were combined in a sealed flask and heated at 130° C., for 18 h. At rt, the mixture was filtered and the filtrate was diluted with EtOAc (30 mL), washed with brine (3×10 mL), dried with $Na_2SO_4$. The crude was purified by HPLC to afford the title compound (yellow microcrystal, 15 mg, 2.2%). $^1$H NMR (D6-DMSO) δ 1.68 (s, 3H), 1.73-1.82 (m, 2H), 2.14 (s, 3H), 2.18 (t, J=6.7 Hz, 2H), 2.25 (t, J=6.1 Hz, 2H), 6.42 (d, J=7.3 Hz, 1H), 6.70 (d, J=6.1 Hz, 1H), 7.09 (t, J=7.9 Hz, 3H), 7.20 (t, J=7.9 Hz, 1H), 7.23 (s, 1H), 7.28 (d, J=7.3 Hz, 1H), 7.97 (s, 1H). $^{13}$C NMR (D6-DMSO) δ 8.8, 17.7, 21.3, 26.8, 36.4, 106.2, 112.9, 118.4, 118.7, 124.4, 124.5, 126.8, 127.1, 130.9, 132.6, 137.9, 140.0, 143.3, 159.0, 194.2. LCMS t=5.1 min, m/z Calcd for $C_{20}H_{22}ClN_2O$; $C_{20}H_{21}ClN_2NaO$; $C_{40}H_{43}Cl_2N_4O_2$; 341.142; 363.124; 703.258 [M+H]$^+$; [M+Na]$^+$; [2M+Na]$^+$, Found 341.146; 363.124; 703.258.

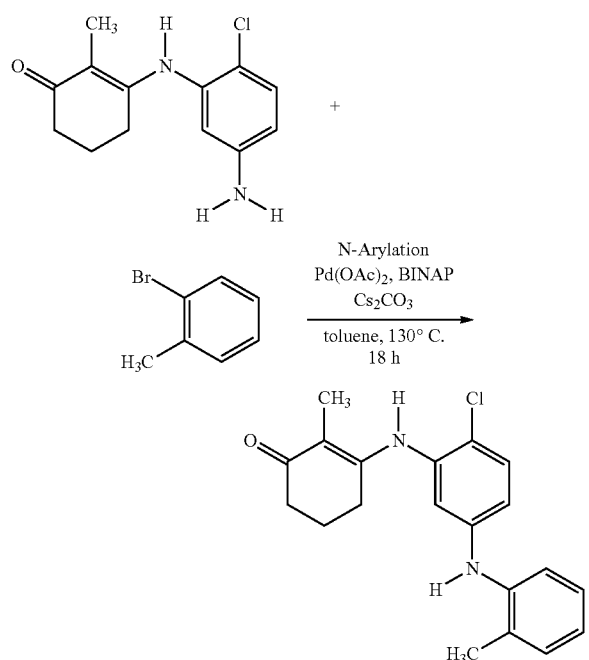

Example 05-81

Preparation of 3-((2-chloro-5-(o-tolylamino)phenyl)amino)-2-methylcyclohex-2-enone (05-81)

The title compound was prepared from Example 02-10 according to the procedure of Example 05-80 (mp=165-168° C.). $^1$H NMR (D6-DMSO) δ 1.64 (s, 3H), 1.76 (quin, J=6.1 Hz, 2H), 2.14-2.17 (m, 2H), 2.19 (s, 3H), 2.22 (t, J=5.5 Hz, 2H), 6.66 (d, J=2.4 Hz, 1H), 6.71-6.76 (m, 1H), 6.98 (t, J=7.9 Hz, 1H), 7.13-7.20 (m, 2H), 7.23 (d, J=7.3 Hz, 1H), 7.28 (d, J=8.5 Hz, 1H), 7.70 (s, 1H), 7.90 (s, 1H). $^{13}$C NMR (D6-DMSO) δ 8.8, 17.9, 21.2, 26.8, 36.4, 106.4, 114.2, 115.1, 119.3, 121.3, 123.1, 126.7, 129.9, 130.7, 131.1, 137.4, 140.2, 145.1, 158.9, 194.3. LCMS t=5.0 min, m/z Calcd for $C_{20}H_{22}ClN_2O$; $C_{20}H_{21}ClN_2NaO$; $C_{40}H_{42}Cl_2N_4NaO_2$ 341.142; 363.124; 703.258 [M+H]$^+$; [M+Na]$^+$; [2M+Na]$^+$, Found 341.142; 363.124; 703.258.

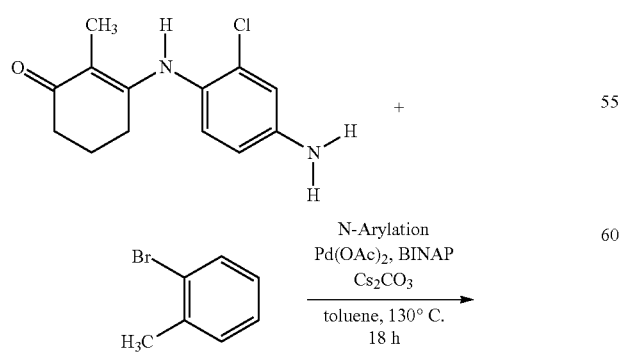

Example 05-82

Preparation of 3-((2-chloro-4-(o-tolylamino)phenyl)amino)-2-methylcyclohex-2-enone (05-82)

The title compound was prepared from Example 02-12 according to the procedure of Example 05-80 (mp=68-70° C.). $^1$H NMR (D6-DMSO) δ 1.67 (s, 3H), 1.74 (quin, J=6.4 Hz, 2H), 2.10-2.16 (m, 4H), 2.19 (s, 3H), 6.77 (dd, J=8.5, 2.4 Hz, 1H), 6.89 (d, J=2.4 Hz, 1H), 6.98-7.03 (m, 1H), 7.12 (d, J=8.5 Hz, 1H), 7.15-7.21 (m, 2H), 7.25 (d, J=7.3 Hz, 1H), 7.80 (s, 1H), 7.85 (s, 1H). $^{13}$C NMR (D6-DMSO) δ 8.5, 17.9, 21.3, 26.4, 36.3, 104.7, 113.7, 114.7, 114.7, 121.7, 123.4, 126.7, 130.9, 131.0, 131.1, 132.6, 139.9, 145.5, 160.3, 193.7. LCMS t=5.1 min, m/z Calcd for $C_{20}H_{22}ClN_2O$; $C_{40}H_{42}Cl_2N_4NaO_2$ 341.142; 703.258 [M+H]$^+$; [2M+Na]$^+$, Found 341.142; 703.261.

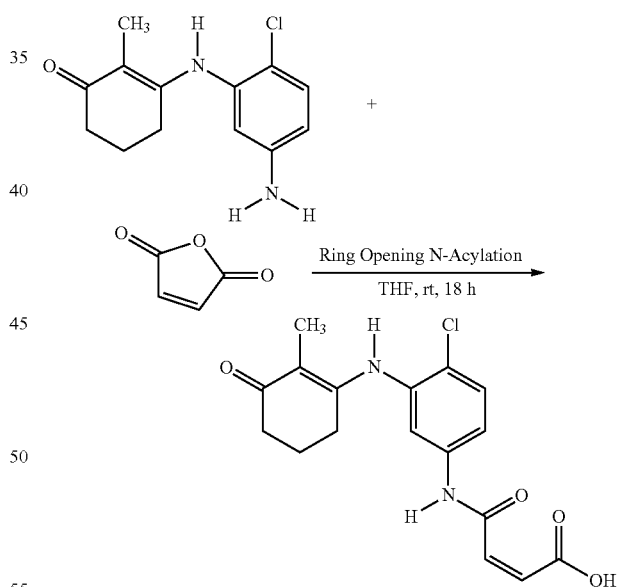

Example 05-83

Preparation of (Z)-4-((4-chloro-3-((2-methyl-3-oxocyclohex-1-en-1-yl)amino)phenyl)-amino)-4-oxobut-2-enoic acid (05-83)

Example 02-10 (0.5 g, 2.0 mmol) and furan-2,5-dione (0.196 g, 2.0 mmol) were stirred in THF (10 mL) at rt, for 18 h. The solvent was removed under vacuum and purified by HPLC to afford the title compound (0.19 g, 27.3% yield, mp=182-185° C.). $^1$H NMR (D6-DMSO) δ 1.64 (s, 3H), 1.73-1.81 (m, 2H), 2.19 (t, J=6.1 Hz, 2H), 2.23 (t, J=5.5 Hz, 2H), 6.31 (d, J=12.2 Hz, 1H), 6.40 (d, J=12.2 Hz, 1H), 7.41-7.52 (m, 2H), 7.61 (d, J=2.4 Hz, 1H), 8.02 (s, 1H), 10.89 (br s, 1H), 12.73 (br s, 1H). $^{13}$C NMR (D6-DMSO) δ 9.1, 21.2, 27.0, 36.4, 107.2, 118.0, 119.2, 124.6, 129.8, 131.0, 131.4, 137.3, 138.2, 158.3, 163.5, 167.0, 194.6. LCMS t=3.9 min, m/z Calcd for $C_{17}H_{18}ClN_2O_4$; $C_{17}H_{17}ClN_2NaO_4$; $C_{34}H_{35}Cl_2N_4O_8$; $C_{34}H_{34}Cl_2N_4NaO_8$ 349.096; 371.078; 697.183; 719.165 [M+H]$^+$; [M+Na]$^+$; [2M+H]$^+$; [2M+Na]$^+$, Found 349.096; 371.075; 697.176; 719.166.

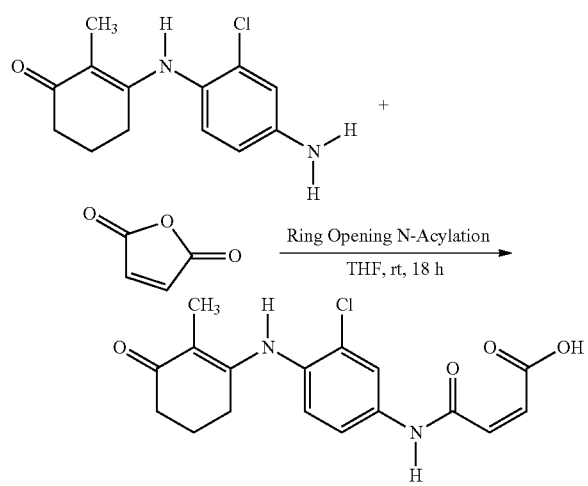

Example 05-84

Preparation of (Z)-4-((3-chloro-4-((2-methyl-3-oxo-cyclohex-1-en-1-yl)amino)phenyl)-amino)-4-oxobut-2-enoic acid (05-84)

The title compound was prepared from Example 02-12 according to the procedure of Example 05-83 (mp=200-202° C.). $^1$H NMR (D6-DMSO) δ 1.66 (s, 3H), 1.72-1.77 (m, 2H), 2.10-2.19 (m, 4H), 6.33 (d, J=12.2 Hz, 1H), 6.47 (d, J=12.2 Hz, 1H), 7.29 (d, J=8.5 Hz, 1H), 7.49 (dd, J=8.5, 2.4 Hz, 1H), 7.94 (d, J=2.4 Hz, 1H), 7.97 (s, 1H), 10.58 (br s, 1H), 12.92 (br s, 1H). $^{13}$C NMR (D6-DMSO) δ 8.8, 21.2, 26.7, 36.3, 106.0, 118.4, 119.7, 130.0, 130.2, 131.4, 131.6, 132.3, 137.9, 159.2, 163.5, 166.9, 194.2. LCMS t=3.9 min, m/z Calcd for $C_{17}H_{18}ClN_2O_4$; $C_{17}H_{17}ClN_2NaO_4$; $C_{34}H_{34}Cl_2N_4NaO_8$ 349.096; 371.078; 719.165 [M+H]$^+$; [M+Na]$^+$; [2M+Na]$^+$, Found 349.096; 371.078; 719.164.

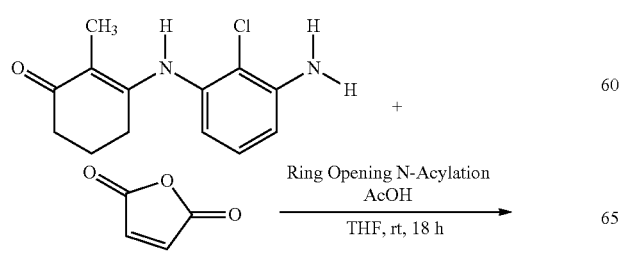

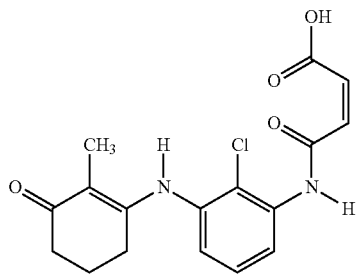

Example 05-85

Preparation of (Z)-4-((2-chloro-3-((2-methyl-3-oxo-cyclohex-1-en-1-yl)amino)phenyl)-amino)-4-oxobut-2-enoic acid (05-85)

Example 02-11 (0.2 g, 0.8 mmol), furan-2,5-dione (0.392 g, 4.0 mmol) and AcOH (1 mL) were stirred in THF (10 mL) was stirred at rt, for 18 h. The solvent was removed under vacuum and purified by HPLC to afford the title compound (0.14 g, 50.3% yield). $^1$H NMR (D6-DMSO) δ 1.67 (s, 3H), 1.73-1.79 (m, 2H), 2.15-2.22 (m, 4H), 4.06 (br s, 0.5H), 5.77 (d, J=13.4 Hz, 1H), 6.19 (d, J=13.4 Hz, 1H), 7.04 (d, J=7.3 Hz, 1H), 7.12-7.33 (m, 3H), 7.80 (d, J=7.3 Hz, 1H), 8.01 (s, 0.5H). LCMS t=3.6 min, m/z Calcd for $C_{17}H_{18}ClN_2O_4$; $C_{17}H_{17}ClN_2NaO_4$ 349.096; 371.078 [M+H]$^+$; [M+Na]$^+$, Found 349.096; 371.078.

Examples 06-01 to 06-011

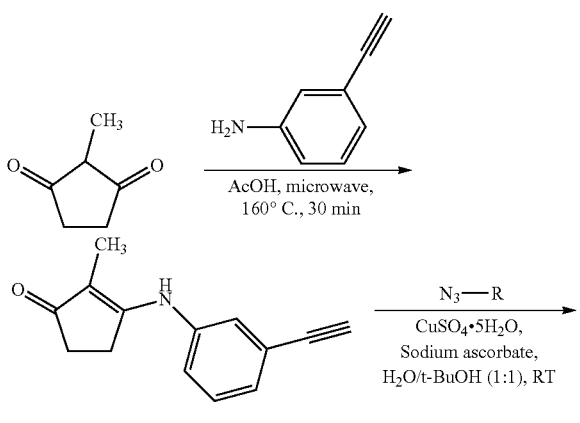

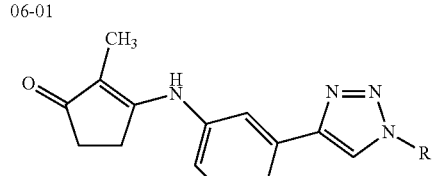

| Example 06-# | TITLE COMPOUND NAME | R |
|---|---|---|
| 01 | 3-((3-ethynylphenyl)amino)-2-methylcyclopent-2-enone | |
| 02 | 2-methyl-3-((3-(1-phenyl-1H-1,2,3-triazol-4-yl)phenyl)amino)cyclopent-2-enone | Ph |
| 03 | 3-((3-(1-(4-methoxyphenyl)-1H-1,2,3-triazol-4-yl)phenyl)amino)-2-methylcyclopent-2-enone | 4-OCH$_3$Ph |
| 04 | 3-((3-(1-benzyl-1H-1,2,3-triazol-4-yl)phenyl)amino)-2-methylcyclopent-2-enone | CH$_2$Ph |
| 05 | 2-methyl-3-((3-(1-(4-methylbenzyl)-1H-1,2,3-triazol-4-yl)phenyl)amino)cyclopent-2-enone | CH$_2$ 4-CH$_3$Ph |
| 06 | 3-((3-(1-(4-fluorobenzyl)-1H-1,2,3-triazol-4-yl)phenyl)amino)-2-methylcyclopent-2-enone | CH$_2$ 4-FPh |
| 07 | 3-((3-(1-(3-fluorobenzyl)-1H-1,2,3-triazol-4-yl)phenyl)amino)-2-methylcyclopent-2-enone | CH$_2$ 3-FPh |
| 08 | 3-((3-(1-(2-fluorobenzyl)-1H-1,2,3-triazol-4-yl)phenyl)amino)-2-methylcyclopent-2-enone | CH$_2$ 2-FPh |
| 09 | 4-((4-(3-((2-methyl-3-oxocyclopent-1-en-1-yl)amino)phenyl)-1H-1,2,3-triazol-1-yl)methyl)benzamide | CH$_2$ 4-CONH$_2$Ph |
| 10 | 2-methyl-3-((3-(1-(2-methylbenzyl)-1H-1,2,3-triazol-4-yl)phenyl)amino)cyclopent-2-enone | CH$_2$ 2-CH$_3$Ph |
| 11 | 2-methyl-3-((3-(1-(pyridin-3-ylmethyl)-1H-1,2,3-triazol-4-yl)phenyl)amino)cyclopent-2-enone | CH$_2$ 3-Pyridyl |

Example 06-01

Preparation of 3-((3-ethynylphenyl)amino)-2-methylcyclopent-2-enone (06-01)

2-methylcyclopentane-1,3-dione (0.112 g, 0.996 mmol), 3-ethynylaniline (0.112 mL, 0.996 mmol), and acetic acid (0.029 mL, 0.499 mmol), were added to a 0.5-2 mL Biotage® microwave vial. The biotage Intiator® microwave reactor was programmed to heat at 160° C. for 30 min. The reaction mixture was dissolved in dichloromethane, concentrated in vacuo, purified by combiflash (SiO$_2$, 7% methanol in dichloromethane), triturated with ethylacetate, and filtered to give 3-((3-ethynylphenyl)amino)-2-methylcyclopent-2-enone (0.046 g, 22%) as a yellow solid. $^1$H NMR (600 MHz, MeOD) δ 7.37-7.35 (2H, m), 7.31-7.27 (2H, m), 3.55-3.54 (1H, m), 2.72 (2H, bs), 2.40-2.38 (2H, m), 1.66 (3H, s); $^{13}$C NMR (150 MHz, MeOD) δ 205.3, 173.7, 139.6, 129.2, 128.7, 126.9, 124.2, 123.5, 110.2, 82.4, 78.2, 32.7, 25.8, 5.6; LCMS m/z 212.1827 ([M+H$^+$], C$_{14}$H$_{14}$NO requires 212.1070).

General synthesis procedure for 3-((3-(1-substituted-1H-1,2,3-triazol-4-yl)phenyl)amino)-2-methylcyclopent-2-enones—06-02 to 06-011. To a suspension of 3-((3-ethynylphenyl)amino)-2-methylcyclopent-2-enone (1 Eq) and substituted azide (2 Eq) in a mixture of water and tert-butyl alcohol (1:1, 0.071 mmol/mL) was added sodium ascorbate (0.01 Eq, 1 M solution in water), followed by copper (II) sulfate pentahydrate (0.01 Eq). The heterogeneous mixture was stirred at RT for the specified time. The reaction mixture was diluted with water and cooled in an ice bath. The precipitate formed was filtered and washed with water. The precipitate was then dissolved in dichloromethane, dried (Na$_2$SO$_4$), concentrated, and purified as specified.

Example 06-02

Preparation of 2-methyl-3-((3-(1-phenyl-1H-1,2,3-triazol-4-yl)phenyl)amino)cyclopent-2-enone (06-02)

Using the general procedure, a suspension of 3-((3-ethynylphenyl)amino)-2-methylcyclopent-2-enone (0.015 g, 0.071 mmol) and azidobenzene (0.017 g, 0.142 mmol), sodium ascorbate, and copper (II) sulfate pentahydrate in a mixture of water and tert-butyl alcohol were stirred at RT for 14 h. Purification was done by washing the solid precipitate with dichloromethane to afford 2-methyl-3-((3-(1-phenyl-1H-1,2,3-triazol-4-yl)phenyl)amino)cyclopent-2-enone (0.022 g, 96%) as a yellow solid. $^1$H NMR (600 MHz, MeOD) δ 8.97 (1H, s), 7.92 (2H, d, J=7.8 Hz), 7.84 (1H, bs), 7.78 (1H, d, J=7.2 Hz), 7.61 (2H, t, J=7.8 Hz), 7.53-7.49 (2H, m), 7.28 (1H, d, J=7.8 Hz), 2.80 (2H, bs), 2.41 (2H, bs), 1.70 (3H, s); $^{13}$C NMR (150 MHz, MeOD) δ 205.2, 174.0, 140.1, 137.2, 131.4, 129.8, 128.9, 123.8, 122.6, 120.9, 120.2, 119.5, 33.0, 29.5, 25.8, 5.7; LCMS m/z 331.2967 ([M+H$^+$], C$_{20}$H$_{19}$N$_4$O requires 331.1554).

Example 06-03

Preparation of 3-((3-(1-(4-methoxyphenyl)-1H-1,2,3-triazol-4-yl)phenyl)amino)-2-methylcyclopent-2-enone (06-03)

Using the general procedure, a suspension of 3-((3-ethynylphenyl)amino)-2-methylcyclopent-2-enone (0.050 g, 0.236 mmol) and 1-azido-4-methoxybenzene (0.070 g, 0.473 mmol), sodium ascorbate, and copper (II) sulfate pentahydrate in a mixture of water and tert-butyl alcohol were stirred at RT for 15 h. Purification was done by combiflash (SiO$_2$, 90% ethylacetate in hexanes) to yield 3-((3-(1-(4-methoxyphenyl)-1H-1,2,3-triazol-4-yl)phenyl)amino)-2-methylcyclopent-2-enone (0.015 g, 18%) as a white solid. $^1$H NMR (600 MHz, MeOD) δ 8.87 (1H, s), 7.83-7.76 (4H, m), 7.52-7.49 (1H, m), 7.29 (1H, dd, J=1.8, 7.8 Hz), 7.15-7.13 (1H, m), 3.89 (3H, s), 2.82-2.80 (2H, m), 2.43-2.41 (2H, m), 1.71 (3H, s); LCMS m/z 361.3447 ([M+H$^+$], C$_{21}$H$_{21}$N$_4$O$_2$ requires 361.1660).

Example 06-04

Preparation of 3-((3-(1-benzyl-1H-1,2,3-triazol-4-yl)phenyl)amino)-2-methylcyclopent-2-enone (06-04)

Using the general procedure, a suspension of 3-((3-ethynylphenyl)amino)-2-methylcyclopent-2-enone (0.050 g, 0.236 mmol) and (azidomethyl)benzene (0.063 g, 0.472 mmol), sodium ascorbate, and copper (II) sulfate pentahydrate in a mixture of water and tert-butyl alcohol were stirred at RT for 14 h. Purification was done by combiflash (SiO$_2$, 2%-5% methanol in dichloromethane) to yield 3-((3-(1-benzyl-1H-1,2,3-triazol-4-yl)phenyl)amino)-2-methylcyclopent-2-enone (0.040 g, 49%) as a white solid. $^1$H NMR (600 MHz, MeOD) δ 8.36 (1H, s), 7.70 (1H, s), 7.62 (1H, d, J=7.8 Hz), 7.43-7.40 (1H, m), 7.35-7.32 (4H, m), 7.21 (1H, d, J=7.8 Hz), 5.61 (2H, d, J=1.8 Hz), 2.72 (2H, bs), 2.36-2.35 (2H, m), 1.67 (3H, s); $^{13}$C NMR (150 MHz, MeOD) δ 205.1, 173.9, 147.2, 140.0, 135.5, 131.6, 129.7, 128.8, 128.4, 127.9, 123.4, 122.4, 121.4, 120.6, 53.8, 32.7, 25.8, 5.7; LCMS m/z 345.3331 ([M+H$^+$], $C_{21}H_{21}N_4O$ requires 345.1710).

Example 06-05

Preparation of 2-methyl-3-((3-(1-(4-methylbenzyl)-1H-1,2,3-triazol-4-yl)phenyl)amino)cyclopent-2-enone (06-05)

Using the general procedure, a suspension of 3-((3-ethynylphenyl)amino)-2-methylcyclopent-2-enone (0.075 g, 0.355 mmol) and 1-(azidomethyl)-4-methylbenzene (0.104 g, 0.710 mmol), sodium ascorbate, and copper (II) sulfate pentahydrate in a mixture of water and tert-butyl alcohol were stirred at RT for 11 h. Purification was done by combiflash (SiO$_2$, 3%-5% methanol in dichloromethane) to yield 2-methyl-3-((3-(1-(4-methylbenzyl)-1H-1,2,3-triazol-4-yl)phenyl)amino)cyclopent-2-enone (0.103 g, 81%) as a white solid. $^1$H NMR (600 MHz, MeOD) δ 8.33 (1H, bs), 7.70 (1H, s), 7.63 (1H, d, J=7.8 Hz), 7.43 (1H, t, J=7.8 Hz), 7.26-7.18 (5H, m), 5.57 (2H, s), 2.74 (2H, bs), 2.38-2.37 (2H, m), 2.31 (3H, s), 1.68 (3H, s); $^{13}$C NMR (150 MHz, MeOD) δ205.1, 174.0, 147.2, 140.0, 138.5, 132.4, 131.6, 129.7, 129.4, 127.9, 123.5, 122.4, 121.3, 120.7, 110.0, 53.7, 32.7, 25.8, 19.9, 5.7; LCMS m/z 359.4512 ([M+H$^+$], $C_{22}H_{23}N_4O$ requires 359.1867).

Example 06-06

Preparation of 3-((3-(1-(4-fluorobenzyl)-1H-1,2,3-triazol-4-yl)phenyl)amino)-2-methylcyclopent-2-enone (06-06)

Using the general procedure, a suspension of 3-((3-ethynylphenyl)amino)-2-methylcyclopent-2-enone (0.075 g, 0.355 mmol) and 1-(azidomethyl)-4-fluorobenzene (0.107 g, 0.710 mmol), sodium ascorbate, and copper (II) sulfate pentahydrate in a mixture of water and tert-butyl alcohol were stirred at RT for 11 h. Purification was done by combiflash (SiO$_2$, 3%-5% methanol in dichloromethane) to yield 3-((3-(1-(4-fluorobenzyl)-1H-1,2,3-triazol-4-yl)phenyl)amino)-2-methylcyclopent-2-enone (0.063 g, 49%). $^1$H NMR (600 MHz, MeOD) δ 8.39 (1H, bs), 7.72 (1H, s), 7.65 (1H, d, J=7.2 Hz), 7.46-7.42 (3H, m), 7.24 (1H, d, J=7.8 Hz), 7.14-7.11 (2H, m), 5.63 (2H, s), 2.76 (2H, bs), 2.40-2.39 (2H, m), 1.68 (3H, s); $^{13}$C NMR (150 MHz, MeOD) δ 205.2, 174.1, 147.3, 140.0, 131.6, 131.5, 130.1, 129.7, 123.6, 122.5, 121.3, 120.7, 115.6, 115.5, 109.9, 53.0, 32.7, 25.8, 5.7; LCMS m/z 363.4738 ([M+H$^+$], $C_{21}H_{20}FN_4O$ requires 363.1616).

Example 06-07

Preparation of 3-((3-(1-(3-fluorobenzyl)-1H-1,2,3-triazol-4-yl)phenyl)amino)-2-methylcyclopent-2-enone (06-07)

Using the general procedure, a suspension of 3-((3-ethynylphenyl)amino)-2-methylcyclopent-2-enone (0.075 g, 0.355 mmol) and 1-(azidomethyl)-3-fluorobenzene (0.107 g, 0.710 mmol), sodium ascorbate, and copper (II) sulfate pentahydrate in a mixture of water and tert-butyl alcohol were stirred at RT for 11 h. Purification was done by combiflash (SiO$_2$, 3%-5% methanol in dichloromethane) to yield 3-((3-(1-(3-fluorobenzyl)-1H-1,2,3-triazol-4-yl)phenyl)amino)-2-methylcyclopent-2-enone (0.115 g, 90%). $^1$H NMR (600 MHz, MeOD) δ 8.42 (1H, bs), 7.74-7.73 (1H, m), 7.66 (1H, dd, J=1.2, 6.6 Hz), 7.47-7.40 (2H, m), 7.25 (1H, dd, J=2.4, 8.4 Hz), 7.19 (1H, d, J=7.8 Hz), 7.14-7.10 (2H, m), 5.67 (2H, s), 2.78-2.77 (2H, m), 2.41-2.39 (2H, m), 1.69 (3H, s); $^{13}$C NMR (150 MHz, MeOD) δ 205.2, 174.1, 147.3, 140.0, 138.1, 131.5, 130.8, 130.7, 129.7, 123.6, 122.5, 121.6, 120.7, 115.2, 115.1, 114.7, 114.6, 53.1, 32.7, 25.8, 5.7; LCMS m/z 363.4598 ([M+H$^+$], $C_{21}H_{20}FN_4O$ requires 363.1616).

Example 06-08

Preparation of 3-((3-(1-(2-fluorobenzyl)-1H-1,2,3-triazol-4-yl)phenyl)amino)-2-methylcyclopent-2-enone (06-08)

Using the general procedure, a suspension of 3-((3-ethynylphenyl)amino)-2-methylcyclopent-2-enone (0.075 g, 0.355 mmol) and 1-(azidomethyl)-2-fluorobenzene (0.107 g, 0.710 mmol), sodium ascorbate, and copper (II) sulfate pentahydrate in a mixture of water and tert-butyl alcohol were stirred at RT for 11 h. Purification was done by combiflash (SiO$_2$, 3%-5% methanol in dichloromethane) to yield 3-((3-(1-(2-fluorobenzyl)-1H-1,2,3-triazol-4-yl)phenyl)amino)-2-methylcyclopent-2-enone (0.115 g, 90%). $^1$H NMR (600 MHz, DMSO-d$^6$) δ 9.05 (1H, bs), 7.71 (1H, s), 7.59 (1H, d, J=7.8 Hz), 7.44-7.38 (1H, m), 7.28-7.18 (3H, m), 5.70 (2H, s), 2.63 (2H, bs), 2.21-2.20 (2H, m), 1.56 (3H, s); $^{13}$C NMR (150 MHz, DMSO-d$^6$) δ 202.5, 169.9, 146.8, 141.0, 131.9, 131.4, 130.2, 125.5, 123.4, 123.3, 122.7, 122.5, 121.4, 119.9, 116.4, 116.2, 110.5, 47.7, 33.5, 26.3, 8.0; LCMS m/z 363.3012 ([M+H$^+$], $C_{21}H_{20}FN_4O$ requires 363.1616).

Example 06-09

Preparation of 4-((4-(3-((2-methyl-3-oxocyclopent-1-en-1-yl)amino)phenyl)-1H-1,2,3-triazol-1-yl)methyl)benzamide (06-09)

Using the general procedure, a suspension of 3-((3-ethynylphenyl)amino)-2-methylcyclopent-2-enone (0.075 g, 0.355 mmol) and 4-(azidomethyl)benzamide (0.125 g, 0.710 mmol), sodium ascorbate, and copper (II) sulfate pentahydrate in a mixture of water and tert-butyl alcohol were stirred at RT for 20 h. Purification was done by washing the solid precipitate with dichloromethane to afford 4-((4-(3-((2-methyl-3-oxocyclopent-1-en-1-yl)amino)phenyl)-1H-1,2,3-triazol-1-yl)methyl)benzamide (0.120 g, 88%) as a white solid. $^1$H NMR (600 MHz, DMSO-d$^6$) δ 9.05 (1H, bs), 8.68 (1H, s), 7.97 (1H, s), 7.86 (1H, d, J=7.8 Hz), 7.71 (1H, s), 7.58 (1H, d, J=7.2 Hz), 7.41-7.38 (2H, m), 7.18 (1H, d, J=7.2 Hz), 5.70 (2H, s), 2.68 (2H, bs), 2.21-2.20 (2H, m), 1.56 (3H, s); $^{13}$C NMR (150 MHz, DMSO-d$^6$) δ 202.5, 169.8, 168.0, 147.0, 141.0, 139.6, 134.7, 132.0, 128.6, 128.3, 122.6, 121.3, 119.9, 110.5, 53.3, 33.5, 26.3, 8.0; LCMS m/z 388.3432 ([M+H$^+$], C$_{22}$H$_{22}$N$_5$O$_2$ requires 388.1768).

Example 06-10

Preparation of 2-methyl-3-((3-(1-(2-methylbenzyl)-1H-1,2,3-triazol-4-yl)phenyl)amino)cyclopent-2-enone (06-10)

Using the general procedure, a suspension of 3-((3-ethynylphenyl)amino)-2-methylcyclopent-2-enone (0.075 g, 0.355 mmol) and 1-(azidomethyl)-2-methylbenzene (0.104 g, 0.710 mmol), sodium ascorbate, and copper (II) sulfate pentahydrate in a mixture of water and tert-butyl alcohol were stirred at RT for 60 h. Purification was done by combiflash (SiO$_2$, 3%-7% methanol in dichloromethane) to yield 2-methyl-3-((3-(1-(2-methylbenzyl)-1H-1,2,3-triazol-4-yl)phenyl)amino)cyclopent-2-enone (0.074 g, 58%). $^1$H NMR (600 MHz, MeOD) δ 8.23 (1H, bs), 7.70 (1H, s), 7.62 (1H, d, J=6.6 Hz), 7.41-7.40 (1H, m), 7.22-7.20 (4H, m), 5.64 (2H, s), 2.72 (2H, bs), 2.35-2.34 (5H, m), 1.66 (3H, s); LCMS m/z 359.4657 ([M+H$^+$], C$_{22}$H$_{23}$N$_4$O requires 359.1867).

Example 06-11

Preparation of 2-methyl-3-((3-(1-(pyridin-3-ylmethyl)-1H-1,2,3-triazol-4-yl) phenyl) amino) cyclopent-2-enone (06-11)

Using the general procedure, a suspension of 3-((3-ethynylphenyl)amino)-2-methylcyclopent-2-enone (0.075 g, 0.355 mmol) and 3-(azidomethyl)pyridine (0.095 g, 0.710 mmol), sodium ascorbate, and copper (II) sulfate pentahydrate in a mixture of water and tert-butyl alcohol were stirred at RT for 60 h. Purification was done by washing the solid precipitate with dichloromethane to afford 2-methyl-3-((3-(1-(pyridin-3-ylmethyl)-1H-1,2,3-triazol-4-yl)phenyl) amino)cyclopent-2-enone (0.067 g, 55%). $^1$H NMR (600 MHz, MeOD) δ 8.63 (1H, s), 8.54-8.53 (1H, m), 8.45 (1H, s), 7.85 (1H, dd, J=1.2, 7.8 Hz), 7.72 (1H, s), 7.64 (1H, dd, J=0.6, 7.8 Hz), 7.47-7.42 (2H, m), 7.24-7.23 (1H, m), 5.73 (2H, s), 2.74 (2H, bs), 2.38-2.37 (2H, m), 1.67 (3H, s); LCMS m/z 346.2856 ([M+H$^+$], C$_{20}$H$_{20}$N$_5$O requires 346.1663).

Examples 06-12 and 06-13

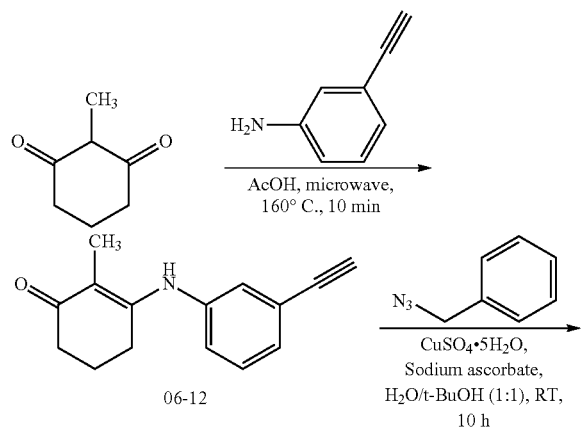

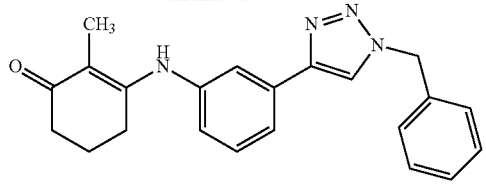

06-13

| Example 06-# | TITLE COMPOUND NAME |
|---|---|
| 12 | 3-((3-ethynylphenyl)amino)-2-methylcyclohex-2-enone |
| 13 | 3-((3-(1-benzyl-1H-1,2,3-triazol-4-yl)phenyl)amino)-2-methylcyclohex-2-enone |

Example 06-12

Preparation of 3-((3-ethynylphenyl)amino)-2-methylcyclohex-2-enone (06-12)

2-methylcyclohexane-1,3-dione (0.200 g, 1.58 mmol), 3-ethynylaniline (0.178 mL, 1.58 mmol), acetic acid (0.181 mL, 3.17 mmol), were added to a 0.5-2 mL Biotage® microwave vial. The biotage Intiator® microwave reactor was programmed to heat at 160° C. for 10 min. The reaction mixture was dissolved in methanol, concentrated in vacuo, purified by combiflash (SiO$_2$, 2%-4% methanol in dichloromethane), to give 3-((3-ethynylphenyl)amino)-2-methylcyclohex-2-enone (0.176 g, 49%) as a white solid. $^1$H NMR (600 MHz, MeOD) δ 7.34 (1H, t, J=7.8 Hz), 7.30 (1H, d, J=7.8 Hz), 7.25 (1H, bs), 7.17 (1H, d, J=8.4 Hz), 3.54 (1H, s), 2.47 (2H, t, J=6 Hz), 2.34 (2H, t, J=6.6 Hz), 1.88-1.84 (2H, m), 1.77 (3H, s); $^{13}$C NMR (150 MHz, MeOD) δ 197.6, 162.0, 139.6, 129.0, 128.8, 128.4, 125.8, 123.4, 107.1, 82.5, 78.2, 36.0, 27.3, 21.7, 7.6; LCMS m/z 226.4831 ([M+H$^+$], C$_{15}$H$_{16}$NO requires 226.1227).

Example 06-13

Preparation of 3-((3-(1-benzyl-1H-1,2,3-triazol-4-yl) phenyl)amino)-2-methylcyclohex-2-enone (06-13)

To a suspension of 3-((3-ethynylphenyl)amino)-2-methylcyclohex-2-enone (0.075 g, 0.332 mmol) and (azidomethyl)benzene (0.089 g, 0.666 mmol) in a mixture of water and tert-butyl alcohol (1:1, 1.5 mL) was added sodium ascorbate (0.035 mL, 0.036 mmol, 1 M solution in water), followed by copper (II) sulfate pentahydrate (0.001 g, 0.004 mmol). The heterogeneous mixture was stirred at RT for 10 h. The reaction mixture was diluted with water (5 mL) and cooled in an ice bath. The ppt formed was filtered and washed with water and dichloromethane. The filtrate was extracted with dichloromethane, and the ppt was dissolved in dichloromethane. The combined dichloromethane layers were dried (Na$_2$SO$_4$) and purified by combiflash (SiO$_2$, 2%-5% methanol in dichloromethane) to give 3-((3-(1-benzyl-1H-1,2,3-triazol-4-yl)phenyl)amino)-2-methylcyclohex-2-enone (0.048 g, 40%) as a white solid. $^1$H NMR (600 MHz, MeOD) δ 8.35 (1H, bs), 7.63 (1H, d, J=7.8 Hz), 7.61 (1H, s), 7.40 (1H, t, J=7.8 Hz), 7.37-7.32 (5H, m), 7.12 (1H, d, J=7.8 Hz), 5.62 (1H, d, J=10.8 Hz), 2.49 (2H, t, J=5.4 Hz), 2.31 (2H, t, J=6 Hz), 1.83-1.81 (2H, m), 1.79 (s, 3H); $^{13}$C NMR (150 MHz, MeOD) δ 197.4, 162.5, 147.2, 140.0, 135.5, 131.4, 129.5, 128.8, 128.4, 127.9, 125.1, 122.6, 122.3, 121.4, 106.7, 53.8, 36.0, 27.3, 21.8, 7.6; LCMS m/z 359.5227 ([M+H$^+$], C$_{22}$H$_{23}$N$_4$O requires 359.1867).

Examples 06-14 to 06-27

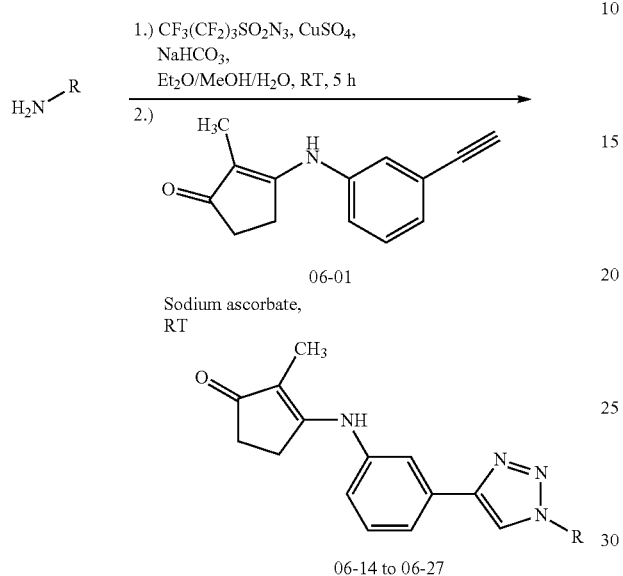

General synthesis procedure for 3-((3-(1-substituted-1H-1,2,3-triazol-4-yl)phenyl)amino)-2-methylcyclopent-2-enones—06-14 to 06-27. To a solution of substituted amine (1 Eq) in water (0.75 mmol/mL) was added in sequence methanol (0.27 mmol/mL), NaHCO$_3$ (4 Eq), a solution of 1,1,2,2,3,3,4,4,4-nonafluorobutane-1-sulfonyl azide (1.5 Eq) in Et$_2$O (0.50 mmol/mL) and copper sulfate pentahydrate (0.1 Eq). The reaction mixture was stirred at RT for 5 h. To the reaction mixture was added 3-((3-ethynylphenyl)amino)-2-methylcyclopent-2-enone (1.1 Eq) and sodium ascorbate (1.5 Eq). The reaction mixture was stirred at RT for the specified time. The reaction mixture was filtered, washed with dichloromethane (10 mL×3), filtrate was concentrated in vacuo and purified as specified.

Example 06-14

Preparation of 3-((3-(1-(4-chlorobenzyl)-1H-1,2,3-triazol-4-yl)phenyl)amino)-2-methylcyclopent-2-enone (06-14)

Using the general procedure (4-chlorophenyl)methanamine (0.085 g, 0.6 mmol) was stirred for 60 h. Purification was done by combiflash (SiO$_2$, 2%-7% methanol in dichloromethane) to yield 3-((3-(1-(4-chlorobenzyl)-1H-1,2,3-triazol-4-yl)phenyl)amino)-2-methylcyclopent-2-enone (0.092 g, 41%). $^1$H NMR (600 MHz, MeOD) δ 8.39 (1H, bs), 7.72 (1H, s), 7.65 (1H, d, J=7.2 Hz), 7.46-7.38 (4H, m), 7.24 (1H, d, J=8.4 Hz), 5.64 (2H, s), 2.77 (2H, bs), 2.40-2.39 (2H, m), 1.68 (3H, s); LCMS m/z 379.2597 ([M+H$^+$], C$_{21}$H$_{20}$ClN$_4$O requires 379.1321).

Example 06-15

Preparation of 3-((3-(1-(4-methoxybenzyl)-1H-1,2,3-triazol-4-yl)phenyl)amino)-2-methylcyclopent-2-enone (06-15)

Using the general procedure (4-methoxyphenyl)methanamine (0.082 g, 0.6 mmol) was stirred for 60 h. Purification was done by combiflash (SiO$_2$, 3%-7% methanol in dichloromethane) to yield 3-((3-(1-(4-methoxybenzyl)-1H-1,2,3-triazol-4-yl)phenyl)amino)-2-methylcyclopent-2-enone (0.117 g, 53%). $^1$H NMR (600 MHz, MeOD) δ 8.32 (1H, bs), 7.71 (1H, s), 7.64 (1H, d, J=7.2 Hz), 7.44 (1H, t, J=7.8 Hz), 7.34 (2H, d, J=8.4 Hz), 7.24 (1H, d, J=7.2 Hz), 6.94

| Example 06-# | TITLE COMPOUND NAME | R |
|---|---|---|
| 14 | 3-((3-(1-(4-chlorobenzyl)-1H-1,2,3-triazol-4-yl)phenyl)amino)-2-methylcyclopent-2-enone | CH$_2$ 4-ClPh |
| 15 | 3-((3-(1-(4-methoxybenzyl)-1H-1,2,3-triazol-4-yl)phenyl)amino)-2-methylcyclopent-2-enone | CH$_2$ 4-OCH$_3$Ph |
| 16 | 2-methyl-3-((3-(1-(naphthalen-1-ylmethyl)-1H-1,2,3-triazol-4-yl)phenyl)amino)cyclopent-2-enone | CH$_2$ 1-Naphthyl |
| 17 | 2-methyl-3-((3-(1-(4-(trifluoromethyl)benzyl)-1H-1,2,3-triazol-4-yl)phenyl)amino)cyclopent-2-enone | CH$_2$ 4-CF$_3$Ph |
| 18 | 2-methyl-3-((3-(1-(1-phenylethyl)-1H-1,2,3-triazol-4-yl)phenyl)amino)cyclopent-2-enone | CH$_2$ CH(CH$_3$)Ph |
| 19 | 2-methyl-3-((3-(1-phenethyl-1H-1,2,3-triazol-4-yl)phenyl)amino)cyclopent-2-enone | CH$_2$ CH$_2$Ph |
| 20 | 3-((3-(1-(2-chlorobenzyl)-1H-1,2,3-triazol-4-yl)phenyl)amino)-2-methylcyclopent-2-enone | CH$_2$ 2-ClPh |
| 21 | 3-((3-(1-(3-chlorobenzyl)-1H-1,2,3-triazol-4-yl)phenyl)amino)-2-methylcyclopent-2-enone | CH$_2$ 3-ClPh |
| 22 | 3-((3-(1-(2-methoxybenzyl)-1H-1,2,3-triazol-4-yl)phenyl)amino)-2-methylcyclopent-2-enone | CH$_2$ 2-OCH$_3$Ph |
| 23 | 3-((3-(1-(3-methoxybenzyl)-1H-1,2,3-triazol-4-yl)phenyl)amino)-2-methylcyclopent-2-enone | CH$_2$ 3-OCH$_3$Ph |
| 24 | 2-methyl-3-((3-(1-(3-methylbenzyl)-1H-1,2,3-triazol-4-yl)phenyl)amino)cyclopent-2-enone | CH$_2$ 3-CH$_3$Ph |
| 25 | 3-((3-(1-(4-bromobenzyl)-1H-1,2,3-triazol-4-yl)phenyl)amino)-2-methylcyclopent-2-enone | CH$_2$ 4-BrPh |
| 26 | (R)-2-(4-(3-((2-methyl-3-oxocyclopent-1-en-1-yl)amino)phenyl)-1H-1,2,3-triazol-1-yl)-3-phenylpropanoic acid | CH(COOH)Bn |
| 27 | (S)-2-(4-(3-((2-methyl-3-oxocyclopent-1-en-1-yl)amino)phenyl)-1H-1,2,3-triazol-1-yl)-3-phenylpropanoic acid | CH(COOH)Bn |

(2H, d, J=8.4 Hz), 5.56 (2H, s), 3.78 (3H, s), 2.76 (2H, bs), 2.39 (2H, bs), 1.68 (3H, s); LCMS m/z 375.3921 ([M+H$^+$], $C_{22}H_{23}N_4O_2$ requires 375.1816).

Example 06-16

Preparation of 2-methyl-3-((3-(1-(naphthalen-1-ylmethyl)-1H-1,2,3-triazol-4-yl)phenyl)amino)cyclopent-2-enone (06-16)

Using the general procedure Naphthalen-1-ylmethanamine (0.094 g, 0.6 mmol) was stirred for 40 h. Purification was done by combiflash (SiO$_2$, 2%-7% methanol in dichloromethane) to yield 2-methyl-3-((3-(1-(naphthalen-1-ylmethyl)-1H-1,2,3-triazol-4-yl)phenyl)amino)cyclopent-2-enone (0.220 g, 94%). $^1$H NMR (600 MHz, MeOD) δ 8.24 (1H, bs), 8.12 (1H, d, J=7.8 Hz), 7.89 (2H, d, J=6.6 Hz), 7.65 (1H, bs), 7.57-7.48 (5H, m), 7.37 (1H, t, J=3.6 Hz), 7.17 (2H, d, J=7.2 Hz), 6.08 (2H, s), 2.67 (2H, bs), 2.31 (2H, bs), 1.65 (3H, s); LCMS m/z 395.2784 ([M+H$^+$], $C_{25}H_{23}N_4O$ requires 395.1867).

Example 06-17

Preparation of 2-methyl-3-((3-(1-(4-(trifluoromethyl)benzyl)-1H-1,2,3-triazol-4-yl)phenyl)amino)cyclopent-2-enone (06-17)

Using the general procedure (4-(trifluoromethyl)phenyl)methanamine (0.105 g, 0.6 mmol) was stirred for 40 h. Purification was done by combiflash (SiO$_2$, 3%-5% methanol in dichloromethane) to yield 2-methyl-3-((3-(1-(4-(trifluoromethyl)benzyl)-1H-1,2,3-triazol-4-yl)phenyl)amino)cyclopent-2-enone (0.201 g, 81%). $^1$H NMR (600 MHz, MeOD) δ 8.43 (1H, bs), 7.72-7.63 (4H, m), 7.52 (2H, d, J=7.2 Hz), 7.42 (1H, t, J=7.2 Hz), 7.22 (1H, d, J=7.2 Hz), 5.74 (2H, s), 2.72 (2H, bs), 2.36 (2H, bs), 1.66 (3H, s); LCMS m/z 413.4756 ([M+H$^+$], $C_{22}H_{20}F_3N_4O$ requires 413.1584).

Example 06-18

Preparation of 2-methyl-3-((3-(1-(1-phenylethyl)-1H-1,2,3-triazol-4-yl)phenyl)amino)cyclopent-2-enone (06-18)

Using the general procedure 1-phenylethanamine (0.073 g, 0.6 mmol) was stirred for 40 h. Purification was done by combiflash (SiO$_2$, 2%-7% methanol in dichloromethane) to yield 2-methyl-3-((3-(1-(1-phenylethyl)-1H-1,2,3-triazol-4-yl)phenyl)amino)cyclopent-2-enone (0.162 g, 75%). $^1$H NMR (600 MHz, MeOD) δ 8.44 (1H, bs), 7.72 (1H, s), 7.65 (1H, d, J=7.2 Hz), 7.43 (1H, t, J=7.8 Hz), 7.38-7.31 (5H, m), 7.22 (1H, d, J=7.8 Hz), 5.94-5.93 (1H, m), 2.73 (2H, bs), 2.36 (2H, bs), 2.00 (3H, d, J=6.6 Hz), 1.67 (3H, s); LCMS m/z 359.4603 ([M+H$^+$], $C_{22}H_{23}N_4O$ requires 359.1867).

Example 06-19

Preparation of 2-methyl-3-((3-(1-phenethyl-1H-1,2,3-triazol-4-yl)phenyl)amino)cyclopent-2-enone (06-19)

Using the general procedure 2-phenylethanamine (0.073 g, 0.6 mmol) was stirred for 40 h. Purification was done by combiflash (SiO$_2$, 2%-7% methanol in dichloromethane) to yield 2-methyl-3-((3-(1-phenethyl-1H-1,2,3-triazol-4-yl)phenyl)amino)cyclopent-2-enone (0.132 g, 61%). $^1$H NMR (600 MHz, MeOD) δ 8.14 (1H, bs), 7.65 (1H, s), 7.59 (1H, d, J=6 Hz), 7.45-7.44 (1H, m), 7.26-7.17 (6H, m), 4.70-4.69 (2H, m), 3.28-3.27 (2H, m), 2.77 (2H, bs), 2.41 (2H, bs), 1.69 (3H, s); LCMS m/z 359.4236 ([M+H$^+$], $C_{22}H_{23}N_4O$ requires 359.1867).

Example 06-20

Preparation of 3-((3-(1-(2-chlorobenzyl)-1H-1,2,3-triazol-4-yl)phenyl)amino)-2-methylcyclopent-2-enone (06-20)

Using the general procedure (2-chlorophenyl)methanamine (0.085 g, 0.6 mmol) was stirred for 40 h. Purification was done by combiflash (SiO$_2$, 2%-7% methanol in dichloromethane) to yield 3-((3-(1-(2-chlorobenzyl)-1H-1,2,3-triazol-4-yl)phenyl)amino)-2-methylcyclopent-2-enone (0.116 g, 65%). $^1$H NMR (600 MHz, MeOD) δ 8.35 (1H, bs), 7.73 (1H, s), 7.66 (1H, d, J=7.2 Hz), 7.50-7.31 (5H, m), 7.25 (1H, d, J=7.8 Hz), 5.79 (2H, s), 2.77 (2H, bs), 2.40 (2H, bs), 1.69 (3H, s); LCMS m/z 379.2943 ([M+H$^+$], $C_{21}H_{20}ClN_4O$ requires 379.1321).

Example 06-21

Preparation of 3-((3-(1-(3-chlorobenzyl)-1H-1,2,3-triazol-4-yl)phenyl)amino)-2-methylcyclopent-2-enone (06-21)

Using the general procedure (3-chlorophenyl)methanamine (0.085 g, 0.6 mmol) was stirred for 40 h. Purification was done by combiflash (SiO$_2$, 2%-7% methanol in dichloromethane) to yield 3-((3-(1-(3-chlorobenzyl)-1H-1,2,3-triazol-4-yl)phenyl)amino)-2-methylcyclopent-2-enone (0.130 g, 73%). $^1$H NMR (600 MHz, MeOD) δ 8.41 (1H, bs), 7.73 (1H, s), 7.66 (1H, bs), 7.45-7.26 (6H, m), 5.65 (2H, s), 2.77 (2H, bs), 2.40 (2H, bs), 1.68 (3H, s); LCMS m/z 379.2314 ([M+H$^+$], $C_{21}H_{20}ClN_4O$ requires 379.1321).

Example 06-22

Preparation of 3-((3-(1-(2-methoxybenzyl)-1H-1,2,3-triazol-4-yl)phenyl)amino)-2-methylcyclopent-2-enone (06-22)

Using the general procedure (2-methoxyphenyl)methanamine (0.085 g, 0.6 mmol) was stirred for 40 h. Purification was done by combiflash (SiO$_2$, 2%-7% methanol in dichloromethane) to yield 3-((3-(1-(2-methoxybenzyl)-1H-1,2,3-triazol-4-yl)phenyl)amino)-2-methylcyclopent-2-enone (0.059 g, 33%). $^1$H NMR (600 MHz, MeOD) δ 8.26 (1H, bs), 7.70 (1H, s), 7.64 (1H, d, J=7.8 Hz), 7.43 (1H, dt, J=3, 7.8 Hz), 7.38-7.35 (1H, m), 7.27-7.22 (2H, m), 7.04 (1H, dd, J=2.4, 8.1 Hz), 6.98-6.97 (1H, m), 5.62 (2H, d, J=3 Hz), 3.88 (3H, t, J=1.8 Hz), 2.76 (2H, bs), 2.40-2.38 (2H, m), 1.68 (3H, s); LCMS m/z 375.4430 ([M+H$^+$], $C_{22}H_{23}N_4O_2$ requires 375.1816).

Example 06-23

Preparation of 3-((3-(1-(3-methoxybenzyl)-1H-1,2,3-triazol-4-yl)phenyl)amino)-2-methylcyclopent-2-enone (06-23)

Using the general procedure (3-methoxyphenyl)methanamine (0.082 g, 0.6 mmol) was stirred for 40 h. Purification was done by combiflash (SiO$_2$, 3%-5% methanol in dichloromethane) to yield 3-((3-(1-(3-methoxybenzyl)-1H-1,2,3-triazol-4-yl)phenyl)amino)-2-methylcyclopent-2-enone (0.152 g, 86%). $^1$H NMR (600 MHz, MeOD) δ 8.36 (1H, bs), 7.72 (1H, s), 7.65 (1H, d, J=7.2 Hz), 7.45-7.24 (3H, m), 6.93-6.91 (3H, m), 5.61 (2H, s), 3.78 (3H, s), 2.76 (2H, bs), 2.39 (2H, bs), 1.68 (3H, s); LCMS m/z 375.4525 ([M+H$^+$], C$_{22}$H$_{23}$N$_4$O$_2$ requires 375.1816).

Example 06-24

Preparation of 2-methyl-3-((3-(1-(3-methylbenzyl)-1H-1,2,3-triazol-4-yl)phenyl)amino)cyclopent-2-enone (06-24)

Using the general procedure m-tolylmethanamine (0.073 g, 0.6 mmol) was stirred for 40 h. Purification was done by combiflash (SiO$_2$, 2%-7% methanol in dichloromethane) to yield 2-methyl-3-((3-(1-(3-methylbenzyl)-1H-1,2,3-triazol-4-yl)phenyl)amino)cyclopent-2-enone (0.144 g, 85%). $^1$H NMR (600 MHz, MeOD) δ 8.35 (1H, bs), 7.71 (1H, s), 7.65 (1H, d, J=7.8 Hz), 7.44 (1H, t, J=8.4 Hz), 7.27-7.15 (5H, m), 5.61 (2H, s), 2.76 (2H, bs), 2.39 (2H, bs), 2.34 (3H, s), 1.68 (3H, s); LCMS m/z 359.3305 ([M+H$^+$], C$_{22}$H$_{23}$N$_4$O requires 359.1867).

Example 06-25

Preparation of 3-((3-(1-(4-bromobenzyl)-1H-1,2,3-triazol-4-yl)phenyl)amino)-2-methylcyclopent-2-enone (06-25)

Using the general procedure (4-bromophenyl)methanamine (0.112 g, 0.6 mmol) was stirred for 40 h. Purification was done by combiflash (SiO$_2$, 2%-7% methanol in dichloromethane) to yield 3-((3-(1-(4-bromobenzyl)-1H-1,2,3-triazol-4-yl)phenyl)amino)-2-methylcyclopent-2-enone (0.147 g, 74%). $^1$H NMR (600 MHz, MeOD) δ 8.39 (1H, s), 7.72 (1H, t, J=1.8 Hz), 7.65 (1H, d, J=7.2 Hz), 7.56-7.55 (2H, m), 7.45 (1H, t, J=7.8 Hz), 7.31 (2H, d, J=8.4 Hz), 7.25 (1H, dd, J=1.8, 7.8 Hz), 5.63 (2H, s), 2.77-2.76 (2H, m), 2.41-2.39 (2H, m), 1.68 (3H, s); LCMS m/z 423.1297 ([M+H$^+$], C$_{21}$H$_{20}$BrN$_4$O requires 423.0815).

Example 06-26

Preparation of (R)-2-(4-(3-((2-methyl-3-oxocyclopent-1-en-1-yl)amino)phenyl)-1H-1,2,3-triazol-1-yl)-3-phenylpropanoic acid (06-26)

Using the general procedure (R)-2-amino-3-phenylpropanoic acid (0.099 g, 0.6 mmol) was stirred for 40 h. The reaction mixture acidified to pH 1 with 1 M HCl, filtered and washed with dichloromethane to give (R)-2-(4-(3-((2-methyl-3-oxocyclopent-1-en-1-yl)amino)phenyl)-1H-1,2,3-triazol-1-yl)-3-phenylpropanoic acid (0.091 g, 48%). $^1$H NMR (600 MHz, MeOD) δ 8.38 (1H, s), 7.67 (1H, s), 7.61 (1H, d, J=7.8 Hz), 7.44 (1H, t, J=7.8 Hz), 7.24-7.13 (6H, m), 5.71 (1H, dd, J=4.2, 10.5 Hz), 3.69 (1H, dd, J=4.8, 14.4 Hz), 3.56 (1H, dd, J=10.8, 15.9 Hz), 2.77 (2H, bs), 2.41-2.40 (2H, m), 1.69 (3H, s); LCMS m/z 403.3882 ([M+H$^+$], C$_{23}$H$_{23}$N$_4$O$_3$ requires 403.1765).

Example 06-27

Preparation of (S)-2-(4-(3-((2-methyl-3-oxocyclopent-1-en-1-yl)amino)phenyl)-1H-1,2,3-triazol-1-yl)-3-phenylpropanoic acid (06-27)

Using the general procedure (S)-2-amino-3-phenylpropanoic acid (0.099 g, 0.6 mmol) was stirred for 40 h. The reaction mixture acidified to pH 1 with 1 M HCl, filtered and washed with dichloromethane to give (S)-2-(4-(3-((2-methyl-3-oxocyclopent-1-en-1-yl)amino)phenyl)-1H-1,2,3-triazol-1-yl)-3-phenylpropanoic acid (0.040 g, 21%). $^1$H NMR (600 MHz, MeOD) δ 8.38 (1H, d, J=3 Hz), 7.67 (1H, d, J=1.8 Hz), 7.62-7.60 (1H, m), 7.46-7.42 (1H, m), 7.24-7.13 (6H, m), 5.72-5.70 (1H, m), 3.69 (1H, dd, J=4.2, 14.4 Hz), 3.56 (1H, dd, J=10.8, 14.4 Hz), 2.78-2.77 (2H, m), 2.41-2.40 (2H, m), 1.69 (3H, s); LCMS m/z 403.4457 ([M+H$^+$], C$_{23}$H$_{23}$N$_4$O$_3$ requires 403.1765).

Example 06-28

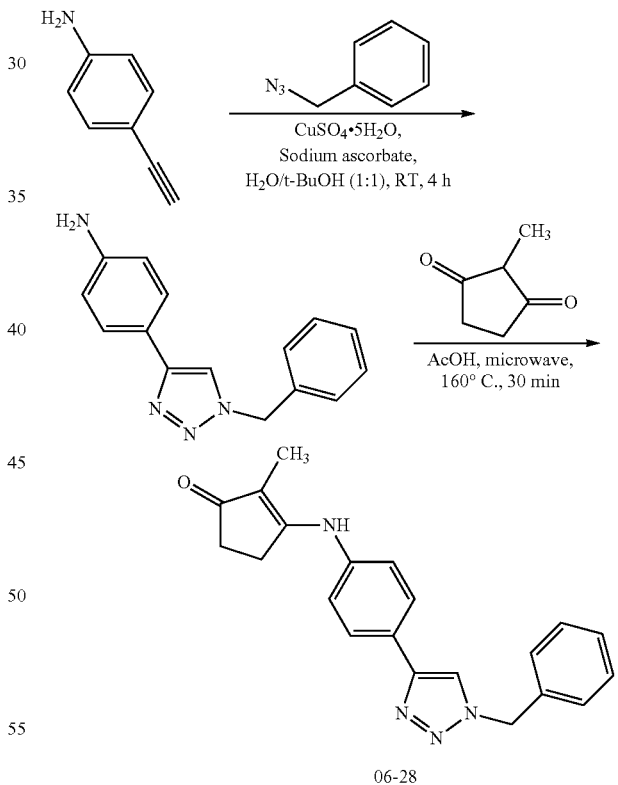

| Example 06-# | TITLE COMPOUND NAME |
|---|---|
| 28 | 3-((4-(1-benzyl-1H-1,2,3-triazol-4-yl)phenyl)amino)-2-methylcyclopent-2-enone |

Example 06-28

Preparation of 3-((4-(4-benzyl-1H-1,2,3-triazol-1-yl)phenyl)amino)-2-methylcyclopent-2-enone (06-28)

To a suspension of 4-ethynylaniline (0.117 g, 0.998 mmol) and (azidomethyl)benzene (0.266 g, 1.996 mmol) in a mixture of water and tert-butyl alcohol (1:1, 4 mL) was added sodium ascorbate (0.095 mL, 0.099 mmol, 1 M solution in water), followed by copper (II) sulfate pentahydrate (0.002 g, 0.009 mmol). The heterogeneous mixture was stirred at RT for 4 h. The reaction mixture was diluted with 5 mL water and cooled in an ice bath. The precipitate formed was filtered and washed with water and dichloromethane, extracted with dichloromethane, dried ($Na_2SO_4$) and purified by combiflash ($SiO_2$, 2%-4% methanol in dichloromethane) to give 4-(1-benzyl-1H-1,2,3-triazol-4-yl)aniline (0.042 g, 17%) which was used for the next step without further purification. LCMS m/z 251.3345 ([M+H$^+$], $C_{20}H_{20}N_5O$ requires 251.1292).

2-methylcyclopentane-1,3-dione (0.019 g, 0.167 mmol), 4-(4-benzyl-1H-1,2,3-triazol-1-yl)aniline (0.042 g, 0.167 mmol), acetic acid (0.019 mL, 0.334 mmol), were added to a 0.5-2 mL Biotage® microwave vial. The biotage Intiator® microwave reactor was programmed to heat at 160° C. for 30 min. The reaction mixture was purified by combiflash ($SiO_2$, 2%-5% methanol in dichloromethane), to give 3-((4-(4-benzyl-1H-1,2,3-triazol-1-yl)phenyl)amino)-2-methylcyclopent-2-enone (0.032 g, 55%). $^1$H NMR (600 MHz, MeOD) δ 8.31 (1H, s), 7.83-7.82 (2H, m), 7.38-7.32 (6H, m), 5.64 (2H, s), 2.76 (2H, bs), 2.39 (2H, bs), 1.68 (3H, s); LCMS m/z 345.3646 ([M+H$^+$], $C_{21}H_{21}N_4O$ requires 345.1710).

Biological Assays

Fluorescence Anisotropy Binding Assay

Expression and purification of the first bromodomain (BrD1) of human BRD4 in poly-His tag form was performed using a procedure described in the literature [See Zeng et al. Structure 16, 643-652 (2008) and Zhang et al., J Biol Chem 287, 28840-28851 (2012).] The protein was purified by using affinity chromatography on a nickel-IDA column (Invitrogen), followed by the removal of poly-His tag by thrombin cleavage.

Binding affinity of the newly synthesized compounds to the BRD4 BrD1 was assessed in a fluorescence anisotropy assay using a fluorescein isothiocyanate (FITC)-labeled MS417 as an assay probe (Zhang et al. 2008 op.cit.). Competition binding was performed with a BrD protein (0.25 to 1 μM) and the fluorescent probe (80 nM), and increasing concentration of unlabeled competing ligand in a PBS buffer (pH 7.4) in total volume of 80 μL. Measurements were obtained after 1 hour incubation of the fluorescent ligand and the protein at 25° C. with Safire 2 microplate reader (Tecan). In the assay, fluorescent ligand concentration was <2$K_d$, and protein concentration was set at which 50-80% of fluorescent ligand is bound. Dissociation constant of a competing ligand was calculated with the correction to Cheng-Prussoff equation introduced by Nikolovska-Coleska and colleagues [Nikolovska-Coleska, Z. et al., Anal Biochem 332, 261-273 (2004). Assuming one-site competitive binding model, the equation used to calculate $K_i$'s from $IC_{50}$ values recovered from fitting data using Prism:

$$K_i = \frac{[I_{50}]}{\frac{[L_{50}]}{K_d} + \frac{[P_0]}{K_d} + 1},$$

where [$I_{50}$] is the concentration of free inhibitor at 50% inhibition, [$L_{50}$], the concentration of free labeled ligand at 50% inhibition, and [$P_0$], concentration of free protein at 0% inhibition. Note that $K_d$ for each protein-probe pair is the limit of resolvable $K_i$ in a competition assay. The binding results for examples above are listed in Table 1.

TABLE 1

| Examples 01-# | BRD4_1 IC$_{50}$ | BRD4_2 IC$_{50}$ | Examples 02-# | BRD4_1 IC$_{50}$ | BRD4_2 IC$_{50}$ | Examples 03-# | BRD4_1 IC$_{50}$ | BRD4_2 IC$_{50}$ |
|---|---|---|---|---|---|---|---|---|
| 01-1 | ++ | ++ | 02-1 | ++ | + | 03-1 | ++ | ++ |
| 01-2 | ++ | ++ | 02-2 | ++ | ++ | 03-2 | + | + |
| 01-3 | + | ++ | 02-3 | + | + | 03-3 | n.t. | n.t. |
| 01-4 | ++ | + | 02-4 | + | + | 03-4 | n.t. | n.t. |
| 01-5 | ++ | ++ | 02-5 | + | + | 03-5 | n.t. | n.t. |
| 01-6 | + | + | 02-6 | ++ | + | 03-6 | ++ | ++ |
| 01-7 | + | + | 02-7 | ++ | + | 03-7 | ++ | ++ |
| 01-8 | n.t. | n.t. | 02-8 | ++ | ++ | 03-8 | n.t. | n.t. |
| 01-9 | ++ | + | 02-9 | + | + | 03-9 | ++ | ++ |
| 01-10 | + | + | 02-10 | ++ | ++ | 03-10 | ++ | ++ |
| 01-11 | ++ | ++ | 02-11 | ++ | + | 03-11 | ++ | + |
| 01-12 | ++ | ++ | 02-12 | ++ | ++ | 03-12 | n.t. | n.t. |
| 01-13 | ++ | ++ | 02-13 | ++ | ++ | 03-13 | n.t. | n.t. |
| 01-14 | ++ | ++ | 02-14 | ++ | ++ | 03-14 | n.t. | n.t. |
| 01-15 | n.t. | n.t. | 02-15 | ++ | ++ | 03-15 | n.t. | n.t. |
| 01-16 | + | + | 03-16 | ++ | ++ | | | |
| 01-17 | n.t. | n.t. | 03-17 | n.t. | n.t. | | | |
| 01-18 | + | + | 03-18 | ++ | ++ | | | |
| 01-19 | + | + | 03-19 | ++ | ++ | | | |
| 01-20 | + | + | 03-20 | + | + | | | |
| 01-21 | ++ | + | 03-21 | n.t. | n.t. | | | |
| 01-22 | ++ | ++ | 03-22 | n.t. | n.t. | | | |
| 01-23 | + | + | 03-23 | ++ | ++ | | | |
| 01-24 | ++ | + | | | | | | |
| 01-25 | ++ | + | | | | | | |
| 01-26 | ++ | ++ | | | | | | |
| 01-27 | ++ | ++ | | | | | | |

TABLE 1-continued

| | | |
|---|---|---|
| 01-28 | + | + |
| 01-29 | + | + |
| 01-30 | ++ | ++ |
| 01-31 | ++ | ++ |
| 01-32 | + | + |
| 01-33 | + | + |
| 01-34 | + | + |
| 01-35 | ++ | ++ |
| 01-36 | + | + |
| 01-37 | + | + |
| 01-38 | n.t. | n.t. |
| 01-39 | n.t. | n.t. |
| 01-40 | n.t. | n.t. |
| 01-41 | ++ | ++ |
| 01-42 | +++ | ++ |
| 01-43 | ++ | ++ |
| 01-44 | ++ | + |
| 01-45 | ++ | ++ |
| 01-46 | ++ | ++ |
| 01-47 | + | + |
| 01-48 | ++ | + |
| 01-49 | ++ | + |
| 01-50 | + | + |
| 01-51 | ++ | + |
| 01-52 | ++ | ++ |
| 01-53 | +++ | ++ |
| 01-54 | ++ | ++ |
| 01-55 | ++ | ++ |
| 01-56 | ++ | + |
| 01-57 | ++ | ++ |
| 01-58 | ++ | ++ |
| 01-59 | ++ | + |
| 01-60 | ++ | ++ |
| 01-61 | + | + |
| 01-62 | +++ | ++ |
| 01-63 | ++ | ++ |
| 01-64 | +++ | ++ |

| Examples 04-# | BRD4_1 IC$_{50}$ | BRD4_2 IC$_{50}$ | Examples 05-# | BRD4_1 IC$_{50}$ | BRD4_2 IC$_{50}$ | Examples 06-# | BRD4_1 IC$_{50}$ | BRD4_2 IC$_{50}$ |
|---|---|---|---|---|---|---|---|---|
| 04-1 | ++ | ++ | 05-1 | n.t. | n.t. | 06-1 | ++ | + |
| 04-2 | ++ | ++ | 05-2 | n.t. | n.t. | 06-2 | ++ | ++ |
| 04-3 | ++ | + | 05-3 | n.t. | n.t. | 06-3 | n.t. | n.t. |
| 04-4 | ++ | ++ | 05-4 | n.t. | n.t. | 06-4 | +++ | ++ |
| 04-5 | ++ | ++ | 05-5 | n.t. | n.t. | 06-5 | n.t. | n.t. |
| 04-6 | ++ | + | 05-6 | n.t. | n.t. | 06-6 | n.t. | n.t. |
| 04-7 | ++ | + | 05-7 | n.t. | n.t. | 06-7 | n.t. | n.t. |
| 04-8 | ++ | ++ | 05-8 | n.t. | n.t. | 06-8 | +++ | ++ |
| 04-9 | n.t. | n.t. | 05-9 | n.t. | n.t. | 06-9 | n.t. | n.t. |
| 04-10 | n.t. | n.t. | 05-10 | n.t. | n.t. | 06-10 | +++ | ++ |
| 04-11 | n.t. | n.t. | 05-11 | n.t. | n.t. | 06-11 | n.t. | n.t. |
| 04-12 | n.t. | n.t. | 05-12 | ++ | ++ | 06-12 | n.t. | n.t. |
| 04-13 | ++ | ++ | 05-13 | n.t. | n.t. | 06-13 | n.t. | n.t. |
| 04-14 | +++ | ++ | 05-14 | +++ | ++ | 06-14 | n.t. | n.t. |
| 04-15 | +++ | ++ | 05-15 | +++ | ++ | 06-15 | +++ | ++ |
| 04-16 | ++ | ++ | 05-16 | n.t. | n.t. | 06-16 | n.t. | n.t. |
| 04-17 | +++ | ++ | 05-17 | ++ | ++ | 06-17 | n.t. | n.t. |
| 04-18 | +++ | ++ | 05-18 | +++ | ++ | 06-18 | n.t. | n.t. |
| 04-19 | +++ | ++ | 05-19 | n.t. | n.t. | 06-19 | n.t. | n.t. |
| 04-20 | +++ | ++ | 05-20 | n.t. | n.t. | 06-20 | n.t. | n.t. |
| 04-21 | +++ | ++ | 05-21 | n.t. | n.t. | 06-21 | n.t. | n.t. |
| 04-22 | ++ | ++ | 05-22 | n.t. | n.t. | 06-22 | n.t. | n.t. |
| 04-23 | n.t. | n.t. | 05-23 | n.t. | n.t. | 06-23 | n.t. | n.t. |
| 04-24 | n.t. | n.t. | 05-24 | n.t. | n.t. | 06-24 | n.t. | n.t. |
| 04-25 | n.t. | n.t. | 05-25 | n.t. | n.t. | 06-25 | n.t. | n.t. |
| 04-26 | + | + | 05-26 | n.t. | n.t. | 06-26 | n.t. | n.t. |
| 04-27 | n.t. | n.t. | 05-27 | n.t. | n.t. | 06-27 | n.t. | n.t. |
| 04-28 | n.t. | n.t. | 05-28 | n.t. | n.t. | 06-28 | +++ | ++ |
| 04-29 | n.t. | n.t. | 05-29 | n.t. | n.t. | | | |
| 04-30 | + | + | 05-30 | n.t. | n.t. | | | |
| 04-31 | n.t. | n.t. | 05-31 | n.t. | n.t. | | | |
| 04-32 | + | + | 05-32 | + | + | | | |
| 04-33 | n.t. | n.t. | 05-33 | + | + | | | |
| 04-34 | n.t. | n.t. | 05-34 | + | + | | | |
| 04-35 | n.t. | n.t. | 05-35 | + | + | | | |
| 04-36 | + | + | 05-36 | + | + | | | |
| 04-37 | n.t. | n.t. | 05-37 | +++ | + | | | |
| 04-38 | n.t. | n.t. | 05-38 | +++ | +++ | | | |
| 04-39 | n.t. | n.t. | 05-39 | +++ | ++ | | | |

TABLE 1-continued

| | | | | | |
|---|---|---|---|---|---|
| 04-40 | + | + | 05-40 | +++ | +++ |
| 04-41 | n.t. | n.t. | 05-41 | +++ | ++ |
| 04-42 | n.t. | n.t. | 05-42 | +++ | ++ |
| 04-43 | + | + | 05-43 | + | + |
| 04-44 | ++ | + | 05-44 | +++ | ++ |
| 04-45 | + | + | 05-45 | +++ | ++ |
| 04-46 | ++ | + | 05-46 | +++ | ++ |
| 04-47 | + | + | 05-47 | +++ | ++ |
| 04-48 | ++ | ++ | 05-48 | +++ | ++ |
| 04-49 | ++ | + | 05-49 | +++ | ++ |
| 04-50 | + | + | 05-50 | ++ | + |
| 04-51 | + | + | 05-51 | ++ | + |
| 04-52 | + | + | 05-52 | +++ | ++ |
| 04-53 | ++ | ++ | 05-53 | ++ | ++ |
| 04-54 | ++ | ++ | 05-54 | +++ | +++ |
| 04-55 | ++ | ++ | 05-55 | +++ | ++ |
| 04-56 | ++ | ++ | 05-56 | +++ | +++ |
| 04-57 | ++ | ++ | 05-57 | +++ | +++ |
| 04-58 | ++ | ++ | 05-58 | +++ | +++ |
| 04-59 | ++ | ++ | 05-59 | +++ | +++ |
| 04-60 | ++ | ++ | 05-60 | +++ | +++ |
| 04-61 | ++ | ++ | 05-61 | +++ | +++ |
| 04-62 | ++ | ++ | 05-62 | +++ | ++ |
| 04-63 | n.t. | n.t. | 05-63 | +++ | ++ |
| 04-64 | n.t. | n.t. | 05-64 | +++ | ++ |
| 04-65 | ++ | ++ | 05-65 | +++ | ++ |
| 04-66 | ++ | ++ | 05-66 | +++ | +++ |
| 04-67 | +++ | + | 05-67 | +++ | +++ |
| 04-68 | ++ | ++ | 05-68 | +++ | ++ |
| 04-69 | +++ | + | 05-69 | +++ | ++ |
| 04-70 | ++ | ++ | 05-70 | +++ | + |
| 04-71 | ++ | ++ | 05-71 | +++ | ++ |
| 04-72 | +++ | ++ | 05-72 | +++ | +++ |
| 04-73 | ++ | ++ | 05-73 | ++ | ++ |
| 04-74 | ++ | ++ | 05-74 | +++ | +++ |
| 04-75 | n.t. | n.t. | 05-75 | +++ | ++ |
| 04-76 | n.t. | n.t. | 05-76 | ++ | + |
| 04-77 | ++ | + | 05-77 | ++ | ++ |
| 04-78 | ++ | ++ | 05-78 | +++ | ++ |
| 04-79 | ++ | ++ | 05-79 | ++ | + |
| 04-80 | ++ | ++ | 05-80 | +++ | ++ |
| 04-81 | ++ | ++ | 05-81 | +++ | ++ |
| 04-82 | ++ | ++ | 05-82 | +++ | + |
| 04-83 | ++ | ++ | 05-83 | ++ | + |
| 04-84 | ++ | ++ | 05-84 | ++ | + |
| 04-85 | ++ | ++ | 05-85 | +++ | + |
| 04-86 | ++ | ++ | | | |
| 04-87 | n.t. | n.t. | | | |
| 04-88 | n.t. | n.t. | | | |
| 04-89 | +++ | ++ | | | |
| 04-90 | n.t. | n.t. | | | |
| 04-91 | ++ | ++ | | | |
| 04-92 | ++ | + | | | |
| 04-93 | ++ | ++ | | | |
| 04-94 | n.t. | n.t. | | | |
| 04-95 | + | + | | | |
| 04-96 | ++ | + | | | |
| 04-97 | ++ | + | | | |
| 04-98 | + | + | | | |
| 04-99 | ++ | ++ | | | |
| 04-100 | n.t. | n.t. | | | |
| 04-101 | n.t. | n.t. | | | |
| 04-102 | n.t. | n.t. | | | |
| 04-103 | n.t. | n.t. | | | |
| 04-104 | +++ | ++ | | | |
| 04-105 | +++ | ++ | | | |
| 04-106 | +++ | ++ | | | |

Note:
n.t. = not tested;
(+) = >10 uM;
(++) = 1-10 uM;
(+++) = <1 uM

LPS-Induced IL-6 Secretion in Murine Macrophage Raw264.7 Cells RAW264.7 cells were cultivated in Dulbecco's modified Eagle medium (DMEM) (Hyclone, Logan, Utah) supplemented with 10% FBS (fetal bovine serum) (Hyclone, Logan, Utah) at 37° C. in a humidified atmosphere of 5% $CO_2$. Cells in 96-well plates (0.1 ml, $3\times10^5$ cells/ml) were treated with the test compounds. After 30 min, all supernatants were removed and cells were treated with LPS (lipopolysaccharide) (1 µg/ml) (Sigma-Aldrich Chemical Co., St. Louis, Mo.) and compounds. After 24 hours, the supernatant was collected and mouse IL-6 protein level was measured using ELISA (enzyme-linked immunosorbent assay) (Thermo Scientific, Pittsburgh, Pa.). The compounds dissolved in DMSO were diluted with culture medium to concentrations from 0.28 to 50,000 nM. The final concentration of DMSO was adjusted to 0.05% (v/v). The assay was measured by an absorption reading at 570 nm using EnVison 2104 Multilabel Reader (PerkinElmer, Inc., Waltham, Mass.). Each experiment was performed at least in triplicate, and plotted using Prim, and an $IC_{50}$ value was calculated. Examples 04-19 and 04-20 were tested in this assay and found to have $IC_{50}$ values in the range of 0.2-1 µM.

LPS-Induced Transcriptional Activation of Cytokines in Murine Macrophage Cells RAW264.7 cells were cultivated with or without a treatment of the compounds as described above. Total RNA was isolated the cells using TRIzol reagent (Gibco, Grand Island, N.Y.) for homogenization. The concentration and integrity of RNA were determined by measuring absorbance at a 260 nm/280 nm ratio. Quantitative PCR was performed to determine the mRNA transcript levels of cytokines IL-6, IL-1β and TNFα with specific primers for these target genes. Each experiment was performed at least in triplicate, and plotted using Prim, and an $IC_{50}$ value was calculated. Examples 01-36, 04-15, 04-17, 04-19, 04-20, 04-89, 04-91, 04-98, 05-15, and 06-4 were tested in this assay and found to have $IC_{50}$ values in the range of 0.1-5 µM in inhibition of transcriptional activation of the cytokines IL-6, IL-1β and TNFα.

LPS-Stimulated Nitric Oxide (NO) Release in Murine Macrophage RAW264.7 Cells

RAW264.7 cells was cultivated in DMEM supplemented with 10% FBS at 37° C. in a humidified atmosphere of 5% $CO_2$. Cells in 96-well plates (0.1 ml, $3 \times 10^5$ cells/ml) were treated with the test compounds. After 30 min, all supernatants were removed and cells were treated with LPS (1 µg/ml) and the test compounds. After 24 hours, the level of nitrite was measured using Griess reaction G2930 (Promega Corp., Madison, Wis.) [see Bredt and Snyder, *Ann Rev Biochem* 63, 175-195 (1994)]. The test compounds dissolved in DMSO were diluted with culture medium to concentrations from 0.28 to 50,000 nM. The final concentration of DMSO was adjusted to 0.05% (v/v). The nitrite production was measured by spectrophotometry at 520 nm using EnVison 2104 Multilabel Reader (PerkinElmer, Inc., Waltham, Mass.). Each experiment was performed at least in triplicate and plotted using Prism. Examples 01-36, 04-15, 04-17, 04-19, 04-20, 04-89, 04-91, 04-98, 05-15, and 06-4 were tested in this assay and found to have $IC_{50}$ values in the range of 0.1-5 µM in inhibition of LPS-induced NO release in RAW264.7 cells.

ELISA Assay Assessing IL-8 Expression in BLBCs

Compounds of the Examples listed in Table 1 ("test compounds") were evaluated for their activity to inhibit expression of IL-8 in human basal-like breast cancer cells (BLBCs). The human BLBCs were cultivated in DMEM (Hyclone, Logan, Utah) supplemented with 10% FBS (Hyclone, Logan, Utah) at 37° C. in a humidified atmosphere of 5% $CO_2$. Upon 60-80% confluency of the culturing dish, the cells were trypsinized, centrifuged at 1000 rpm for 5 min, and resuspended with fresh culturing medium for seeding of cells in a 96-well plate (0.1 ml, $3 \times 10^5$ cells/ml) and incubated at the above-mentioned culturing conditions overnight. The following day upon cells adhesion to the plate bottom, all supernatants were carefully discarded followed by adding test compounds diluted in culturing medium. The test compounds dissolved in DMSO (Sigma-Aldrich Chemical Co., St. Louis, Mo.) were diluted with culturing medium in a 2-fold serial dilution from 1000 nM to 125 nM. The final concentration of DMSO was adjusted to 0.05% (v/v). At the end of 24-hour incubation, all supernatants were carefully removed and stored at −80° C. if the subsequent steps would not be performed immediately. The Human IL-8 ELISA Ready-Set-Go! ($2^{nd}$ generation) is used (Catalog No. 88-8086) against the prepared samples. The samples along with the Standard Human IL-8 Recombinant Protein (prepared in duplicates in a 2-fold serial dilution from 250 pg/ml to 2 pg/ml) were incubated overnight for maximal sensitivity. The assay was measured by an absorption reading at 450 nm using EnVision 2104 Multilabel Reader (PerkinElmer, Inc., Waltham, Mass.). Each experiment was performed at least in duplicate and plotted using Prism. The curve fitting equation used was "log(inhibitor) vs. response-variable slope (four parameters)". Examples 05-57, 05-68, and 05-70 were tested in this assay in a panel of human BLBC cells consisting of MDA-MB-435S, MDA-MB-231, BT-549, MDA-MB-157, HS578T, and SUM1315, and found to have $IC_{50}$ values in the range of 0.1-1 µM.

Human, Rat, and Mouse Microsome Stability Assay

Microsome stability assays were performed on Compounds of the Examples listed in Table 1 ("test compounds"). Human, rat, and mouse liver microsomal incubations were carried out at 37° C. with a final incubation volume of 135 µL. Human liver microsomes (mixed gender, Catalog No, H12610) were obtained from XenoTech. Rat liver microsomes (male Sprague-Dawley, Catalog No. 452501) were obtained from BD Gentest. Mouse liver microsomes (male CD1, Catalog No. 452701) were obtained from BD Gentest. Incubations were conducted using a test compound (initially dissolved in DMSO at 5 µM concentration) concentration of 0.5 µM and 0.25 mg/mL microsomal protein in 50 mM phosphate buffer at pH 7.4. Time zero samples were prepared by transferring 13.5 µL of compound-microsomal mix to the quench plates containing 45 µL of quench solution made of 10 nM Buspirone (Sigma) or 50 nM Carbutamide (Princeton Bio) as internal standard in 1:1 methanol:acetonitrile. An aliquot of 1.5 µL Nicotinamide adenine dinucleotide phosphate reduced tetrasodium salt (NADPH) was also added to the time zero plates. The reaction was then initiated by the addition of 13.5 µL NADPH to the compound-microsomal mix. At each of the remaining time points (5, 10, 15, 20, 30, 45 and 60 min) 15 µL of incubation mixture was added to 45 µL of quench solution. Samples were centrifuged for 15-30 minutes at 3800 rpm. Samples were then pooled for 6 per group. An aliquot of 60 µL of supernatant was transferred to 96-well plate, and a 5 µL aliquot was injected and analyzed by LC-MS (Applied Biosystems API 5500 QTrap). The intrinsic clearance of a compound was calculated by converting the peak area ratios (analyte peak area/IS peak area) to % parent remaining using the area ratio at time 0 as 100%. The slope (k) was determined from the plot of the % parent remaining versus incubation time, from which the half life (t½; minutes), intrinsic clearance (CLint; µL/min/mg protein for liver microsomes and µL/min/million cells for hepatocytes) and scaled intrinsic clearance (scaled CLint; L/h/kg) were then derived. Examples 01-41, 01-47, 05-57, 05-66, 05-68, and 05-70 were tested in this assay and found to have the intrinsic clearance CLint values in the range of 25-250 L/min/mg protein.

T-Cell-Transfer Colitis Study and Histopathology

Figure 2:
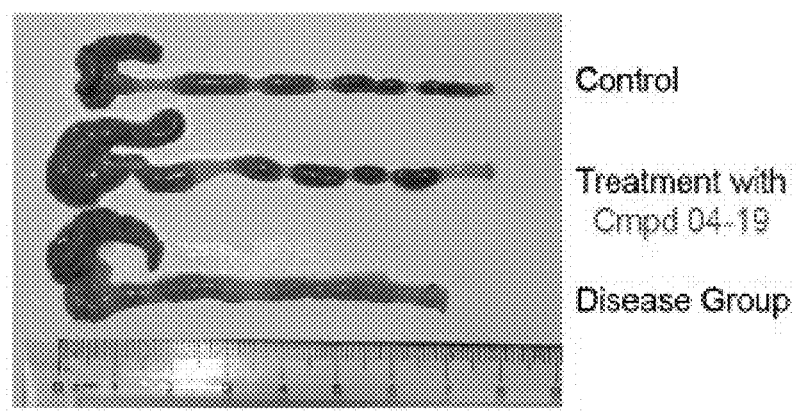
FIG. 2 is a gray-scale rendering of a photograph showing the gross morphology of the intestines for treated and untreated mice in which inflammatory colitis has been induced compared to a normal (control) intestine.

Compound of Example 04-19 inhibits the development of colitis in mice as examined in the established T-cell-transfer colitis model [See (Totsuka, T. et al. *J Immunol* 178, 4737-4748 (2007) and Powrie, F. et al. *International immunology* 5, 1461-1471 (1993).] Briefly, purified $CD4^+$ $CD45RB^{hi}$ T cells from C57BL/6 mice were injected intraperitoneally into $Rag1^{-/-}$ recipients ($5\times10^5$ cells per mouse in 200 μl sterile PBS per injection). Mice were weighed every week throughout the course of experiments. FIG. 1 presents the results in graph form. It can be seen that compound 04-19 significantly (P<0.05) inhibits the loss of body weight. After 5-7 weeks, mice were killed and colon tissues were excised. Tissues were fixed in 10% buffered formalin and paraffin embedded. The sections (5 m) of tissue samples stained with hematoxylin and eosin. All the slides were read and scored by an experienced pathologist without previous knowledge of the type of treatment. The degree of inflammation in the epithelium, submucosa and muscularis propria was scored separately. It can be seen from FIG. 2 that the gross morphology of the intestines is preserved in the treated mice and lost in the disease group.

What is claimed:

1. A method for treating a disease or disorder arising from inappropriate activity of proteins containing an acetyl-lysine residue, said method comprising administering to a patient in need thereof a therapeutically effective amount of a compound of formula I

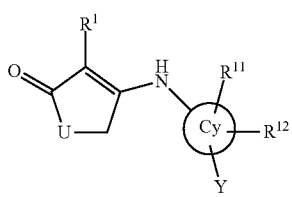

wherein:
U is $(CH_2)_n$, where n=1, 2 or 3;
$R^1$ is selected from the group consisting of: $(C_1-C_{10})$alkyl, substituted $(C_1-C_{10})$alkyl, and nitrile;
Cy is a carbocycle or heterocycle;
$R^{11}$ and $R^{12}$ are independently selected from the group consisting of: H, $(C_1-C_{10})$alkyl, $(C_1-C_{10})$perfluoroalkyl, halogen, nitrile, hydroxy, $(C_1-C_{10})$alkoxy, perfluoro$(C_1-C_{10})$alkoxy, $(C_1-C_{10})$alkylthio, amino, $(C_1-C_{10})$alkylamino, $(C_1-C_{10})$acylamino, aryl, heteroaryl, aminocarbonyl, carboxyl, and $(C_1-C_{10})$alkoxycarbonyl; or
taken together, $R^{11}$ and $R^{12}$ may form a 5, 6, or 7-membered carbocycle or heterocycle wherein said carbocycle or heterocycle may be optionally substituted with $R^2$;
$R^2$ is selected from the group consisting of: halogen, $(C_1-C_4)$alkyl, halo$(C_1-C_4)$alkyl, hydroxy, $(C_1-C_4)$alkoxy, halo$(C_1-C_4)$alkoxy, carboxy, amino, $(C_1-C_4)$alkylamino and di$(C_1-C_4)$alkylamino;
Y is selected from,

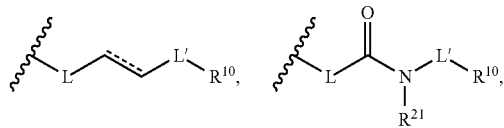

-continued

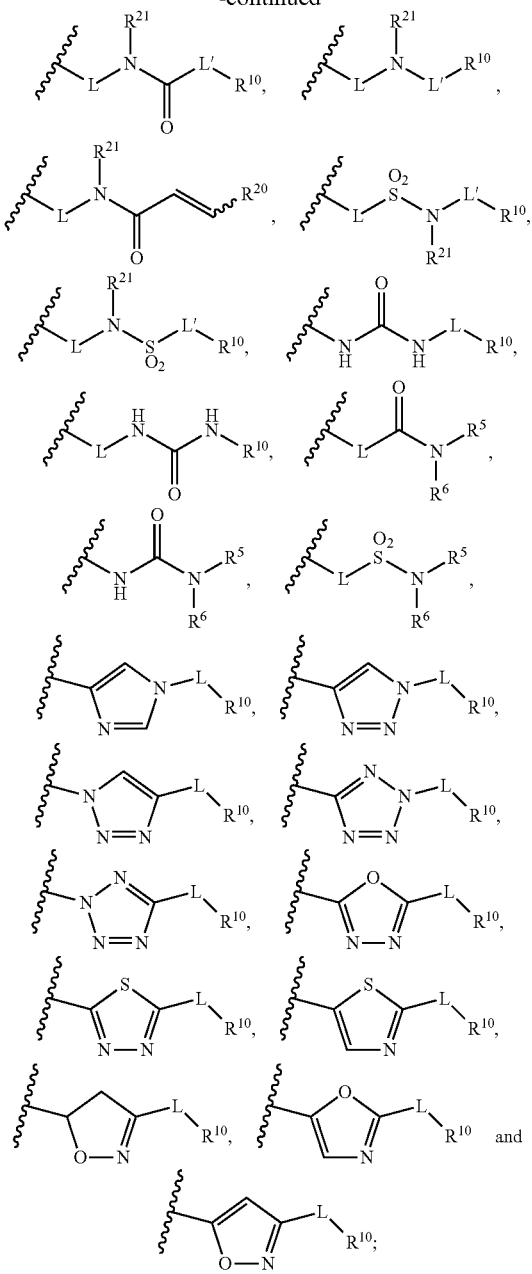

L and L' are independently a bond or $(CR^3R^4)_m$ where $R^3$ and $R^4$ are independently selected from the group consisting of H and $(C_1-C_4)$alkyl, and m is 1 or 2;
$R^{10}$ is chosen from alkyl, carbocycle and heterocycle, wherein said alkyl, carbocycle or heterocycle is optionally substituted with $R^7$ and/or $R^8$;
$R^{20}$ is $—C(=O)OR^{21}$;
$R^{21}$ is chosen from H and $(C_1-C_4)$alkyl;
$R^5$ and $R^6$ are independently selected from the group consisting of hydrogen, hydroxy, $(C_1-C_{10})$ hydrocarbyl, halo$(C_1-C_{10})$hydrocarbyl, and $(C_1-C_{10})$alkoxy;
$R^7$ and $R^8$ are independently selected from the group consisting of: hydroxy, halogen, $(C_1-C_4)$alkyl, halo$(C_1-C_4)$alkyl, hydroxy$(C_1-C_4)$alkyl, $(C_1-C_4)$alkoxy, halo$(C_1-C_4)$alkoxy, $(C_1-C_4)$alkylthio, $(C_1-C_4)$alkylcarbonyl, aryl, heteroaryl, cycloalkyl, heterocycloalkyl, cyano, oxo, $(C_1-C_4)$alkylsulfonyl, amino, $(C_1-C_4)$alkylamino, di$(C_1-C_4)$alkylamino, $(C_1-C_4)$acylamino, aminocarbonyl, carboxyl, and $(C_1-C_4)$alkoxycarbonyl, where each said alkyl, aryl, heteroaryl, cycloalkyl, or heterocycloalkyl, may be further optionally substituted with hydroxy, oxo, carboxy, carboxy$(C_1-C_4)$alkyl, hydroxy$(C_1-C_4)$alkyl, $(C_1-C_4)$alkoxy, $(C_1-C_4)$alkoxycarbonyl, $(C_1-C_4)$alkoxycarbonyl$(C_1-C_4)$alkyl, amino, $(C_1-C_4)$alkylamino, di $(C_1-C_4)$alkylamino, amido, $(C_1-C_4)$alkylamido, di $(C_1-C_4)$alkylamido, halogen, $(C_1-C_4)$alkyl, halo$(C_1-C_4)$alkyl, aryl, heteroaryl, heterocycloalkyl, or cycloalkyl;

or, taken together, $R^5$ and $R^6$, or $R^7$ and $R^8$ may form a 5, 6, or 7-membered carbocycle or heterocycle, wherein said carbocycle or heterocycle is optionally substituted with $R^9$;

$R^9$ is selected from the group consisting of: halogen, $(C_1-C_4)$alkyl, halo$(C_1-C_4)$alkyl, hydroxy, $(C_1-C_4)$alkoxy, halo$(C_1-C_4)$alkoxy, amino, $(C_1-C_4)$alkylamino and di$(C_1-C_4)$alkylamino.

2. The method of claim 1, wherein the disease or disorder is chronic inflammation.

3. The method of claim 2 wherein the disease or disorder is inflammatory colitis.

4. The method of claim 1, wherein the treatment of a disease or a disorder further comprises administering an additional therapeutic agent.

5. A method for inhibiting bromodomain in a cell, comprising contacting the cell with an inhibitory amount of a compound of formula I

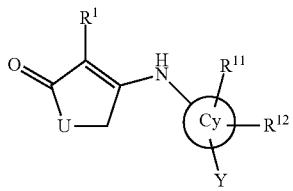

wherein:

U is $(CH_2)_n$, where n=1, 2 or 3;

$R^1$ is selected from the group consisting of: $(C_1-C_{10})$alkyl, substituted $(C_1-C_{10})$alkyl, and nitrile;

Cy is a carbocycle or heterocycle;

$R^{11}$ and $R^{12}$ are independently selected from the group consisting of: H, $(C_1-C_{10})$alkyl, $(C_1-C_{10})$perfluoroalkyl, halogen, nitrile, hydroxy, $(C_1-C_{10})$alkoxy, perfluoro$(C_1-C_{10})$alkoxy, $(C_1-C_{10})$alkylthio, amino, $(C_1-C_{10})$alkylamino, $(C_1-C_{10})$acylamino, aryl, heteroaryl, aminocarbonyl, carboxyl, and $(C_1-C_{10})$alkoxycarbonyl; or taken together, $R^{11}$ and $R^{12}$ may form a 5, 6, or 7-membered carbocycle or heterocycle wherein said carbocycle or heterocycle may be optionally substituted with $R^2$;

$R^2$ is selected from the group consisting of: halogen, $(C_1-C_4)$alkyl, halo$(C_1-C_4)$alkyl, hydroxy, $(C_1-C_4)$alkoxy, halo$(C_1-C_4)$alkoxy, carboxy, amino, $(C_1-C_4)$alkylamino and di$(C_1-C_4)$alkylamino;

Y is selected from,

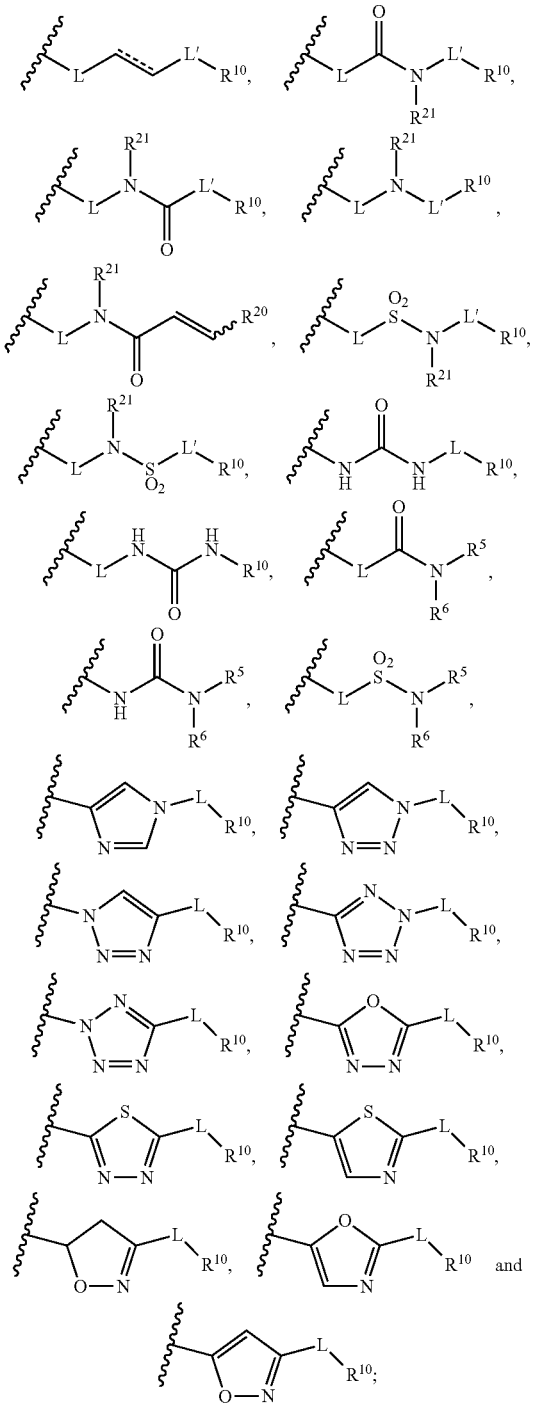

L and L' are independently a bond or $(CR^3R^4)_m$ where $R^3$ and $R^4$ are independently selected from the group consisting of H and $(C_1-C_4)$alkyl, and m is 1 or 2;

$R^{10}$ is chosen from alkyl, carbocycle and heterocycle, wherein said alkyl, carbocycle or heterocycle is optionally substituted with $R^7$ and/or $R^8$;

$R^{20}$ is —C(=O)OR$^{21}$;

$R^{21}$ is chosen from H and $(C_1-C_4)$alkyl;

$R^5$ and $R^6$ are independently selected from the group consisting of hydrogen, hydroxy, $(C_1-C_{10})$ hydrocarbyl, halo$(C_1-C_{10})$hydrocarbyl, and $(C_1-C_{10})$alkoxy;

$R^7$ and $R^8$ are independently selected from the group consisting of: hydroxy, halogen, $(C_1-C_4)$alkyl, halo$(C_1-C_4)$alkyl, hydroxy$(C_1-C_4)$alkyl, $(C_1-C_4)$alkoxy, halo $(C_1-C_4)$alkoxy, $(C_1-C_4)$alkylthio, $(C_1-C_4)$alkylcarbonyl, aryl, heteroaryl, cycloalkyl, heterocycloalkyl, cyano, oxo, $(C_1-C_4)$alkylsulfonyl, amino, $(C_1-C_4)$alkylamino, di$(C_1-C_4)$alkylamino, $(C_1-C_4)$acylamino, aminocarbonyl, carboxyl, and $(C_1-C_4)$alkoxycarbonyl, where each said alkyl, aryl, heteroaryl, cycloalkyl, or heterocycloalkyl, may be further optionally substituted with hydroxy, oxo, carboxy, carboxy$(C_1-C_4)$alkyl, hydroxy$(C_1-C_4)$alkyl, $(C_1-C_4)$alkoxy, $(C_1-C_4)$alkoxycarbonyl, $(C_1-C_4)$alkoxycarbonyl$(C_1-C_4)$alkyl, amino, $(C_1-C_4)$alkylamino, di $(C_1-C_4)$alkylamino, amido, $(C_1-C_4)$alkylamido, di $(C_1-C_4)$alkylamido, halogen, $(C_1-C_4)$alkyl, halo$(C_1-C_4)$alkyl, aryl, heteroaryl, heterocycloalkyl, or cycloalkyl;

or, taken together, $R^5$ and $R^6$, or $R^7$ and $R^8$ may form a 5, 6, or 7-membered carbocycle or heterocycle, wherein said carbocycle or heterocycle is optionally substituted with $R^9$;

$R^9$ is selected from the group consisting of: halogen, $(C_1-C_4)$alkyl, halo$(C_1-C_4)$alkyl, hydroxy, $(C_1-C_4)$alkoxy, halo$(C_1-C_4)$alkoxy, amino, $(C_1-C_4)$alkylamino and di$(C_1-C_4)$alkylamino 6. The method of claim 1, wherein the disease or disorder is autoimmune disease.

7. The method of claim 1, wherein the disease or disorder is cancer.

8. The method of claim 7, wherein the cancer is selected from breast cancer, triple negative breast cancer, prostate cancer, acute leukemia, chronic leukemia, chronic lymphocytic leukemia, colon cancer, colorectal cancer, multiple myeloma, glioblastoma, lung cancer, and liver cancer.

9. The method of claim 2, wherein the disease or disorder is selected from multiple sclerosis, inflammatory bowel disease, Crohn's disease, ulcerative colitis, type I diabetes, rheumatoid arthritis, AIDS, and asthma.

10. The method of claim 3, wherein:

$R^1$ is selected from the group consisting of: $(C_1-C_{10})$alkyl, $(C_1-C_{10})$alkyl substituted with one or more fluorine, and nitrile;

Cy is selected from the group consisting of: phenyl, naphthalene, pyridine, quinoline, isoquinoline, indole, or benzimidazole;

$R^{11}$ and $R^{12}$ are independently selected from the group consisting of: H, $(C_1-C_{10})$alkyl, $(C_1-C_{10})$perfluoroalkyl, halogen, $(C_1-C_{10})$alkoxy, amino, hydroxy, $(C_1-C_{10})$alkylamino, $(C_1-C_{10})$acylamino, aryl, heteroaryl, aminocarbonyl, carboxyl, and $(C_1-C_{10})$alkoxycarbonyl; or taken together, $R^{11}$ and $R^{12}$ may form a 5, 6, or 7-membered carbocycle or heterocycle wherein said carbocycle or heterocycle may be optionally substituted with $R^2$; and Y is selected from:

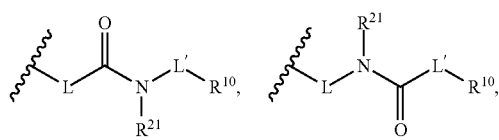

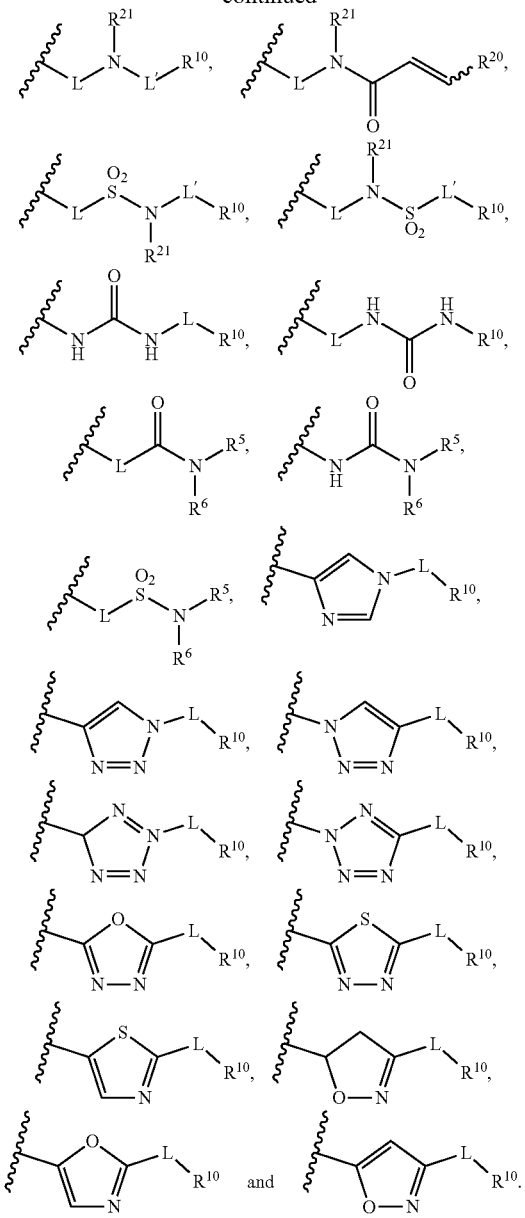

11. The method of claim 10, wherein the disease or disorder is chronic inflammation.

12. The method of claim 11, wherein the disease or disorder is inflammatory colitis.

13. The method of claim 10, wherein the treatment of a disease or a disorder further comprises administering an additional therapeutic agent.

14. The method of claim 5, wherein:

$R^1$ is selected from the group consisting of: $(C_1-C_{10})$alkyl, $(C_1-C_{10})$alkyl substituted with one or more fluorine, and nitrile;

Cy is selected from the group consisting of: phenyl, naphthalene, pyridine, quinoline, isoquinoline, indole, or benzimidazole;

$R^{11}$ and $R^{12}$ are independently selected from the group consisting of: H, $(C_1-C_{10})$alkyl, $(C_1-C_{10})$perfluoroalkyl, halogen, $(C_1-C_{10})$alkoxy, amino, hydroxy, $(C_1-$ $C_{10}$)alkylamino, ($C_1$-$C_{10}$)acylamino, aryl, heteroaryl, aminocarbonyl, carboxyl, and ($C_1$-$C_{10}$)alkoxycarbonyl; or taken together, $R^{11}$ and $R^{12}$ may form a 5, 6, or 7-membered carbocycle or heterocycle wherein said carbocycle or heterocycle may be optionally substituted with $R^2$; and Y is selected from:

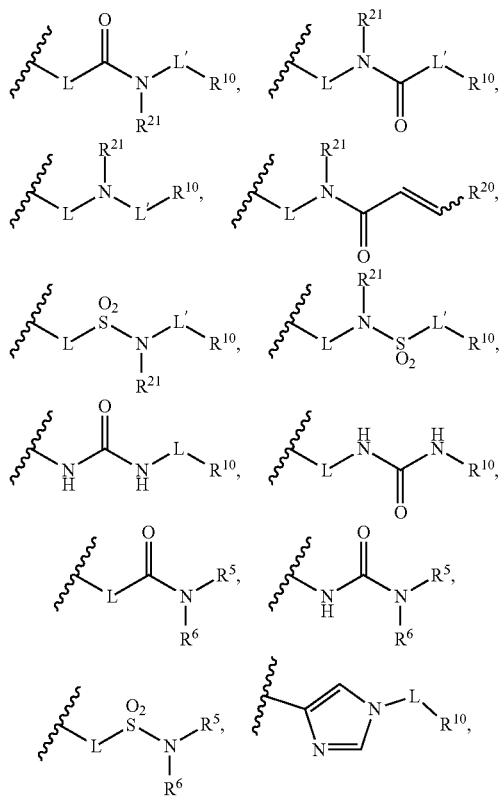

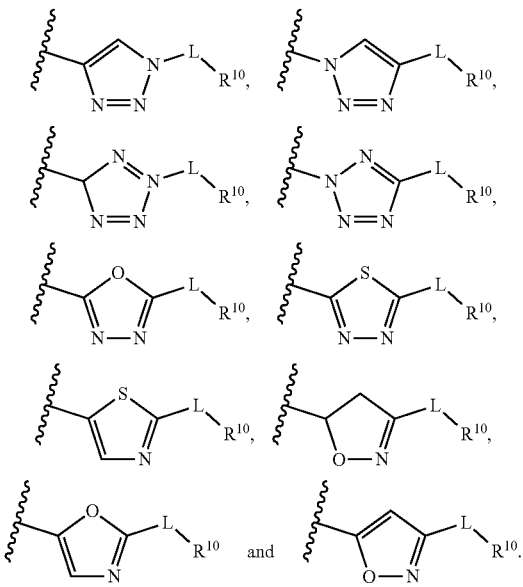

15. The method of claim 10, wherein the disease or disorder is autoimmune disease.

16. The method of claim 10, wherein the disease or disorder is cancer.

17. The method of claim 16, wherein the cancer is selected from breast cancer, triple negative breast cancer, prostate cancer, acute leukemia, chronic leukemia, chronic lymphocytic leukemia, colon cancer, colorectal cancer, multiple myeloma, glioblastoma, lung cancer, and liver cancer.

18. The method of claim 11, wherein the disease or disorder is selected from multiple sclerosis, inflammatory bowel disease, Crohn's disease, ulcerative colitis, type I diabetes, rheumatoid arthritis, AIDS, and asthma.

* * * * *

UNITED STATES PATENT AND TRADEMARK OFFICE
CERTIFICATE OF CORRECTION

PATENT NO. : 10,351,511 B2
APPLICATION NO. : 15/842032
DATED : July 16, 2019
INVENTOR(S) : Zhou et al.

Page 1 of 1

It is certified that error appears in the above-identified patent and that said Letters Patent is hereby corrected as shown below:

In the Claims

Column 203, Line 42: Claim 10, Delete "claim 3" and insert -- claim 1 --

Signed and Sealed this
Third Day of September, 2019

Andrei Iancu
*Director of the United States Patent and Trademark Office*